(12) United States Patent
Guiles et al.

(10) Patent No.: US 8,148,380 B2
(45) Date of Patent: Apr. 3, 2012

(54) ANTIBACTERIAL AMIDE AND SULFONAMIDE SUBSTITUTED HETEROCYCLIC UREA COMPOUNDS

(75) Inventors: Joseph Guiles, Lafayette, CO (US); Thale Jarvis, Boulder, CO (US); Sarah Strong, Louisville, CO (US); Xicheng Sun, Broomfield, CO (US); Jian Qiu, Longmont, CO (US); John C. Rohloff, Boulder, CO (US)

(73) Assignee: Crestone, Inc., Boulder, CO (US)

( * ) Notice: Subject to any disclaimer, the term of this patent is extended or adjusted under 35 U.S.C. 154(b) by 176 days.

(21) Appl. No.: 12/669,634

(22) PCT Filed: Jul. 23, 2008

(86) PCT No.: PCT/US2008/070893
§ 371 (c)(1),
(2), (4) Date: May 6, 2010

(87) PCT Pub. No.: WO2009/015208
PCT Pub. Date: Jan. 29, 2009

(65) Prior Publication Data
US 2012/0015941 A1  Jan. 19, 2012

Related U.S. Application Data

(60) Provisional application No. 60/961,634, filed on Jul. 23, 2007, provisional application No. 61/022,725, filed on Jan. 22, 2008.

(51) Int. Cl.
| | |
|---|---|
| *A61K 31/497* | (2006.01) |
| *A61K 31/433* | (2006.01) |
| *A61K 31/427* | (2006.01) |
| *A61K 31/4439* | (2006.01) |
| *A61K 31/506* | (2006.01) |
| *A61K 31/513* | (2006.01) |
| *A61K 31/426* | (2006.01) |
| *A61P 31/04* | (2006.01) |
| *C07D 285/08* | (2006.01) |
| *C07D 417/12* | (2006.01) |
| *C07D 277/28* | (2006.01) |
| *C07D 239/47* | (2006.01) |

(52) U.S. Cl. ............ 514/255.05; 514/361; 514/371; 514/342; 514/272; 514/274; 544/405; 544/316; 544/298; 546/270.7; 548/128; 548/196

(58) Field of Classification Search ............ None
See application file for complete search history.

(56) References Cited

U.S. PATENT DOCUMENTS

| | | | |
|---|---|---|---|
| 4,522,811 A | 6/1985 | Eppstein et al. | |
| 6,100,282 A | 8/2000 | Alig et al. | |
| 6,569,874 B1 | 5/2003 | Pruitt et al. | |
| 7,105,508 B1 * | 9/2006 | Kling et al. | ............ 514/212.04 |
| 2005/0261294 A1 | 11/2005 | Mjalli et al. | |
| 2007/0155706 A1 | 7/2007 | Andersch et al. | |
| 2008/0207703 A1 | 8/2008 | Guiles et al. | |
| 2010/0286169 A1 | 11/2010 | Guiles et al. | |

FOREIGN PATENT DOCUMENTS

| | | |
|---|---|---|
| WO | WO 00/66618 | 11/2000 |
| WO | WO 01/10847 | 2/2001 |
| WO | WO 0110847 A2 * | 2/2001 |
| WO | WO/2006/071255 | 7/2006 |
| WO | WO 2008/011191 | 1/2008 |
| WO | WO 2009/015193 | 1/2009 |
| WO | WO 2009/015208 | 1/2009 |

OTHER PUBLICATIONS

Nov. 25, 2011 EP Supplemental Search Report with respect to EP Appl. 08782264.9 (EP 2200440 Publication).
Office Action received Oct. 14, 2010 with respect to U.S. Appl. No. 11/880,501.
Kennedy and Harkin (1999) "Data to Access Public Health Threat from Resistant Bacteria are Limited" Antimicrobial Resistance, General Accounting Office (GAO/RCED-99-132).
Berge et al (1977) "Pharmaceeutical Salts" Journal of Pharmaceutical Sciences 66(1):1-19.
Gould (1986) "Salt Selection for Basic Drugs" International J. of Pharmaceutics 33:201-217.
Jacobsen et al (1999) "Synthesis of a Series of Stromelysin-Selective Thiadiazole Urea Matrix Metalloproteinase Inhibitors" J. Med. Chem. 42:1525-1536.
Lange et al (2002) "Synthesis of Highly Potent and Selective Hetaryl Ureas as Integrin $\alpha_v\beta_3$-Receptor Antagonists" Bioorganic & Medicinal Chemistry Letters 12:1379-1382.
Ochsner et al (2005) "Mode of Action and Biochemical Characterization of REP8839, a Novel Inhibitor of Methionyl-tRNA Synthetase" Antimicrobial Agents Chemo. 49:4253-62.
Office Action received Mar. 26, 2010 with respect to U.S. Appl. No. 11/880,501.

\* cited by examiner

*Primary Examiner* — Yong Chu
(74) *Attorney, Agent, or Firm* — Swanson & Bratschun, L.L.C.

(57) ABSTRACT

The present invention provides novel amide and sulfonamide substituted heterocyclic urea compounds having useful antibacterial activity. Use of these compounds as pharmaceutical compositions and method of their production are also provided.

23 Claims, No Drawings

SEQUENCE LISTING

<160> NUMBER OF SEQ ID NOS: 2

<210> SEQ ID NO 1
<211> LENGTH: 19
<212> TYPE: DNA
<213> ORGANISM: Artificial

```
<220> FEATURE:
<223> OTHER INFORMATION: Synthetic

<400> SEQUENCE: 1
accagtgaga cgggcaaca                                            19

<210> SEQ ID NO 2
<211> LENGTH: 33
<212> TYPE: DNA
<213> ORGANISM: Artificial
<220> FEATURE:
<223> OTHER INFORMATION: Synthetic

<400> SEQUENCE: 2
tgaattatag gccctgttgc ccgtctcact ggt                            33
```

ANTIBACTERIAL AMIDE AND SULFONAMIDE SUBSTITUTED HETEROCYCLIC UREA COMPOUNDS

RELATED APPLICATIONS

This application is a 35 U.S.C. §371 national phase application of PCT/US2008/070893 (WO 2009/015208), filed on Jul. 23, 2008, entitled "Antibacterial Amide and Sulfonamide Substituted Heterocyclic Urea Compounds", which application claims the benefit of U.S. Provisional Application Ser. No. 60/961,634, filed Jul. 23, 2007, and claims benefit of U.S. Provisional Application Ser. No. 61/022,725, filed Jan. 22, 2008, each of which is incorporated herein by reference in its entirety.

TECHNICAL FIELD

The present invention relates to novel heterocyclic urea compounds and in particular to novel amide and sulfonamide substituted heterocyclic urea compounds and to their uses in the treatment of bacterial infections.

BACKGROUND OF THE INVENTION

Antibacterials kill or inhibit the growth of bacteria by interfering with major processes of cellular function that are essential for survival. The development of antibacterial agents has significantly reduced the morbidity and mortality associated with bacterial infections over the last century, particularly in developed countries. However, the emergence of drug-resistant bacterial strains threatens the resurgence of bacterial-borne diseases long thought to have been conquered.

Resistance to antibacterials can occur when the target of a drug mutates so that it can still function, but is no longer inhibited by the drug (e.g., mutations in the quinolone resistance determining regions of bacterial gyrases and topisomerase enzymes that confer resistance to the fluoroquinolones). In a recent congressional report, the General Accounting Office (GAO) has summarized the current and future public health burden resulting from drug-resistant bacteria (Antimicrobial Resistance (1999). General Accounting Office (GAO/RCED-99-132)). According to this report, the number of patients treated in a hospital setting for an infection with drug-resistant bacteria has doubled from 1994 to 1996 and again almost doubled from 1996 to 1997. The same GAO report also provides clear evidence that previously susceptible bacteria are increasingly becoming resistant and spreading around the world. As a consequence of the increase and prevalence of resistant bacteria there is a growing need to identify new antibacterial agents.

SUMMARY OF THE INVENTION

It has now been found that amide and sulfonamide substituted heterocyclic urea compounds are useful in the treatment of bacterial infections. The present invention relates to these antibacterial compounds and salts thereof, pharmaceutical compositions comprising these compounds and methods of use thereof in the treatment of bacterial infections, including resistant bacterial infections.

In one aspect the invention provides compounds of Formula (I):

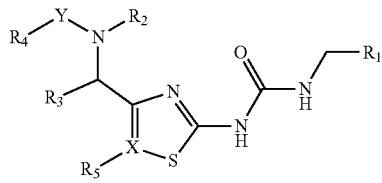

in which:
$R_1$ is selected from the group consisting of a substituted or unsubstituted aryl, substituted or unsubstituted arylalkyl and substituted or unsubstituted heteroaryl;
X is selected from the group consisting of a C and N atom;
Y is selected from the group consisting of CO and $SO_2$;
$R_2$, $R_3$ and $R_4$ are independently selected from the group consisting of, H, OH, substituted or unsubstituted aryl, substituted or unsubstituted arylalkyl, substituted or unsubstituted linear, cyclic or branched alkyl, cyano, and perfluoroalkyl;
and further, optionally
wherein $R_2$, $R_4$, Y, and N together can form a substituted or unsubstituted 4-7 member saturated ring;
or alternatively, optionally
wherein $R_2$, $R_3$ and N together can form a substituted or unsubstituted 4-7 member saturated ring; and
$R_5$ is selected from the group consisting of H, halogen, alkyl, cyano and null, wherein $R_5$ is null when X is N.

These and various other features as well as advantages which characterize the invention will be apparent from a reading of the following detailed description and a review of the appended claims.

DETAILED DESCRIPTION OF THE INVENTION

The present invention relates to antibacterial compounds and salts thereof, pharmaceutical compositions comprising these compounds and methods of use thereof. The compounds of the present invention are useful in the protection of patients from bacterial infections, including antibiotic resistant bacterial infections.

In particular, antibacterial compounds of the invention include amide and sulfonamide substituted heterocyclic urea compounds.

In one embodiment, the invention provides compounds of Formula (I):

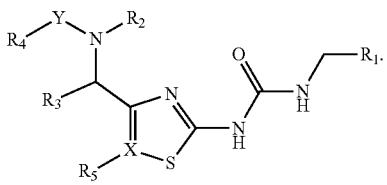

In one embodiment, $R_1$ is preferably a substituted or unsubstituted phenyl or thiophene group, for example, a phenyl group which has one or more substituents independently selected from halogen, cyano, $(C_{1-6})$alkyl, mono to perfluoro $(C_{1-3})$alkyl, $(C_{3-7})$cycloalkyl, $(C_{2-6})$alkenyl, $(C_{1-6})$alkoxy, $(C_{2-6})$alkenoxy, hydroxy, amino, mono- or di-$(C_{1-6})$alkylamino, acylamino, nitro, carboxy, $(C_{1-6})$alkoxycarbonyl, $(C_{1-6})$alkenyloxycarbonyl, $(C_{1-6})$alkoxycarbonyl$(C_{1-6})$alkyl, carboxy$(C_{1-6})$alkyl, $(C_{1-6})$alkylcarbonyloxy, carboxy$(C_{1-6})$ alkyloxy, $(C_{1-6})$alkoxycarbonyl$(C_{1-6})$alkoxy, $(C_{1-6})$alkylthio, $(C_{1-6})$alkylsulphinyl, $(C_{1-6})$alkylsulphonyl, sulphamoyl, mono- and di-$(C_{1-6})$-alkylsulphamoyl, and carbamoyl.

Suitable identities for $R_1$ include, but are not limited to, 3-fluorophenyl, 4-fluorophenyl, 3-chlorophenyl, 4-chlorophenyl, 3-bromophenyl, 4-bromophenyl, 3-iodophenyl, 4-iodophenyl, 3-methoxyphenyl, 4-methoxyphenyl, 3-methylphenyl, 4-methylphenyl, 3-trifluoromethylphenyl, 4-trifluoromethylphenyl, 3-4-methylendioxyphenyl, 3-4-difluorophenyl, 3-4-dichlorophenyl, 3-4-dibromophenyl, 3-4-dimethylphenyl, 3-4-(—CH$_2$CH$_2$CH$_2$—)phenyl, 3-4-(—OCH$_2$CH$_2$O—)phenyl, 3-chloro-4-fluorophenyl, benzo[1,3]dioxyl-5-yl, and 3-3-cyanophenyl, 3-5 difluorophenyl, thiophen-2-yl, thiophen-3-yl, 4,5-di-bromo-thiophen-2-yl, 5-chloro-thiophen-2-yl, and 5-bromo-thiophen-2-yl, 5-fluoro-thiophen-2-yl, 5-chloro-thiophen-3-yl, 1,1,-difluoro-benzo[1,3]dioxyl-5-yl, 7-chlorobenzo[1,3]dioxol-5-yl, 3-nitrophenyl, 2,1,3-benzoxadiazol-5-yl, and 4-nitrophenyl.

X is selected from the group consisting of C and N atom.

Y is selected from the group consisting of CO, and SO$_2$.

$R_5$ is selected from the group consisting of H, halogen, alkyl, cyano and null, wherein $R_5$ is null when X is N.

$R_2$, $R_3$ and $R_4$ are independently selected from the group consisting of, H, OH, substituted or unsubstituted aryl, substituted or unsubstituted arylalkyl, substituted or unsubstituted linear, cyclic or branched alkyl, cyano, and perfluoroalkyl.

Suitable identities for $R_2$, and $R_3$, include, but are not limited to, H, methyl, ethyl, 2-hydroxyethyl, 2-hydroxymethyl, 2,2-Difluoro-ethyl, 2-methoxyethyl, 2-aminoethyl, propyl, cyclopropyl, isopropyl, 2,4-dimethoxybenzyl, 2-methanesulfonylaminoethyl and 3,5-dimethylisoxazole-4-yl-methyl.

Suitable identities for $R_4$, include, but are not limited to methyl, 2-(2-methoxyethoxy)-methyl, 2-methoxymethyl, 4-methylisoxazole-5-yl, isoxazole-5-yl, 3-phenylpropanyl, furan-2-yl, 4-phenoxybutanyl, 1,1-dioxo-tetrahydro-1-lamda6-thiophen-3-ylmethylaminoyl, 3,5-dimethylisoxazole-4-yl, 1-methyl-1H-imidazole-5-yl, furan-3-yl, 3-methylfuran-2-yl, 5-methyl-3-phenylisoxazole-4-yl, 5-methyl-2-phenyl-2H-1,2,3-triazole-4-yl, 5-methylisoxazole-3-yl, 3-methyl-5-phenylisoxazole-4-yl, 3-methyl-5-(4-methyl-1,2,3-thiadiazol-5-yl)isoxazole-4-yl, 2-(2H-tetrazol-5-yl)methyl, benzofuran-2-yl, 1,2,5-oxadiazole-3-yl, (3,5-dimethylisoxazol-4-yl)-methyl, 3-methylisoxazole-4-yl, 5-methylisoxazole-4-yl, 5-cyclopropyl-isoxazole-4-yl, 2,6-dimethylphenyl, 5-(furan-2-yl)-isoxazole-3-yl, 2,5-dimethyloxazole-4-yl, 2-phenylthiazole-4-yl, 2-(thiophen-2-yl)thiazole-4-yl, 3-hydroxy-isoxazole-5-yl, 5-phenyl-1,3,4-oxadiazole-2-yl, 5-methylfuran-2-yl, 4-methyl-1,2,5-oxadiazole-3-yl, 4-methyl-2-(pyrazin-2-yl)thiazole-5-yl, 2,4-dimethoxy-phenyl, 4-methoxy-phenyl, 3,4-dimethoxy-phenyl, benzo[1,3]dioxole-5-yl, 3,4,5-trimethoxy-phenyl, 5-methyl-3-(trifluoromethyl)isoxazole-4-yl, pyridin-3-ylmethyl, 2,4-dimethylpyridine-3-yl, 2,4,6-trimethylphenyl, 5-(methoxymethyl)-3-methylisoxazole-4-yl, 2-methoxymethyl, 2-methoxyformyl, 3-ethyl-5-methylisoxazole-4-yl, pyrimidine-5-yl, pyrazine-2-yl, 5-methylpyrazine-2-yl, furan-3-yl, 4-methyloxazole-5-yl, 2-tosylmethyl, 3-ethylcarboxy-5-methylisoxazole-4-yl, 3-carboxy-5-methylisoxazole-4-yl, 2-methylpyridine-3-yl, 4-methylpyridine-3-yl, 3-chloro-4-(methylsulfonyl)thiophene-2-yl, 4-methylthiazole-5-yl, 5-oxo-3,5-dihydro-2H-thiazolo[3,2-a]pyrimidine-6-yl, 4-methyl-2-(methylthio)pyrimidine-5-yl, 2-methyl-prop-1-enyl, 2-methylphenyl, quinoxaline-2,3-methylpyridine-4-yl, 3-methylisoxazole-4-yl, 4-aminopyrimidine-5-yl, 2-amino-4-methylpyrimidine-5-yl, 4,6-dimethyl-2-oxo-1,2-dihydropyridine-3-yl, 2,4,6-trimethylpyrimidine-5-yl, 3-methylpyrazine-2-yl, 4-Boc-amino-1-methyl-1H-imidazole-2-yl, 4-amino-1-methyl-1H-imidazole-2-yl, 4-acetamido-1-methyl-1H-imidazole-2-yl, 4,6-dimethylpyrimidine-5-yl, 3-(hydroxymethyl)-5-methylisoxazole-4-yl, 3-methylpyridine-2-yl, 2-amino-4,6-dimethylpyrimidine-5-yl, 2-methylimidazo[1,2-a]pyridine-3-yl, tetrahydrofuran-2-yl, 2-methoxypyridine-3-yl, tetrahydrofuran-3-yl, methoxyformyl, 2-chloropyridine-3-yl, 1,3,5-tetramethyl-1H-pyrazole-4-yl, (S)-tetrahydrofuran-2-yl, (R)-tetrahydrofuran-2-yl, 3-propoxypyridine-4-yl, N-Boc-morpholine-2-yl, morpholine-2-yl, pyridazine-4-yl, 3,5-dimethyl-1H-pyrazole-4-yl, pyridazine-3-yl, tetrahydro-2H-pyran-4-yl, 1,5-dimethyl-1H-pyrazole-4-yl, morpholine-3-yl, 4-methylpyrrolidine-3-yl, (S)-pyrrolidine-2-yl, 1,1-Dioxo-tetrahydro-1-lamda6-thiophene-3-yl, 4-methylphenyl, methyl, ethyl, propyl, butyl, cyclopropyl, and 1,1-Dioxo-1-isothiazolidin-2-yl, 2-methyl-5,6-dihydro-4H-pyran-3-yl, 2-methyl-5-morpholin-4-ylmethyl-furan-3-yl, 2-methyl-but-2-enyl, [1,2,3]thiadiazole-4-yl, 2-pyridin-3-yl-thiazole-4-yl, 2,5-dimethyl-2H-pyrazole-3-yl, 4-methylfurazan-3-yl, 2-morpholin-4-ylmethyl-furan-3-yl, 1-methylpyrrolidine-2-yl, 1-methyl-1H-pyrrole-2-yl, 1,5-dimethyl-1H-[1,2,3]-triazole-4-yl, 5-fluoro-thiophene-2-yl, 4-methylpyrimidine-5-yl, 4-methyl-2-phenyl-pyrimidine-5-yl, 2-methylsulfanyl-nicotinyl, acetonitrile, 6-morpholin-4-yl-nicotinyl, 4-methyl-thiazole-5-yl, 3-methyl-1H-pyrazole-4-yl, 2,4-dimethyl-pyrimidine-5-yl, 2-methyl-[1,6]naphthyridine-3-yl, 6-(4-methoxy-phenyl)-pyridazine-3-yl, 2,6-bis-dimethylamino-pyrimidine-4-yl, 2,6-di-morpholin-4-yl-pyrimidine-4-yl, 3-pyridin-3-yl-acrylonitrile-2-yl, 2-methyl-[1,8]naphthyridine-3-yl, 2-dimethylamino-6-methyl-pyrimidine-4-yl, acetic acid 1-yl-ethyl ester, 1-ethyl-3-methyl-1H-pyrazole-4-yl, 2-methyl-pyrazolo[1,5-a]pyrimidine-3-yl, 1-hydroxy-ethyl, 1-ethyl-5-methyl-1H-pyrazole-4-yl, 5,7-dimethyl-pyrazolo[1,5-a]pyrimidine-3-yl, 1-methyl-1H-indole-3-yl, 1-methyl-1H-indazole-3-yl, pyrazolo[1,5-a]pyridine-3-yl, 2-furan-2-yl-oxo, 5-oxo-pyrrolidine-2-yl, 4-methyl-pyridazine-3-yl, 5-methyl-pyridazine-4-yl, 3-amino-1H-pyrazole-4-yl, 3,6-dimethoxy-pyridazine-4-yl, 3,6-dichloro-pyridazine-4-yl, pyridine-3-yl, pyridine-2-yl, 1-methyl-1H-imidazole-4-yl, 1,2-dimethyl-1H-imidazole-4-yl, pyridin-3-yl-methyl, 3-chloro-6-methoxy-pyridazin-4-yl, 3,5-dimethyl-pyridazin-4-yl, 1-methyl-3-trifluoromethyl-1H-pyrazol-4-yl, 3-chloro-6-hydroxy-pyridazin-4-yl, 2-methyl-tetrahydrofuran-2-yl, 4-chloro-1-methyl-1H-pyrazol-3-yl, 5-chloro-1-methyl-1H-pyrazol-4-yl, 4-chloro-2-methyl-2H-pyrazol-3-yl, 4-chloro-1H-pyrazol-3-yl, 1,3,6-trimethyl-1H-pyrazolo[3,4-b]pyridin-3-yl, 2-methyl-5-sulfamoyl-phenyl, 1-methyl-6-oxo-1,4,5,6-tetrahydropyridazin-3-yl, 1-phenyl-cyclobutyl, 3-methyl-4-oxo-3,4-dihydrophthalazin-1-yl, 7-chloro-benzo[1,3]dioxol-5-yl, 6-[1,2,4]triazol-1-yl-pyridin-3-yl, 1-(2-methoxyethyl)-6-oxo-1,6-dihydropyridazin-3-yl, 2-(2,4-dioxo-3,4-dihydropyrimidin-1-(2H)-yl)methyl, 6-chloro-3-hydroxy-pyridazin-4-yl, 3-cyano-2-hydroxy-6-methyl-pyridin-4-yl, 1-methyl-5-(1H-pyrrol-1-yl)-1H-pyrazol-4-yl, 4-oxo-3,4-dihydrophthalazin-1-yl, 4,6-dimethyl-2-oxo-2H-pyran-5-yl, 1-methyl-4-sulfamoyl-1H-pyrrol-2-yl, (5,7-dimethyl-[1,2,4]triazolo[1,5-a]pyrimidin-6-yl)methyl, 3,6-dimethyl-4-oxo-3,4-dihydrofuro[2,3-d]pyrimidin-5-yl, 5-methyl-4-oxo-3,4-dihydrothieno[2,3-b]pyrimidin-6-yl, phenyl-difluoromethyl, 4-hydroxyl-1-carbamoyl-pyrrolidin-2-yl, 2-(1-morpholino)-pyridin-3-yl, 1-(3-fluorophenyl)-cyclobutyl, 1-methyl-5-trifluoromethyl-1H-pyrazol-4-yl, (S)-1-methoxyethyl, 3-methyl-5,6-dihydro-1,4-dioxin-2-yl, (R)-5-oxotetrahydrofuran-2-yl, 5-chloro-1,3-dimethyl-1H-pyraozol-4-yl, 2-methoxy-ethyl, 1-(2-hydroxyethyl)-3,5-dimethyl-1H-pyrazol-4-yl, (R)-1-methoxy-ethyl, 1-(2-methoxyethyl)-3,5-dimethyl-1H-pyrazol-4-yl, tetrahydro-2H-pyran-2-yl, 3,6-dimethylisoxazolo[5,4-b]pyridine-4-yl, 5-methoxy-tetrahydrofuran-2-yl, 1-(4-methoxybutyl)-3,5-dimethyl-1H-pyrazol-4-yl, 1-(3-methoxypropyl)-3,5-dimethyl-1H-pyrazol-4-yl, 1-(4-fluorophenyl)-cyclobutyl, 5-methyl-tetrahydrofuran-2-yl, 3-methyl-oxetan-3-yl, 5-chloro-1H-pyrazol-4-yl, (R)-2,2-dimethyl-1,3-dioxolan-4-yl, (S)-2,2-dimethyl-1,3-dioxolan-4-yl, 3,6-dichloro-5-methyl-pyridazin-4-yl, 6-methoxyl-3-methyl-pyridazin-4-yl, 1-methyl-5-nitro-1H pyrazol-4-yl, 2,3-dihydrobenzofuran-2-yl, 6-hydroxy-3-methyl-pyridazin-4-yl, 2-(1-pyrrolidinyl)-pyridin-3-yl, 3-oxo-3-(2-thiophenyl)-propyl, 3-oxo-3-phenyl-propyl, 3-fluoro-4-methoxy-benzyl, 3,4-dimethoxy-benzyl, 4-(hydroxymethyl)-phenoxy-methyl, 3-methylsulfonyl-benzyl, 2-mercapto-4-methyl-thiazol-5-yl, 5-trifluoromethyl-furan-2-yl, 6-hydroxy-3-methylamino-pyridazin-4-yl, 3-(dimethylamino)-6-methoxy-pyridazin-4-yl, 2,2-dimethyl-tetrahydro-2H-pyran-4-yl, 4-(dimethylamino)-benzyl, 7-hydroxy-1,2,3,4-tetrahydroisoquinolin-3-yl, 1H-benzoimidazol-2-yl, naphthalene-2-yl-methyl, 4-methoxy-3-methyl-benzyl, 1-amino-2-benzyloxy-ethyl, 1,4-dioxo-1,2,3,4-tetrahydrophthalazin-6-yl, 2,4-dioxo-3,4-dihydropyrimidin-1(2H)-yl)-methyl, 5-nitro-1H-pyrazol-4-yl, (S)-3,3-difluoro-tetrahydrofuran-2-yl, chroman-2-yl, 3,5-dimethyl-1H-pyrazol-4-yl, 4-butynyl, 2-methyl-1,2,34-tetrahydroisoquinolin-3-yl, (S)-2-(4-pyridinyl), 1-amino-ethyl, cis-3-methoxy-tetrahydrofuran-2-yl, 1-cyano-cyclopropyl, ethynyl, 1-ethoxy-ethyl, 1-(4-methoxy-phenoxy)ethyl, 1-(cyclopropylmethoxy)ethyl, 1,4-diamino-butyl, 1-(2-phenoxyethoxy)ethyl, cyclopropylmethyl, 3-ethyl-3-oxetan-3-yl, 1-(2,2-difluoroethoxy)ethyl, 1-(4-fluoro-benzyloxy)ethyl, 1-(2,2,2-trifluoroethoxy)ethyl, 1-(prop-2-ynyloxy)ethyl, 5-methyl-isoxazol-3-yl, 1-((1-methyl-pyrrolidin-3-yl)oxy)ethyl, 1-(2-hydroxyethoxy)ethyl, cyclopentyl, 1-hydroxy-cyclopropyl, cyclohexyl, 2-methyl cyclohexyl, 2-oxo-2,3-dihydrobenzoxazol-6-yl, 2,2,2-trifluoroethyl, 1-hydroxy-1-methyl-ethyl, (R)-5-(hydroxymethyl)tetrahydrofuran-2-yl, (4-hydroxy-2-oxo-pyrrolidin-1-yl)methyl, 1,2,2,2-tetrafluoroethyl, 1-carbamoyl-cyclopropyl, 2-methyl-cyclopropyl, 5-chloro-1,3-dimethyl-1H-pyrazol-4-yl, 5-isopropyl-3-methyl-isoxazol-4-yl, and 1,3,5-trimethyl-1H-pyrazolo[4,3-b]pyridin-7-yl.

In alternative embodiments, $R_2$, $R_4$, Y, and N together form a substituted or unsubstituted 4-7 member saturated ring. Suitable identities for such a substituted or unsubstituted 4-7 member saturated rings include, but are not limited to, 2,4-dioxothiazolidin-3-yl and 2-oxooxazolidin-3-yl.

In other alternative embodiments, $R_2$, $R_3$ and N together form a substituted or unsubstituted 4-7 member saturated ring. Suitable identities for such a substituted or unsubstituted 4-7 member saturated rings include, but are not limited to, 4-acetoxy-1-(methylsulfonyl)pyrrolidin-2-yl and 4-hydroxy-1-(methylsulfonyl)pyrrolidin-2-yl.

When used herein, the term "alkyl" and similar terms such as "alkoxy" include all straight chain, branched, and cyclic isomers. Representative examples thereof include methyl, ethyl, n-propyl, iso-propyl, cyclobutyl, cyclopropyl, cyclopentyl, cyclohexyl, n-butyl, sec-butyl, iso-butyl, t-butyl, n-pentyl and n-hexyl. Optionally fluorosubstituted alkyls may have 1 or more substitutions of F for H on the alkyl chain. A representative example of an optionally fluorosubstituted alkyl is trifluoromethyl.

When used herein, the terms "alkenyl" and "alkynyl" include all straight chain, branched and cyclic isomers. Representative examples thereof include vinyl, ethynyl and 1-propynyl. Optionally fluorosubstituted alkenyls may have 1 or more substitutions of F for H on the alkenyl chain. A representative example of an optionally fluorosubstituted alkenyl is fluorovinyl.

Preferred substituents for alkyl and alkenyl groups include, for example, and unless otherwise defined, halogen, cyano, azido, nitro, carboxy, $(C_{1-6})$alkoxycarbonyl, carbamoyl, mono- or di-$(C_{1-6})$alkylcarbamoyl, sulpho, sulphamoyl, mono- or di-$(C_{1-6})$alkylsulphamoyl, amino, mono- or di-$(C_{1-6})$alkylamino, acylamino (e.g., pyridyloxy), ureido, $(C_{1-6})$alkoxycarbonylamino, 2,2,2-trichloroethoxycarbonylamino, aryl, heteroaryl, heterocyclyl, hydroxy, $(C_{1-6})$alkoxy (e.g., ethoxy, isopropoxy), acyloxy (e.g., phenyloxy, benzyloxy, phenethoxy), oxo, acyl, 2-thienoyl, $(C_{1-6})$alkylthio, $(C_{1-6})$alkylsulphinyl, $(C_{1-6})$alkylsulphonyl, hydroxyimino, $(C_{1-6})$alkoxyimino, hydrazino, hydrazono, benzohydroximoyl, guanidino, amidino and iminoalkylamino Also preferred are 4-formyl-piperazin-1-yl, 4-methylpiperazin-1-yl-, 4-ethylpiperazin-1-yl-, 4-phenylpiperazin-1-yl-, 4-pyrimidin-2-yl-piperazin-1-yl, Hexahydroxy-pyrrolo[1,2-a]imidazole-1-yl, Morpholin-4-yl, 3-(2-methoxy-ethyl)-methyl-amino, and 3-(2-methoxy-ethyl)-methyl-amino. Other appropriate substituents include alkylthio meaning an alkyl-S— group in which the alkyl group is as previously described. Non-limiting examples of suitable alkylthio groups include methylthio and ethylthio. The bond to the parent moiety is through the sulfur. Substituents further include alkoxycarbonyl meaning an alkyl-O—CO— group. Non-limiting examples of suitable alkoxycarbonyl groups include methoxycarbonyl and ethoxycarbonyl. The bond to the parent moiety is through the carbonyl. Another suitable substituent is alkylsulfonyl meaning an alkyl-$SO_2$ group. Preferred alkylsulfonyl groups are those in which the alkyl group is a lower alkyl. The bond to the parent moiety is through the sulfonyl.

When used herein, the term "aryl" means an aromatic monocyclic or multicyclic ring system with each ring comprising from about 6 to about 14 carbon atoms, preferably about 6 to about 10 carbon atoms. The aryl group can be optionally substituted with one or more "ring system substituents" and optionally substituted with up to five, preferably up to three substituents which may be the same or different, and are as defined herein. Non-limiting examples of suitable aryl groups include phenyl, naphthyl, anthracenyl, phenanthrenyl, indanyl, indenyl, and the like. Aryl moieties are well known and described, for example, in Hawley's Condensed Chemical Dictionary (13 ed.), R. J. Lewis, ed., J. Wiley & Sons, Inc., New York (1997). Aryl groups can be substituted or unsubstituted.

When substituted, an aryl group may have up to three substituents. Preferred substituents for an aryl group (a "ring system substituent") include, for example, and unless otherwise defined, halogen, cyano, $(C_{1-6})$alkyl, mono to perfluoro $(C_{1-3})$alkyl, $(C_{3-7})$cycloalkyl, $(C_{2-6})$alkenyl, $(C_{1-6})$alkoxy, $(C_{2-6})$alkenoxy, aryl$C_{(1-6)}$alkoxy, halo$(C_{1-6})$alkyl, hydroxy, amino, mono- or di-$(C_{1-6})$alkylamino, acylamino, nitro, carboxy, $(C_{1-6})$alkoxycarbonyl, $(C_{1-6})$alkenyloxycarbonyl, $(C_{1-6})$alkoxycarbonyl$(C_{1-6})$alkyl, carboxy$(C_{1-6})$alkyl, $(C_{1-6})$alkylcarbonyloxy, carboxy$(C_{1-6})$alkyloxy, $(C_{1-6})$alkoxycarbonyl$(C_{1-6})$alkoxy, $(C_{1-6})$alkylthio, $(C_{1-6})$alkylsulphinyl, $(C_{1-6})$alkylsulphonyl, sulphamoyl, mono- and di-$(C_{1-6})$-alkylsulphamoyl, carbamoyl, mono- and di-$(C_{1-6})$alkylcarbamoyl, heteroaryl and heterocyclyl. Other preferred aryl groups include arylalkyl meaning an alkyl substituted aryl group. Other preferred aryl groups include aryloxy meaning an aryl-O— group in which the aryl group is as previously described. Non-limiting examples of suitable aryloxy groups include phenoxy and naphthoxy. The bond to the parent moiety is through the ether oxygen. Arylalkyloxy meaning an arylalkyl-O— group in which the arylalkyl group is as previously described. Non-limiting examples of suitable arylalkyloxy groups include benzyloxy and phenethyloxy. The bond to the parent moiety is through the ether oxygen. Another preferred aryl is an arylthio meaning an aryl-S— group in which the aryl group is as previously described. Non-limiting examples of suitable arylthio groups include phenylthio and naphthylthio. The bond to the parent moiety is through the sulfur. Other preferred aryls include arylalkylthio meaning an arylalkyl-S— group in which the arylalkyl group is as previously described. Non-limiting example of a suitable arylalkylthio group is benzylthio. The bond to the parent moiety is through the sulfur. Other preferred aryls is an aryloxycarbonyl meaning an aryl-O—C(O)— group. Non-limiting examples of suitable aryloxycarbonyl groups include phenoxycarbonyl and naphthoxycarbonyl. The bond to the parent moiety is through the carbonyl. Another such group is an arylalkoxycarbonyl meaning an arylalkyl-O—C(O)— group. Non-limiting example of a suitable arylkoxycarbonyl group is benzyloxycarbonyl. The bond to the parent moiety is through the carbonyl. Yet another such group is an arylsulfonyl meaning an aryl-SO$_2$— group. The bond to the parent moiety is through the sulfonyl.

When used herein, the term "heteroaryl" monocyclic and polycyclic aromatic hydrocarbons include at least one heteroatom ring member such as sulfur, oxygen, or nitrogen alone or in combination. Preferably the heteroaryl ring comprises from 4 to 7, and preferably 5 to 6, ring atoms. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-5-oxide, 2,3-dihydrobenzothienyl-5-dioxide, benzoxazolin-2-on-yl, indolinyl, benzodioxolanyl, benzodioxane, and the like. Heteroaryl groups can be substituted or unsubstituted. A fused heteroaryl ring system may include carbocyclic rings and need only include one heterocyclic ring.

When used herein, the term "heterocyclyl" means an aromatic or non-aromatic saturated monocyclic or multicyclic (preferably bicyclic) ring system comprising about 3 to about 10 ring atoms, preferably about 5 to about 10 ring atoms, in which one or more of the atoms in the ring system is an element other than carbon, for example nitrogen, oxygen or sulfur, alone or in combination. Suitably the heterocyclic ring comprises from 4 to 7, preferably 5 to 6, ring atoms. A fused heterocyclic ring system may include carbocyclic rings and need only include one heterocyclic ring. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protected moieties are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, pyrimidyl, oxazolidinyl, and the like.

When substituted, a heteroaryl or a heterocyclyl group may have up to three substituents. Preferred such substituents include those previously mentioned for an aryl group as well as oxo.

When used herein, the terms "halogen" and "halo" include fluorine, chlorine, bromine and iodine and fluoro, chloro, bromo and iodo, respectively.

When used herein, the term "acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

When used herein, the term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent. The term "optionally substituted" means optional substitution with the specified groups, radicals or moieties.

It should also be noted that any heteroatom with unsatisfied valences in the text, schemes, examples and Tables herein is assumed to have the hydrogen atom to satisfy the valences. When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in Organic Synthesis (1991), Wiley, N.Y.

When any variable (e.g., aryl, heterocycle, $R_2$, etc.) occurs more than one time in any constituent or in Formula (I), its definition on each occurrence is independent of its definition at every other occurrence.

When used herein, the term "composition" is intended to encompass a product comprising the specified ingredients in the specified amounts, as well as any product which results, directly or indirectly, from combination of the specified ingredients in the specified amounts.

The compounds according to the invention are suitably provided in substantially pure form, for example at least 50% pure, suitably at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

It will be appreciated that certain compounds of the present invention may comprise one or more chiral centers so that compounds may exist as stereoisomers, including diastereoisomers and enantiomers. The present invention covers all such stereoisomers, and mixtures thereof, including racemates.

In some aspects of the present invention provides compounds of Formula (Ia):

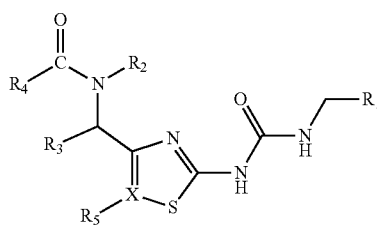

(Ia)

in which:

$R_1$, $R_2$, $R_3$, $R_4$, $R_5$ and X are as previously described herein.

In addition, aspects of the present invention provide compounds of Formula (Ib):

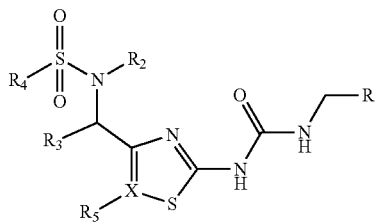

(Ib)

in which:

$R_1$, $R_2$, $R_3$, $R_4$, $R_5$ and X are as previously described herein.
Accordingly, the invention provides the following compounds:

N-((2-(3-(3,4-dichlorobenzyl)ureido)thiazol-4-yl)methyl)-N-(2-methoxyethyl)acetamide;

3-(N-((2-(3-(3,4-dichlorobenzyl)ureido)thiazol-4-yl)methyl)acetamido)propylphosphonic acid;

N-((2-(3-(3,4-dichlorobenzyl)ureido)thiazol-4-yl)methyl)-2-(2-methoxyethoxy)-N-methylacetamide;

N-((2-(3-(3,4-dichlorobenzyl)ureido)thiazol-4-yl)methyl)-2-methoxy-N-methylacetamide;

N-((2-(3-(3,4-dichlorobenzyl)ureido)thiazol-4-yl)methyl)-N,4-dimethylisoxazole-5-carboxamide;

N-((2-(3-(3,4-dichlorobenzyl)ureido)thiazol-4-yl)methyl)-N-methylisoxazole-5-carboxamide;

N-((2-(3-(3,4-dichlorobenzyl)ureido)thiazol-4-yl)methyl)-N-methyl-3-phenylpropanamide;

N-((2-(3-(3,4-dichlorobenzyl)ureido)thiazol-4-yl)methyl)-N-methylfuran-2-carboxamide;

N-((2-(3-(3,4-dichlorobenzyl)ureido)thiazol-4-yl)methyl)-N-methyl-4-phenoxybutanamide;

1-(3,4-Dichloro-benzyl)-3-{4-[3-(1,1-dioxo-tetrahydro-116-thiophen-3-ylmethyl)-1-methyl-ureidomethyl]-thiazol-2-yl}-urea;

N-((2-(3-(3,4-dichlorobenzyl)ureido)thiazol-4-yl)methyl)-N,3,5-trimethylisoxazole-4-carboxamide;

N-((2-(3-(3,4-dichlorobenzyl)ureido)thiazol-4-yl)methyl)-N,1-dimethyl-1H-imidazole-5-carboxamide;

N-((2-(3-(3,4-dichlorobenzyl)ureido)thiazol-4-yl)methyl)-N-methylfuran-3-carboxamide;

N-((2-(3-(3,4-dichlorobenzyl)ureido)thiazol-4-yl)methyl)-N,3-dimethylfuran-2-carboxamide;

N-((2-(3-(3,4-dichlorobenzyl)ureido)thiazol-4-yl)methyl)-N,5-dimethyl-3-phenylisoxazole-4-carboxamide;

N-((2-(3-(3,4-dichlorobenzyl)ureido)thiazol-4-yl)methyl)-N-ethyl-3,5-dimethylisoxazole-4-carboxamide;

N-((2-(3-(3,4-dichlorobenzyl)ureido)thiazol-4-yl)methyl)-N-isopropyl-3,5-dimethylisoxazole-4-carboxamide;

N-((2-(3-(3,4-dichlorobenzyl)ureido)thiazol-4-yl)methyl)-N,5-dimethyl-2-phenyl-2H-1,2,3-triazole-4-carboxamide;

N-((2-(3-(3,4-dichlorobenzyl)ureido)thiazol-4-yl)methyl)-N,5-dimethylisoxazole-3-carboxamide;

N-((2-(3-(3,4-dichlorobenzyl)ureido)thiazol-4-yl)methyl)-N,3-dimethyl-5-phenylisoxazole-4-carboxamide;

N-((2-(3-(3,4-dichlorobenzyl)ureido)thiazol-4-yl)methyl)-N,3-dimethyl-5-(4-methyl-1,2,3-thiadiazol-5-yl)isoxazole-4-carboxamide;

N-((2-(3-(3,4-dichlorobenzyl)ureido)thiazol-4-yl)methyl)-N-methyl-2-(2H-tetrazol-5-yl)acetamide;

N-((2-(3-(3,4-dichlorobenzyl)ureido)thiazol-4-yl)methyl)-N-methylbenzofuran-2-carboxamide;

N-(1-(2-(3-(3,4-dichlorobenzyl)ureido)thiazol-4-yl)ethyl)-N,3,5-trimethylisoxazole-4-carboxamide;

N-((2-(3-(3,4-dichlorobenzyl)ureido)thiazol-4-yl)methyl)-N-methyl-1,2,5-oxadiazole-3-carboxamide;

N-((2-(3-(3,4-dichlorobenzyl)ureido)thiazol-4-yl)methyl)-2-(3,5-dimethylisoxazol-4-yl)-N-methylacetamide;

N-((2-(3-(3,4-dichlorobenzyl)ureido)thiazol-4-yl)methyl)-3-ethyl-N,5-dimethylisoxazole-4-carboxamide;

N-((2-(3-(3,4-dichlorobenzyl)ureido)thiazol-4-yl)methyl)-N,3-dimethylisoxazole-4-carboxamide;

N-((2-(3-(3,4-dichlorobenzyl)ureido)thiazol-4-yl)methyl)-N,5-dimethylisoxazole-4-carboxamide;

5-cyclopropyl-N-((2-(3-(3,4-dichlorobenzyl)ureido)thiazol-4-yl)methyl)-N-methylisoxazole-4-carboxamide;

N-((2-(3-(3,4-dichlorobenzyl)ureido)thiazol-4-yl)methyl)-N,2,6-trimethylbenzamide;

N-((2-(3-(3,4-dichlorobenzyl)ureido)thiazol-4-yl)methyl)-5-(furan-2-yl)-N-methylisoxazole-3-carboxamide;

N-((2-(3-(3,4-dichlorobenzyl)ureido)thiazol-4-yl)methyl)-N,2,5-trimethyloxazole-4-carboxamide;

N-((2-(3-(3,4-dichlorobenzyl)ureido)thiazol-4-yl)methyl)-N-methyl-2-phenylthiazole-4-carboxamide;

N-((2-(3-(3,4-dichlorobenzyl)ureido)thiazol-4-yl)methyl)-N-(2,4-dimethoxybenzyl)-3,5-dimethylisoxazole-4-carboxamide;

N-((2-(3-(3,4-dichlorobenzyl)ureido)thiazol-4-yl)methyl)-N-(2-methoxyethyl)-3,5-dimethylisoxazole-4-carboxamide;

N-((2-(3-(3,4-dichlorobenzyl)ureido)thiazol-4-yl)methyl)-N-methyl-2-(thiophen-2-yl)thiazole-4-carboxamide;

N-((2-(3-(3,4-dichlorobenzyl)ureido)thiazol-4-yl)methyl)-3-hydroxy-N-methylisoxazole-5-carboxamide;

N-((2-(3-(3,4-dichlorobenzyl)ureido)thiazol-4-yl)methyl)-N-methyl-5-phenyl-1,3,4-oxadiazole-2-carboxamide;

N-((2-(3-(3,4-dichlorobenzyl)ureido)thiazol-4-yl)methyl)-N,5-dimethylfuran-2-carboxamide;

N-((2-(3-(3,4-dichlorobenzyl)ureido)thiazol-4-yl)methyl)-N,4-dimethyl-1,2,5-oxadiazole-3-carboxamide;

4-Methyl-2-pyrazin-2-yl-thiazole-5-carboxylic acid {2-[3-(3,4-dichlorobenzyl)ureido]-thiazol-4-ylmethyl}-methyl-amide;

N-((2-(3-(3,4-dichlorobenzyl)ureido)thiazol-4-yl)methyl)-2,4-dimethoxy-N-methylbenzamide;

N-((2-(3-(3,4-dichlorobenzyl)ureido)thiazol-4-yl)methyl)-4-methoxy-N-methylbenzamide;
N-((2-(3-(3,4-dichlorobenzyl)ureido)thiazol-4-yl)methyl)-3,4-dimethoxy-N-methylbenzamide;
N-((2-(3-(3,4-dichlorobenzyl)ureido)thiazol-4-yl)methyl)-N-methylbenzo[1,3]dioxole-5-carboxamide;
N-((2-(3-(3,4-dichlorobenzyl)ureido)thiazol-4-yl)methyl)-3,4,5-trimethoxy-N-methylbenzamide;
N-((2-(3-(3,4-dichlorobenzyl)ureido)thiazol-4-yl)methyl)-N,5-dimethyl-3-(trifluoromethyl)isoxazole-4-carboxamide;
N-((2-(3-(3,4-dichlorobenzyl)ureido)thiazol-4-yl)methyl)-N-methyl-2-(pyridin-3-yl)acetamide;
N-(1-(2-(3-(3,4-dichlorobenzyl)ureido)thiazol-4-yl)-2-(methylamino)-2-oxoethyl)-N,3,5-trimethylisoxazole-4-carboxamide;
N-((2-(3-(3,4-dichlorobenzyl)ureido)thiazol-4-yl)methyl)-N,2,4-trimethylnicotinamide;
N-((2-(3-(3,4-dichlorobenzyl)ureido)thiazol-4-yl)methyl)-N,2,4,6-tetramethylbenzamide;
N-((2-(3-(3,4-dichlorobenzyl)ureido)thiazol-4-yl)methyl)-N-(2-hydroxyethyl)-3,5-dimethylisoxazole-4-carboxamide;
N-((2-(3-(3-fluorobenzyl)ureido)thiazol-4-yl)methyl)-N,3,5-trimethylisoxazole-4-carboxamide;
N-((2-(3-(3-fluorobenzyl)ureido)thiazol-4-yl)methyl)-5-(methoxymethyl)-N,3-dimethylisoxazole-4-carboxamide;
N-((2-(3-(3,4-dichlorobenzyl)ureido)thiazol-4-yl)methyl)-5-(methoxymethyl)-N,3-dimethylisoxazole-4-carboxamide;
N-((2-(3-(3-fluorobenzyl)ureido)thiazol-4-yl)methyl)-2-methoxy-N-methylacetamide;
methyl 2-(((2-(3-(3-fluorobenzyl)ureido)thiazol-4-yl)methyl)(methyl)amino)-2-oxoacetate;
N-((2-(3-(3-fluorobenzyl)ureido)thiazol-4-yl)methyl)-N,3-dimethylisoxazole-4-carboxamide;
3-ethyl-N-((2-(3-(3-fluorobenzyl)ureido)thiazol-4-yl)methyl)-N,5-dimethylisoxazole-4-carboxamide;
N-((2-(3-(3-fluorobenzyl)ureido)thiazol-4-yl)methyl)-N,2,4-trimethylnicotinamide;
N-((2-(3-(3-fluorobenzyl)ureido)thiazol-4-yl)methyl)-N-methylpyrazine-2-carboxamide;
N-((2-(3-(3,4-dichlorobenzyl)ureido)thiazol-4-yl)methyl)-N-methylpyrimidine-5-carboxamide;
N-((2-(3-(3-fluorobenzyl)ureido)thiazol-4-yl)methyl)-N-methylpyrimidine-5-carboxamide;
N-((2-(3-(3,4-dichlorobenzyl)ureido)thiazol-4-yl)methyl)-N-methylpyrazine-2-carboxamide;
N-((2-(3-(3-fluorobenzyl)ureido)thiazol-4-yl)methyl)-N-methylacetamide;
N-((2-(3-(3-fluorobenzyl)ureido)thiazol-4-yl)methyl)-N,5-dimethylpyrazine-2-carboxamide;
N-((2-(3-(3-fluorobenzyl)ureido)thiazol-4-yl)methyl)-N-methylfuran-3-carboxamide;
N-((2-(3-(3-fluorobenzyl)ureido)thiazol-4-yl)methyl)-N,4-dimethyloxazole-5-carboxamide;
N-((2-(3-(3-fluorobenzyl)ureido)thiazol-4-yl)methyl)-N,5-dimethylisoxazole-3-carboxamide;
N-((2-(3-(3-fluorobenzyl)ureido)thiazol-4-yl)methyl)-N-methyl-2-tosylacetamide;
Ethyl 4-(((2-(3-(3-fluorobenzyl)ureido)thiazol-4-yl)methyl)(methyl)carbamoyl)-5-methylisoxazole-3-carboxylate;
4-(((2-(3-(3-fluorobenzyl)ureido)thiazol-4-yl)methyl)(methyl)carbamoyl)-5-methylisoxazole-3-carboxylic acid;
N-((2-(3-(3-fluorobenzyl)ureido)thiazol-4-yl)methyl)-N,2-dimethylnicotinamide;
N-((2-(3-(3-fluorobenzyl)ureido)thiazol-4-yl)methyl)-N,5-dimethylisoxazole-4-carboxamide;
N-((2-(3-(3-fluorobenzyl)ureido)thiazol-4-yl)methyl)-N,4-dimethylnicotinamide;
3-chloro-N-((2-(3-(3-fluorobenzyl)ureido)thiazol-4-yl)methyl)-N-methyl-4-(methylsulfonyl)thiophene-2-carboxamide;
N-((2-(3-(3-fluorobenzyl)ureido)thiazol-4-yl)methyl)-N,4-dimethylthiazole-5-carboxamide;
N-((2-(3-(3-fluorobenzyl)ureido)thiazol-4-yl)methyl)-N-methyl-5-oxo-3,5-dihydro-2H-thiazolo[3,2-a]pyrimidine-6-carboxamide;
N-((2-(3-(3-fluorobenzyl)ureido)thiazol-4-yl)methyl)-N,4-dimethyl-2-(methylthio)pyrimidine-5-carboxamide;
N-((2-(3-(3-fluorobenzyl)ureido)thiazol-4-yl)methyl)-N,3-dimethylbut-2-enamide;
N-((2-(3-(3-fluorobenzyl)ureido)thiazol-4-yl)methyl)-N,2-dimethylbenzamide;
N-((2-(3-(3-fluorobenzyl)ureido)thiazol-4-yl)methyl)-N-methylquinoxaline-2-carboxamide;
N-((2-(3-(3-fluorobenzyl)ureido)thiazol-4-yl)methyl)-N,3-dimethylpicolinamide;
N-((2-(3-(3-fluorobenzyl)ureido)thiazol-4-yl)methyl)-5-((4-methoxybenzyloxy)methyl)-N,3-dimethylisoxazole-4-carboxamide;
N-(2-Aminoethyl)-N-((2-(3-(3-fluorobenzyl)ureido)thiazol-4-yl)methyl)-3,5-dimethylisoxazole-4-carboxamide;
4-amino-N-((2-(3-(3-fluorobenzyl)ureido)thiazol-4-yl)methyl)-N-methylpyrimidine-5-carboxamide;
2-amino-N-((2-(3-(3-fluorobenzyl)ureido)thiazol-4-yl)methyl)-N,4-dimethylpyrimidine-5-carboxamide;
N-((2-(3-(3-fluorobenzyl)ureido)thiazol-4-yl)methyl)-3,5-dimethyl-N-(2-(methylsulfonamido)ethyl)isoxazole-4-carboxamide;
N-((2-(3-(3-fluorobenzyl)ureido)thiazol-4-yl)methyl)-N,4,6-trimethyl-2-oxo-1,2-dihydropyridine-3-carboxamide;
N-((2-(3-(3-fluorobenzyl)ureido)thiazol-4-yl)methyl)-N,2,4,6-tetramethylpyrimidine-5-carboxamide;
N-((2-(3-(3-fluorobenzyl)ureido)thiazol-4-yl)methyl)-N,3-dimethylpyrazine-2-carboxamide;
tert-butyl 2-(((2-(3-(3-fluorobenzyl)ureido)thiazol-4-yl)methyl)(methyl)carbamoyl)-1-methyl-1H-imidazol-4-ylcarbamate;
4-amino-N-((2-(3-(3-fluorobenzyl)ureido)thiazol-4-yl)methyl)-N,1-dimethyl-1H-imidazole-2-carboxamide;
4-acetamido-N-((2-(3-(3-fluorobenzyl)ureido)thiazol-4-yl)methyl)-N,1-dimethyl-1H-imidazole-2-carboxamide;
N-((2-(3-(3-fluorobenzyl)ureido)thiazol-4-yl)methyl)-N,4,6-trimethylpyrimidine-5-carboxamide;
N-((2-(3-(3-fluorobenzyl)ureido)thiazol-4-yl)methyl)-3-(hydroxymethyl)-N,5-dimethylisoxazole-4-carboxamide;
N-((2-(3-(4-fluorobenzyl)ureido)thiazol-4-yl)methyl)-N,3,5-trimethylisoxazole-4-carboxamide;
N-((2-(3-(3,5-difluorobenzyl)ureido)thiazol-4-yl)methyl)-N,3,5-trimethylisoxazole-4-carboxamide;
N-((2-(3-(3-fluorobenzyl)ureido)thiazol-4-yl)methyl)-N,3-dimethylisonicotinamide;
N-((2-(3-(3-chlorobenzyl)ureido)thiazol-4-yl)methyl)-N,3,5-trimethylisoxazole-4-carboxamide;
N-((2-(3-(benzo[1,3]dioxol-5-ylmethyl)ureido)thiazol-4-yl)methyl)-N,3,5-trimethylisoxazole-4-carboxamide;
2-amino-N-((2-(3-(3-fluorobenzyl)ureido)thiazol-4-yl)methyl)-N,4,6-trimethylpyrimidine-5-carboxamide;
N-((2-(3-(2,2-difluorobenzo[1,3]dioxol-5-yl)methyl)ureido)thiazol-4-yl)methyl)-N,3,5-trimethylisoxazole-4-carboxamide;

N-((2-(3-(3-fluorobenzyl)ureido)thiazol-4-yl)methyl)-N,2-dimethylimidazo[1,2-a]pyridine-3-carboxamide;

N,3,5-trimethyl-N-((2-(3-(3-(N-methylacetamido)benzyl)ureido)thiazol-4-yl)methyl)isoxazole-4-carboxamide;

N-((2-(3-((5-chlorothiophen-2-yl)methyl)ureido)thiazol-4-yl)methyl)-N,3,5-trimethylisoxazole-4-carboxamide;

N-((2-(3-(3-fluorobenzyl)ureido)thiazol-4-yl)methyl)-N-methyltetrahydrofuran-2-carboxamide;

1-(4-((2,4-dioxothiazolidin-3-yl)methyl)thiazol-2-yl)-3-(3-fluorobenzyl)urea;

N-((2-(3-(3-fluorobenzyl)ureido)thiazol-4-yl)methyl)-2-methoxy-N-methylnicotinamide;

N-((2-(3-(3-fluorobenzyl)ureido)thiazol-4-yl)methyl)-N-methyltetrahydrofuran-3-carboxamide;

N,3,5-trimethyl-N-((2-(3-(thiophen-3-ylmethyl)ureido)thiazol-4-yl)methyl)isoxazole-4-carboxamide;

methyl (2-(3-(3-fluorobenzyl)ureido)thiazol-4-yl)methyl(2-hydroxyethyl)carbamate;

N-((2-(3-(3-fluorobenzyl)ureido)thiazol-4-yl)methyl)-N-(2-hydroxyethyl)-3-methylisonicotinamide;

1-(3-fluorobenzyl)-3-(4-((2-oxooxazolidin-3-yl)methyl)thiazol-2-yl)urea;

2-chloro-N-((2-(3-(3-fluorobenzyl)ureido)thiazol-4-yl)methyl)-N-methylnicotinamide;

N-((2-(3-(3-fluorobenzyl)ureido)thiazol-4-yl)methyl)-N,1,3,5-tetramethyl-1H-pyrazole-4-carboxamide;

(S)—N-((2-(3-(3-fluorobenzyl)ureido)thiazol-4-yl)methyl)-N-methyltetrahydrofuran-2-carboxamide;

(R)—N-((2-(3-(3-fluorobenzyl)ureido)thiazol-4-yl)methyl)-N-methyltetrahydrofuran-2-carboxamide;

N-((2-(3-(3-fluorobenzyl)ureido)thiazol-4-yl)methyl)-N-methyl-3-propoxypicolinamide;

tert-butyl 2-(((2-(3-(3-fluorobenzyl)ureido)thiazol-4-yl)methyl)(methyl)carbamoyl)morpholine-4-carboxylate;

N-((2-(3-(3-fluorobenzyl)ureido)thiazol-4-yl)methyl)-N-methylmorpholine-2-carboxamide;

N-((2-(3-(3,5-difluorobenzyl)ureido)thiazol-4-yl)methyl)-N,3-dimethylpyrazine-2-carboxamide;

N-((2-(3-(3,5-difluorobenzyl)ureido)thiazol-4-yl)methyl)-N,3-dimethylisonicotinamide;

N-((2-(3-(3-fluorobenzyl)ureido)thiazol-4-yl)methyl)-N-methylpyridazine-4-carboxamide;

N-((2-(3-(3-fluorobenzyl)ureido)thiazol-4-yl)methyl)-N,3,5-trimethyl-1H-pyrazole-4-carboxamide;

N-((2-(3-(3-fluorobenzyl)ureido)thiazol-4-yl)methyl)-N-methylpyridazine-3-carboxamide;

N-((2-(3-(3-fluorobenzyl)ureido)thiazol-4-yl)methyl)-N-methyltetrahydro-2H-pyran-4-carboxamide;

N-((2-(3-(3-fluorobenzyl)ureido)thiazol-4-yl)methyl)-N,1,5-trimethyl-1H-pyrazole-4-carboxamide;

N-((2-(3-((5-chlorofuran-2-yl)methyl)ureido)thiazol-4-yl)methyl)-N,3,5-trimethylisoxazole-4-carboxamide;

N-((2-(3-(3-fluorobenzyl)ureido)thiazol-4-yl)methyl)-N-methylmorpholine-3-carboxamide;

N-((2-(3-(3-fluorobenzyl)ureido)thiazol-4-yl)methyl)-N,4-dimethylpyrrolidine-3-carboxamide;

(S)—N-((2-(3-(3-fluorobenzyl)ureido)thiazol-4-yl)methyl)-N-methylpyrrolidine-2-carboxamide;

2-Methyl-5,6-dihydro-4H-pyran-3-carboxylic acid {2-[3-(3-fluoro-benzyl)-ureido]-thiazol-4-ylmethyl}-methyl-amide;

2-Methyl-5-morpholin-4-ylmethyl-furan-3-carboxylic acid {2-[3-(3-fluoro-benzyl)-ureido]-thiazol-4-ylmethyl}-methyl-amide;

2-Methyl-but-2-enoic acid {2-[3-(3-fluoro-benzyl)-ureido]-thiazol-4-ylmethyl}-methyl-amide;

1,2,3-Thiadiazole-4-carboxylic acid {2-[3-(3-fluoro-benzyl)-ureido]-thiazol-4-ylmethyl}-methyl-amide;

3,5-Dimethyl-isoxazole-4-carboxylic acid {2-[3-(5-fluoro-thiophen-2-ylmethyl)-ureido]-thiazol-4-ylmethyl}-methyl-amide;

2-Pyridin-3-yl-thiazole-4-carboxylic acid {2-[3-(3-fluoro-benzyl)-ureido]-thiazol-4-ylmethyl}-methyl-amide;

2,5-Dimethyl-2H-pyrazole-3-carboxylic acid {2-[3-(3-fluoro-benzyl)-ureido]-thiazol-4-ylmethyl}-methyl-amide;

4-Methyl-furazan-3-carboxylic acid {2-[3-(3-fluoro-benzyl)-ureido]-thiazol-4-ylmethyl}-methyl-amide;

2-Morpholin-4-ylmethyl-furan-3-carboxylic acid {2-[3-(3-fluoro-benzyl)-ureido]-thiazol-4-ylmethyl}-methyl-amide;

1-Methyl-pyrrolidine-2-carboxylic acid {2-[3-(3-fluoro-benzyl)-ureido]-thiazol-4-ylmethyl}-methyl-amide;

1-Methyl-1H-pyrrole-2-carboxylic acid {2-[3-(3-fluoro-benzyl)-ureido]-thiazol-4-ylmethyl}-methyl-amide;

1,5-Dimethyl-1H-[1,2,3]triazole-4-carboxylic acid {2-[3-(3-fluoro-benzyl)-ureido]-thiazol-4-ylmethyl}-methyl-amide;

5-Fluoro-thiophene-2-carboxylic acid {2-[3-(3-fluoro-benzyl)-ureido]-thiazol-4-ylmethyl}-methyl-amide;

4-Methyl-pyrimidine-5-carboxylic acid {2-[3-(3-fluoro-benzyl)-ureido]-thiazol-4-ylmethyl}-methyl-amide;

4-Methyl-2-phenyl-pyrimidine-5-carboxylic acid {2-[3-(3-fluoro-benzyl)-ureido]-thiazol-4-ylmethyl}-methyl-amide;

N-{2-[3-(3-Fluoro-benzyl)-ureido]-thiazol-4-ylmethyl}-N-methyl-2-methylsulfanyl-nicotinamide;

2-Cyano-N-{2-[3-(3-fluoro-benzyl)-ureido]-thiazol-4-ylmethyl}-N-methyl-acetamide;

3,5-Dimethyl-isoxazole-4-carboxylic acid {5-bromo-2-[3-(3-fluoro-benzyl)-ureido]-thiazol-4-ylmethyl}-methyl-amide;

N-{2-[3-(3-Fluoro-benzyl)-ureido]-thiazol-4-ylmethyl}-N-methyl-6-morpholin-4-yl-nicotinamide;

4-Methyl-thiazole-5-carboxylic acid {2-[3-(3-fluoro-benzyl)-ureido]-thiazol-4-ylmethyl}-methyl-amide;

3-Methyl-1H-pyrazole-4-carboxylic acid {2-[3-(3-fluoro-benzyl)-ureido]-thiazol-4-ylmethyl}-methyl-amide;

2,4-Dimethyl-pyrimidine-5-carboxylic acid {2-[3-(3-fluoro-benzyl)-ureido]-thiazol-4-ylmethyl}-methyl-amide;

2-Methyl-[1,6]naphthyridine-3-carboxylic acid {2-[3-(3-fluoro-benzyl)-ureido]-thiazol-4-ylmethyl}-methyl-amide;

6-(4-Methoxy-phenyl)-pyridazine-3-carboxylic acid {2-[3-(3-fluoro-benzyl)-ureido]-thiazol-4-ylmethyl}-methyl-amide;

3-Methyl-pyrazine-2-carboxylic acid {5-bromo-2-[3-(3-fluoro-benzyl)-ureido]-thiazol-4-ylmethyl}-methyl-amide;

3-Methyl-pyrazine-2-carboxylic acid {5-chloro-2-[3-(3-fluoro-benzyl)-ureido]-thiazol-4-ylmethyl}-methyl-amide;

2,6-Bis-dimethylamino-pyrimidine-4-carboxylic acid {2-[3-(3-fluoro-benzyl)-ureido]-thiazol-4-ylmethyl}-methyl-amide;

2,6-Di-morpholin-4-yl-pyrimidine-4-carboxylic acid {2-[3-(3-fluoro-benzyl)-ureido]-thiazol-4-ylmethyl}-methyl-amide;

2-Cyano-N-{2-[3-(3-fluoro-benzyl)-ureido]-thiazol-4-ylmethyl}-N-methyl-3-pyridin-3-yl-acrylamide;

2-Methyl-[1,8]naphthyridine-3-carboxylic acid {2-[3-(3-fluoro-benzyl)-ureido]-thiazol-4-ylmethyl}-methyl-amide;

2-Dimethylamino-6-methyl-pyrimidine-4-carboxylic acid {2-[3-(3-fluoro-benzyl)-ureido]-thiazol-4-ylmethyl}-methyl-amide;
N-{2-[3-(3-Fluoro-benzyl)-ureido]-thiazol-4-ylmethyl}-2-methoxy-N-methyl-2-phenyl-acetamide;
3-Methyl-pyrazine-2-carboxylic acid {2-[3-(5-fluoro-thiophen-2-ylmethyl)-ureido]-thiazol-4-ylmethyl}-methyl-amide;
3-Methyl-pyrazine-2-carboxylic acid methyl-[2-(3-thiophen-3-ylmethyl-ureido)-thiazol-4-ylmethyl]-amide;
3,5-Dimethyl-isoxazole-4-carboxylic acid {5-cyano-2-[3-(3-fluoro-benzyl)-ureido]-thiazol-4-ylmethyl}-methyl-amide;
Acetic acid 1-({2-[3-(3-fluoro-benzyl)-ureido]-thiazol-4-ylmethyl}-methyl-carbamoyl)-ethyl ester;
1-Ethyl-3-methyl-1H-pyrazole-4-carboxylic acid {2-[3-(3-fluoro-benzyl)-ureido]-thiazol-4-ylmethyl}-methyl-amide;
2-Methyl-pyrazolo[1,5-a]pyrimidine-3-carboxylic acid {2-[3-(3-fluoro-benzyl)-ureido]-thiazol-4-ylmethyl}-methyl-amide;
N-{2-[3-(3-Fluoro-benzyl)-ureido]-thiazol-4-ylmethyl}-2-hydroxy-N-methyl-propionamide;
3,5-Dimethyl-isoxazole-4-carboxylic acid (1-{2-[3-(3-fluoro-benzyl)-ureido]-thiazol-4-yl}-ethyl)-amide;
1-Ethyl-5-methyl-1H-pyrazole-4-carboxylic acid {2-[3-(3-fluoro-benzyl)-ureido]-thiazol-4-ylmethyl}-methyl-amide;
5,7-Dimethyl-pyrazolo[1,5-a]pyrimidine-3-carboxylic acid {2-[3-(3-fluoro-benzyl)-ureido]-thiazol-4-ylmethyl}-methyl-amide;
3,5-Dimethyl-isoxazole-4-carboxylic acid (1-{2-[3-(3-fluoro-benzyl)-ureido]-thiazol-4-yl}-2-hydroxy-ethyl)-amide;
1-Methyl-1H-indole-3-carboxylic acid {2-[3-(3-fluoro-benzyl)-ureido]-thiazol-4-ylmethyl}-methyl-amide;
1-Methyl-1H-indazole-3-carboxylic acid {2-[3-(3-fluoro-benzyl)-ureido]-thiazol-4-ylmethyl}-methyl-amide;
Pyrazolo[1,5-a]pyridine-3-carboxylic acid {2-[3-(3-fluoro-benzyl)-ureido]-thiazol-4-ylmethyl}-methyl-amide;
N-{2-[3-(3-Fluoro-benzyl)-ureido]-thiazol-4-ylmethyl}-2-furan-2-yl-N-methyl-2-oxo-acetamide;
3,5-Dimethyl-isoxazole-4-carboxylic acid [2-(3-benzyl-ureido)-thiazol-4-ylmethyl]-methyl-amide;
3-Methyl-pyrazine-2-carboxylic acid {2-[3-(5-chloro-thiophen-2-ylmethyl)-ureido]-thiazol-4-ylmethyl}-methyl-amide;
3,5-Dimethyl-isoxazole-4-carboxylic acid {2-[3-(3-fluoro-benzyl)-ureido]-5-isopropyl-thiazol-4-ylmethyl}-methyl-amide;
5-Oxo-pyrrolidine-2-carboxylic acid {2-[3-(3-fluoro-benzyl)-ureido]-thiazol-4-ylmethyl}-methyl-amide;
3-Methyl-pyrazine-2-carboxylic acid {2-[3-(5-chloro-thiophen-3-ylmethyl)-ureido]-thiazol-4-ylmethyl}-methyl-amide;
3,5-Dimethyl-isoxazole-4-carboxylic acid (2,2-difluoro-ethyl)-{2-[3-(3-fluoro-benzyl)-ureido]-thiazol-4-ylmethyl}-amide;
4-Methyl-pyridazine-3-carboxylic acid {2-[3-(3-fluoro-benzyl)-ureido]-thiazol-4-ylmethyl}-methyl-amide;
5-Methyl-pyridazine-4-carboxylic acid {2-[3-(3-fluoro-benzyl)-ureido]-thiazol-4-ylmethyl}-methyl-amide;
3-Amino-1H-pyrazole-4-carboxylic acid {2-[3-(3-fluoro-benzyl)-ureido]-thiazol-4-ylmethyl}-methyl-amide;
3,6-Dimethoxy-pyridazine-4-carboxylic acid {2-[3-(3-fluoro-benzyl)-ureido]-thiazol-4-ylmethyl}-methyl-amide;
(3,5-Dimethyl-isoxazol-4-ylmethyl)-{2-[3-(3-fluoro-benzyl)-ureido]-thiazol-4-ylmethyl}-carbamic acid methyl ester;
(R)-Tetrahydro-furan-2-carboxylic acid {2-[3-(5-chloro-thiophen-2-ylmethyl)-ureido]-thiazol-4-ylmethyl}-methyl-amide;
5-Methyl-pyridazine-4-carboxylic acid {2-[3-(5-chloro-thiophen-2-ylmethyl)-ureido]-thiazol-4-ylmethyl}-methyl-amide;
3,5-Dimethyl-1H-pyrazole-4-carboxylic acid {2-[3-(5-chloro-thiophen-2-ylmethyl)-ureido]-thiazol-4-ylmethyl}-methyl-amide;
5-Methyl-pyridazine-4-carboxylic acid {2-[3-(5-chloro-thiophen-3-ylmethyl)-ureido]-thiazol-4-ylmethyl}-methyl-amide;
Tetrahydro-furan-2-carboxylic acid {2-[3-(5-chloro-thiophen-3-ylmethyl)-ureido]-thiazol-4-ylmethyl}-methyl-amide;
3,5-Dimethyl-1H-pyrazole-4-carboxylic acid {2-[3-(5-chloro-thiophen-3-ylmethyl)-ureido]-thiazol-4-ylmethyl}-methyl-amide;
1,3,5-Trimethyl-1H-pyrazole-4-carboxylic acid {2-[3-(5-chloro-thiophen-3-ylmethyl)-ureido]-thiazol-4-ylmethyl}-methyl-amide;
3,6-Dichloro-pyridazine-4-carboxylic acid {2-[3-(3-fluoro-benzyl)-ureido]-thiazol-4-ylmethyl}-methyl-amide;
3-Chloro-6-methoxy-pyridazine-4-carboxylic acid {2-[3-(3-fluoro-benzyl)-ureido]-thiazol-4-ylmethyl}-methyl-amide;
3,5-Dimethyl-isoxazole-4-carboxylic acid {5-fluoro-2-[3-(3-fluoro-benzyl)-ureido]-thiazol-4-ylmethyl}-methyl-amide;
(R)-Tetrahydro-furan-2-carboxylic acid {5-fluoro-2-[3-(3-fluoro-benzyl)-ureido]-thiazol-4-ylmethyl}-methyl-amide;
3,5-Dimethyl-pyridazine-4-carboxylic acid {2-[3-(3-fluoro-benzyl)-ureido]-thiazol-4-ylmethyl}-methyl-amide;
N-{5-Fluoro-2-[3-(3-fluoro-benzyl)-ureido]-thiazol-4-ylmethyl}-N-methyl-acetamide;
1-Methyl-3-trifluoromethyl-1H-pyrazole-4-carboxylic acid {2-[3-(3-fluoro-benzyl)-ureido]-thiazol-4-ylmethyl}-methyl-amide;
1,3,5-Trimethyl-1H-pyrazole-4-carboxylic acid {5-fluoro-2-[3-(3-fluoro-benzyl)-ureido]-thiazol-4-ylmethyl}-methyl-amide;
1,3,5-Trimethyl-1H-pyrazole-4-carboxylic acid {2-[3-(5-chloro-thiophen-2-ylmethyl)-ureido]-thiazol-4-ylmethyl}-methyl-amide;
3-Chloro-6-hydroxy-pyridazine-4-carboxylic acid {2-[3-(3-fluoro-benzyl)-ureido]-thiazol-4-ylmethyl}-methyl-amide;
2-Methyl-tetrahydro-furan-2-carboxylic acid {2-[3-(3-fluoro-benzyl)-ureido]-thiazol-4-ylmethyl}-methyl-amide;
4-Chloro-1-methyl-1H-pyrazole-3-carboxylic acid {2-[3-(3-fluoro-benzyl)-ureido]-thiazol-4-ylmethyl}-methyl-amide;
5-Chloro-1-methyl-1H-pyrazole-4-carboxylic acid {2-[3-(3-fluoro-benzyl)-ureido]-thiazol-4-ylmethyl}-methyl-amide;
4-Chloro-2-methyl-2H-pyrazole-3-carboxylic acid {2-[3-(3-fluoro-benzyl)-ureido]-thiazol-4-ylmethyl}-methyl-amide;
4-Chloro-1H-pyrazole-3-carboxylic acid {2-[3-(3-fluoro-benzyl)-ureido]-thiazol-4-ylmethyl}-methyl-amide;

3,5-Dimethyl-isoxazole-4-carboxylic acid (cyano-{2-[3-(3-fluoro-benzyl)-ureido]-thiazol-4-yl}-methyl)-methyl-amide;

1-Methyl-3-trifluoromethyl-1H-pyrazole-4-carboxylic acid {2-[3-(5-chloro-thiophen-2-ylmethyl)-ureido]-thiazol-4-ylmethyl}-methyl-amide;

1-Methyl-3-trifluoromethyl-1H-pyrazole-4-carboxylic acid {2-[3-(5-chloro-thiophen-2-ylmethyl)-ureido]-thiazol-4-ylmethyl}-methyl-amide;

1,3,6-Trimethyl-1H-pyrazolo[3,4-b]pyridine-4-carboxylic acid {2-[3-(5-chloro-thiophen-2-ylmethyl)-ureido]-thiazol-4-ylmethyl}-methyl-amide;

N-{2-[3-(5-Chloro-thiophen-2-ylmethyl)-ureido]-thiazol-4-ylmethyl}-2,N-dimethyl-5-sulfamoyl-benzamide;

1-Methyl-6-oxo-1,4,5,6-tetrahydro-pyridazine-3-carboxylic acid {2-[3-(5-chloro-thiophen-2-ylmethyl)-ureido]-thiazol-4-ylmethyl}-methyl-amide;

1-Phenyl-cyclobutanecarboxylic acid {2-[3-(5-chloro-thiophen-2-ylmethyl)-ureido]-thiazol-4-ylmethyl}-methyl-amide;

3-Methyl-4-oxo-3,4-dihydro-phthalazine-1-carboxylic acid {2-[3-(5-chloro-thiophen-2-ylmethyl)-ureido]-thiazol-4-ylmethyl}-methyl-amide;

7-Chloro-benzo[1,3]dioxole-5-carboxylic acid {2-[3-(5-chloro-thiophen-2-ylmethyl)-ureido]-thiazol-4-ylmethyl}-methyl-amide;

N-{2-[3-(5-Chloro-thiophen-2-ylmethyl)-ureido]-thiazol-4-ylmethyl}-N-methyl-6-[1,2,4]triazol-1-yl-nicotinamide;

1-(2-Methoxy-ethyl)-6-oxo-1,6-dihydro-pyridazine-3-carboxylic acid {2-[3-(5-chloro-thiophen-2-ylmethyl)-ureido]-thiazol-4-ylmethyl}-methyl-amide;

N-((2-(3-((5-chlorothiophen-2-yl)methyl)ureido)thiazol-4-yl)methyl)-2-(2,4-dioxo-3,4-dihydropyrimidin-1(2H)-yl)-N-methylacetamide;

1,1-Dioxo-tetrahydrothiophene-3-carboxylic acid {2-[3-(5-chlorothiophen-2-yl)methyl)-ureido]-thiazol-4-ylmethyl}-methyl-amide;

6-chloro-N-((2-(3-(3-fluorobenzyl)ureido)thiazol-4-yl)methyl)-3-hydroxy-N-methylpyridazine-4-carboxamide;

5-chloro-N-((2-(3-(3-fluorobenzyl)ureido)thiazol-4-yl)methyl)-N,1,3-trimethyl-1H-pyrazole-4-carboxamide;

N-((2-(3-(3-fluorobenzyl)ureido)thiazol-4-yl)methyl)-5-isopropyl-N,3-dimethylisoxazole-4-carboxamide;

3-cyano-N-((2-(3-(3-fluorobenzyl)ureido)thiazol-4-yl)methyl)-2-hydroxy-N,6-dimethylisonicotinamide;

6-chloro-N-((2-(3-(3-fluorobenzyl)ureido)thiazol-4-yl)methyl)-N-methyl-3-oxo-2,3-dihydropyridazine-4-carboxamide;

N-((2-(3-(3-fluorobenzyl)ureido)thiazol-4-yl)methyl)-N,1-dimethyl-5-(1H-pyrrol-1-yl)-1H-pyrazole-4-carboxamide;

N-((2-(3-(3-fluorobenzyl)ureido)thiazol-4-yl)methyl)-N,2-dimethyl-5-sulfamoylbenzamide;

N-((2-(3-(3-fluorobenzyl)ureido)thiazol-4-yl)methyl)-N-methyl-1-phenylcyclobutanecarboxamide;

N-((2-(3-(3-fluorobenzyl)ureido)thiazol-4-yl)methyl)-N-methyl-4-oxo-3,4-dihydrophthalazine-1-carboxamide;

N-((2-(3-(3-fluorobenzyl)ureido)thiazol-4-yl)methyl)-N,4,6-trimethyl-2-oxo-2H-pyran-5-carboxamide;

7-chloro-N-((2-(3-(3-fluorobenzyl)ureido)thiazol-4-yl)methyl)-N-methylbenzo[1,3]dioxole-5-carboxamide;

N-((2-(3-(3-fluorobenzyl)ureido)thiazol-4-yl)methyl)-N,1-dimethyl-4-sulfamoyl-1H-pyrrole-2-carboxamide;

2-(5,7-dimethyl-[1,2,4]triazolo[1,5-a]pyrimidin-6-yl)-N-((2-(3-(3-fluorobenzyl)ureido)thiazol-4-yl)methyl)-N-methylacetamide;

N-((2-(3-(3-fluorobenzyl)ureido)thiazol-4-yl)methyl)-N,3,6-trimethyl-4-oxo-3,4-dihydrofuro[2,3-d]pyrimidine-5-carboxamide;

N-((2-(3-(3-fluorobenzyl)ureido)thiazol-4-yl)methyl)-N,5-dimethyl-4-oxo-3,4-dihydrothieno[2,3-d]pyrimidine-6-carboxamide;

2,2-difluoro-N-((2-(3-(3-fluorobenzyl)ureido)thiazol-4-yl)methyl)-N-methyl-2-phenylacetamide;

N2-((2-(3-(3-fluorobenzyl)ureido)thiazol-4-yl)methyl)-4-hydroxy-N2-methylpyrrolidine-1,2-dicarboxamide;

N-((2-(3-((5-chlorothiophen-2-yl)methyl)ureido)thiazol-4-yl)methyl)-N-methyl-2-morpholinonicotinamide;

N-((2-(3-((5-chlorothiophen-2-yl)methyl)ureido)thiazol-4-yl)methyl)-N-methyl-4-oxo-3,4-dihydrophthalazine-1-carboxamide;

N-((2-(3-((5-chlorothiophen-2-yl)methyl)ureido)thiazol-4-yl)methyl)-N,4,6-trimethyl-2-oxo-2H-pyran-5-carboxamide;

N-((2-(3-((5-chlorothiophen-2-yl)methyl)ureido)thiazol-4-yl)methyl)-N,1-dimethyl-4-sulfamoyl-1H-pyrrole-2-carboxamide;

N-((2-(3-((5-chlorothiophen-2-yl)methyl)ureido)thiazol-4-yl)methyl)-2-(5,7-dimethyl-[1,2,4]triazolo[1,5-a]pyrimidin-6-yl)-N-methylacetamide;

N-((2-(3-((5-chlorothiophen-2-yl)methyl)ureido)thiazol-4-yl)methyl)-N,5-dimethyl-4-oxo-3,4-dihydrothieno[2,3-d]pyrimidine-6-carboxamide;

N-((2-(3-((5-chlorothiophen-2-yl)methyl)ureido)thiazol-4-yl)methyl)-1-(3-fluorophenyl)-N-methylcyclobutanecarboxamide;

N-((2-(3-((5-chlorothiophen-2-yl)methyl)ureido)thiazol-4-yl)methyl)-2,2-difluoro-N-methyl-2-phenylacetamide;

N-((2-(3-(3-fluorobenzyl)ureido)thiazol-4-yl)methyl)-N-methyl-5-(trifluoromethyl)-1H-pyrazole-4-carboxamide;

N-((2-(3-(3-fluorobenzyl)ureido)thiazol-4-yl)methyl)-N,1-dimethyl-5-(trifluoromethyl)-1H-pyrazole-4-carboxamide;

(S)—N-((2-(3-(3-fluorobenzyl)ureido)thiazol-4-yl)methyl)-2-methoxy-N-methylpropanamide;

N-((2-(3-(3-fluorobenzyl)ureido)thiazol-4-yl)methyl)-N,3-dimethyl-5,6-dihydro-1,4-dioxine-2-carboxamide;

(R)—N-((2-(3-(3-fluorobenzyl)ureido)thiazol-4-yl)methyl)-N-methyl-5-oxotetrahydrofuran-2-carboxamide;

5-chloro-N-((2-(3-((5-chlorothiophen-2-yl)methyl)ureido)thiazol-4-yl)methyl)-N,1,3-trimethyl-1H-pyrazole-4-carboxamide;

N-((2-(3-(3-fluorobenzyl)ureido)thiazol-4-yl)methyl)-N,1-dimethyl-6-oxo-1,4,5,6-tetrahydropyridazine-3-carboxamide;

N-((2-(3-(3-fluorobenzyl)ureido)thiazol-4-yl)methyl)-N,3-dimethyl-4-oxo-3,4-dihydrophthalazine-1-carboxamide;

N-((2-(3-((5-chlorothiophen-2-yl)methyl)ureido)thiazol-4-yl)methyl)-N,1-dimethyl-5-(1H-pyrrol-1-yl)-1H-pyrazole-4-carboxamide;

N-((2-(3-((5-chlorothiophen-2-yl)methyl)ureido)thiazol-4-yl)methyl)-N,3,6-trimethyl-4-oxo-3,4-dihydrofuro[2,3-d]pyrimidine-5-carboxamide;

N-((2-(3-(3-fluorobenzyl)ureido)thiazol-4-yl)methyl)-3-methoxy-N-methylpropanamide;

N-((2-(3-(3-fluorobenzyl)ureido)thiazol-4-yl)methyl)-1-(2-hydroxyethyl)-N,3,5-trimethyl-1H-pyrazole-4-carboxamide;

(R)—N-((2-(3-(3-fluorobenzyl)ureido)thiazol-4-yl)methyl)-2-methoxy-N-methylpropanamide;

N-((2-(3-(3-fluorobenzyl)ureido)thiazol-4-yl)methyl)-1-(2-methoxyethyl)-N,3,5-trimethyl-1H-pyrazole-4-carboxamide;

N-((2-(3-(3-fluorobenzyl)ureido)thiazol-4-yl)methyl)-N-methyltetrahydro-2H-pyran-2-carboxamide;
N-(cyano(2-(3-(3-fluorobenzyl)ureido)thiazol-4-yl)methyl)-N,3-dimethylpyrazine-2-carboxamide;
N-(cyano(2-(3-(3-fluorobenzyl)ureido)thiazol-4-yl)methyl)-N-methyltetrahydrofuran-2-carboxamide;
N-((2-(3-((5-chlorothiophen-2-yl)methyl)ureido)thiazol-4-yl)methyl)-N,3,6-trimethylisoxazolo[5,4-b]pyridine-4-carboxamide;
N-((2-(3-(3-fluorobenzyl)ureido)thiazol-4-yl)methyl)-5-methoxy-N-methyltetrahydrofuran-2-carboxamide;
N-((2-(3-(3-fluorobenzyl)ureido)thiazol-4-yl)methyl)-1-(4-methoxybutyl)-N,3,5-trimethyl-1H-pyrazole-4-carboxamide;
N-((2-(3-(3-fluorobenzyl)ureido)thiazol-4-yl)methyl)-1-(3-methoxypropyl)-N,3,5-trimethyl-1H-pyrazole-4-carboxamide;
N-((5-fluoro-2-(3-(3-fluorobenzyl)ureido)thiazol-4-yl)methyl)-N,3,5-trimethylpyridazine-4-carboxamide;
N-((2-(3-(3-fluorobenzyl)ureido)thiazol-4-yl)methyl)-N-methyl-2-morpholinonicotinamide;
N-((2-(3-(3-fluorobenzyl)ureido)thiazol-4-yl)methyl)-N,3,6-trimethylisoxazolo[5,4-b]pyridine-4-carboxamide;
N-((2-(3-(3-fluorobenzyl)ureido)thiazol-4-yl)methyl)-1-(4-fluorophenyl)-N-methylcyclobutanecarboxamide;
1,1-Dioxo-tetrahydrothiophene-3-carboxylic acid {2-[3-(3-fluoro-benzyl)-ureido]-thiazol-4-ylmethyl}-methyl-amide;
N-((2-(3-(3-fluorobenzyl)ureido)thiazol-4-yl)methyl)-N,5-dimethyltetrahydrofuran-2-carboxamide;
N-((2-(3-(3-fluorobenzyl)ureido)thiazol-4-yl)methyl)-N,3-dimethyloxetane-3-carboxamide;
5-chloro-N-((2-(3-(3-fluorobenzyl)ureido)thiazol-4-yl)methyl)-N-methyl-1H-pyrazole-4-carboxamide;
(R)—N-((2-(3-(3-fluorobenzyl)ureido)thiazol-4-yl)methyl)-N,2,2-trimethyl-1,3-dioxolane-4-carboxamide;
(S)—N-((2-(3-(3-fluorobenzyl)ureido)thiazol-4-yl)methyl)-N,2,2-trimethyl-1,3-dioxolane-4-carboxamide;
N-(2-amino-1-(2-(3-(3-fluorobenzyl)ureido)thiazol-4-yl)ethyl)-N-methyltetrahydrofuran-2-carboxamide;
(R)—N-((2-(3-((5-fluorothiophen-2-yl)methyl)ureido)thiazol-4-yl)methyl)-N-methyltetrahydrofuran-2-carboxamide;
3,6-dichloro-N-((2-(3-(3-fluorobenzyl)ureido)thiazol-4-yl)methyl)-N,5-dimethylpyridazine-4-carboxamide;
N-((2-(3-(3-fluorobenzyl)ureido)thiazol-4-yl)methyl)-6-methoxy-N,3-dimethylpyridazine-4-carboxamide;
N-((2-(3-(3-fluorobenzyl)ureido)thiazol-4-yl)methyl)-N,1,3,6-tetramethyl-1H-pyrazolo[3,4-b]pyridine-4-carboxamide;
N-((2-(3-(3-fluorobenzyl)ureido)thiazol-4-yl)methyl)-N,1-dimethyl-5-nitro-1H-pyrazole-4-carboxamide;
N-((2-(3-(3-fluorobenzyl)ureido)thiazol-4-yl)methyl)-N-methyl-2,3-dihydrobenzofuran-2-carboxamide;
N-((2-(3-((5-chlorothiophen-2-yl)methyl)ureido)thiazol-4-yl)methyl)-N-methyl-2,3-dihydrobenzofuran-2-carboxamide;
N-((2-(3-(3-fluorobenzyl)ureido)thiazol-4-yl)methyl)-6-hydroxy-N,3-dimethylpyridazine-4-carboxamide;
N-((2-(3-(3-fluorobenzyl)ureido)thiazol-4-yl)methyl)-N-methyl-2-(pyrrolidin-1-yl)nicotinamide;
N-((2-(3-(3-fluorobenzyl)ureido)thiazol-4-yl)methyl)-N-methyl-4-oxo-4-(thiophen-2-yl)butanamide;
N-((2-(3-(3-fluorobenzyl)ureido)thiazol-4-yl)methyl)-N-methyl-4-oxo-4-phenylbutanamide;
2-(3-fluoro-4-methoxyphenyl)-N-((2-(3-(3-fluorobenzyl)ureido)thiazol-4-yl)methyl)-N-methylacetamide;
2-(3,4-dimethoxyphenyl)-N-((2-(3-(3-fluorobenzyl)ureido)thiazol-4-yl)methyl)-N-methylacetamide;
N-((2-(3-(3-fluorobenzyl)ureido)thiazol-4-yl)methyl)-2-(4-(hydroxymethyl)phenoxy)-N-methylacetamide;
N-((2-(3-(3-fluorobenzyl)ureido)thiazol-4-yl)methyl)-N-methyl-2-(3-(methylsulfonyl)phenyl)acetamide;
N-((2-(3-(3-fluorobenzyl)ureido)thiazol-4-yl)methyl)-2-(2-mercapto-4-methylthiazol-5-yl)-N-methylacetamide;
N-((2-(3-(3-fluorobenzyl)ureido)thiazol-4-yl)methyl)-N-methyl-5-(trifluoromethyl)furan-2-carboxamide;
(R)—N-((5-fluoro-2-(3-(3-fluorobenzyl)ureido)thiazol-4-yl)methyl)-2-methoxy-N-methylpropanamide;
N-((2-(3-(3-fluorobenzyl)ureido)thiazol-4-yl)methyl)-6-hydroxy-N-methyl-3-(methylamino)pyridazine-4-carboxamide;
3-(dimethylamino)-N-((2-(3-(3-fluorobenzyl)ureido)thiazol-4-yl)methyl)-6-methoxy-N-methylpyridazine-4-carboxamide;
N-((2-(3-(3-fluorobenzyl)ureido)thiazol-4-yl)methyl)-1-(2-methoxyethyl)-N-methyl-6-oxo-1,6-dihydropyridazine-3-carboxamide;
N-((2-(3-((5-chlorothiophen-2-yl)methyl)ureido)thiazol-4-yl)methyl)-N-methyl-2-(pyrrolidin-1-yl)nicotinamide;
N-((2-(3-(3-fluorobenzyl)ureido)thiazol-4-yl)methyl)-N,2,2-trimethyltetrahydro-2H-pyran-4-carboxamide;
N-((2-(3-((5-chlorothiophen-2-yl)methyl)ureido)thiazol-4-yl)methyl)-N,2,2-trimethyltetrahydro-2H-pyran-4-carboxamide;
N-((2-(3-((1H-indol-5-yl)methyl)ureido)thiazol-4-yl)methyl)-N,3,5-trimethylisoxazole-4-carboxamide;
N-((2-(3-(benzo[1,2,5]oxadiazol-5-ylmethyl)ureido)thiazol-4-yl)methyl)-N,3,5-trimethylisoxazole-4-carboxamide;
N-((2-(3-(benzo[1,2,5]thiadiazol-5-ylmethyl)ureido)thiazol-4-yl)methyl)-N,3,5-trimethylisoxazole-4-carboxamide;
2-(4-(dimethylamino)phenyl)-N-((2-(3-(3-fluorobenzyl)ureido)thiazol-4-yl)methyl)-N-methylacetamide;
N-((2-(3-(3-fluorobenzyl)ureido)thiazol-4-yl)methyl)-7-hydroxy-N-methyl-1,2,3,4-tetrahydroisoquinoline-3-carboxamide;
3-(1H-benzoimidazol-2-yl)-N-((2-(3-(3-fluorobenzyl)ureido)thiazol-4-yl)methyl)-N-methylpropanamide;
N-((2-(3-(3-fluorobenzyl)ureido)thiazol-4-yl)methyl)-N-methyl-2-(naphthalen-2-yl)acetamide;
N-((2-(3-(3-fluorobenzyl)ureido)thiazol-4-yl)methyl)-2-(4-methoxy-3-methylphenyl)-N-methylacetamide;
2-amino-3-(benzyloxy)-N-((2-(3-(3-fluorobenzyl)ureido)thiazol-4-yl)methyl)-N-methylpropanamide;
N-((2-(3-(3-fluorobenzyl)ureido)thiazol-4-yl)methyl)-N-methyl-1,4-dioxo-1,2,3,4-tetrahydrophthalazine-6-carboxamide;
N-((2-(3-(3-fluorobenzyl)ureido)thiazol-4-yl)methyl)-N-methyl-6-(1H-1,2,4-triazol-1-yl)nicotinamide;
2-(2,4-dioxo-3,4-dihydropyrimidin-1(2H)-yl)-N-((2-(3-(3-fluorobenzyl)ureido)thiazol-4-yl)methyl)-N-methylacetamide;
N-((2-(3-((5-chlorothiophen-2-yl)methyl)ureido)thiazol-4-yl)methyl)-N-methyl-1,4-dioxo-1,2,3,4-tetrahydrophthalazine-6-carboxamide;
N2-((2-(3-((5-chlorothiophen-2-yl)methyl)ureido)thiazol-4-yl)methyl)-4-hydroxy-N2-methylpyrrolidine-1,2-dicarboxamide;
N-((2-(3-((5-chlorothiophen-2-yl)methyl)ureido)thiazol-4-yl)methyl)-N,1-dimethyl-5-nitro-1H-pyrazole-4-carboxamide;
(S)-3,3-difluoro-N-((2-(3-(3-fluorobenzyl)ureido)thiazol-4-yl)methyl)-N-methyltetrahydrofuran-2-carboxamide;

N-((2-(3-(3-fluorobenzyl)ureido)thiazol-4-yl)methyl)-N-methylchroman-2-carboxamide;
4-(3,5-dimethyl-1H-pyrazol-4-yl)-N-((2-(3-(3-fluorobenzyl)ureido)thiazol-4-yl)methyl)-N-methylbenzamide;
N-((2-(3-(3-fluorobenzyl)ureido)thiazol-4-yl)methyl)-N-methylpent-4-ynamide;
N-((2-(3-(3-fluorobenzyl)ureido)thiazol-4-yl)methyl)-N,2-dimethyl-1,2,3,4-tetrahydroisoquinoline-3-carboxamide;
(S)-2-amino-N-((2-(3-(3-fluorobenzyl)ureido)thiazol-4-yl)methyl)-N-methyl-3-(pyridin-4-yl)propanamide;
cis-N-((2-(3-(3-fluorobenzyl)ureido)thiazol-4-yl)methyl)-3-methoxy-N-methyltetrahydrofuran-2-carboxamide;
1-cyano-N-((2-(3-(3-fluorobenzyl)ureido)thiazol-4-yl)methyl)-N-methylcyclopropanecarboxamide;
N-((2-(3-(3-fluorobenzyl)ureido)thiazol-4-yl)methyl)-N-methylpropiolamide;
N-((2-(3-((1H-indol-2-yl)methyl)ureido)thiazol-4-yl)methyl)-N,3,5-trimethylisoxazole-4-carboxamide;
N-((2-(3-(benzoxazol-6-ylmethyl)ureido)thiazol-4-yl)methyl)-N,3,5-trimethylisoxazole-4-carboxamide;
2-ethoxy-N-((2-(3-(3-fluorobenzyl)ureido)thiazol-4-yl)methyl)-N-methylpropanamide;
N-((2-(3-(3-fluorobenzyl)ureido)thiazol-4-yl)methyl)-2-(4-methoxyphenoxy)-N-methylpropanamide;
2-(cyclopropylmethoxy)-N-((2-(3-(3-fluorobenzyl)ureido)thiazol-4-yl)methyl)-N-methylpropanamide;
2,5-diamino-N-((2-(3-(3-fluorobenzyl)ureido)thiazol-4-yl)methyl)-N-methylpentanamide;
N-((2-(3-(3-fluorobenzyl)ureido)thiazol-4-yl)methyl)-N-methyl-2-(2-phenoxyethoxy)propanamide;
2-cyclopropyl-N-((2-(3-(3-fluorobenzyl)ureido)thiazol-4-yl)methyl)-N-methylacetamide;
N,3,5-trimethyl-N-((2-(3-(4-nitrobenzyl)ureido)thiazol-4-yl)methyl)isoxazole-4-carboxamide;
N,3,5-trimethyl-N-((2-(3-(3-nitrobenzyl)ureido)thiazol-4-yl)methyl)isoxazole-4-carboxamide;
3-ethyl-N-((2-(3-(3-fluorobenzyl)ureido)thiazol-4-yl)methyl)-N-methyloxetane-3-carboxamide;
2-(2,2-difluoroethoxy)-N-((2-(3-(3-fluorobenzyl)ureido)thiazol-4-yl)methyl)-N-methylpropanamide;
N-((2-(3-(3-fluorobenzyl)ureido)thiazol-4-yl)methyl)-2-(4-fluorobenzyloxy)propanamide;
2-(2,2,2-trifluoroethoxy)-N-((2-(3-(3-fluorobenzyl)ureido)thiazol-4-yl)methyl)-N-methylpropanamide;
N-((2-(3-(3-fluorobenzyl)ureido)thiazol-4-yl)methyl)-2-(prop-2-ynyloxy)propanamide;
N-((2-(3-(3-fluorobenzyl)ureido)thiazol-4-yl)methyl)-N-methyl-2-((5-methylisoxazol-3-yl)methoxy)propanamide;
N-((2-(3-(3-fluorobenzyl)ureido)thiazol-4-yl)methyl)-N-methyl-2-(1-methylpyrrolidin-3-yloxy)propanamide;
N-((2-(3-(3-fluorobenzyl)ureido)thiazol-4-yl)methyl)-2-(2-hydroxyethoxy)propanamide;
N-((2-(3-((5-chlorothiophen-2-yl)methyl)ureido)thiazol-4-yl)methyl)-N-methylcyclopentanecarboxamide;
N-((2-(3-((5-chlorothiophen-2-yl)methyl)ureido)thiazol-4-yl)methyl)-1-hydroxy-N-methylcyclopropanecarboxamide;
N-((2-(3-((5-chlorothiophen-2-yl)methyl)ureido)thiazol-4-yl)methyl)-N-methylcyclohexanecarboxamide;
1-cyano-N-((5-fluoro-2-(3-(3-fluorobenzyl)ureido)thiazol-4-yl)methyl)-N-methylcyclopropanecarboxamide;
N-((2-(3-(3-fluorobenzyl)ureido)thiazol-4-yl)methyl)-N-methylcyclopentanecarboxamide;
N-((2-(3-(3-fluorobenzyl)ureido)thiazol-4-yl)methyl)-N,2-dimethylcyclohexanecarboxamide;
N-((2-(3-(3-fluorobenzyl)ureido)thiazol-4-yl)methyl)-N-methylcyclohexanecarboxamide;
N-((2-(3-(3-fluorobenzyl)ureido)thiazol-4-yl)methyl)-N-methyl-2-oxo-2,3-dihydrobenzoxazole-6-carboxamide;
3,3,3-trifluoro-N-((2-(3-(3-fluorobenzyl)ureido)thiazol-4-yl)methyl)-N-methylpropanamide;
N-((2-(3-(3-fluorobenzyl)ureido)thiazol-4-yl)methyl)-2-hydroxy-N,2-dimethylpropanamide;
2,3-cis-N-((2-(3-(3-fluorobenzyl)ureido)thiazol-4-yl)methyl)-N,3-dimethyltetrahydrofuran-2-carboxamide;
(5R)—N-((2-(3-(3-fluorobenzyl)ureido)thiazol-4-yl)methyl)-5-(hydroxymethyl)-N-methyltetrahydrofuran-2-carboxamide;
N-((2-(3-((5-chlorothiophen-2-yl)methyl)ureido)thiazol-4-yl)methyl)-2-hydroxy-N,2-dimethylpropanamide;
N-((2-(3-(5-chlorothiophen-2-yl)methyl)ureido)thiazol-4-yl)methyl)-N-methyl-2-oxo-2,3-dihydrobenzoxazole-6-carboxamide;
(S)—N-((2-(3-((5-chlorothiophen-2-yl)methyl)ureido)thiazol-4-yl)methyl)-2-(4-hydroxy-2-oxopyrrolidin-1-yl)-N-methylacetamide;
(R)—N-((2-(3-(benzo[1,2,5]oxadiazol-5-ylmethyl)ureido)thiazol-4-yl)methyl)-N-methyltetrahydrofuran-2-carboxamide;
(R)—N-((2-(3-((7-chlorobenzo[1,3]dioxol-5-yl)methyl)ureido)thiazol-4-yl)methyl)-N-methyltetrahydrofuran-2-carboxamide;
2,3,3,3-tetrafluoro-N-((2-(3-(3-fluorobenzyl)ureido)thiazol-4-yl)methyl)-N-methylpropanamide;
N-((2-(3-(3-fluorobenzyl)ureido)thiazol-4-yl)methyl)-N-methylcyclopropanecarboxamide;
N-((2-(3-(3-fluorobenzyl)ureido)thiazol-4-yl)methyl)-N-methylcyclopropane-1,1-dicarboxamide;
N-((2-(3-(3-fluorobenzyl)ureido)thiazol-4-yl)methyl)-N,2-dimethylcyclopropanecarboxamide;
(S)—N-((2-(3-(3-fluorobenzyl)ureido)thiazol-4-yl)methyl)-2-(4-hydroxy-2-oxopyrrolidin-1-yl)-N-methylacetamide;
N-((5-(3-(3-fluorobenzyl)ureido)-1,2,4-thiadiazol-3-yl)methyl)-N,3,5-trimethylisoxazole-4-carboxamide;
N-((5-(3-(3-fluorobenzyl)ureido)-1,2,4-thiadiazol-3-yl)methyl)-N,2,6-trimethylbenzamide;
N-((5-(3-(3-fluorobenzyl)ureido)-1,2,4-thiadiazol-3-yl)methyl)-N,3-dimethylisonicotinamide;
N-((5-(3-(3-fluorobenzyl)ureido)-1,2,4-thiadiazol-3-yl)methyl)-N,3-dimethylpyrazine-2-carboxamide;
1,3,5-Trimethyl-1H-pyrazole-4-carboxylic acid {5-[3-(3-fluoro-benzyl)-ureido]-[1,2,4]thiadiazol-3-ylmethyl}-methyl-amide;
5-Chloro-1,3-dimethyl-1H-pyrazole-4-carboxylic acid {5-[3-(3-fluoro-benzyl)-ureido]-[1,2,4]thiadiazol-3-ylmethyl}-methyl-amide;
5-Isopropyl-3-methyl-isoxazole-4-carboxylic acid {5-[3-(3-fluoro-benzyl)-ureido]-[1,2,4]thiadiazol-3-ylmethyl}-methyl-amide;
1,3,5-Trimethyl-1H-pyrazolo[4,3-b]pyridine-7-carboxylic acid {5-[3-(5-chloro-thiophen-2-ylmethyl)-ureido]-[1,2,4]thiadiazol-3-ylmethyl}-methyl-amide;
1-Methyl-5-pyrrol-1-yl-1H-pyrazole-4-carboxylic acid {5-[3-(3-fluoro-benzyl)-ureido]-[1,2,4]thiadiazol-3-ylmethyl}-methyl-amide;
3-Methyl-4-oxo-3,4-dihydro-phthalazine-1-carboxylic acid {5-[3-(3-fluoro-benzyl)-ureido]-[1,2,4]thiadiazol-3-ylmethyl}-methyl-amide;
2,4-Dimethyl-6-oxo-6H-pyran-3-carboxylic acid {5-[3-(3-fluoro-benzyl)-ureido]-[1,2,4]thiadiazol-3-ylmethyl}-methyl-amide;

3,6-Dimethyl-isoxazolo[5,4-b]pyridine-4-carboxylic acid {5-[3-(3-fluoro-benzyl)-ureido]-[1,2,4]thiadiazol-3-ylmethyl}-methyl-amide;

2-(5,7-Dimethyl-[1,2,4]triazolo[1,5-a]pyrimidin-6-yl)-N-{5-[3-(3-fluoro-benzyl)-ureido]-[1,2,4]thiadiazol-3-ylmethyl}-N-methyl-acetamide;

3,6-Dimethyl-4-oxo-3,4-dihydro-furo[2,3-d]pyrimidine-5-carboxylic acid {5-[3-(3-fluoro-benzyl)-ureido]-[1,2,4]thiadiazol-3-ylmethyl}-methyl-amide;

N-{5-[3-(3-Fluoro-benzyl)-ureido]-[1,2,4]thiadiazol-3-ylmethyl}-N-methyl-6-[1,2,4]triazol-1-yl-nicotinamide;

1-(2-Methoxy-ethyl)-6-oxo-1,6-dihydro-pyridazine-3-carboxylic acid {5-[3-(3-fluoro-benzyl)-ureido]-[1,2,4]thiadiazol-3-ylmethyl}-methyl-amide;

1-Methyl-4-sulfamoyl-1H-pyrrole-2-carboxylic acid {5-[3-(5-chloro-thiophen-2-ylmethyl)-ureido]-[1,2,4]thiadiazol-3-ylmethyl}-methyl-amide;

N-{5-[3-(5-Chloro-thiophen-2-ylmethyl)-ureido]-[1,2,4]thiadiazol-3-ylmethyl}-2-(5,7-dimethyl-[1,2,4]triazolo[1,5-a]pyrimidin-6-yl)-N-methyl-acetamide;

3,6-Dimethyl-4-oxo-3,4-dihydro-furo[2,3-d]pyrimidine-5-carboxylic acid{5-[3-(5-chloro-thiophen-2-ylmethyl)-ureido]-[1,2,4]thiadiazol-3-ylmethyl}-methyl-amide;

(R)-Tetrahydro-furan-2-carboxylic acid {5-[3-(3-fluoro-benzyl)-ureido]-[1,2,4]thiadiazol-3-ylmethyl}-methyl-amide;

1,3,5-Trimethyl-1H-pyrazolo[4,3-b]pyridine-7-carboxylic acid {5-[3-(3-fluoro-benzyl)-ureido]-[1,2,4]thiadiazol-3-ylmethyl}-methyl-amide;

1-Methyl-3-trifluoromethyl-1H-pyrazole-4-carboxylic acid {5-[3-(5-chloro-thiophen-2-ylmethyl)-ureido]-[1,2,4]thiadiazol-3-ylmethyl}-methyl-amide;

N-{5-[3-(5-Chloro-thiophen-2-ylmethyl)-ureido]-[1,2,4]thiadiazol-3-ylmethyl}-3-cyano-2-hydroxy-6,N-dimethyl-isonicotinamide;

6-Chloro-3-oxo-2,3-dihydro-pyridazine-4-carboxylic acid {5-[3-(3-fluoro-benzyl)-ureido]-[1,2,4]thiadiazol-3-ylmethyl}-methyl-amide;

1-Methyl-6-oxo-1,4,5,6-tetrahydro-pyridazine-3-carboxylic acid {5-[3-(3-fluoro-benzyl)-ureido]-[1,2,4]thiadiazol-3-ylmethyl}-methyl-amide;

7-Chloro-benzo[1,3]dioxole-5-carboxylic acid {5-[3-(3-fluoro-benzyl)-ureido]-[1,2,4]thiadiazol-3-ylmethyl}-methyl-amide;

5-Methyl-4-oxo-3,4-dihydro-thieno[2,3-d]pyrimidine-6-carboxylic acid {5-[3-(3-fluoro-benzyl)-ureido]-[1,2,4]thiadiazol-3-ylmethyl}-methyl-amide;

1-Methyl-5-pyrrol-1-yl-1H-pyrazole-4-carboxylic acid {5-[3-(5-chloro-thiophen-2-ylmethyl)-ureido]-[1,2,4]thiadiazol-3-ylmethyl}-methyl-amide;

1-Methyl-6-oxo-1,4,5,6-tetrahydro-pyridazine-3-carboxylic acid {5-[3-(5-chloro-thiophen-2-ylmethyl)-ureido]-[1,2,4]thiadiazol-3-ylmethyl}-methyl-amide;

3-Methyl-4-oxo-3,4-dihydro-phthalazine-1-carboxylic acid {5-[3-(5-chloro-thiophen-2-ylmethyl)-ureido]-[1,2,4]thiadiazol-3-ylmethyl}-methyl-amide;

2,4-Dimethyl-6-oxo-6H-pyran-3-carboxylic acid {5-[3-(5-chloro-thiophen-2-ylmethyl)-ureido]-[1,2,4]thiadiazol-3-ylmethyl}-methyl-amide;

5-Methyl-4-oxo-3,4-dihydro-thieno[2,3-d]pyrimidine-6-carboxylic acid {5-[3-(5-chloro-thiophen-2-ylmethyl)-ureido]-[1,2,4]thiadiazol-3-ylmethyl}-methyl-amide;

N-{5-[3-(5-Chloro-thiophen-2-ylmethyl)-ureido]-[1,2,4]thiadiazol-3-ylmethyl}-N-methyl-6-[1,2,4]triazol-1-yl-nicotinamide;

1-(2-Methoxy-ethyl)-6-oxo-1,6-dihydro-pyridazine-3-carboxylic acid {5-[3-(5-chloro-thiophen-2-ylmethyl)-ureido]-[1,2,4]thiadiazol-3-ylmethyl}-methyl-amide;

N-{5-[3-(5-Chloro-thiophen-2-ylmethyl)-ureido]-[1,2,4]thiadiazol-3-ylmethyl}-2,2-difluoro-N-methyl-2-phenyl-acetamide;

(R)-Tetrahydro-furan-2-carboxylic acid [5-(3-benzo[1,2,5]oxadiazol-5-ylmethyl-ureido)-[1,2,4]thiadiazol-3-ylmethyl]-methyl-amide;

3,5-Dimethyl-1H-pyrazole-4-carboxylic acid {5-[3-(3-fluoro-benzyl)-ureido]-[1,2,4]thiadiazol-3-ylmethyl}-methyl-amide;

3,5-Dimethyl-pyridazine-4-carboxylic acid {5-[3-(3-fluoro-benzyl)-ureido]-[1,2,4]thiadiazol-3-ylmethyl}-methyl-amide;

5-Isopropyl-3-methyl-isoxazole-4-carboxylic acid {5-[3-(5-chloro-thiophen-2-ylmethyl)-ureido]-[1,2,4]thiadiazol-3-ylmethyl}-methyl-amide;

N-{5-[3-(3-Fluoro-benzyl)-ureido]-[1,2,4]thiadiazol-3-ylmethyl}-2,N-dimethyl-5-sulfamoyl-benzamide;

1,1-Dioxo-tetrahydrothiophene-3-carboxylic acid {5-[3-(3-fluoro-benzyl)-ureido]-[1,2,4]thiadiazol-3-ylmethyl}-methyl-amide;

N-{5-[3-(5-Chloro-thiophen-2-ylmethyl)-ureido]-[1,2,4]thiadiazol-3-ylmethyl}-N-methyl-2-morpholin-4-yl-nicotinamide;

1-Phenyl-cyclobutanecarboxylic acid {5-[3-(5-chloro-thiophen-2-ylmethyl)-ureido]-[1,2,4]thiadiazol-3-ylmethyl}-methyl-amide;

4-Oxo-3,4-dihydro-phthalazine-1-carboxylic acid {5-[3-(5-chloro-thiophen-2-ylmethyl)-ureido]-[1,2,4]thiadiazol-3-ylmethyl}-methyl-amide;

7-Chloro-benzo[1,3]dioxole-5-carboxylic acid {5-[3-(5-chloro-thiophen-2-ylmethyl)-ureido]-[1,2,4]thiadiazol-3-ylmethyl}-methyl-amide;

1-(4-Fluoro-phenyl)-cyclobutanecarboxylic acid {5-[3-(5-chloro-thiophen-2-ylmethyl)-ureido]-[1,2,4]thiadiazol-3-ylmethyl}-methyl-amide;

1-Methyl-3-trifluoromethyl-1H-pyrazole-4-carboxylic acid {5-[3-(3-fluoro-benzyl)-ureido]-[1,2,4]thiadiazol-3-ylmethyl}-methyl-amide;

5-Chloro-1,3-dimethyl-1H-pyrazole-4-carboxylic acid {5-[3-(5-chloro-thiophen-2-ylmethyl)-ureido]-[1,2,4]thiadiazol-3-ylmethyl}-methyl-amide;

1-Phenyl-cyclobutanecarboxylic acid {5-[3-(3-fluoro-benzyl)-ureido]-[1,2,4]thiadiazol-3-ylmethyl}-methyl-amide;

4-Oxo-3,4-dihydro-phthalazine-1-carboxylic acid {5-[3-(3-fluoro-benzyl)-ureido]-[1,2,4]thiadiazol-3-ylmethyl}-methyl-amide;

1-(4-Fluoro-phenyl)-cyclobutanecarboxylic acid {5-[3-(3-fluoro-benzyl)-ureido]-[1,2,4]thiadiazol-3-ylmethyl}-methyl-amide;

2,2-Difluoro-N-{5-[3-(3-fluoro-benzyl)-ureido]-[1,2,4]thiadiazol-3-ylmethyl}-N-methyl-2-phenyl-acetamide;

1,1-Dioxo-tetrahydro-thiophene-3-carboxylic acid {5-[3-(5-chloro-thiophen-2-ylmethyl)-ureido]-[1,2,4]thiadiazol-3-ylmethyl}-methyl-amide;

2,2-Dimethyl-tetrahydro-pyran-4-carboxylic acid {5-[3-(5-chloro-thiophen-2-ylmethyl)-ureido]-[1,2,4]thiadiazol-3-ylmethyl}-methyl-amide;

2,3-Dihydro-benzofuran-2-carboxylic acid {5-[3-(3-fluoro-benzyl)-ureido]-[1,2,4]thiadiazol-3-ylmethyl}-methyl-amide;

(R)-Tetrahydro-furan-2-carboxylic acid {5-[3-(5-chloro-thiophen-2-ylmethyl)-ureido]-[1,2,4]thiadiazol-3-ylmethyl}-methyl-amide;

2,2-Dimethyl-tetrahydro-pyran-4-carboxylic acid {5-[3-(3-fluoro-benzyl)-ureido]-[1,2,4]thiadiazol-3-ylmethyl}-methyl-amide;
1-Methyl-5-nitro-1H-pyrazole-4-carboxylic acid {5-[3-(3-fluoro-benzyl)-ureido]-[1,2,4]thiadiazol-3-ylmethyl}-methyl-amide;
1-Methyl-5-nitro-1H-pyrazole-4-carboxylic acid {5-[3-(5-chloro-thiophen-2-ylmethyl)-ureido]-[1,2,4]thiadiazol-3-ylmethyl}-methyl-amide;
2,3-Dihydro-benzofuran-2-carboxylic acid {5-[3-(5-chloro-thiophen-2-ylmethyl)-ureido]-[1,2,4]thiadiazol-3-ylmethyl}-methyl-amide;
(R)—N-{5-[3-(3-Fluoro-benzyl)-ureido]-[1,2,4]thiadiazol-3-ylmethyl}-2-methoxy-N-methyl-propionamide;
(R)—N-{5-[3-(5-chloro-thiophen-2-ylmethyl)-ureido]-[1,2,4]thiadiazol-3-ylmethyl}-2-methoxy-N-methyl-propionamide;
N-{5-[3-(3-Fluoro-benzyl)-ureido]-[1,2,4]thiadiazol-3-ylmethyl}-N-methyl-2-morpholin-4-yl-nicotinamide;
N-{5-[3-(3-Fluoro-benzyl)-ureido]-[1,2,4]thiadiazol-3-ylmethyl}-N-methyl-2-pyrrolidin-1-yl-nicotinamide;
N-{5-[3-(5-Chloro-thiophen-2-ylmethyl)-ureido]-[1,2,4]thiadiazol-3-ylmethyl}-2,N-dimethyl-5-sulfamoyl-benzamide;
N-{5-[3-(5-chloro-thiophen-2-ylmethyl)-ureido]-[1,2,4]thiadiazol-3-ylmethyl}-N-methyl-2-pyrrolidin-1-yl-nicotinamide;
2,2-Difluoro-N-{5-[3-(3-fluoro-benzyl)-ureido]-[1,2,4]thiadiazol-3-ylmethyl}-N-methyl-2-pyridin-2-yl-acetamide;
1-Methyl-4-sulfamoyl-1H-pyrrole-2-carboxylic acid {5-[3-(3-fluoro-benzyl)-ureido]-[1,2,4]thiadiazol-3-ylmethyl}-methyl-amide;
4-Hydroxy-pyrrolidine-1,2-dicarboxylic acid 1-amide 2-({5-[3-(3-fluoro-benzyl)-ureido]-[1,2,4]thiadiazol-3-ylmethyl}-methyl-amide);
Cyclopentanecarboxylic acid {5-[3-(3-fluoro-benzyl)-ureido]-[1,2,4]thiadiazol-3-ylmethyl}-methyl-amide;
2-Methyl-cyclohexanecarboxylic acid {5-[3-(3-fluoro-benzyl)-ureido]-[1,2,4]thiadiazol-3-ylmethyl}-methyl-amide;
Cyclohexanecarboxylic acid {5-[3-(3-fluoro-benzyl)-ureido]-[1,2,4]thiadiazol-3-ylmethyl}-methyl-amide;
2,6-Dioxo-hexahydro-pyrimidine-4-carboxylic acid {5-[3-(3-fluoro-benzyl)-ureido]-[1,2,4]thiadiazol-3-ylmethyl}-methyl-amide;
1-Cyano-cyclopropanecarboxylic acid {5-[3-(5-chloro-thiophen-2-ylmethyl)-ureido]-[1,2,4]thiadiazol-3-ylmethyl}-methyl-amide;
1-Hydroxy-cyclopropanecarboxylic acid {5-[3-(3-fluoro-benzyl)-ureido]-[1,2,4]thiadiazol-3-ylmethyl}-methyl-amide;
2-Oxo-2,3-dihydro-benzooxazole-6-carboxylic acid {5-[3-(3-fluoro-benzyl)-ureido]-[1,2,4]thiadiazol-3-ylmethyl}-methyl-amide;
N-{5-[3-(3-Fluoro-benzyl)-ureido]-[1,2,4]thiadiazol-3-ylmethyl}-2-hydroxy-2,N-dimethyl-propionamide;
1-Cyano-cyclopropanecarboxylic acid {5-[3-(3-fluoro-benzyl)-ureido]-[1,2,4]thiadiazol-3-ylmethyl}-methyl-amide;
N-{5-[3-(3-Fluoro-benzyl)-ureido]-[1,2,4]thiadiazol-3-ylmethyl}-2-((S)-4-hydroxy-2-oxo-pyrrolidin-1-yl)-N-methyl-acetamide;
1,1-Dioxo-tetrahydro-1,6-thiophene-3-sulfonic acid {2-[3-(3,4-dichloro-benzyl)-ureido]-thiazol-4-ylmethyl}-methyl-amide;
N-((2-(3-(3,4-dichlorobenzyl)ureido)thiazol-4-yl)methyl)-N,4-dimethylbenzenesulfonamide;
N-((2-(3-(3,4-dichlorobenzyl)ureido)thiazol-4-yl)methyl)-N,3,5-trimethylisoxazole-4-sulfonamide;
N-((2-(3-(3,4-dichlorobenzyl)ureido)thiazol-4-yl)methyl)-N-methylmethanesulfonamide;
N-((2-(3-(3-fluorobenzyl)ureido)thiazol-4-yl)methyl)-N-methylmethanesulfonamide;
N-((2-(3-(3-fluorobenzyl)ureido)thiazol-4-yl)methyl)-N-methylpropane-1-sulfonamide;
5-(2-(3-(3,4-dichlorobenzyl)ureido)thiazol-4-yl)-1-(methylsulfonyl)pyrrolidin-3-yl acetate;
1-(3,4-dichlorobenzyl)-3-(4-(4-hydroxy-1-(methylsulfonyl)pyrrolidin-2-yl)thiazol-2-yl)urea;
N-((2-(3-(3-fluorobenzyl)ureido)thiazol-4-yl)methyl)-N-methylbutane-1-sulfonamide;
N-((2-(3-(3-fluorobenzyl)ureido)thiazol-4-yl)methyl)-N-methylethanesulfonamide;
N-((2-(3-(3-fluorobenzyl)ureido)thiazol-4-yl)methyl)-N,3,5-trimethylisoxazole-4-sulfonamide;
N-((2-(3-(3-fluorobenzyl)ureido)thiazol-4-yl)methyl)-N-methylcyclopropanesulfonamide;
N-((2-(3-(3-fluorobenzyl)ureido)thiazol-4-yl)methyl)-N-(2-(methylsulfonamido)ethyl)methanesulfonamide;
1-[4-(1,1-Dioxo-116-isothiazolidin-2-ylmethyl)-thiazol-2-yl]-3-(3-fluoro-benzyl)-urea;
1-(3-Fluoro-benzyl)-3-{4-[1-(propane-1-sulfonyl)-pyrrolidin-2-yl]-thiazol-2-yl}-urea;
Ethanesulfonic acid {5-bromo-2-[3-(3-fluoro-benzyl)-ureido]-thiazol-4-ylmethyl}-methyl-amide;
N-{2-[3-(3-Fluoro-benzyl)-ureido]-thiazol-4-ylmethyl}-N-methyl-4-morpholin-4-yl-benzenesulfonamide;
Furan-2-sulfonic acid {2-[3-(3-fluoro-benzyl)-ureido]-thiazol-4-ylmethyl}-methyl-amide;
Thiophene-2-sulfonic acid {2-[3-(3-fluoro-benzyl)-ureido]-thiazol-4-ylmethyl}-methyl-amide;
Pyridine-3-sulfonic acid {2-[3-(3-fluoro-benzyl)-ureido]-thiazol-4-ylmethyl}-methyl-amide;
Pyridine-2-sulfonic acid {2-[3-(3-fluoro-benzyl)-ureido]-thiazol-4-ylmethyl}-methyl-amide;
1-Methyl-1H-imidazole-4-sulfonic acid {2-[3-(3-fluoro-benzyl)-ureido]-thiazol-4-ylmethyl}-methyl-amide;
1,2-Dimethyl-1H-imidazole-4-sulfonic acid {2-[3-(3-fluoro-benzyl)-ureido]-thiazol-4-ylmethyl}-methyl-amide;
N-{2-[3-(3-Fluoro-benzyl)-ureido]-thiazol-4-ylmethyl}-N-methyl-C-pyridin-3-yl-methanesulfonamide; and
N-(3,5-Dimethyl-isoxazol-4-ylmethyl)-N-{2-[3-(3-fluoro-benzyl)-ureido]-thiazol-4-ylmethyl}-methanesulfonamide.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula (I) (note that Formula (I) includes Formula (Ia) and Formula (Ib)) or a salt and/or solvate thereof. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

When used herein, the term "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid.

"Solvate" encompasses both solution-phase and isolatable solvates. Non-limiting examples of suitable solvates include ethanolates, methanolates, and the like.

When used herein, the term "hydrate" is a solvate wherein the solvent molecule is $H_2O$.

As used herein, the phrases "effective amount" or "therapeutically effective amount" are meant to describe an amount of compound or a composition of the present invention effective in inhibiting bacterial replication and thus producing the desired therapeutic, ameliorative, inhibitory or preventative effect.

The compounds of Formula (I) (as defined herein Formula (I) includes Formula (Ia) and (1b)) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates, or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, Journal of Pharmaceutical Sciences (1977) 66(1) 1 19; P. Gould, International J. of Pharmaceutics (1986) 33 201 217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), arylalkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

Compounds of Formula (I) and salts, solvates and prodrugs thereof, may exist in their tautomeric form (for example, as an amide or imino ether). All such tautomeric forms are contemplated herein as part of the present invention. All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Compounds of Formula (I) are inhibitors of PolC, a type II DNA Polymerase III, which is the major replicative polymerase responsible for chromosomal replication in low GC Gram-positive bacteria. Compounds of Formula (I) are generally selective for PolC, showing little or no inhibition of the eukaryotic replicative polymerase, i.e., provides an optimal combination of high activity against various pathogenic bacteria and low or no activity against mammalian calls, allowing the use of compounds of the invention in the treatment of mammals, and in particular humans.

Compounds of the present invention show antibacterial activity against clinically relevant Gram-positive pathogens, including *S. pyogenes, S. aureus, S. pneumoniae* and *E. faecalis*. Compounds of the present invention demonstrate preferential inhibition of DNA synthesis over RNA, protein, or cell wall synthesis in whole cell assays. Therapeutic compositions of the present invention have antibacterial activity against clinically important Gram-positive pathogens, including staphylococci and streptococci, and particularly including isolates resistant to currently marketed agents.

Another aspect of this invention is a method of protecting a patient from a bacterial infection. A patient may be an animal, preferably a mammal and even more preferably a human having or susceptible to a disease or condition associated with a bacterial infection. Protecting may be prophylactic, i.e., administering a compound of the present invention in the absence of a diagnosed bacterial infection, or therapeutic, i.e., administering a compound of the present invention upon diagnosis of a bacterial infection. Protection may be achieved by administering a therapeutically effective amount of at least one compound of Formula (I), or a pharmaceutically acceptable salt or solvate of said compound to the patient. A preferred dosage is about 0.001 to 500 mg/kg of body weight/day of the compound of Formula (I) or a pharmaceutically acceptable salt or solvate of said compound. An especially preferred dosage is about 0.01 to 25 mg/kg of body weight/day of a compound of Formula (I), or a pharmaceutically acceptable salt or solvate of said compound.

Methods to diagnose bacterial infection in patients are known in the art. Preferred bacterial infections to treat include bacterial infections caused by any bacteria type or species against which the compounds of the present invention have an antibacterial effect. Particularly preferred bacteria types or species include Gram-positive and Gram-negative bacteria and most preferred bacterial types include Gram-positive bacteria.

In order to protect an animal from bacterial infection, a therapeutic or prophylactic composition of the present invention is administered to the animal in an effective manner such that bacterial infection is minimized and/or reduced. Preferably, the bacterial infection and/or bacterial burden of the infectious bacteria is reduced by at least about 50%, at least about 70%, and more preferably at least about 90%, 95% or 97%.

Suitable patients to treat include humans; birds such as chickens, ostriches, quail, and turkeys; other mammals such as companion animals (including dogs, cats, and rodents) and economic food and/or fur or other product animals, such as horses, cattle, llamas, chinchillas, ferrets, goats, sheep, rodents, minks, rabbits, raccoons, and swine.

The compounds of this invention can also be useful in combination (administered together or sequentially) with one or more of antibacterial treatments, such as, for example, treatment with other known antibacterial drug classes such as, for example, β-lactams, glycopeptides, oxazolidinones, macrolides, ketolides, quinolones, fluoroquinolones, aminoglycosides, tetracyclines, and lipopeptides. If formulated as a fixed dose, such combination products employ the compounds of this invention within the dosage range described herein and the other pharmaceutically active agent or treatment within its dosage range. Compounds of Formula (I) may also be administered sequentially with known antibacterial agents when a combination formulation is inappropriate. The invention is not limited in the sequence of administration; compounds of Formula (I) may be administered either prior to or after administration of the known antibacterial agent. Such techniques are within the skills of persons skilled in the art as well as attending physicians.

Accordingly, in an aspect, this invention includes combinations comprising an amount of at least one compound of Formula (I), or a pharmaceutically acceptable salt or solvate thereof, and an amount of one or more antibacterial agents or treatments listed above wherein the amounts of the compounds/treatments result in desired therapeutic effect. The pharmacological properties of the compounds of this invention may be confirmed by a number of pharmacological assays. The exemplified pharmacological assays which are described herein have been carried out with compounds according to the invention and/or their salts.

In another aspect, the invention includes pharmaceutical compositions which comprise at least one compound of Formula (I), or a pharmaceutically acceptable salt or solvate of said compound, and at least one pharmaceutically acceptable carrier. Accordingly, the present invention further includes compositions comprising one or more compounds of Formula (I) and a pharmaceutically acceptable carrier.

When used herein, the phrase "pharmaceutically acceptable carrier" refers to media generally accepted in the art for the delivery of biologically active agents to patients, in particular, mammals Pharmaceutically acceptable carriers are typically formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Remington's Pharmaceutical Sciences, 17th ed., Mack Publishing Company, Easton, Pa., 1985, which is incorporated herein by reference in its entirety.

Preparation of Pharmaceutical Compositions of the Invention Include inclusion of inert, solid or liquid pharmaceutically acceptable carriers. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, silica, sucrose, lactose, starch, or cellulose derivatives. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa. incorporated herein by reference.

Liquid form preparations include solutions, suspensions and emulsions. As an example, water or water-propylene glycol solutions for parenteral injection or addition of sweeteners and opacifiers for oral solutions, suspensions and emulsions, can be used. Liquid form preparations may also include solutions for intranasal administration. Gelatin capsules can be used to contain the active ingredient and a suitable carrier such as, but not limited to, lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract. Liquid dose forms for oral administration can also contain coloring or flavoring agents to increase patient acceptance.

Typically, water, pharmaceutically acceptable oils, saline, aqueous dextrose, and related sugar solutions and glycols, such as propylene glycol or polyethylene glycol, are suitable carriers for parenteral solutions. Solutions for parenteral administration can contain, for example, a water soluble salt of the active ingredient and suitable stabilizing agent(s). Antioxidizing agents, such as sodium bisulfite, sodium sulfite, or ascorbic acid, either alone or in combination, can act as suitable stabilizing agents. Also suitable as stabilizing agents are citric acid and its salts, and EDTA. In addition, parenteral solutions can contain preservatives such as, for example, benzalkonium chloride, methyl- or propyl-paraben, and chlorobutanol.

Oral compositions are preferred and will generally include an inert diluent or an edible carrier and may be compressed into tablets or enclosed in gelatin capsules. The oral dosage forms are administered to the patient weekly, twice weekly, three times weekly, four times weekly, five times weekly, six times weekly, or 1, 2, 3, or 4 times daily. It is preferred that the compounds of the invention be administered either three or fewer times daily, more preferably once or twice daily. For purposes of oral therapeutic administration, the active compound or compounds can be incorporated with excipients and used in the form of tablets, capsules, lozenges, or troches. Pharmaceutically compatible binding agents and adjuvant materials can be included as part of the composition. The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes, colorings, and flavors. The active materials can also be mixed with other active materials that do not impair the desired action, or with materials that supplement the desired action.

Solutions or suspensions used for parenternal, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenternal preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known, for example, as described in U.S. Pat. No. 4,522,811, which is incorporated by reference herein.

The active compounds may be prepared with carriers that protect the compound against rapid elimination from the body, such as time-release formulations or coatings such as enteric coatings to protect the compounds of the present invention from the acidic environment of the stomach. Enteric coated tablets are well known to those skilled in the art. In addition, capsules filled with small spheres, each coated to protect from the acidic stomach, are also well known to those skilled in the art. Other such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds of the invention can be administered orally, parenterally (IV, IM, depo-IM, SQ, and depo-SQ), sublingually, intranasally (inhalation), intrathecally, topically, or rectally. Dosage forms known to those skilled in the art are suitable for delivery of the compounds of the invention.

When administered orally, compounds of the invention can be administered in usual dosage forms for oral administration as is well known to those skilled in the art and are described more fully herein. These dosage forms include the usual solid unit dosage forms of tablets and capsules as well as liquid dosage forms such as solutions, suspensions, and elixirs. When the solid dosage forms are used, it is preferred that they be of the sustained release type so that the compounds of the invention need to be administered only once or twice daily.

The compounds of the invention can be administered parenterally, for example, by IV, IM, depo-IM, SC, or depo-SC. When administered parenterally, a therapeutically effective amount for humans of about 0.5 to about 100 mg/day, preferably from about 5 to about 50 mg daily should be delivered. When a depot formulation is used for injection once a month or once every two weeks, the dose for humans should be about 0.5 mg/day to about 50 mg/day, or a monthly dose of from about 15 mg to about 1,500 mg. Dosing for other types of patients can be estimated from the appropriate human dose.

The compounds of the invention can be administered sublingually. When given sublingually, the compounds of the invention should be given one to four times daily in the amounts described above for IM administration.

The compounds of the invention can also be administered intranasally. When given by this route, the appropriate dosage forms are a nasal spray or dry powder, as is known to those skilled in the art. The dosage of the compounds of the invention for intranasal administration is the amount described above for IM administration.

The compounds of the invention can be administered intrathecally. When given by this route the appropriate dosage form can be a parenteral dosage form as is known to those skilled in the art. The dosage of the compounds of the invention for intrathecal administration is the amount described above for IM administration.

The compounds of the invention can be administered topically. When given by this route, the appropriate dosage form is a cream, ointment, or patch. When administered topically, the dosage is from about 0.5 mg/day to about 200 mg/day. The compounds of the invention can be administered rectally by suppository as is known to those skilled in the art. When administered by suppository, the therapeutically effective amount is from about 0.5 mg to about 500 mg for humans. The compounds of the invention can be administered by implants as is known to those skilled in the art. When administering a compound of the invention by implant, the therapeutically effective amount is the amount described above for depot administration.

The invention herein is the novel compounds of the invention and new methods of using the compounds of the invention. Given a particular compound of the invention and a desired dosage form, one skilled in the art would know how to prepare and administer the appropriate dosage form.

Where the compounds of the invention exhibit insufficient solubility, methods for solubilizing may be used. Such methods are known and include, but are not limited to, using cosolvents such as dimethylsulfoxide (DMSO), using surfactants such as polysorbates including Tween® and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration. A suitable single dose is a dose that is capable of reducing bacterial infection and/or bacterial burden with the infectious bacteria when administered one or more times over a suitable time period. For example, a preferred single dose of a compound of Formula (I) ranges from about 1 microgram to about 10 milligrams, but can range up to 100 milligrams of the composition per kilogram body weight of the patient.

The active compound is typically included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound of the invention in lyophilized form, and a suitable diluent, may be provided as separated components for combination prior to use. A kit may include a compound of the invention and a second therapeutic agent for co-administration. The compound of the invention and second therapeutic agent may be provided as separate component parts.

A kit herein may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampules, vials, and the like for parenternal administration; and patches, medipads, creams, ointments, and the like for topical administration.

The concentration of active compound in the drug composition will depend on absorption, inactivation, and excretion rates of the active compound, the dosage schedule, and amount administered as well as other factors known to those of skill in the art. The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data.

It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the composition(s), and that the concentration ranges set forth herein are exemplary only and are not intended to limit the scope or practice of the claimed compositions.

Compounds of the invention can be prepared as described in the following Examples.

The invention disclosed herein is exemplified by the following preparations and examples which should not be construed to limit the scope of the disclosure. Alternative mechanistic pathways and analogous structures will be apparent to those skilled in the art.

EXAMPLES

Examples 1-478

The following abbreviations are used throughout the Example section and are not meant to limit the scope of the disclosure.
TLC=thin layer chromatography
eq.=equivalents
equiv.=equivalents
THF=tetrahydrofuran
DIPEA=diisopropylethylamine
DIEA=diisopropylethylamine
DCM=dichloromethane
MeOH=methanol
EtOAc=ethyl acetate
BOC$_2$O=di-tert-butyl dicarbonate
mCPBA=3-chloroperbenzoic acid
DMAP=4-(Dimethylamino)pyridine
TFA=trifluoroacetic acid
DMA=N,N-dimethylacetamide
TBTU=O-(Benzotriazol-1-yl)-N,N,N',N'-tetramethyluronium tetrafluoroborate
DMSO=dimethyl sulfoxide
Et$_2$O=diethyl ether
MeCN=acetonitrile
DMF=N,N-dimethylformamide
NMP=1-Methyl-2-pyrrolidinone The compounds of Examples 1-475, shown below in Tables 1 (thiazoyl amides), 2 (thiadiazolyl amides) and 3 (thiazoyl sulfonamides) were prepared by the methods described in Example 477 as indicated in the Tables using intermediates described in Example 476.

TABLE 1

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 1 | N-((2-(3-(3,4-dichlorobenzyl)ureido)thiazol-4-yl)methyl)-N-(2-methoxyethyl)acetamide | C17H20Cl2N4O3S | 431.3 | 431, 433 | 3 | Int. 12 | Acetyl chloride |
| 2 | 3-(N-((2-(3-(3,4-dichlorobenzyl)ureido)thiazol-4-yl)methyl) acetamido) propylphosphonic acid | C17H21Cl2N4O5PS | 495.3 | 495, 497 | 3 | Int. 23 | Acetyl chloride |
| 3 | N-((2-(3-(3,4-dichlorobenzyl)ureido)thiazol-4-yl)methyl)-2-(2-methoxyethoxy)-N-methylacetamide | C18H22Cl2N4O4S | 461.4 | 461, 463 | 3 | Int. 3 | 2-(2-Methoxyethoxy)acetyl chloride |
| 4 | N-((2-(3-(3,4-dichlorobenzyl)ureido)thiazol-4-yl)methyl)-2-methoxy-N-methylacetamide | C16H18Cl2N4O3S | 417.3 | 417, 419 | 3 | Int. 3 | 2-Methoxyacetyl chloride |
| 5 | N-((2-(3-(3,4-dichlorobenzyl)ureido)thiazol-4-yl)methyl)-N,4-dimethylisoxazole-5-carboxamide | C18H17Cl2N5O3S | 454.3 | 454, 456 | 3 | Int. 3 | 4-Methyl-isoxazole-5-carboxylic acid chloride |
| 6 | N-((2-(3-(3,4-dichlorobenzyl)ureido)thiazol-4-yl)methyl)-N-methylisoxazole-5-carboxamide | C17H15Cl2N5O3S | 440.3 | 440, 442 | 3 | Int. 3 | Isoxazole-5-carboxylic acid chloride |
| 7 | N-((2-(3-(3,4-dichlorobenzyl)ureido)thiazol-4-yl)methyl)-N-methyl-3-phenylpropanamide | C22H22Cl2N4O2S | 477.4 | 477, 479 | 3 | Int. 3 | 3-Phenylpropionyl chloride |
| 8 | N-((2-(3-(3,4-dichlorobenzyl)ureido)thiazol-4-yl)methyl)-N-methylfuran-2-carboxamide | C18H16Cl2N4O3S | 439.3 | 439, 441 | 3 | Int. 3 | 2-Furoyl chloride |
| 9 | N-((2-(3-(3,4-dichlorobenzyl)ureido)thiazol-4-yl)methyl)-N-methyl-4-phenoxybutanamide | C23H24Cl2N4O3S | 507.4 | 507, 509 | 3 | Int. 3 | 4-Phenoxy-butyryl chloride |
| 10 | 1-(3,4-Dichloro-benzyl)-3-{4-[3-(1,1-dioxo-tetrahydro-1l6-thiophen-3-ylmethyl)-1-methyl-ureidomethyl]-thiazol-2-yl}-urea | C19H23Cl2N5O4S2 | 520.5 | 520, 522 | 3 | Int. 3 | N-(1,1-Dioxo-tetrahydrothiophen-3-yl-methyl)carbamoyl chloride |
| 11 | N-((2-(3-(3,4-dichlorobenzyl)ureido)thiazol-4-yl)methyl)-N,3,5-trimethylisoxazole-4-carboxamide | C19H19Cl2N5O3S | 468.4 | 468, 470 | 3 | Int. 3 | 3,5-Dimethyl-isoxazole-4-carboxylic acid chloride |
| 12 | N-((2-(3-(3,4-dichlorobenzyl)ureido)thiazol-4-yl)methyl)-N,1-dimethyl-1H-imidazole-5-carboxamide | C18H18Cl2N6O2S | 453.4 | 453, 455 | 3 | Int. 3 | 1-Methyl-imidazole-5-carboxylic acid chloride |
| 13 | N-((2-(3-(3,4-dichlorobenzyl)ureido)thiazol-4-yl)methyl)-N-methylfuran-3-carboxamide | C18H16Cl2N4O3S | 439.3 | 439, 441 | 3 | Int. 3 | 3-Furoyl chloride |
| 14 | N-((2-(3-(3,4-dichlorobenzyl)ureido)thiazol-4-yl)methyl)-N,3-dimethylfuran-2-carboxamide | C19H18Cl2N4O3S | 453.3 | 453, 455 | 3 | Int. 3 | 3-Methyl-2-furoyl chloride |
| 15 | N-((2-(3-(3,4-dichlorobenzyl)ureido)thiazol-4-yl)methyl)-N,5-dimethyl-3-phenylisoxazole-4-carboxamide | C24H21Cl2N5O3S | 530.4 | 530, 532 | 3 | Int. 3 | 5-Methyl-3-phenyl-isoxazole-4-carboxylic acid chloride |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 16 | N-((2-(3-(3,4-dichlorobenzyl)ureido)thiazol-4-yl)methyl)-N-ethyl-3,5-dimethylisoxazole-4-carboxamide | C20H21Cl2N5O3S | 482.4 | 482, 484 | 3 | Int. 8 | 3,5-Dimethyl-isoxazole-4-carboxylic acid chloride |
| 17 | N-((2-(3-(3,4-dichlorobenzyl)ureido)thiazol-4-yl)methyl)-N-isopropyl-3,5-dimethylisoxazole-4-carboxamide | C21H23Cl2N5O3S | 496.4 | 496, 498 | 3 | Int. 9 | 3,5-Dimethyl-isoxazole-4-carboxylic acid chloride |
| 18 | N-((2-(3-(3,4-dichlorobenzyl)ureido)thiazol-4-yl)methyl)-N,5-dimethyl-2-phenyl-2H-1,2,3-triazole-4-carboxamide | C23H21Cl2N7O2S | 530.4 | 530, 532 | 3 | Int. 3 | 5-Methyl-2-phenyl-2H-1,2,3-triazole-4-carboxylic acid chloride |
| 19 | N-(2-(3-(3,4-dichlorobenzyl)ureido)thiazol-4-yl)methyl)-N,5-dimethylisoxazole-3-carboxamide | C18H17Cl2N5O3S | 454.3 | 454, 456 | 3 | Int. 3 | 5-Methylisoxazole-3-carboxylic acid chloride |
| 20 | N-((2-(3-(3,4-dichlorobenzyl)ureido)thiazol-4-yl)methyl)-N,3-dimethyl-5-phenylisoxazole-4-carboxamide | C24H21Cl2N5O3S | 530.4 | 530, 532 | 3 | Int. 3 | 3-Methyl-5-phenylisoxazole-4-carboxylic acid chloride |
| 21 | N-((2-(3-(3,4-dichlorobenzyl)ureido)thiazol-4-yl)methyl)-N,3-dimethyl-5-(4-methyl-1,2,3-thiadiazol-5-yl)isoxazole-4-carboxamide | C21H19Cl2N7O3S2 | 552.5 | 552, 554 | 3 | Int. 3 | 3-Methyl-5-(4-methyl-1,2,3-thiadiazol-5-yl)isoxazole-4-carboxylic acid chloride |
| 22 | N-(2-(3-(3,4-dichlorobenzyl)ureido)thiazol-4-yl)methyl)-N-methyl-2-(2H-tetrazol-5-yl)acetamide | C16H16Cl2N8O2S | 455.3 | 455/457 | 2 | Int. 3 | 2-(2H-Tetrazol-5-yl)acetic acid |
| 23 | N-((2-(3-(3,4-dichlorobenzyl)ureido)thiazol-4-yl)methyl)-N-methylbenzofuran-2-carboxamide | C22H18Cl2N4O3S | 489.4 | 489, 491 | 3 | Int. 3 | Benzofuran-2-carboxylic acid chloride |
| 24 | N-(1-(2-(3-(3,4-dichlorobenzyl)ureido)thiazol-4-yl)ethyl)-N,3,5-trimethylisoxazole-4-carboxamide | C20H21Cl2N5O3S | 482.4 | 482/484 | 3 | Int. 10a | 3,5-Dimethyl-isoxazole-4-carboxylic acid chloride |
| 25 | N-((2-(3-(3,4-dichlorobenzyl)ureido)thiazol-4-yl)methyl)-N-methyl-1,2,5-oxadiazole-3-carboxamide | C16H14Cl2N6O3S | 441.3 | 441/443 | 2 | Int. 3 | 1,2,5-Oxadiazole-3-carboxylic acid chloride |
| 26 | N-(2-(3-(3,4-dichlorobenzyl)ureido)thiazol-4-yl)methyl)-2-(3,5-dimethylisoxazol-4-yl)-N-methylacetamide | C20H21Cl2N5O3S | 482.4 | 482, 484 | 2 | Int. 3 | 2-(3,5-Dimethylisoxazol-4-yl)acetic acid |
| 27 | N-((2-(3-(3,4-dichlorobenzyl)ureido)thiazol-4-yl)methyl)-3-ethyl-N,5-dimethylisoxazole-4-carboxamide | C20H21Cl2N5O3S | 482.4 | 482, 484 | 2 | Int. 3 | 3-Ethyl-5-methylisoxazole-4-carboxylic acid |
| 28 | N-((2-(3-(3,4-dichlorobenzyl)ureido)thiazol-4-yl)methyl)-N,3-dimethylisoxazole-4-carboxamide | C18H17Cl2N5O3S | 454.3 | 454, 456 | 2 | Int. 3 | 3-Methylisoxazole-4-carboxylic acid |
| 29 | N-((2-(3-(3,4-dichlorobenzyl)ureido)thiazol-4-yl)methyl)-N,5-dimethylisoxazole-4-carboxamide | C18H17Cl2N5O3S | 454.3 | 454, 456 | 2 | Int. 3 | 5-Methylisoxazole-4-carboxylic acid chloride |
| 30 | 5-cyclopropyl-N-((2-(3-(3,4-dichlorobenzyl)ureido)thiazol-4-yl)methyl)-N-methylisoxazole-4-carboxamide | C20H19Cl2N5O3S | 480.4 | 480, 482 | 2 | Int. 3 | 5-Cyclopropylisoxazole-4-carboxylic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 31 | N-((2-(3-(3,4-dichlorobenzyl)ureido)thiazol-4-yl)methyl)-N,2,6-trimethylbenzamide | C22H22Cl2N4O2S | 477.4 | 477, 479 | 3 | Int. 3 | 2,6-Dimethylbenzoyl chloride |
| 32 | N-((2-(3-(3,4-dichlorobenzyl)ureido)thiazol-4-yl)methyl)-5-(furan-2-yl)-N-methylisoxazole-3-carboxamide | C21H17Cl2N5O4S | 506.4 | 506, 508 | 3 | Int. 3 | 5-(Furan-2-yl)isoxazole-3-carboxylic acid chloride |
| 33 | N-((2-(3-(3,4-dichlorobenzyl)ureido)thiazol-4-yl)methyl)-N,2,5-trimethyloxazole-4-carboxamide | C19H19Cl2N5O3S | 468.4 | 468, 470 | 3 | Int. 3 | 2,5-Dimethyloxazole-4-carboxylic acid chloride |
| 34 | N-((2-(3-(3,4-dichlorobenzyl)ureido)thiazol-4-yl)methyl)-N-methyl-2-phenylthiazole-4-carboxamide | C23H19Cl2N5O2S2 | 532.5 | 532, 534 | 3 | Int. 3 | 2-Phenylthiazole-4-carboxylic acid chloride |
| 35 | N-((2-(3-(3,4-dichlorobenzyl)ureido)thiazol-4-yl)methyl)-N-(2,4-dimethoxybenzyl)-3,5-dimethylisoxazole-4-carboxamide | C27H27Cl2N5O5S | 604.5 | 604, 606 | 3 | Int. 3 | 3,5-Dimethyl-isoxazole-4-carboxylic acid chloride |
| 36 | N-((2-(3-(3,4-dichlorobenzyl)ureido)thiazol-4-yl)methyl)-N-(2-methoxyethyl)-3,5-dimethylisoxazole-4-carboxamide | C21H23Cl2N5O4S | 512.4 | 512, 514 | 3 | Int. 3 | 3,5-Dimethyl-isoxazole-4-carboxylic acid chloride |
| 37 | N-((2-(3-(3,4-dichlorobenzyl)ureido)thiazol-4-yl)methyl)-N-methyl-2-(thiophen-2-yl)thiazole-4-carboxamide | C21H17Cl2N5O2S3 | 538.5 | 538, 540 | 3 | Int. 11 | 2-(Thiophen-2-yl)thiazole-4-carboxylic acid chloride |
| 38 | N-((2-(3-(3,4-dichlorobenzyl)ureido)thiazol-4-yl)methyl)-3-hydroxy-N-methylisoxazole-5-carboxamide | C17H15Cl2N5O4S | 456.3 | 456/458 | 2 | Int. 12 | 3-Hydroxyisoxazole-5-carboxylic acid |
| 39 | N-((2-(3-(3,4-dichlorobenzyl)ureido)thiazol-4-yl)methyl)-N-methyl-5-phenyl-1,3,4-oxadiazole-2-carboxamide | C22H18Cl2N6O3S | 517.4 | 517, 519 | 3 | Int. 3 | 5-Phenyl-1,3,4-oxadiazole-2-carboxylic acid chloride |
| 40 | N-((2-(3-(3,4-dichlorobenzyl)ureido)thiazol-4-yl)methyl)-N,5-dimethylfuran-2-carboxamide | C19H18Cl2N4O3S | 453.3 | 453, 455 | 3 | Int. 3 | 5-Methyl-2-furoyl chloride |
| 41 | N-((2-(3-(3,4-dichlorobenzyl)ureido)thiazol-4-yl)methyl)-N,4-dimethyl-1,2,5-oxadiazole-3-carboxamide | C17H16Cl2N6O3S | 455.3 | 455, 457 | 2 | Int. 3 | 4-Methyl-1,2,5-oxadiazole-3-carboxylic acid |
| 42 | 4-Methyl-2-pyrazin-2-yl-thiazole-5-carboxylic acid {2-[3-(3,4-dichlorobenzyl)ureido]-thiazol-4-ylmethyl}-methyl-amide | C22H19Cl2N7O2S2 | 548.5 | 548, 550 | 3 | Int. 3 | 2-(Pyrazin-2-yl)-4-methylthiazole-5-carboxylic acid chloride |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 43 | N-((2-(3-(3,4-dichlorobenzyl)ureido)thiazol-4-yl)methyl)-2,4-dimethoxy-N-methylbenzamide | C22H22Cl2N4O4S | 509.4 | 509, 511 | 3 | Int. 3 | 2,4-Dimethoxybenzoyl chloride |
| 44 | N-((2-(3-(3,4-dichlorobenzyl)ureido)thiazol-4-yl)methyl)-4-methoxy-N-methylbenzamide | C21H20Cl2N4O3S | 497.4 | 479, 481 | 3 | Int. 3 | 4-Methoxybenzoyl chloride |
| 45 | N-((2-(3-(3,4-dichlorobenzyl)ureido)thiazol-4-yl)methyl)-3,4-dimethoxy-N-methylbenzamide | C22H22Cl2N4O4S | 509.4 | 509, 511 | 3 | Int. 3 | 3,4-Dimethoxybenzoyl chloride |
| 46 | N-((2-(3-(3,4-dichlorobenzyl)ureido)thiazol-4-yl)methyl)-N-methylbenzo[1,3]dioxole-5-carboxamide | C21H18Cl2N4O4S | 493.4 | 493, 495 | 3 | Int. 3 | 3,4-Methylenedioxybenzoyl chloride |
| 47 | N-((2-(3-(3,4-dichlorobenzyl)ureido)thiazol-4-yl)methyl)-3,4,5-trimethoxy-N-methylbenzamide | C23H24Cl2N4O5S | 539.4 | 539, 541 | 3 | Int. 3 | 3,4,5-Trimethoxybenzoyl chloride |
| 48 | N-((2-(3-(3,4-dichlorobenzyl)ureido)thiazol-4-yl)methyl)-N,5-dimethyl-3-(trifluoromethyl)isoxazole-4-carboxamide | C19H16Cl2F3N5O3S | 522.3 | 522, 524 | 2 | Int. 3 | 5-Methyl-3-trifluoromethyl-isoxazole-4-carboxylic acid |
| 49 | N-((2-(3-(3,4-dichlorobenzyl)ureido)thiazol-4-yl)methyl)-N-methyl-2-(pyridin-3-yl)acetamide | C20H19Cl2N5O2S | 464.4 | 464, 466 | 2 | Int. 3 | 2-(Pyridin-3-yl)acetic acid |
| 50 | N-(1-(2-(3-(3,4-dichlorobenzyl)ureido)thiazol-4-yl)-2-(methylamino)-2-oxoethyl)-N,3,5-trimethylisoxazole-4-carboxamide | C21H22Cl2N6O4S | 525.4 | 525, 527 | 3 | Int. 13 | 3,5-Dimethyl-isoxazole-4-carboxylic acid chloride |
| 51 | N-((2-(3-(3,4-dichlorobenzyl)ureido)thiazol-4-yl)methyl)-N,2,4-trimethylnicotinamide | C21H21Cl2N5O2S | 478.4 | 478, 480 | 2 | Int. 3 | 2,4-Dimethylnicotinic acid |
| 52 | N-((2-(3-(3,4-dichlorobenzyl)ureido)thiazol-4-yl)methyl)-N,2,4,6-tetramethylbenzamide | C23H24Cl2N4O2S | 491.4 | 491, 493 | 3 | Int. 3 | 2,4,6-Trimethylbenzoyl chloride |
| 53 | N-((2-(3-(3,4-dichlorobenzyl)ureido)thiazol-4-yl)methyl)-N-(2-hydroxyethyl)-3,5-dimethylisoxazole-4-carboxamide | C20H21Cl2N5O4S | 498.4 | 498, 500 | 3 | Int. 14 | 3,5-Dimethyl-isoxazole-4-carboxylic acid chloride |
| 54 | N-((2-(3-(3-fluorobenzyl)ureido)thiazol-4-yl)methyl)-N,3,5-trimethylisoxazole-4-carboxamide | C19H20FN5O3S | 417.5 | 418 | 3 | Int. 5 | 3,5-Dimethyl-isoxazole-4-carboxylic acid chloride |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 55 | N-((2-(3-(3-fluorobenzyl)ureido)thiazol-4-yl)methyl)-5-(methoxymethyl)-N,3-dimethylisoxazole-4-carboxamide | C20H22FN5O4S | 447.5 | 448 | 2 | Int. 5 | Int. 31 |
| 56 | N-((2-(3-(3,4-dichlorobenzyl)ureido)thiazol-4-yl)methyl)-5-(methoxymethyl)-N,3-dimethylisoxazole-4-carboxamide | C20H21Cl2N5O4S | 498.4 | 498, 500 | 2 | Int. 3 | Int. 31 |
| 57 | N-((2-(3-(3-fluorobenzyl)ureido)thiazol-4-yl)methyl)-2-methoxy-N-methylacetamide | C16H19FN4O3S | 366.4 | 367 | 3 | Int. 5 | 2-Methoxyacetyl chloride |
| 58 | methyl 2-(((2-(3-(3-fluorobenzyl)ureido)thiazol-4-yl)methyl)(methyl)amino)-2-oxoacetate | C16H17FN4O4S | 380.4 | 381 | 3 | Int. 5 | Methyl chlorooxoacetate |
| 59 | N-((2-(3-(3-fluorobenzyl)ureido)thiazol-4-yl)methyl)-N,3-dimethylisoxazole-4-carboxamide | C18H18FN5O3S | 403.4 | 404 | 2 | Int. 5 | 3-Methylisoxazole-4-carboxylic acid |
| 60 | 3-ethyl-N-((2-(3-(3-fluorobenzyl)ureido)thiazol-4-yl)methyl)-N,5-dimethylisoxazole-4-carboxamide | C20H22FN5O3S | 431.5 | 432 | 2 | Int. 5 | 3-Ethyl-5-methylisoxazole-4-carboxylic acid |
| 61 | N-((2-(3-(3-fluorobenzyl)ureido)thiazol-4-yl)methyl)-N,2,4-trimethylnicotinamide | C21H22FN5O2S | 427.5 | 428 | 2 | Int. 5 | 2,4-Dimethylnicotinic acid |
| 62 | N-((2-(3-(3-fluorobenzyl)ureido)thiazol-4-yl)methyl)-N-methylpyrazine-2-carboxamide | C18H17FN6O2S | 400.4 | 401 | 2 | Int. 5 | Pyrazine-2-carboxylic acid |
| 63 | N-((2-(3-(3,4-dichlorobenzyl)ureido)thiazol-4-yl)methyl)-N-methylpyrimidine-5-carboxamide | C18H16Cl2N6O2S | 451.3 | 451, 453 | 2 | Int. 3 | Pyrimidine-5-carboxylic acid |
| 64 | N-((2-(3-(3-fluorobenzyl)ureido)thiazol-4-yl)methyl)-N-methylpyrimidine-5-carboxamide | C18H17FN6O2S | 400.4 | 401 | 2 | Int. 5 | Pyrimidine-5-carboxylic acid |
| 65 | N-((2-(3-(3,4-dichlorobenzyl)ureido)thiazol-4-yl)methyl)-N-methylpyrazine-2-carboxamide | C18H16Cl2N6O2S | 451.3 | 451, 453 | 2 | Int. 3 | Pyrazine-2-carboxylic acid |
| 66 | N-((2-(3-(3-fluorobenzyl)ureido)thiazol-4-yl)methyl)-N-methylacetamide | C15H17FN4O2S | 336.4 | 337 | 3 | Int. 5 | Acetyl chloride |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 67 | N-((2-(3-(3-fluorobenzyl)ureido)thiazol-4-yl)methyl)-N,5-dimethylpyrazine-2-carboxamide | C19H19FN6O2S | 414.5 | 415 | 2 | Int. 5 | 5-Methylpyrazine-2-carboxylic acid |
| 68 | N-((2-(3-(3-fluorobenzyl)ureido)thiazol-4-yl)methyl)-N-methylfuran-3-carboxamide | C18H17FN4O3S | 388.4 | 389 | 3 | Int. 5 | 3-Furoyl chloride |
| 69 | N-((2-(3-(3-fluorobenzyl)ureido)thiazol-4-yl)methyl)-N,4-dimethyloxazole-5-carboxamide | C18H18FN5O3S | 403.4 | 404 | 3 | Int. 5 | 4-Methyloxazole-5-carboxylic acid chloride |
| 70 | N-((2-(3-(3-fluorobenzyl)ureido)thiazol-4-yl)methyl)-N,5-dimethylisoxazole-3-carboxamide | C18H18FN5O3S | 403.4 | 404 | 3 | Int. 5 | 5-Methylisoxazole-3-carboxylic acid chloride |
| 71 | N-((2-(3-(3-fluorobenzyl)ureido)thiazol-4-yl)methyl)-N-methyl-2-tosylacetamide | C22H23FN4O4S2 | 490.6 | 491 | 2 | Int. 5 | 2-(4-Methylphenylsulfonyl)acetic acid |
| 72 | Ethyl 4-((2-(3-(3-fluorobenzyl)ureido)thiazol-4-yl)methyl)(methyl)carbamoyl)-5-methylisoxazole-3-carboxylate | C21H22FN5O5S | 475.5 | 476 | 2 | Int. 5 | Int. 35 |
| 73 | 4-(((2-(3-(3-fluorobenzyl)ureido)thiazol-4-yl)methyl)(methyl)carbamoyl)-5-methylisoxazole-3-carboxylic acid | C19H18FN5O5S | 447.4 | 448 | 9 | Ethyl 4-(((2-(3-(3-fluorobenzyl)ureido)thiazol-4-yl)methyl)(methyl)carbamoyl)-5-methylisoxazole-3-carboxylate (EX# 72) | None |
| 74 | N-((2-(3-(3-fluorobenzyl)ureido)thiazol-4-yl)methyl)-N,2-dimethylnicotinamide | C20H20FN5O2S | 413.5 | 414 | 2 | Int. 5 | 2-Methylnicotinic acid |
| 75 | N-((2-(3-(3-fluorobenzyl)ureido)thiazol-4-yl)methyl)-N,5-dimethylisoxazole-4-carboxamide | C18H18FN5O3S | 403.4 | 404 | 2 | Int. 5 | 5-Methylisoxazole-4-carboxylic acid |
| 76 | N-((2-(3-(3-fluorobenzyl)ureido)thiazol-4-yl)methyl)-N,4-dimethylnicotinamide | C20H20FN5O2S | 413.5 | 414 | 2 | Int. 5 | 4-Methylnicotinic acid |
| 77 | 3-chloro-N-(2-(3-(3-fluorobenzyl)ureido)thiazol-4-yl)methyl)-N-methyl-4-(methylsulfonyl)thiophene-2-carboxamide | C19H18ClFN4O4S3 | 517.0 | 517, 519 | 3 | Int. 5 | 3-Methyl-4-(methylsulfonyl)thiophene-2-carboxylic acid chloride |
| 78 | N-((2-(3-(3-fluorobenzyl)ureido)thiazol-4-yl)methyl)-N,4-dimethylthiazole-5-carboxamide | C18H18FN5O2S2 | 419.5 | 421 | 3 | Int. 5 | 4-Methylthiazole-5-carboxylic acid chloride |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 79 | N-((2-(3-(3-fluorobenzyl)ureido)thiazol-4-yl)methyl)-N-methyl-5-oxo-3,5-dihydro-2H-thiazolo[3,2-a]pyrimidine-6-carboxamide | C20H19FN6O3S2 | 474.5 | 475 | 2 | Int. 5 | 5-Oxo-3,5-dihydro-5H-thiazolo[3,2-a]pyrimidine-6-carboxylic acid |
| 80 | N-((2-(3-(3-fluorobenzyl)ureido)thiazol-4-yl)methyl)-N,4-dimethyl-2-(methylthio)pyrimidine-5-carboxamide | C20H21FN6O2S2 | 460.6 | 461 | 2 | Int. 5 | 4-methyl-2-methylthio-pyrimidine-5-carboxylic acid |
| 81 | N-(2-(3-(3-fluorobenzyl)ureido)thiazol-4-yl)methyl)-N,3-dimethylbut-2-enamide | C18H21FN4O2S | 376.5 | 377 | 3 | Int. 5 | 3-Methyl-but-2-enoyl chloride |
| 82 | N-((2-(3-(3-fluorobenzyl)ureido)thiazol-4-yl)methyl)-N,2-dimethylbenzamide | C21H21FN4O2S | 412.5 | 413 | 3 | Int. 5 | 2-Methylbenzoyl chloride |
| 83 | N-((2-(3-(3-fluorobenzyl)ureido)thiazol-4-yl)methyl)-N-methylquinoxaline-2-carboxamide | C22H19FN6O2S | 450.5 | 451 | 2 | Int. 5 | Quinoxaline-2-carboxylic acid |
| 84 | N-((2-(3-(3-fluorobenzyl)ureido)thiazol-4-yl)methyl)-N,3-dimethylpicolinamide | C20H20FN5O2S | 413.5 | 414 | 2 | Int. 5 | 3-Methylpicolinic acid |
| 85 | N-((2-(3-(3-fluorobenzyl)ureido)thiazol-4-yl)methyl)-5-((4-methoxybenzyloxy)methyl)-N,3-dimethylisoxazole-4-carboxamide | C27H28FN5O5S | 553.6 | 554 | 2 | Int. 5 | 5-((4-methoxybenzyloxy)methyl)-3-methylisoxazole-4-carboxylic acid |
| 86 | N-(2-Aminoethyl)-N-((2-(3-(3-fluorobenzyl)ureido)thiazol-4-yl)methyl)-3,5-dimethylisoxazole-4-carboxamide | C20H23FN6O3S | 446.5 | 447 | 3; 1 | Int. 15 | 3,5-Dimethyl-isoxazole-4-carboxylic acid chloride |
| 87 | 4-amino-N-((2-(3-(3-fluorobenzyl)ureido)thiazol-4-yl)methyl)-N-methylpyrimidine-5-carboxamide | C18H18FN7O2S | 415.5 | 416 | 2 | Int. 5 | 4-Aminopyrimidine-5-carboxylic acid |
| 88 | 2-amino-N-((2-(3-(3-fluorobenzyl)ureido)thiazol-4-yl)methyl)-N,4-dimethylpyrimidine-5-carboxamide | C19H20FN7O2S | 429.5 | 430 | 2 | Int. 5 | 2-Amino-4-methyl-pyrimidine-5-carboxylic acid |
| 89 | N-((2-(3-(3-fluorobenzyl)ureido)thiazol-4-yl)methyl)-3,5-dimethyl-N-(2-(methylsulfonamido)ethyl)isoxazole-4-carboxamide | C21H25FN6O5S2 | 524.6 | 526 | 5 | N-(2-Aminoethyl)-N-((2-(3-(3-fluorobenzyl)ureido)thiazol-4-yl)methyl)3,5-dimethylisoxazole-4-carboxamide (EX# 86) | Methanesulfonyl chloride |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 90 | N-((2-(3-fluorobenzyl)ureido)thiazol-4-yl)methyl)-N,4,6-trimethyl-2-oxo-1,2-dihydropyridine-3-carboxamide | C21H22FN5O3S | 443.5 | 444 | 2 | Int. 5 | 4,6-Dimethyl-2-oxo-1,2-dihydropyridine-3-carboxylic acid |
| 91 | N-((2-(3-(3-fluorobenzyl)ureido)thiazol-4-yl)methyl)-N,2,4,6-tetramethylpyrimidine-5-carboxamide | C21H23FN6O2S | 442.5 | 443 | 2 | Int. 5 | 2,4,6-Trimethylpyrimidine-5-carboxylic acid |
| 92 | N-((2-(3-(3-fluorobenzyl)ureido)thiazol-4-yl)methyl)-N,3-dimethylpyrazine-2-carboxamide | C19H19FN6O2S | 414.5 | 415 | 2 | Int. 5 | 3-Methylpyrazine-2-carboxylic acid (Int. 34) |
| 93 | tert-butyl 2-(((2-(3-(3-fluorobenzyl)ureido)thiazol-4-yl)methyl)(methyl)carbamoyl)-1-methyl-1H-imidazole-4-ylcarbamate | C23H28FN7O4S | 517.6 | Andras | 2 | Int. 5 | 4-tert-Butoxycarbonylamino-1-methyl-1H-imidazole-2-carboxylic acid |
| 94 | 4-amino-N-((2-(3-(3-fluorobenzyl)ureido)thiazol-4-yl)methyl)-N,1-dimethyl-1H-imidazole-2-carboxamide | C18H20FN7O2S | 417.5 | 418 | 1 | tert-butyl 2-(((2-(3-(3-fluorobenzyl)ureido)thiazol-4-yl)methyl)carbamoyl)-1-methyl-1H-imidazol-4-ylcarbamate (EX# 93) | None |
| 95 | 4-acetamido-N-((2-(3-(3-fluorobenzyl)ureido)thiazol-4-yl)methyl)-N,1-dimethyl-1H-imidazole-2-carboxamide | C20H22FN7O3S | 459.5 | 460 | 3 | 4-amino-N-((2-(3-(3-fluorobenzyl)ureido)thiazol-4-yl)methyl)-N,1-dimethyl-1H-imidazole-2-carboxamide (EX# 94) | Acetyl chloride |
| 96 | N-((2-(3-(3-fluorobenzyl)ureido)thiazol-4-yl)methyl)-N,4,6-trimethylpyrimidine-5-carboxamide | C20H21FN6O2S | 428.5 | 429 | 2 | Int. 5 | 4,6-Dimethylpyrimidine-5-carboxylic acid |
| 97 | N-(2-(3-(3-fluorobenzyl)ureido)thiazol-4-yl)methyl)-3-(hydroxymethyl)-N,5-dimethylisoxazole-4-carboxamide | C19H20FN5O4S | 433.5 | 434 | 12 | Ethyl 4-(((2-(3-(3-fluorobenzyl)ureido)thiazol-4-yl)methyl)(methyl)carbamoyl)-5-methylisoxazole-3-carboxylate (EX# 72) | Lithium borohydride |
| 98 | N-((2-(3-(4-fluorobenzyl)ureido)thiazol-4-yl)methyl)-N,3,5-trimethylisoxazole-4-carboxamide | C19H20FN5O3S | 417.5 | 418 | 8 | Int. 18 | 3-Fluorobenzylamine |
| 99 | N-((2-(3-(3,5-difluorobenzyl)ureido)thiazol-4-yl)methyl)-N,3,5-trimethylisoxazole-4-carboxamide | C19H19F2N5O3S | 435.5 | 436 | 8 | Int. 18 | 3,5-Difluorobenzylamine |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 100 | N-((2-(3-(3-fluorobenzyl)ureido)thiazol-4-yl)methyl)-N,3-dimethylisonicotinamide | C20H20FN5O2S | 413.5 | 414 | 2 | Int. 5 | 3-Methyl-isonicotinic acid |
| 101 | N-((2-(3-(3-chlorobenzyl)ureido)thiazol-4-yl)methyl)-N,3,5-trimethylisoxazole-4-carboxamide | C19H20ClN5O3S | 433.9 | 434 | 8 | Int. 18 | 3-Chlorobenzylamine |
| 102 | N-((2-(3-(benzo[1,3]dioxol-5-yl)methyl)ureido)thiazol-4-yl)methyl)-N,3,5-trimethylisoxazole-4-carboxamide | C20H21N5O5S | 443.5 | 444 | 8 | Int. 18 | Piperonylamine |
| 103 | 2-amino-N-((2-(3-(3-fluorobenzyl)ureido)thiazol-4-yl)methyl)-N,4,6-trimethylpyrimidine-5-carboxamide | C20H22FN7O2S | 443.5 | 444 | 2 | Int. 5 | 2-Amino-4,6-dimethylpyrimidine-5-carboxylic acid |
| 104 | N-((2-(3-((2,2-difluorobenzo[1,3]dioxol-5-yl)methyl)ureido)thiazol-4-yl)methyl)-N,3,5-trimethylisoxazole-4-carboxamide | C20H19F2N5O5S | 479.5 | 480 | 8; 10 | Int. 18 | 2,4-Dimethoxybenzyl(C-2,2-difluoro-benzo[1,3]dioxol-5-yl)methyl)amine (per Method 13) |
| 105 | N-((2-(3-(3-fluorobenzyl)ureido)thiazol-4-yl)methyl)-N,2-dimethylimidazo[1,2-a]pyridine-3-carboxamide | C22H21FN6O2S | 452.5 | 453 | 2 | Int. 5 | 2-Methylimidazo[1,2-a]pyridine-3-carboxylic acid |
| 106 | N-3,5-trimethyl-N-(2-(3-(N-methylacetamido)benzyl)ureido)thiazol-4-yl)methyl)isoxazole-4-carboxamide | C22H26N6O4S | 470.6 | 471 | 8 | Int. 18 | 3-(N-Acetyl-methylamino)benzylamine |
| 107 | N-((2-(3-((5-chlorothiophen-2-yl)methyl)ureido)thiazol-4-yl)methyl)-N,3,5-trimethylisoxazole-4-carboxamide | C17H18ClN5O3S2 | 439.9 | 440, 442 | 8; 10 | Int. 18 | (5-Chlorothiophen-2-yl-methyl)(2,4-dimethoxybenzyl)amine (per Method 13) |
| 108 | N-((2-(3-(3-fluorobenzyl)ureido)thiazol-4-yl)methyl)-N-methyltetrahydrofuran-2-carboxamide | C18H21FN4O3S | 392.5 | 393 | 2 | Int. 5 | Tetrahydro-2-furoic acid |
| 109 | 1-(4-((2,4-dioxothiazolidin-3-yl)methyl)thiazol-2-yl)-3-(3-fluorobenzyl)urea | C15H13FN4O3S2 | 380.4 | 381 | 14 | Int. 7 | Thiazolidine-2,4-dione |
| 110 | N-((2-(3-(3-fluorobenzyl)ureido)thiazol-4-yl)methyl)-2-methoxy-N-methylnicotinamide | C20H20FN5O3S | 429.5 | 430 | 2 | Int. 5 | 2-Methoxynicotinic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 111 | N-((2-(3-(3-fluorobenzyl)ureido)thiazol-4-yl)methyl)-N-methyltetrahydrofuran-3-carboxamide | C18H21FN4O3S | 392.5 | 393 | 2 | Int. 5 | Tetrahydro-3-furoic acid |
| 112 | N,3,5-trimethyl-N-(2-(3-(thiophen-3-ylmethyl)ureido)thiazol-4-yl)methyl)isoxazole-4-carboxamide | C17H19N5O3S2 | 405.5 | 406 | 8 | Int. 18 | Thiophen-3-yl-methylamine |
| 113 | methyl (2-(3-(3-fluorobenzyl)ureido)thiazol-4-yl)methyl(2-hydroxyethyl)carbamate | C16H19FN4O4S | 382.4 | 383 | 3 | Int. 19 | Methyl chloroformate |
| 114 | N-((2-(3-(3-fluorobenzyl)ureido)thiazol-4-yl)methyl)-N-(2-hydroxyethyl)-3-methylisonicotinamide | C21H22FN5O3S | 443.5 | 444 | 2 | Int. 19 | 3-Methyl-isonicotinic acid |
| 115 | 1-(3-fluorobenzyl)-3-(4-((2-oxooxazolidin-3-yl)methyl)thiazol-2-yl)urea | C15H15FN4O3S | 350.4 | 351 | 15 | Int. 21 | Oxazolidin-2-one |
| 116 | 2-chloro-N-((2-(3-(3-fluorobenzyl)ureido)thiazol-4-yl)methyl)-N-methylnicotinamide | C19H17ClFN5O2S | 433.9 | 434 | 2 | Int. 5 | 2-Chloronicotinic acid |
| 117 | N-((2-(3-(3-fluorobenzyl)ureido)thiazol-4-yl)methyl)-N,1,3,5-tetramethyl-1H-pyrazole-4-carboxamide | C20H23FN6O2S | 430.5 | 431 | 2 | Int. 5 | 1,3,5-Trimethyl-1H-pyrazole-4-carboxylic acid |
| 118 | (S)-N-((2-(3-(3-fluorobenzyl)ureido)thiazol-4-yl)methyl)-N-methyltetrahydrofuran-2-carboxamide | C18H21FN4O3S | 392.5 | 393 | 2 | Int. 5 | (S)-Tetrahydro-2-furoic acid |
| 119 | (R)-N-((2-(3-(3-fluorobenzyl)ureido)thiazol-4-yl)methyl)-N-methyltetrahydrofuran-2-carboxamide | C18H21FN4O3S | 392.5 | 393 | 2 | Int. 5 | (R)-Tetrahydro-2-furoic acid |
| 120 | N-((2-(3-(3-fluorobenzyl)ureido)thiazol-4-yl)methyl)-N-methyl-3-propoxypicolinamide | C22H24FN5O3S | 457.5 | 458 | 2 | Int. 5 | 3-n-Propoxylpicolinic acid |
| 121 | tert-butyl 2-(((2-(3-(3-fluorobenzyl)ureido)thiazol-4-yl)methyl)(methyl)carbamoyl)morpholine-4-carboxylate | C23H30FN5O5S | 507.6 | 508 | 2 | Int. 5 | N-(tert-Butoxycarbonyl)morpholine-2-carboxylic acid |
| 122 | N-((2-(3-(3-fluorobenzyl)ureido)thiazol-4-yl)methyl)-N-methylmorpholine-2-carboxamide | C18H22FN5O3S | 407.5 | 408 | 1 | tert-butyl 2-(((2-(3-(3-fluorobenzyl)ureido)thiazol-4-yl)methyl)(methyl)carbamoyl)morpholine-4-carboxylate (EX# 121) | none |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 123 | N-((2-(3-(3,5-difluorobenzyl)ureido)thiazol-4-yl)methyl)-N,3-dimethylpyrazine-2-carboxamide | C19H18F2N6O2S | 432.5 | 433 | 2 | Int. 20 | 3-Methyl-pyrazine-2-carboxylic acid (Int. 34) |
| 124 | N-((2-(3-(3,5-difluorobenzyl)ureido)thiazol-4-yl)methyl)-N,3-dimethylisonicotinamide | C20H19F2N5O2S | 431.5 | 432 | 2 | Int. 20 | 3-Methyl-isonicotinic acid |
| 125 | N-((2-(3-(3-fluorobenzyl)ureido)thiazol-4-yl)methyl)-N-methylpyridazine-4-carboxamide | C18H17FN6O2S | 400.4 | 401 | 2 | Int. 5 | Pyridazine-4-carboxylic acid |
| 126 | N-((2-(3-(3-fluorobenzyl)ureido)thiazol-4-yl)methyl)-N,3,5-trimethyl-1H-pyrazole-4-carboxamide | C19H21FN6O2S | 416.5 | 417 | 2 | Int. 5 | 3,5-Dimethyl-1H-pyrazole-4-carboxylic acid |
| 127 | N-((2-(3-(3-fluorobenzyl)ureido)thiazol-4-yl)methyl)-N-methylpyridazine-3-carboxamide | C18H17FN6O2S | 400.4 | 401 | 2 | Int. 5 | Pyridazine-3-carboxylic acid |
| 128 | N-((2-(3-(3-fluorobenzyl)ureido)thiazol-4-yl)methyl)-N-methyltetrahydro-2H-pyran-4-carboxamide | C19H23FN4O3S | 406.5 | 407 | 2 | Int. 5 | Tetrahydro-2H-pyran-4-carboxylic acid |
| 129 | N-((2-(3-(3-fluorobenzyl)ureido)thiazol-4-yl)methyl)-N,1,5-trimethyl-1H-pyrazole-4-carboxamide | C19H21FN6O2S | 416.5 | 417 | 2 | Int. 5 | 1,5-Dimethylpyrazole-4-carboxylic acid |
| 130 | N-((2-(3-((5-chlorofuran-2-yl)methyl)ureido)thiazol-4-yl)methyl)-N,3,5-trimethylisoxazole-4-carboxamide | C17H18ClN5O4S | 423.9 | 425 | 8; 10 | Int. 18 | (5-Chlorothiophen-2-yl-methyl)(2,4-dimethoxybenzyl)amine (per Method 13) |
| 131 | N-(2-(3-(3-fluorobenzyl)ureido)thiazol-4-yl)methyl)-N-methylmorpholine-3-carboxamide | C18H22FN5O3S | 407.5 | 408 | 4 | Int. 5 | N-(tert-Butoxycarbonyl)morpholine-3-carboxylic acid |
| 132 | N-(2-(3-(3-fluorobenzyl)ureido)thiazol-4-yl)methyl)-N,4-dimethylpyrrolidine-3-carboxamide | C19H24FN5O2S | 405.5 | 406 | 4 | Int. 5 | N-(tert-Butoxycarbonyl)-4-methylpyrrolidine-3-carboxylic acid |
| 133 | (S)-N-(2-(3-(3-fluorobenzyl)ureido)thiazol-4-yl)methyl)-N-methylpyrrolidine-2-carboxamide | C18H22FN5O2S | 391.5 | 392 | 4 | Int. 5 | (S)-N-(tert-Butoxycarbonyl)pyrrolidine-2-carboxylic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 134 | 2-Methyl-5,6-dihydro-4H-pyran-3-carboxylic acid {2-[3-(3-fluoro-benzyl)-ureido]-thiazol-4-ylmethyl}-methyl-amide | $C_{20}H_{23}FN_4O_3S$ | 418.5 | 419 | 2 | Int.5 | 2-Methyl-5,6-dihydro-4H-pyran-3-carboxylic acid |
| 135 | 2-Methyl-5-morpholin-4-ylmethyl-furan-3-carboxylic acid {2-[3-(3-fluoro-benzyl)-ureido]-thiazol-4-ylmethyl}-methyl-amide | $C_{24}H_{28}FN_5O_4S$ | 501.6 | 502 | 2 | Int.5 | 2-Methyl-5-(morpholin-4-ylmethyl)furan-3-carboxylic acid |
| 136 | 2-Methyl-but-2-enoic acid {2-[3-(3-fluoro-benzyl)-ureido]-thiazol-4-ylmethyl}-methyl-amide | $C_{18}H_{21}FN_4O_2S$ | 376.4 | 377 | 2 | Int.5 | 2-Methyl-but-2-enoic acid |
| 137 | 1,2,3-Thiadiazole-4-carboxylic acid {2-[3-(3-fluoro-benzyl)-ureido]-thiazol-4-ylmethyl}-methyl-amide | $C_{16}H_{15}FN_6O_2S_2$ | 406.5 | 407 | 2 | Int.5 | 1,2,3-Thiadiazole-4-carboxylic acid |
| 138 | 3,5-Dimethyl-isoxazole-4-carboxylic acid {2-[3-(5-fluoro-thiophen-2-ylmethyl)-ureido]-thiazol-4-ylmethyl}-methyl-amide | $C_{17}H_{18}FN_5O_3S_2$ | 423.5 | 424 | 8 | Int.18 | C-(5-Fluoro-thiophen-2-yl)methylamine (Int. 36) |
| 139 | 2-Pyridin-3-yl-thiazole-4-carboxylic acid {2-[3-(3-fluoro-benzyl)-ureido]-thiazol-4-ylmethyl}-methyl-amide | $C_{22}H_{19}FN_6O_2S_2$ | 482.6 | 483 | 2 | Int.5 | 2-Pyridin-3-yl-thiazole-4-carboxylic acid |
| 140 | 2,5-Dimethyl-2H-pyrazole-3-carboxylic acid {2-[3-(3-fluoro-benzyl)-ureido]-thiazol-4-ylmethyl}-methyl-amide | $C_{19}H_{21}FN_6O_2S$ | 416.5 | 417 | 2 | Int.5 | 2,5-Dimethyl-2H-pyrazole-3-carboxylic acid |
| 141 | 4-Methyl-furazan-3-carboxylic acid {2-[3-(3-fluoro-benzyl)-ureido]-thiazol-4-ylmethyl}-methyl-amide | $C_{17}H_{17}FN_6O_3S$ | 404.4 | 405 | 2 | Int.5 | 4-Methyl-furazan-3-carboxylic acid |
| 142 | 2-Morpholin-4-ylmethyl-furan-3-carboxylic acid {2-[3-(3-fluoro-benzyl)-ureido]-thiazol-4-ylmethyl}-methyl-amide | $C_{23}H_{26}FN_5O_4S$ | 487.5 | 488 | 2 | Int.5 | 2-Morpholin-4-ylmethyl-3-furoic acid |
| 143 | 1-Methyl-pyrrolidine-2-carboxylic acid {2-[3-(3-fluoro-benzyl)-ureido]-thiazol-4-ylmethyl}-methyl-amide | $C_{19}H_{24}FN_5O_2S$ | 405.5 | 406 | 2 | Int.5 | 1-Methyl-pyrrolidine-2-carboxylic acid |
| 144 | 1-Methyl-1H-pyrrole-2-carboxylic acid {2-[3-(3-fluoro-benzyl)-ureido]-thiazol-4-ylmethyl}-methyl-amide | $C_{19}H_{20}FN_5O_2S$ | 401.5 | 402 | 2 | Int.5 | 1-Methyl-1H-pyrrole-2-carboxylic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 145 | 1,5-Dimethyl-1H-[1,2,3]triazole-4-carboxylic acid {2-[3-(3-fluoro-benzyl)-ureido]-thiazol-4-ylmethyl}-methyl-amide | $C_{18}H_{20}FN_7O_2S$ | 417.5 | 418 | 2 | Int.5 | 1,5-Dimethyl-1H-[1,2,3]triazole-4-carboxylic acid |
| 146 | 5-Fluoro-thiophene-2-carboxylic acid {2-[3-(3-fluoro-benzyl)-ureido]-thiazol-4-ylmethyl}-methyl-amide | $C_{18}H_{16}F_2N_4O_2S_2$ | 422.5 | 423 | 2 | Int.5 | 5-Fluoro-thiophene-2-carboxylic acid |
| 147 | 4-Methyl-pyrimidine-5-carboxylic acid {2-[3-(3-fluoro-benzyl)-ureido]-thiazol-4-ylmethyl}-methyl-amide | $C_{19}H_{19}FN_6O_2S$ | 414.5 | 415 | 2 | Int.5 | 4-Methyl-pyrimidine-5-carboxylic acid |
| 148 | 4-Methyl-2-phenyl-pyrimidine-5-carboxylic acid {2-[3-(3-fluoro-benzyl)-ureido]-thiazol-4-ylmethyl}-methyl-amide | $C_{25}H_{23}FN_6O_2S$ | 490.6 | 491 | 2 | Int.5 | 4-Methyl-2-phenyl-pyrimidine-5-carboxylic acid |
| 149 | N-{2-[3-(3-Fluoro-benzyl)-ureido]-thiazol-4-ylmethyl}-N-methyl-2-methylsulfanyl-nicotinamide | $C_{20}H_{20}FN_5O_2S_2$ | 445.5 | 446 | 3 | Int.5 | 2-Methylthio-nicotinic acid |
| 150 | 2-Cyano-N-{2-[3-(3-fluoro-benzyl)-ureido]-thiazol-4-ylmethyl}-N-methyl-acetamide | $C_{16}H_{16}FN_5O_2S$ | 361.4 | 362 | 2 | Int.5 | 2-Cyanoacetic acid |
| 151 | 3,5-Dimethyl-isoxazole-4-carboxylic acid {5-bromo-2-[3-(3-fluoro-benzyl)-ureido]-thiazol-4-ylmethyl}-methyl-amide | $C_{19}H_{19}BrFN_5O_3S$ | 496.4 | 498 | 17 | N-((2-(3-(3-Fluorobenzyl)ureido)thiazol-4-yl)methyl)-N,3,5-trimethylisoxazole-4-carboxamide (EX# 54) | Bromine |
| 152 | N-{2-[3-(3-Fluoro-benzyl)-ureido]-thiazol-4-ylmethyl}-N-methyl-6-morpholin-4-yl-nicotinamide | $C_{23}H_{25}FN_6O_3S$ | 484.5 | 485 | 3 | Int.5 | 6-Morpholin-4-yl-nicotinic acid chloride |
| 153 | 4-Methyl-thiazole-5-carboxylic acid {2-[3-(3-fluoro-benzyl)-ureido]-thiazol-4-ylmethyl}-methyl-amide | $C_{18}H_{18}FN_5O_2S_2$ | 419.5 | 420 | 2 | Int.5 | 4-Methylthiazole-5-carboxylic acid |
| 154 | 3-Methyl-1H-pyrazole-4-carboxylic acid {2-[3-(3-fluoro-benzyl)-ureido]-thiazol-4-ylmethyl}-methyl-amide | $C_{18}H_{19}FN_6O_2S$ | 402.4 | 403 | 2 | Int.5 | 3-Methyl-1H-pyrazole-4-carboxylic acid |
| 155 | 2,4-Dimethyl-pyrimidine-5-carboxylic acid {2-[3-(3-fluoro-benzyl)-ureido]-thiazol-4-ylmethyl}-methyl-amide | $C_{20}H_{21}FN_6O_2S$ | 428.5 | 429 | 2 | Int.5 | 2,4-Dimethyl-pyrimidine-5-carboxylic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 156 | 2-Methyl-[1,6]naphthyridine-3-carboxylic acid {2-[3-(3-fluoro-benzyl)-ureido]-thiazol-4-ylmethyl}-methyl-amide | $C_{23}H_{21}FN_6O_2S$ | 464.5 | 465 | 2 | Int. 5 | 2-Methyl[1,6]naphthyridine-3-carboxylic acid |
| 157 | 6-(4-Methoxy-phenyl)-pyridazine-3-carboxylic acid {2-[3-(3-fluoro-benzyl)-ureido]-thiazol-4-ylmethyl}-methyl-amide | $C_{25}H_{23}FN_6O_3S$ | 506.6 | 507 | 2 | Int. 5 | 6-(4-Methoxyphenyl)pyridazine-3-carboxylic acid |
| 158 | 3-Methyl-pyrazine-2-carboxylic acid {5-bromo-2-[3-(3-fluoro-benzyl)-ureido]-thiazol-4-ylmethyl}-methyl-amide | $C_{19}H_{18}BrFN_6O_2S$ | 493.4 | 495 | 17 | N-((2-(3-(3-fluorobenzyl)ureido)thiazol-4-yl)methyl)-N,3-dimethylpyrazine-2-carboxamide (EX# 92) | Bromine |
| 159 | 3-Methyl-pyrazine-2-carboxylic acid {5-chloro-2-[3-(3-fluoro-benzyl)-ureido]-thiazol-4-ylmethyl}-methyl-amide | $C_{19}H_{18}ClFN_6O_2S$ | 448.9 | 449 | 18 | N-((2-(3-(3-fluorobenzyl)ureido)thiazol-4-yl)methyl)-N,3-dimethylpyrazine-2-carboxamide (EX# 92) | N-Chlorosuccinimide |
| 160 | 2,6-Bis-dimethylamino-pyrimidine-4-carboxylic acid {2-[3-(3-fluoro-benzyl)-ureido]-thiazol-4-ylmethyl}-methyl-amide | $C_{22}H_{27}FN_8O_2S$ | 486.6 | 487 | 2 | Int. 5 | 2,6-Bis-dimethylamino-pyrimidine-4-carboxylic acid |
| 161 | 2,6-Di-morpholin-4-yl-pyrimidine-4-carboxylic acid {2-[3-(3-fluoro-benzyl)-ureido]-thiazol-4-ylmethyl}-methyl-amide | $C_{26}H_{31}FN_8O_4S$ | 570.6 | 571 | 2 | Int. 5 | 2,6-Di-morpholin-4-yl-pyrimidine-4-carboxylic acid |
| 162 | 2-Cyano-N-{2-[3-(3-fluoro-benzyl)-ureido]-thiazol-4-ylmethyl}-N-methyl-3-pyridin-3-yl-acrylamide | $C_{22}H_{19}FN_6O_2S$ | 450.5 | 451 | 2 | Int. 5 | 2-Cyano-3-pyridin-3-yl-acrylic acid |
| 163 | 2-Methyl-[1,8]naphthyridine-3-carboxylic acid {2-[3-(3-fluoro-benzyl)-ureido]-thiazol-4-ylmethyl}-methyl-amide | $C_{23}H_{21}FN_6O_2S$ | 464.5 | 465 | 2 | Int. 5 | 2-Methyl-[1,8]naphthyridine-3-carboxylic acid |
| 164 | 2-Dimethylamino-6-methyl-pyrimidine-4-carboxylic acid {2-[3-(3-fluoro-benzyl)-ureido]-thiazol-4-ylmethyl}-methyl-amide | $C_{21}H_{24}FN_7O_2S$ | 457.5 | 458 | 2 | Int. 5 | 2-Dimethylamino-6-methyl-pyrimidine-4-carboxylic acid |
| 165 | N-{2-[3-(3-Fluoro-benzyl)-ureido]-thiazol-4-ylmethyl]-2-methoxy-N-methyl-2-phenyl-acetamide | $C_{22}H_{23}FN_4O_3S$ | 442.5 | 443 | 2 | Int. 5 | 2-Methoxy-2-phenylacetic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 166 | 3-Methyl-pyrazine-2-carboxylic acid {2-[3-(5-fluoro-thiophen-2-ylmethyl)-ureido]-thiazol-4-ylmethyl}-methyl-amide | $C_{17}H_{17}FN_6O_2S_2$ | 420.5 | 421 | 8 | Int. 22 | C-(5-Fluoro-thiophen-2-yl)methylamine (Int. 36) |
| 167 | 3-Methyl-pyrazine-2-carboxylic acid methyl-[2-(3-thiophen-3-ylmethyl-ureido)-thiazol-4-ylmethyl]-amide | $C_{17}H_{18}N_6O_2S_2$ | 402.5 | 403 | 8 | Int. 22 | C-(thiophen-3-yl)methylamine |
| 168 | 3,5-Dimethyl-isoxazole-4-carboxylic acid {5-cyano-2-[3-(3-fluoro-benzyl)-ureido]-thiazol-4-ylmethyl}-methyl-amide | $C_{20}H_{19}FN_6O_3S$ | 442.5 | 443 | 19 | 3,5-Dimethyl-isoxazole-4-carboxylic acid {5-bromo-2-[3-(3-fluoro-benzyl)-ureido]-thiazol-4-ylmethyl}-methyl-amide (EX# 151) | CuCN |
| 169 | Acetic acid 1-({2-[3-(3-fluoro-benzyl)-ureido]-thiazol-4-ylmethyl}-methyl-carbamoyl)-ethyl ester | $C_{18}H_{21}FN_4O_4S$ | 408.4 | 409 | 2 | Int. 5 | 2-Acetoxypropionic acid |
| 170 | 1-Ethyl-3-methyl-1H-pyrazole-4-carboxylic acid {2-[3-(3-fluoro-benzyl)-ureido]-thiazol-4-ylmethyl}-methyl-amide | $C_{20}H_{23}FN_6O_2S$ | 430.5 | 431 | 2 | Int. 5 | 1-Ethyl-3-methyl-1H-pyrazole-4-carboxylid acid |
| 171 | 2-Methyl-pyrazolo[1,5-a]pyrimidine-3-carboxylic acid {2-[3-(3-fluoro-benzyl)-ureido]-thiazol-4-ylmethyl}-methyl-amide | $C_{21}H_{20}FN_7O_2S$ | 453.5 | 454 | 2 | Int. 5 | 2-Methyl-pyrazolo[1,5-a]pyrimidine-3-carboxylic acid |
| 172 | N-{2-[3-(3-Fluoro-benzyl)-ureido]-thiazol-4-ylmethyl}-2-hydroxy-N-methyl-propionamide | $C_{16}H_{19}FN_4O_3S$ | 366.4 | 367 | 20 | Acetic acid 1-({2-[3-(3-fluoro-benzyl)-ureido]-thiazol-4-ylmethyl}-methyl-carbamoyl)-ethyl ester (EX# 169) | none |
| 173 | 3,5-Dimethyl-isoxazole-4-carboxylic acid (1-{2-[3-(3-fluoro-benzyl)-ureido]-thiazol-4-yl]-ethyl)-amide | $C_{19}H_{20}FN_5O_3S$ | 417.5 | 418 | 3 | Int. 10b | 3,5-Dimethyl-isoxazole-4-carboxylic acid chloride |
| 174 | 1-Ethyl-5-methyl-1H-pyrazole-4-carboxylic acid {2-[3-(3-fluoro-benzyl)-ureido]-thiazol-4-ylmethyl}-methyl-amide | $C_{20}H_{23}FN_6O_2S$ | 430.5 | 431 | 2 | Int. 5 | 1-Ethyl-5-methyl-1H-pyrazole-4-carboxylic acid |
| 175 | 5,7-Dimethyl-pyrazolo[1,5-a]pyrimidine-3-carboxylic acid {2-[3-(3-fluoro-benzyl)-ureido]-thiazol-4-ylmethyl}-methyl-amide | $C_{22}H_{22}FN_7O_2S$ | 467.5 | 468 | 2 | Int. 5 | 5,7-Dimethyl-pyrazolo[1,5-a]pyrimidine-3-carboxylic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 176 | 3,5-Dimethyl-isoxazole-4-carboxylic acid (1-{2-[3-(3-fluoro-benzyl)-ureido]-thiazol-4-yl}-2-hydroxy-ethyl)-amide | $C_{19}H_{20}FN_5O_4S$ | 433.5 | 434 | 3 | Int. 24 | 3,5-Dimethyl-isoxazole-4-carboxylic acid chloride |
| 177 | 1-Methyl-1H-indole-3-carboxylic acid {2-[3-(3-fluoro-benzyl)-ureido]-thiazol-4-ylmethyl}-amide | $C_{23}H_{22}FN_5O_2S$ | 451.5 | 452 | 2 | Int. 5 | 1-Methyl-1H-indole-3-carboxylic acid |
| 178 | 1-Methyl-1H-indazole-3-carboxylic acid {2-[3-(3-fluoro-benzyl)-ureido]-thiazol-4-ylmethyl}-amide | $C_{22}H_{21}FN_6O_2S$ | 452.5 | 453 | 2 | Int. 5 | 1-Methyl-1H-indazole-3-carboxylic acid |
| 179 | Pyrazolo[1,5-a]pyridine-3-carboxylic acid {2-[3-(3-fluoro-benzyl)-ureido]-thiazol-4-ylmethyl}-amide | $C_{21}H_{19}FN_6O_2S$ | 438.4 | 439 | 3 | Int. 5 | Pyrazolo[1,5-a]pyridine-3-carboxylic acid chloride |
| 180 | N-{2-[3-(3-Fluoro-benzyl)-ureido]-thiazol-4-ylmethyl}-2-furan-2-yl-N-methyl-2-oxo-acetamide | $C_{19}H_{17}FN_4O_4S$ | 416.4 | 417 | 2 | Int. 5 | 2-Furan-2-yl-2-oxoacetic acid |
| 181 | 3,5-Dimethyl-isoxazole-4-carboxylic acid [2-(3-benzyl-ureido)-thiazol-4-ylmethyl]-amide | $C_{19}H_{21}N_5O_3S$ | 399.5 | 400 | 8 | Int.18 | Benzylamine |
| 182 | 3-Methyl-pyrazine-2-carboxylic acid {2-[3-(5-chloro-thiophen-2-ylmethyl)-ureido]-thiazol-4-ylmethyl}-amide | $C_{17}H_{17}ClN_6O_2S_2$ | 436.9 | 437 | 8; 10 | Int. 22 | (5-Chlorothiophen-2-yl-methyl)(2,4-dimethoxybenzyl)amine (per Method 13) |
| 183 | 3,5-Dimethyl-isoxazole-4-carboxylic acid {2-[3-(3-fluoro-benzyl)-ureido]-5-isopropyl-thiazol-4-ylmethyl}-amide | $C_{22}H_{26}FN_5O_3S$ | 459.5 | 460 | 3 | Int. 25 | 3,5-Dimethyl-isoxazole-4-carboxylic acid chloride |
| 184 | 5-Oxo-pyrrolidine-2-carboxylic acid {2-[3-(3-fluoro-benzyl)-ureido]-thiazol-4-ylmethyl}-amide | $C_{18}H_{20}FN_5O_3S$ | 405.4 | 406 | 2 | Int. 5 | 5-Oxo-pyrrolidine-2-carboxylic acid |
| 185 | 3-Methyl-pyrazine-2-carboxylic acid {2-[3-(5-chloro-thiophen-3-ylmethyl)-ureido]-thiazol-4-ylmethyl}-amide | $C_{17}H_{17}ClN_6O_2S_2$ | 436.9 | 437 | 8 | Int. 22 | (5-Chlorothiophen-3-yl)methanamine hydrochloride (Int. 37) |
| 186 | 3,5-Dimethyl-isoxazole-4-carboxylic acid (2,2-difluoro-ethyl)-{2-[3-(3-fluoro-benzyl)-ureido]-thiazol-4-ylmethyl}-amide | $C_{20}H_{20}F_3N_5O_3S$ | 467.5 | 468 | 3 | Int. 26 | 3,5-Dimethyl-isoxazole-4-carboxylic acid chloride |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 187 | 4-Methyl-pyridazine-3-carboxylic acid {2-[3-(3-fluoro-benzyl)-ureido]-thiazol-4-ylmethyl}-methyl-amide | $C_{19}H_{19}FN_6O_2S$ | 414.5 | 415 | 2 | Int. 5 | 4-Methylpyridazine-3-carboxylic acid (Int. 33) |
| 188 | 5-Methyl-pyridazine-4-carboxylic acid {2-[3-(3-fluoro-benzyl)-ureido]-thiazol-4-ylmethyl}-methyl-amide | $C_{19}H_{19}FN_6O_2S$ | 414.5 | 415 | 2 | Int. 5 | 5-Methylpyridazine-4-carboxylic acid (Int. 32) |
| 189 | 3-Amino-1H-pyrazole-4-carboxylic acid {2-[3-(3-fluoro-benzyl)-ureido]-thiazol-4-ylmethyl}-methyl-amide | $C_{17}H_{18}FN_7O_2S$ | 403.4 | 404 | 2 | Int. 5 | 3-Amino-1H-pyrazole-4-carboxylic acid |
| 190 | 3,6-Dimethoxy-pyridazine-4-carboxylic acid {2-[3-(3-fluoro-benzyl)-ureido]-thiazol-4-ylmethyl}-methyl-amide | $C_{20}H_{21}FN_6O_4S$ | 460.5 | 461 | 2 | Int. 5 | 3,6-Dimethoxy-pyridazine-4-carboxylic acid |
| 191 | (3,5-Dimethyl-isoxazol-4-ylmethyl)-{2-[3-(3-fluoro-benzyl)-ureido]-thiazol-4-ylmethyl}-carbamic acid methyl ester | $C_{20}H_{22}FN_5O_4S$ | 447.5 | 448 | 3 | Int. 61 | Methyl chloroformate |
| 192 | (R)-Tetrahydro-furan-2-carboxylic acid {2-[3-(5-chloro-thiophen-2-ylmethyl)-ureido]-thiazol-4-ylmethyl]-methyl-amide | $C_{16}H_{19}ClN_4O_3S_2$ | 414.9 | 415 | 2 | Int. 29 | (R)-2-Tetrahydrofuroic acid |
| 193 | 5-Methyl-pyridazine-4-carboxylic acid {2-[3-(5-chloro-thiophen-2-ylmethyl)-ureido]-thiazol-4-ylmethyl}-methyl-amide | $C_{17}H_{17}ClN_6O_2S_2$ | 436.9 | 437 | 2 | Int. 29 | 5-Methylpyridazine-4-carboxylic acid (Int. 32) |
| 194 | 3,5-Dimethyl-1H-pyrazole-4-carboxylic acid {2-[3-(5-chloro-thiophen-2-ylmethyl)-ureido]-thiazol-4-ylmethyl}-methyl-amide | $C_{17}H_{19}ClN_6O_2S_2$ | 439.0 | 439 | 2 | Int. 29 | 3,5-Dimethyl-1H-pyrazole-4-carboxylic acid |
| 195 | 5-Methyl-pyridazine-4-carboxylic acid {2-[3-(5-chloro-thiophen-3-ylmethyl)-ureido]-thiazol-4-ylmethyl}-methyl-amide | $C_{17}H_{17}ClN_6O_2S_2$ | 436.9 | 437 | 2 | Int. 30 | 5-Methylpyridazine-4-carboxylic acid (Int. 32) |
| 196 | Tetrahydro-furan-2-carboxylic acid {2-[3-(5-chloro-thiophen-3-ylmethyl)-ureido]-thiazol-4-ylmethyl}-methyl-amide | $C_{16}H_{19}ClN_4O_3S_2$ | 414.9 | 415 | 2 | Int. 30 | (R)-2-Tetrahydrofuroic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|------|------|-------------|------------|------|--------|---------------------------|---------------------------|
| 197 | 3,5-Dimethyl-1H-pyrazole-4-carboxylic acid {2-[3-(5-chloro-thiophen-3-ylmethyl)-ureido]-thiazol-4-ylmethyl]-methyl-amide | C$_{17}$H$_{19}$ClN$_6$O$_2$S$_2$ | 439.0 | 439 | 2 | Int. 30 | 3,5-Dimethyl-1H-pyrazole-4-carboxylic acid |
| 198 | 1,3,5-Trimethyl-1H-pyrazole-4-carboxylic acid {2-[3-(5-chloro-thiophen-3-ylmethyl)-ureido]-thiazol-4-ylmethyl]-methyl-amide | C$_{18}$H$_{21}$ClN$_6$O$_2$S$_2$ | 453.0 | 453 | 2 | Int. 30 | 1,3,5-Trimethyl-1H-pyrazole-4-carboxylic acid |
| 199 | 3,6-Dichloro-pyridazine-4-carboxylic acid {2-[3-(3-fluoro-benzyl)-ureido]-thiazol-4-ylmethyl]-methyl-amide | C$_{18}$H$_{15}$Cl$_2$FN$_6$O$_2$S | 469.3 | 469 | 2 | Int. 5 | 3,6-Dichloro-pyridazine-4-carboxylic acid |
| 200 | 3-Chloro-6-methoxy-pyridazine-4-carboxylic acid {2-[3-(3-fluoro-benzyl)-ureido]-thiazol-4-ylmethyl]-methyl-amide | C$_{19}$H$_{18}$ClFN$_6$O$_3$S | 465.0 | 465 | 44 | 3,6-Dichloropyridazine-4-carboxylic acid {2-[3-(3-fluoro-benzyl)-ureido]-thiazol-4-ylmethyl]-methyl-amide (EX# 199) | MeOH |
| 201 | 3,5-Dimethyl-isoxazole-4-carboxylic acid {5-fluoro-2-[3-(3-fluoro-benzyl)-ureido]-thiazol-4-ylmethyl]-methyl-amide | C$_{19}$H$_{19}$F$_2$N$_5$O$_3$S | 435.0 | 436 | 2 | Int. 40 | 3,5-Dimethyl-isoxazole-4-carboxylic acid |
| 202 | (R)-Tetrahydro-furan-2-carboxylic acid {5-fluoro-2-[3-(3-fluoro-benzyl)-ureido]-thiazol-4-ylmethyl]-methyl-amide | C$_{18}$H$_{20}$F$_2$N$_4$O$_3$S | 410.0 | 411 | 2 | Int. 40 | (R)-Tetrahydro-furan-2-carboxylic acid |
| 203 | 3,5-Dimethyl-pyridazine-4-carboxylic acid {2-[3-(3-fluoro-benzyl)-ureido]-thiazol-4-ylmethyl]-methyl-amide | C$_{20}$H$_{21}$FN$_6$O$_2$S | 428.0 | 429 | 2 | Int. 5 | 3,5-Dimethyl-pyridazine-4-carboxylic acid |
| 204 | N-{5-Fluoro-2-[3-(3-fluoro-benzyl)-ureido]-thiazol-4-ylmethyl}-N-methyl-acetamide | C$_{15}$H$_{16}$F$_2$N$_4$O$_2$S | 354.0 | 355 | 2 | Int. 40 | acetic acid |
| 205 | 1-Methyl-3-trifluoromethyl-1H-pyrazole-4-carboxylic acid {2-[3-(3-fluoro-benzyl)-ureido]-thiazol-4-ylmethyl]-methyl-amide | C$_{19}$H$_{18}$F$_4$N$_6$O$_2$S | 470.0 | 471 | 2 | Int. 5 | 1-Methyl-3-trifluoromethyl-1H-pyrazole-4-carboxylic acid |
| 206 | 1,3,5-Trimethyl-1H-pyrazole-4-carboxylic acid {5-fluoro-2-[3-(3-fluoro-benzyl)-ureido]-thiazol-4-ylmethyl]-methyl-amide | C$_{20}$H$_{22}$F$_2$N$_6$O$_2$S | 448.0 | 449 | 2 | Int. 40 | 1,3,5-Trimethyl-1H-pyrazole-4-carboxylic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 207 | 1,3,5-Trimethyl-1H-pyrazole-4-carboxylic acid {2-[3-(5-chloro-thiophen-2-ylmethyl)-ureido]-thiazol-4-ylmethyl]-methyl-amide | $C_{18}H_{21}ClN_6O_2S_2$ | 453.0 | 453 | 2 | Int. 29 | 1,3,5-Trimethyl-1H-pyrazole-4-carboxylic acid |
| 208 | 3-Chloro-6-hydroxy-pyridazine-4-carboxylic acid {2-[3-(3-fluoro-benzyl)-ureido]-thiazol-4-ylmethyl]-methyl-amide | $C_{18}H_{16}ClFN_6O_3S$ | 451.0 | 451 | 45 | 3-Chloro-6-methoxy-pyridazine-4-carboxylic acid {2-[3-(3-fluoro-benzyl)-ureido]-thiazol-4-ylmethyl]-methyl-amide (EX# 200) | None |
| 209 | 2-Methyl-tetrahydro-furan-2-carboxylic acid {2-[3-(3-fluoro-benzyl)-ureido]-thiazol-4-ylmethyl]-methyl-amide | $C_{19}H_{23}FN_4O_3S$ | 406.5 | 408 | 2 | Int. 5 | 2-Methyl-tetrahydro-furan-2-carboxylic acid |
| 210 | 4-Chloro-1-methyl-1H-pyrazole-3-carboxylic acid {2-[3-(3-fluoro-benzyl)-ureido]-thiazol-4-ylmethyl]-methyl-amide | $C_{18}H_{18}ClFN_6O_2S$ | 437.0 | 437 | 2 | Int. 5 | 4-Chloro-1-methyl-1H-pyrazole-3-carboxylic acid |
| 211 | 5-Chloro-1-methyl-1H-pyrazole-4-carboxylic acid {2-[3-(3-fluoro-benzyl)-ureido]-thiazol-4-ylmethyl]-methyl-amide | $C_{18}H_{18}ClFN_6O_2S$ | 437.0 | 437 | 2 | Int. 5 | 5-Chloro-1-methyl-1H-pyrazole-4-carboxylic acid |
| 212 | 4-Chloro-2-methyl-2H-pyrazole-3-carboxylic acid {2-[3-(3-fluoro-benzyl)-ureido]-thiazol-4-ylmethyl]-methyl-amide | $C_{18}H_{18}ClFN_6O_2S$ | 437.0 | 437 | 2 | Int. 5 | 4-Chloro-2-methyl-2H-pyrazole-3-carboxylic acid |
| 213 | 4-Chloro-1H-pyrazole-3-carboxylic acid {2-[3-(3-fluoro-benzyl)-ureido]-thiazol-4-ylmethyl]-methyl-amide | $C_{17}H_{16}ClFN_6O_2S$ | 423.0 | 423/425 | 2 | Int. 5 | 4-Chloro-1H-pyrazole-3-carboxylic acid |
| 214 | 3,5-Dimethyl-isoxazole-4-carboxylic acid (cyano-{2-[3-(3-fluoro-benzyl)-ureido]-thiazol-4-yl}-methyl)-methyl-amide | $C_{20}H_{19}FN_6O_3S$ | 442.0 | 443 | 2 | Int. 41 | 3,5-Dimethyl-isoxazole-4-carboxylic acid |
| 215 | 1-Methyl-3-trifluoromethyl-1H-pyrazole-4-carboxylic acid {2-[3-(5-chloro-thiophen-2-ylmethyl)-ureido]-thiazol-4-ylmethyl]-methyl-amide | $C_{17}H_{16}ClF_3N_6O_2S_2$ | 493.0 | 493 | 2 | Int. 29 | 1-Methyl-3-trifluoromethyl-1H-pyrazole-4-carboxylic acid |
| 216 | 1-Methyl-3-trifluoromethyl-1H-pyrazole-4-carboxylic acid {2-[3-(5-chloro-thiophen-2-ylmethyl)-ureido]-thiazol-4-ylmethyl]-methyl-amide | $C_{19}H_{22}ClN_5O_3S_2$ | 468.0 | 468 | 2 | Int. 29 | 1-Methyl-3-trifluoromethyl-1H-pyrazole-4-carboxylic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 217 | 1,3,6-Trimethyl-1H-pyrazolo[3,4-b]pyridine-4-carboxylic acid {2-[3-(5-chloro-thiophen-2-ylmethyl)-ureido]-thiazol-4-ylmethyl}-methyl-amide | $C_{21}H_{22}ClN_7O_2S_2$ | 504.0 | 505 | 2 | Int. 29 | 1,3,6-Trimethyl-1H-pyrazolo[3,4-b]pyridine-4-carboxylic acid |
| 218 | N-{2-[3-(5-Chloro-thiophen-2-ylmethyl)-ureido]-thiazol-4-ylmethyl}-2,N-dimethyl-5-sulfamoyl-benzamide | $C_{19}H_{20}ClN_5O_4S_3$ | 514.0 | 514 | 2 | Int. 29 | 2-Methyl-5-sulfamoyl-benzoic acid |
| 219 | 1-Methyl-6-oxo-1,4,5,6-tetrahydro-pyridazine-3-carboxylic acid {2-[3-(5-chloro-thiophen-2-ylmethyl)-ureido]-thiazol-4-ylmethyl}-methyl-amide | $C_{17}H_{19}ClN_6O_3S_2$ | 455.0 | 455 | 2 | Int. 29 | 1-Methyl-6-oxo-1,4,5,6-tetrahydro-pyridazine-3-carboxylic acid |
| 220 | 1-Phenyl-cyclobutanecarboxylic acid {2-[3-(5-chloro-thiophen-2-ylmethyl)-ureido]-thiazol-4-ylmethyl}-methyl-amide | $C_{22}H_{23}ClN_4O_2S_2$ | 475.0 | 475 | 2 | Int. 29 | 1-Phenyl-cyclobutanecarboxylic acid |
| 221 | 3-Methyl-4-oxo-3,4-dihydro-phthalazine-1-carboxylic acid {2-[3-(5-chloro-thiophen-2-ylmethyl)-ureido]-thiazol-4-ylmethyl}-methyl-amide | $C_{21}H_{23}ClN_6O_3S_2$ | 503.0 | 503 | 2 | Int. 29 | 3-Methyl-4-oxo-3,4-dihydro-phthalazine-1-carboxylic acid |
| 222 | 7-Chloro-benzo[1,3]dioxole-5-carboxylic acid {2-[3-(5-chloro-thiophen-2-ylmethyl)-ureido]-thiazol-4-ylmethyl}-methyl-amide | $C_{19}H_{18}Cl_2N_4O_4S_2$ | 499.0 | 499 | 2 | Int. 29 | 7-Chloro-benzo[1,3]dioxole-5-carboxylic acid |
| 223 | N-{2-[3-(5-Chloro-thiophen-2-ylmethyl)-ureido]-thiazol-4-ylmethyl}-N-methyl-6-[1,2,4]triazol-1-yl-nicotinamide | $C_{19}H_{17}ClN_8O_2S_2$ | 489.0 | 489 | 2 | Int. 29 | 6-[1,2,4]triazol-1-yl-nicotinic acid |
| 224 | 1-(2-Methoxy-ethyl)-6-oxo-1,6-dihydro-pyridazine-3-carboxylic acid {2-[3-(5-chloro-thiophen-2-ylmethyl)-ureido]-thiazol-4-ylmethyl}-methyl-amide | $C_{19}H_{21}ClN_6O_4S_2$ | 497.0 | 497 | 2 | Int. 29 | 1-(2-Methoxy-ethyl)-6-oxo-1,6-dihydro-pyridazine-3-carboxylic acid |
| 225 | N-((2-(3-((5-chlorothiophen-2-yl)methyl)ureido)thiazol-4-yl)methyl)-2-(2,4-dioxo-3,4-dihydropyrimidin-1(2H)-yl)-N-methylacetamide | $C_{17}H_{17}ClN_6O_4S_2$ | 467.0 | 467 | 2 | Int. 29 | 2-(2,4-dioxo-3,4-dihydropyrimidin-1(2H)-yl)acetic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 226 | 1,1-Dioxo-tetrahydrothiophene-3-carboxylic acid {2-[3-(5-chlorothiophen-2-yl)methyl)-ureido]-thiazol-4-ylmethyl}-methyl-amide | $C_{16}H_{19}ClN_4O_4S_3$ | 463.0 | 463 | 2 | Int. 29 | 1,1-Dioxo-tetrahydrothiophene-3-carboxylic acid |
| 227 | 6-chloro-N-(2-(3-(3-fluorobenzyl)ureido)thiazol-4-yl)methyl)-3-hydroxy-N-methylpyridazine-4-carboxamide | $C_{18}H_{16}ClFN_6O_3S$ | 451.0 | Structure Confirmed by 1H-NMR | 51 | 3-Chloro-6-methoxy-pyridazine-4-carboxylic acid {2-[3-(3-fluoro-benzyl)-ureido]-thiazol-4-ylmethyl}-methyl-amide (EX# 200) | None |
| 228 | 5-chloro-N-(2-(3-(3-fluorobenzyl)ureido)thiazol-4-yl)methyl)-N,1,3-trimethyl-1H-pyrazole-4-carboxamide | $C_{19}H_{20}ClFN_6O_2S$ | 451.0 | 451 | 2 | Int. 5 | N,1,3-trimethyl-1H-pyrazole-4-carboxylic acid |
| 229 | N-(2-(3-(3-fluorobenzyl)ureido)thiazol-4-yl)methyl)-5-isopropyl-N,3-dimethylisoxazole-4-carboxamide | $C_{21}H_{24}FN_5O_3S$ | 446.0 | 446 | 2 | Int. 5 | N,3-dimethylisoxazole-4-carboxylic acid |
| 230 | 3-cyano-N-(2-(3-(3-fluorobenzyl)ureido)thiazol-4-yl)methyl)-2-hydroxy-N,6-dimethylisonicotinamide | $C_{21}H_{19}FN_6O_3S$ | 454.0 | 455 | 2 | Int. 5 | 3-cyano-2-hydroxy-6-methylisonicotinic acid |
| 231 | 6-chloro-N-(2-(3-(3-fluorobenzyl)ureido)thiazol-4-yl)methyl)-N-methyl-3-oxo-2,3-dihydropyridazine-4-carboxamide | $C_{18}H_{16}ClFN_6O_3S$ | 451.0 | 451 | 2 | Int. 5 | 6-chloro-3-oxo-2,3-dihydropyridazine-4-carboxylic acid |
| 232 | N-((2-(3-(3-fluorobenzyl)ureido)thiazol-4-yl)methyl)-N,1-dimethyl-5-(1H-pyrrol-1-yl)-1H-pyrazole-4-carboxamide | $C_{22}H_{22}FN_7O_2S$ | 468.0 | 468 | 2 | Int. 5 | 1-methyl-5-(1H-pyrrol-1-yl)-1H-pyrazole-4-carboxylic acid |
| 233 | N-(2-(3-(3-fluorobenzyl)ureido)thiazol-4-yl)methyl)-N,2-dimethyl-5-sulfamoylbenzamide | $C_{21}H_{22}FN_5O_4S_2$ | 492.0 | 492 | 2 | Int. 5 | N,2-dimethyl-5-sulfamoylbenzoic acid |
| 234 | N-(2-(3-(3-fluorobenzyl)ureido)thiazol-4-yl)methyl)-N-methyl-1-phenylcyclobutanecarboxamide | $C_{24}H_{25}FN_4O_2S$ | 452.0 | 453 | 2 | Int. 5 | 1-phenylcyclobutane carboxylic acid |
| 235 | N-(2-(3-(3-fluorobenzyl)ureido)thiazol-4-yl)methyl)-N-methyl-4-oxo-3,4-dihydrophthalazine-1-carboxamide | $C_{22}H_{19}FN_6O_3S$ | 466.0 | 467 | 2 | Int. 5 | 4-oxo-3,4-dihydrophthalazine-1-carboxylic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 236 | N-((2-(3-(3-fluorobenzyl)ureido)thiazol-4-yl)methyl)-N,4,6-trimethyl-2-oxo-2H-pyran-5-carboxamide | C₂₁H₂₁FN₄O₄S | 444.0 | 445 | 2 | Int. 5 | 4,6-dimethyl-2-oxo-2H-pyran-5-carboxylic acid |
| 237 | 7-chloro-N-(2-(3-(3-fluorobenzyl)ureido)thiazol-4-yl)methyl)-N-methylbenzo[1,3]dioxole-5-carboxamide | C₂₁H₁₈ClFN₄O₄S | 477.0 | 477 | 2 | Int. 5 | 7-chlorobenzo[1,3]dioxole-5-carboxylic acid |
| 238 | N-((2-(3-(3-fluorobenzyl)ureido)thiazol-4-yl)methyl)-N,1-dimethyl-4-sulfamoyl-1H-pyrrole-2-carboxamide | C₁₉H₂₁FN₆O₅S₂ | 480.0 | 481 | 2 | Int. 5 | 1-methyl-4-sulfamoyl-1H-pyrrole-2-carboxylic acid |
| 239 | 2-(5,7-dimethyl-[1,2,4]triazolo[1,5-a]pyrimidin-6-yl)-N-((2-(3-(3-fluorobenzyl)ureido)thiazol-4-yl)methyl)-N-methylacetamide | C₂₂H₂₃FN₈O₂S | 482.0 | 483 | 2 | Int. 5 | 2-(5,7-dimethyl-[1,2,4]triazolo[1,5-a]pyrimidin-6-yl)acetic acid |
| 240 | N-((2-(3-(3-fluorobenzyl)ureido)thiazol-4-yl)methyl)-N,3,6-trimethyl-4-oxo-3,4-dihydrofuro[2,3-d]pyrimidine-5-carboxamide | C₂₂H₂₁FN₆O₄S | 484.0 | 485 | 2 | Int. 5 | 3,6-dimethyl-4-oxo-3,4-dihydrofuro[2,3-d]pyrimidine-5-carboxylic acid |
| 241 | N-((2-(3-(3-fluorobenzyl)ureido)thiazol-4-yl)methyl)-N,5-dimethyl-4-oxo-3,4-dihydrothieno[2,3-d]pyrimidine-6-carboxamide | C₂₁H₁₉FN₆O₃S₂ | 486.0 | 487 | 2 | Int. 5 | 5-methyl-4-oxo-3,4-dihydrothieno[2,3-d]pyrimidine-6-carboxamide |
| 242 | 2,2-difluoro-N-(2-(3-(3-fluorobenzyl)ureido)thiazol-4-yl)methyl)-N-methyl-2-phenylacetamide | C₂₁H₁₉F₃N₄O₂S | 448.0 | 449 | 2 | Int. 5 | 2,2-difluoro-N-methyl-2-phenylacetic acid |
| 243 | N2-((2-(3-(3-fluorobenzyl)ureido)thiazol-4-yl)methyl)-4-hydroxy-N2-methylpyrrolidine-1,2-dicarboxamide | C₁₉H₂₃FN₆O₄S | 450.0 | 451 | 2 | Int. 5 | 1-carbamoyl-4-hydroxypyrrolidine-2-carboxylic acid |
| 244 | N-((2-(3-(5-chlorothiophen-2-yl)methyl)ureido)thiazol-4-yl)methyl)-N-methyl-2-morpholinonicotinamide | C₂₁H₂₃ClN₆O₃S₂ | 507.0 | 507 | 2 | Int. 29 | 2-morpholinonicotinic acid |
| 245 | N-((2-(3-(5-chlorothiophen-2-yl)methyl)ureido)thiazol-4-yl)methyl)-N-methyl-4-oxo-3,4-dihydrophthalazine-1-carboxamide | C₂₀H₁₇ClN₆O₃S₂ | 489.0 | 489 | 2 | Int. 29 | 4-oxo-3,4-dihydrophthalazine-1-carboxylic acid |
| 246 | N-((2-(3-(5-chlorothiophen-2-yl)methyl)ureido)thiazol-4-yl)methyl)-N,4,6-trimethyl-2-oxo-2H-pyran-5-carboxamide | C₁₉H₁₉ClN₄O₄S₂ | 467.0 | 467 | 2 | Int. 29 | 4,6-dimethyl-2-oxo-2H-pyran-5-carboxylic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 247 | N-((2-(3-((5-chlorothiophen-2-yl)methyl)ureido)thiazol-4-yl)methyl)-N,1-dimethyl-4-sulfamoyl-1H-pyrrole-2-carboxamide | $C_{17}H_{19}ClN_6O_4S_3$ | 503.0 | 503 | 2 | Int. 29 | 1-methyl-4-sulfamoyl-1H-pyrrole-2-carboxylic acid |
| 248 | N-((2-(3-((5-chlorothiophen-2-yl)methyl)ureido)thiazol-4-yl)methyl)-2-(5,7-dimethyl-[1,2,4]triazolo[1,5-a]pyrimidin-6-yl)-N-methylacetamide | $C_{20}H_{21}ClN_8O_2S_2$ | 505.0 | 505 | 2 | Int. 29 | 2-(5,7-dimethyl-[1,2,4]triazolo[1,5-a]pyrimidin-6-yl)acetic acid |
| 249 | N-((2-(3-((5-chlorothiophen-2-yl)methyl)ureido)thiazol-4-yl)methyl)-N,5-dimethyl-4-oxo-3,4-dihydrothieno[2,3-d]pyrimidine-6-carboxamide | $C_{19}H_{17}ClN_6O_3S_3$ | 509.0 | 509 | 2 | Int. 29 | 5-methyl-4-oxo-3,4-dihydrothieno[2,3-d]pyrimidine-6-carboxylic acid |
| 250 | N-((2-(3-((5-chlorothiophen-2-yl)methyl)ureido)thiazol-4-yl)methyl)-1-(3-fluorophenyl)-N-methylcyclobutane carboxamide | $C_{22}H_{22}ClFN_4O_2S_2$ | 493.0 | 493 | 2 | Int. 29 | 1-(3-fluorophenyl)cyclobutane carboxylic acid |
| 251 | N-((2-(3-((5-chlorothiophen-2-yl)methyl)ureido)thiazol-4-yl)methyl)-2,2-difluoro-N-methyl-2-phenylacetamide | $C_{19}H_{17}ClF_2N_4O_2S_2$ | 471.0 | 471 | 2 | Int. 29 | 2,2-difluoro-2-phenylacetic acid |
| 252 | N-((2-(3-(3-fluorobenzyl)ureido)thiazol-4-yl)methyl)-N-methyl-5-(trifluoromethyl)-1H-pyrazole-4-carboxamide | $C_{18}H_{16}F_4N_6O_2S$ | 456.0 | 457 | 2 | Int. 5 | 5-(trifluoromethyl)-1H-pyrazole-4-carboxylic acid |
| 253 | N-((2-(3-(3-fluorobenzyl)ureido)thiazol-4-yl)methyl)-N,1-dimethyl-5-(trifluoromethyl)-1H-pyrazole-4-carboxamide | $C_{19}H_{18}F_4N_6O_2S$ | 470.0 | 472 | 2 | Int. 5 | 1-methyl-5-(trifluoromethyl)-1H-pyrazole-4-carboxylic acid |
| 254 | (S)-N-((2-(3-(3-fluorobenzyl)ureido)thiazol-4-yl)methyl)-2-methoxy-N-methylpropanamide | $C_{17}H_{21}FN_4O_3S$ | 380.0 | 381 | 2 | Int. 5 | (S)-2-methoxypropanoic acid |
| 255 | N-((2-(3-(3-fluorobenzyl)ureido)thiazol-4-yl)methyl)-N,3-dimethyl-5,6-dihydro-1,4-dioxine-2-carboxamide | $C_{19}H_{21}FN_4O_4S$ | 420.0 | 421 | 2 | Int. 5 | 3-methyl-5,6-dihydro-1,4-dioxine-2-carboxylic acid |
| 256 | (R)-N-((2-(3-(3-fluorobenzyl)ureido)thiazol-4-yl)methyl)-N-methyl-5-oxotetrahydrofuran-2-carboxamide | $C_{18}H_{19}FN_4O_4S$ | 406.0 | 407 | 2 | Int. 5 | 5-oxotetrahydrofuran-2-carboxylic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 257 | 5-chloro-N-((2-(3-((5-chlorothiophen-2-yl)methyl)ureido)thiazol-4-yl)methyl)-N,1,3-trimethyl-1H-pyrazole-4-carboxamide | $C_{17}H_{18}Cl_2N_6O_2S_2$ | 473.0 | 475 | 2 | Int. 29 | 5-chloro-1,3-dimethyl-1H-pyrazole-4-carboxylic acid |
| 258 | N-((2-(3-(3-fluorobenzyl)ureido)thiazol-4-yl)methyl)-N,1-dimethyl-6-oxo-1,4,5,6-tetrahydropyridazine-3-carboxamide | $C_{19}H_{21}FN_6O_3S$ | 432.0 | 433 | 2 | Int. 5 | 1-methyl-6-oxo-1,4,5,6-tetrahydropyridazine-3-carboxylic acid |
| 259 | N-((2-(3-(3-fluorobenzyl)ureido)thiazol-4-yl)methyl)-N,3-dimethyl-4-oxo-3,4-dihydrophthalazine-1-carboxamide | $C_{23}H_{21}FN_6O_3S$ | 480.0 | 481 | 2 | Int. 5 | 3-methyl-4-oxo-3,4-dihydrophthalazine-1-carboxylic acid |
| 260 | N-((2-(3-((5-chlorothiophen-2-yl)methyl)ureido)thiazol-4-yl)methyl)-N,1-dimethyl-5-(1H-pyrrol-1-yl)-1H-pyrazole-4-carboxamide | $C_{20}H_{20}ClN_7O_2S_2$ | 490.0 | 490 | 2 | Int. 29 | 1-methyl-5-(1H-pyrrol-1-yl)-1H-pyrazole-4-carboxylic acid |
| 261 | N-((2-(3-((5-chlorothiophen-2-yl)methyl)ureido)thiazol-4-yl)methyl)-N,3,6-trimethyl-4-oxo-3,4-dihydrofuro[2,3-d]pyrimidine-5-carboxamide | $C_{20}H_{19}ClN_6O_4S_2$ | 507.0 | 507 | 2 | Int. 29 | 3,6-dimethyl-4-oxo-3,4-dihydrofuro[2,3-d]pyrimidine-5-carboxylic acid |
| 262 | N-((2-(3-(3-fluorobenzyl)ureido)thiazol-4-yl)methyl)-3-methoxy-N-methylpropanamide | $C_{17}H_{21}FN_4O_3S$ | 380.0 | 381 | 2 | Int. 5 | 3-methoxypropanoic acid |
| 263 | N-((2-(3-(3-fluorobenzyl)ureido)thiazol-4-yl)methyl)-1-(2-hydroxyethyl)-N,3,5-trimethyl-1H-pyrazole-4-carboxamide | $C_{21}H_{25}FN_6O_3S$ | 460.0 | 461 | 2 | Int. 5 | 1-(2-hydroxyethyl)-3,5-dimethyl-1H-pyrazole-4-carboxylic acid |
| 264 | (R)-N-((2-(3-(3-fluorobenzyl)ureido)thiazol-4-yl)methyl)-2-methoxy-N-methylpropanamide | $C_{17}H_{21}FN_4O_3S$ | 380.0 | 381 | 2 | Int. 5 | (R)-2-methoxypropanoic acid |
| 265 | N-((2-(3-(3-fluorobenzyl)ureido)thiazol-4-yl)methyl)-1-(2-methoxyethyl)-N,3,5-trimethyl-1H-pyrazole-4-carboxamide | $C_{22}H_{27}FN_6O_3S$ | 474.0 | 475 | 2 | Int. 5 | 1-(2-methoxyethyl)-3,5-dimethyl-1H-pyrazole-4-carboxylic acid (Int. 42) |
| 266 | N-((2-(3-(3-fluorobenzyl)ureido)thiazol-4-yl)methyl)-N-methyltetrahydro-2H-pyran-2-carboxamide | $C_{19}H_{23}FN_4O_3S$ | 406.0 | 407 | 2 | Int. 5 | Tetrahydro-2H-pyran-2-carboxylic acid (Int. 43) |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 267 | N-(cyano(2-(3-(3-fluorobenzyl)ureido)thiazol-4-yl)methyl)-N,3-dimethylpyrazine-2-carboxamide | $C_{20}H_{18}FN_7O_2S$ | 439.0 | 440 | 2 | Int. 41 | 3-methylpyrazine-2-carboxylic acid |
| 268 | N-(cyano(2-(3-(3-fluorobenzyl)ureido)thiazol-4-yl)methyl)-N-methyltetrahydrofuran-2-carboxamide | $C_{19}H_{20}FN_5O_3S$ | 417.0 | 418 | 2 | Int. 41 | tetrahydrofuran-2-carboxylic acid |
| 269 | N-(2-(3-((5-chlorothiophen-2-yl)methyl)ureido)thiazol-4-yl)methyl)-N,3,6-trimethylisoxazolo[5,4-b]pyridine-4-carboxamide | $C_{20}H_{19}ClN_6O_3S_2$ | 491.0 | 492 | 2 | Int. 29 | 3,6-dimethylisoxazolo[5,4-b]pyridine-4-carboxylic acid |
| 270 | N-((2-(3-(3-fluorobenzyl)ureido)thiazol-4-yl)methyl)-5-methoxy-N-methyltetrahydrofuran-2-carboxamide | $C_{19}H_{23}FN_4O_4S$ | 422.0 | 423 | 2 | Int. 5 | 5-methoxy-tetrahydrofuran-2-carboxylic acid (Int. 44) |
| 271 | N-(2-(3-(3-fluorobenzyl)ureido)thiazol-4-yl)methyl)-1-(4-methoxybutyl)-3,5-trimethyl-1H-pyrazole-4-carboxamide | $C_{24}H_{31}FN_6O_3S$ | 503.0 | 503 | 2 | Int. 5 | 1-(4-methoxybutyl)-3,5-dimethyl-1H-pyrazole-4-carboxylic acid (Int. 45) |
| 272 | N-(2-(3-(3-fluorobenzyl)ureido)thiazol-4-yl)methyl)-1-(3-methoxypropyl)-3,5-trimethyl-1H-pyrazole-4-carboxamide | $C_{23}H_{29}FN_6O_3S$ | 488.0 | 489 | 2 | Int. 5 | 1-(3-methoxypropyl)-3,5-dimethyl-1H-pyrazole-4-carboxylic acid (Int. 46) |
| 273 | N-((5-fluoro-2-(3-(3-fluorobenzyl)ureido)thiazol-4-yl)methyl)-N,3,5-trimethylpyridazine-4-carboxamide | $C_{20}H_{20}F_2N_6O_2S$ | 446.0 | 447 | 2 | Int. 40 | 3,5-dimethylpyridazine-4-carboxylic acid (Int. 50) |
| 274 | N-(2-(3-(3-fluorobenzyl)ureido)thiazol-4-yl)methyl)-N-methyl-2-morpholinonicotinamide | $C_{23}H_{25}FN_6O_3S$ | 484.0 | 485 | 2 | Int. 5 | 2-morpholinonicotinic acid |
| 275 | N-(2-(3-(3-fluorobenzyl)ureido)thiazol-4-yl)methyl)-N,3,6-trimethylisoxazolo[5,4-b]pyridine-4-carboxamide | $C_{22}H_{21}FN_6O_3S$ | 468.0 | 469 | 2 | Int. 5 | 3,6-dimethylisoxazolo[5,4-b]pyridine-4-carboxylic acid |
| 276 | N-((2-(3-(3-fluorobenzyl)ureido)thiazol-4-yl)methyl)-1-(4-fluorophenyl)-N-methylcyclobutane carboxamide | $C_{24}H_{24}F_2N_4O_2S$ | 470.0 | 471 | 2 | Int. 5 | 1-(4-fluorophenyl)cyclobutanecarboxylic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 277 | 1,1-Dioxo-tetrahydrothiophene-3-carboxylic acid {2-[3-(3-fluoro-benzyl)-ureido]-thiazol-4-ylmethyl}-methyl-amide | $C_{18}H_{21}FN_4O_4S_2$ | 440.0 | 441 | 2 | Int. 5 | 1,1-Dioxo-tetrahydrothiophene-3-carboxylic acid |
| 278 | N-((2-(3-(3-fluorobenzyl)ureido)thiazol-4-yl)methyl)-N,5-dimethyltetrahydrofuran-2-carboxamide | $C_{19}H_{23}FN_4O_3S$ | 406.0 | 407 | 2 | Int. 5 | 5-methyltetrahydrofuran-2-carboxylic acid (int. 47) |
| 279 | N-((2-(3-(3-fluorobenzyl)ureido)thiazol-4-yl)methyl)-N,3-dimethyloxetane-3-carboxamide | $C_{18}H_{21}FN_4O_3S$ | 392.0 | 393 | 2 | Int. 5 | 3-methyloxetane-3-carboxylic acid (Int. 48) |
| 280 | 5-chloro-N-((2-(3-(3-fluorobenzyl)ureido)thiazol-4-yl)methyl)-N-methyl-1H-pyrazole-4-carboxamide | $C_{17}H_{16}ClFN_6O_2S$ | 423.0 | 423 | 2 | Int. 5 | 1H-pyrazole-4-carboxylic acid |
| 281 | (R)-N-((2-(3-(3-fluorobenzyl)ureido)thiazol-4-yl)methyl)-N,2,2-trimethyl-1,3-dioxolane-4-carboxamide | $C_{19}H_{23}FN_4O_4S$ | 422.0 | 423 | 2 | Int. 5 | (R)-2,2-dimethyl-1,3-dioxolane-4-carboxylic acid |
| 282 | (S)-N-((2-(3-(3-fluorobenzyl)ureido)thiazol-4-yl)methyl)-N,2,2-trimethyl-1,3-dioxolane-4-carboxamide | $C_{19}H_{23}FN_4O_4S$ | 422.0 | 423 | 2 | Int. 5 | (S)-2,2-dimethyl-1,3-dioxolane-4-carboxylic acid |
| 283 | N-(2-amino-1-(2-(3-(3-fluorobenzyl)ureido)thiazol-4-yl)ethyl)-N-methyltetrahydrofuran-2-carboxamide | $C_{19}H_{24}FN_5O_3S$ | 421.0 | 422 | 46 | N-(Cyano(2-(3-(3-fluorobenzyl)ureido)thiazol-4-yl)methyl)-N-methyltetrahydrofuran-2-carboxamide (EX# 268) | Hydrogen |
| 284 | (R)-N-((2-(3-(5-fluorothiophen-2-yl)methyl)ureido)thiazol-4-yl)methyl)-N-methyltetrahydrofuran-2-carboxamide | $C_{16}H_{19}FN_4O_3S_2$ | 398.0 | 399 | 2 | Int. 41 | (R)-tetrahydrofuran-2-carboxylic acid |
| 285 | 3,6-dichloro-N-((2-(3-(3-fluorobenzyl)ureido)thiazol-4-yl)methyl)-N,5-dimethylpyridazine-4-carboxamide | $C_{19}H_{17}Cl_2FN_6O_2S$ | 483.4 | 483 | 3 | Int. 5 | 3,6-dichloro-5-methylpyridazine-4-carboxylic chloride (Int. 49) |
| 286 | N-((2-(3-(3-fluorobenzyl)ureido)thiazol-4-yl)methyl)-6-methoxy-N,3-dimethylpyridazine-4-carboxamide | $C_{20}H_{21}FN_6O_3S$ | 444.5 | Structure confirmed by 1H-NMR | 47 | 3-Chloro-6-methoxy-pyridazine-4-carboxylic acid {2-[3-(3-fluoro-benzyl)-ureido]-thiazol-4-ylmethyl}-methyl-amide (EX# 200) | Trimethylaluminum |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 287 | N-((2-(3-(3-fluorobenzyl)ureido)thiazol-4-yl)methyl)-N,1,3,6-tetramethyl-1H-pyrazolo[3,4-b]pyridine-4-carboxamide | $C_{23}H_{24}FN_7O_2S$ | 482.0 | 482 | 2 | Int. 5 | 1,3,6-trimethyl-1H-pyrazolo[3,4-b]pyridine-4-carboxylic acid |
| 288 | N-((2-(3-(3-fluorobenzyl)ureido)thiazol-4-yl)methyl)-N,1-dimethyl-5-nitro-1H-pyrazole-4-carboxamide | $C_{18}H_{18}FN_7O_4S$ | 447.0 | 448 | 2 | Int. 5 | 1-methyl-5-nitro-1H-pyrazole-4-carboxylic acid |
| 289 | N-((2-(3-(3-fluorobenzyl)ureido)thiazol-4-yl)methyl)-N-methyl-2,3-dihydrobenzofuran-2-carboxamide | $C_{22}H_{21}FN_4O_3S$ | 440.0 | 441 | 2 | Int. 5 | 2,3-dihydrobenzofuran-2-carboxylic acid |
| 290 | N-(2-(3-((5-chlorothiophen-2-yl)methyl)ureido)thiazol-4-yl)methyl)-N-methyl-2,3-dihydrobenzofuran-2-carboxamide | $C_{20}H_{19}ClN_4O_3S_2$ | 463.0 | 463 | 2 | Int. 29 | 2,3-dihydrobenzofuran-2-carboxylic acid |
| 291 | N-((2-(3-(3-fluorobenzyl)ureido)thiazol-4-yl)methyl)-6-hydroxy-N,3-dimethylpyridazine-4-carboxamide | $C_{19}H_{19}FN_6O_3S$ | 430.0 | 431 | 48 | N-((2-(3-(3-fluorobenzyl)ureido)thiazol-4-yl)methyl)-6-methoxy-N,3-dimethylpyridazine-4-carboxamide (EX# 286) | BBr3 |
| 292 | N-((2-(3-(3-fluorobenzyl)ureido)thiazol-4-yl)methyl)-N-methyl-2-(pyrrolidin-1-yl)nicotinamide | $C_{23}H_{25}FN_6O_2S$ | 468.0 | 469 | 2 | Int. 5 | 2-(pyrrolidin-1-yl)nicotinic acid |
| 293 | N-((2-(3-(3-fluorobenzyl)ureido)thiazol-4-yl)methyl)-N-methyl-4-oxo-4-(thiophen-2-yl)butanamide | $C_{21}H_{21}FN_4O_3S_2$ | 460.0 | 461 | 2 | Int. 5 | 4-oxo-4-(thiophen-2-yl)butanoic acid |
| 294 | N-((2-(3-(3-fluorobenzyl)ureido)thiazol-4-yl)methyl)-N-methyl-4-oxo-4-phenylbutanamide | $C_{23}H_{23}FN_4O_3S$ | 454.0 | 455 | 2 | Int. 5 | 3-benzoylpropionic acid |
| 295 | 2-(3-fluoro-4-methoxyphenyl)-N-(2-(3-(3-fluorobenzyl)ureido)thiazol-4-yl)methyl)-N-methylacetamide | $C_{22}H_{22}F_2N_4O_3S$ | 460.0 | 461 | 2 | Int. 5 | 2-(3-fluoro-4-methoxyphenyl)acetic acid |
| 296 | 2-(3,4-dimethoxyphenyl)-N-((2-(3-(3-fluorobenzyl)ureido)thiazol-4-yl)methyl)-N-methylacetamide | $C_{23}H_{25}FN_4O_4S$ | 472.0 | 473 | 2 | Int. 5 | 2-(3,4-dimethoxyphenyl)acetic acid |
| 297 | N-((2-(3-(3-fluorobenzyl)ureido)thiazol-4-yl)methyl)-2-(4-(hydroxymethyl)phenoxy)-N-methylacetamide | $C_{22}H_{23}FN_4O_4S$ | 458.0 | 459 | 2 | Int. 5 | 2-(4-(hydroxymethyl)phenoxy)acetic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 298 | N-((2-(3-(3-fluorobenzyl)ureido)thiazol-4-yl)methyl)-N-methyl-2-(3-(methylsulfonyl)phenyl)acetamide | C22H23FN4O4S2 | 490.0 | 491 | 2 | Int. 5 | 2-(3-(methylsulfonyl)phenyl)acetic acid |
| 299 | N-(2-(3-(3-fluorobenzyl)ureido)thiazol-4-yl)methyl)-2-(2-mercapto-4-methylthiazol-5-yl)-N-methylacetamide | C19H20FN5O2S3 | 466.0 | 466 | 2 | Int. 5 | 2-(2-mercapto-4-methylthiazol-5-yl)acetic acid |
| 300 | N-(2-(3-(3-fluorobenzyl)ureido)thiazol-4-yl)methyl)-N-methyl-5-(trifluoromethyl)furan-2-carboxamide | C19H16F4N4O3S | 456.0 | 457 | 2 | Int. 5 | 5-(trifluoromethyl)furan-2-carboxylic acid |
| 301 | (R)-N-((5-fluoro-2-(3-(3-fluorobenzyl)ureido)thiazol-4-yl)methyl)-2-methoxy-N-methylpropanamide | C17H20F2N4O3S | 398.0 | 399 | 2 | Int. 40 | (R)-2-methoxypropanoic acid |
| 302 | N-(2-(3-(3-fluorobenzyl)ureido)thiazol-4-yl)methyl)-6-hydroxy-N-methyl-3-(methylamino)pyridazine-4-carboxamide | C19H20FN7O3S | 445.0 | 446 | 50 | 3-(dimethylamino)-N-((2-(3-(3-fluorobenzyl)ureido)thiazol-4-yl)methyl)-6-methoxy-N-methylpyridazine-4-carboxamide (EX# 303) | BBr3 |
| 303 | 3-(dimethylamino)-N-((2-(3-(3-fluorobenzyl)ureido)thiazol-4-yl)methyl)-6-methoxy-N-methylpyridazine-4-carboxamide | C21H24FN7O3S | 474.0 | 474 | 49 | 3-Chloro-6-methoxy-pyridazine-4-carboxylic acid {2-[3-(3-fluoro-benzyl)-ureido]-thiazol-4-ylmethyl}-methyl-amide (EX# 200) | dimethylamine |
| 304 | N-((2-(3-(3-fluorobenzyl)ureido)thiazol-4-yl)methyl)-1-(2-methoxyethyl)-N-methyl-6-oxo-1,6-dihydropyridazine-3-carboxamide | C21H23FN6O4S | 474.0 | 475 | 2 | Int. 5 | 1-(2-methoxyethyl)-6-oxo-1,6-dihydropyridazine-3-carboxylic acid |
| 305 | N-(2-(3-(5-chlorothiophen-2-yl)methyl)ureido)thiazol-4-yl)methyl)-N-methyl-2-(pyrrolidin-1-yl)nicotinamide | C21H23ClN6O2S2 | 491.0 | 491 | 2 | Int. 29 | 2-(pyrrolidin-1-yl)nicotinic acid |
| 306 | N-(2-(3-(3-fluorobenzyl)ureido)thiazol-4-yl)methyl)-N,2,2-trimethyltetrahydro-2H-pyran-4-carboxamide | C21H27FN4O3S | 434.0 | 435 | 2 | Int. 5 | 2,2-dimethyltetrahydro-2H-pyran-4-carboxylic acid |
| 307 | N-(2-(3-(5-chlorothiophen-2-yl)methyl)ureido)thiazol-4-yl)methyl)-N,2,2-trimethyltetrahydro-2H-pyran-4-carboxamide | C19H25ClN4O3S2 | 457.0 | 457 | 2 | Int. 29 | 2,2-dimethyltetrahydro-2H-pyran-4-carboxamide |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 308 | N-((2-(3-((1H-indol-5-yl)methyl)ureido)thiazol-4-yl)methyl)-N,3,5-trimethylisoxazole-4-carboxamide | $C_{21}H_{22}N_6O_3S$ | 438.5 | 437 | 8 | Int. 18 | C-(1H-Indol-5-yl)-methylamine |
| 309 | N-((2-(3-(benzo[1,2,5]oxadiazol-5-ylmethyl)ureido)thiazol-4-yl)methyl)-N,3,5-trimethylisoxazole-4-carboxamide | $C_{19}H_{19}N_7O_4S$ | 441.5 | 440 | 8 | Int. 18 | C-Benzo[1,2,5]oxadiazol-5-yl-methylamine |
| 310 | N-((2-(3-(benzo[1,2,5]thiadiazol-5-ylmethyl)ureido)thiazol-4-yl)methyl)-N,3,5-trimethylisoxazole-4-carboxamide | $C_{19}H_{19}N_7O_3S_2$ | 457.5 | 456 | 8 | Int. 18 | C-Benzo[1,2,5]thiadiazol-5-yl-methylamine |
| 311 | 2-(4-(dimethylamino)phenyl)-N-(2-(3-(3-fluorobenzyl)ureido)thiazol-4-yl)methyl)-N-methylacetamide | $C_{23}H_{26}FN_5O_2S$ | 456.0 | 456 | 2 | Int. 5 | 2-(4-(dimethylamino)phenyl)acetic acid |
| 312 | N-((2-(3-(3-fluorobenzyl)ureido)thiazol-4-yl)methyl)-7-hydroxy-N-methyl-1,2,3,4-tetrahydroisoquinoline-3-carboxamide | $C_{23}H_{24}FN_5O_3S$ | 470.0 | 470 | 2 | Int. 5 | 7-hydroxy-1,2,3,4-tetrahydroisoquinoline-3-carboxylic acid |
| 313 | 3-(1H-benzoimidazol-2-yl)-N-((2-(3-(3-fluorobenzyl)ureido)thiazol-4-yl)methyl)-N-methylpropanamide | $C_{23}H_{23}FN_6O_2S$ | 466.0 | 467 | 2 | Int. 5 | 3-(1H-benzoimidazol-2-yl)propanoic acid |
| 314 | N-((2-(3-(3-fluorobenzyl)ureido)thiazol-4-yl)methyl)-N-methyl-2-(naphthalen-2-yl)acetamide | $C_{25}H_{23}FN_4O_2S$ | 462.0 | 463 | 2 | Int. 5 | 2-(naphthalen-2-yl)acetic acid |
| 315 | N-((2-(3-(3-fluorobenzyl)ureido)thiazol-4-yl)methyl)-2-(4-methoxy-3-methylphenyl)-N-methylacetamide | $C_{23}H_{25}FN_4O_3S$ | 456.0 | 457 | 2 | Int. 5 | 2-(4-methoxy-3-methylphenyl)acetic acid |
| 316 | 2-amino-3-(benzyloxy)-N-((2-(3-(3-fluorobenzyl)ureido)thiazol-4-yl)methyl)-N-methylpropanamide | $C_{23}H_{26}FN_5O_3S$ | 472.0 | 472 | 2 | Int. 5 | 2-amino-3-(benzyloxy)propanoic acid |
| 317 | N-((2-(3-(3-fluorobenzyl)ureido)thiazol-4-yl)methyl)-N-methyl-1,4-dioxo-1,2,3,4-tetrahydrophthalazine-6-carboxamide | $C_{22}H_{19}FN_6O_4S$ | 482.0 | 483 | 2 | Int. 5 | 1,4-dioxo-1,2,3,4-tetrahydrophthalazine-6-carboxylic acid |
| 318 | N-((2-(3-(3-fluorobenzyl)ureido)thiazol-4-yl)methyl)-N-methyl-6-(1H-1,2,4-triazol-1-yl)nicotinamide | $C_{21}H_{19}FN_8O_2S$ | 466.0 | 467 | 2 | Int. 5 | 6-(1H-1,2,4-triazol-1-yl)nicotinic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 319 | 2-(2,4-dioxo-3,4-dihydropyrimidin-1(2H)-yl)-N-((2-(3-(3-fluorobenzyl)ureido)thiazol-4-yl)methyl)-N-methylacetamide | $C_{19}H_{19}FN_6O_4S$ | 446.0 | 447 | 2 | Int. 5 | 2-(2,4-dioxo-3,4-dihydropyrimidin-1(2H)-yl)acetic acid |
| 320 | N-((2-(3-(5-chlorothiophen-2-yl)methyl)ureido)thiazol-4-yl)methyl)-N-methyl-1,4-dioxo-1,2,3,4-tetrahydrophthalazine-6-carboxamide | $C_{20}H_{17}ClN_6O_4S_2$ | 505.0 | 505 | 2 | Int. 29 | 1,4-dioxo-1,2,3,4-tetrahydrophthalazine-6-carboxylic acid |
| 321 | N2-((2-(3-(5-chlorothiophen-2-yl)methyl)ureido)thiazol-4-yl)methyl)-4-hydroxy-N2-methylpyrrolidine-1,2-dicarboxamide | $C_{17}H_{21}ClN_6O_4S_2$ | 473.0 | 473 | 2 | Int. 29 | 1-carbamoyl-4-hydroxypyrrolidine-2-carboxylic acid |
| 322 | N-((2-(3-(5-chlorothiophen-2-yl)methyl)ureido)thiazol-4-yl)methyl)-N,1-dimethyl-5-nitro-1H-pyrazole-4-carboxamide | $C_{16}H_{16}ClN_7O_4S_2$ | 470.0 | 470 | 2 | Int. 29 | 1-methyl-5-nitro-1H-pyrazole-4-carboxylic acid |
| 323 | (S)-3,3-difluoro-N-((2-(3-(3-fluorobenzyl)ureido)thiazol-4-yl)methyl)-N-methyltetrahydrofuran-2-carboxamide | $C_{18}H_{19}F_3N_4O_3S$ | 428.0 | 429 | 2 | Int. 5 | (S)-3,3-difluorotetrahydrofuran-2-carboxylic acid |
| 324 | N-((2-(3-(3-fluorobenzyl)ureido)thiazol-4-yl)methyl)-N-methylchroman-2-carboxamide | $C_{23}H_{23}FN_4O_3S$ | 454.0 | 455 | 2 | Int. 5 | Chroman-2-carboxylic acid |
| 325 | 4-(3,5-dimethyl-1H-pyrazol-4-yl)-N-((2-(3-(3-fluorobenzyl)ureido)thiazol-4-yl)methyl)-N-methylbenzamide | $C_{25}H_{25}FN_6O_2S$ | 492.0 | 493 | 2 | Int. 5 | 4-(3,5-dimethyl-1H-pyrazol-4-yl)benzoic acid |
| 326 | N-((2-(3-(3-fluorobenzyl)ureido)thiazol-4-yl)methyl)-N-methylpent-4-ynamide | $C_{18}H_{19}FN_4O_2S$ | 374.0 | 375 | 2 | Int. 5 | Pent-4-ynoic acid |
| 327 | N-((2-(3-(3-fluorobenzyl)ureido)thiazol-4-yl)methyl)-N,2-dimethyl-1,2,3,4-tetrahydroisoquinoline-3-carboxamide | $C_{24}H_{26}FN_5O_2S$ | 468.0 | 468 | 2 | Int. 5 | 2-methyl-1,2,3,4-tetrahydroisoquinoline-3-carboxylic acid |
| 328 | (S)-2-amino-N-((2-(3-(3-fluorobenzyl)ureido)thiazol-4-yl)methyl)-N-methyl-3-(pyridin-4-yl)propanamide | $C_{21}H_{23}FN_6O_2S$ | 442.0 | 443 | 2; 6 | Int. 5 | N-Fmoc-(S)-2-amino-3-(pyridin-4-yl)propanoic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 329 | cis-N-((2-(3-(3-fluorobenzyl) ureido)thiazol-4-yl)methyl)-3-methoxy-N-methyltetrahydrofuran-2-carboxamide | $C_{19}H_{23}FN_4O_4S$ | 422.0 | 423 | 2 | Int. 5 | cis-3-methoxytetrahydrofuran-2-carboxylic acid (Int. 56) |
| 330 | 1-cyano-N-((2-(3-(3-fluorobenzyl)ureido)thiazol-4-yl)methyl)-N-methylcyclopropane carboxamide | $C_{18}H_{18}FN_5O_2S$ | 387.0 | 388 | 2 | Int. 5 | 1-cyanocyclopropane carboxylic acid |
| 331 | N-((2-(3-(3-fluorobenzyl) ureido)thiazol-4-yl)methyl)-N-methylpropiolamide | $C_{16}H_{15}FN_4O_2S$ | 346.0 | 347 | 2 | Int. 5 | propiolic acid |
| 332 | N-((2-(3-(1H-indol-2-yl)methyl)ureido)thiazol-4-yl)methyl)-N,3,5-trimethylisoxazole-4-carboxamide | $C_{21}H_{22}N_6O_3S$ | 438.5 | 439 | 8 | Int. 18 | C-(1H-Indol-2-yl)-methylamine |
| 333 | N-((2-(benzooxazol-6-ylmethyl)ureido)thiazol-4-yl)methyl)-N,3,5-trimethylisoxazole-4-carboxamide | $C_{20}H_{20}N_6O_4S$ | 440.5 | 439 | 8 | Int. 18 | C-Benzooxazol-6-yl-methylamine [Int. 57] |
| 334 | 2-ethoxy-N-((2-(3-(3-fluorobenzyl)ureido)thiazol-4-yl)methyl)-N-methylpropanamide | $C_{18}H_{23}FN_4O_3S$ | 394.0 | 395 | 2 | Int. 5 | 2-ethoxypropanoic acid |
| 335 | N-((2-(3-(3-fluorobenzyl)ureido)thiazol-4-yl)methyl)-2-(4-methoxyphenoxy)-N-methylpropanamide | $C_{23}H_{25}FN_4O_4S$ | 472.0 | 473 | 2 | Int. 5 | 2-(4-methoxyphenoxy) propanoic acid |
| 336 | 2-(cyclopropylmethoxy)-N-((2-(3-(3-fluorobenzyl) ureido)thiazol-4-yl)methyl)-N-methylpropanamide | $C_{20}H_{25}FN_4O_3S$ | 420.0 | 421 | 2 | Int. 5 | 2-(cyclopropylmethoxy) propanoic acid |
| 337 | 2,5-diamino-N-((2-(3-(3-fluorobenzyl)ureido)thiazol-4-yl)methyl)-N-methylpentanamide | $C_{18}H_{25}FN_6O_2S$ | 408.0 | 409 | 2; 1 | Int. 5 | N,N'-di-(tert-butoxylcarbony)-2,5-diaminopentanoic acid |
| 338 | N-((2-(3-(3-fluorobenzyl) ureido)thiazol-4-yl)methyl)-N-methyl-2-(2-phenoxyethoxy) propanamide | $C_{24}H_{27}FN_4O_4S$ | 486.0 | 487 | 2 | Int. 5 | 2-(2-phenoxyethoxy) propanoic acid |
| 339 | 2-cyclopropyl-N-((2-(3-(3-fluorobenzyl)ureido)thiazol-4-yl)methyl)-N-methylacetamide | $C_{18}H_{21}FN_4O_2S$ | 376.0 | 377 | 2 | Int. 5 | 2-cyclopropylacetic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 340 | N,3,5-trimethyl-N-((2-(3-(4-nitrobenzyl)ureido)thiazol-4-yl)methyl)isoxazole-4-carboxamide | $C_{19}H_{20}N_6O_5S$ | 444.0 | 445 | 8 | Int. 18 | 4-nitrobenzyl amine |
| 341 | N,3,5-trimethyl-N-((2-(3-(3-nitrobenzyl)ureido)thiazol-4-yl)methyl)isoxazole-4-carboxamide | $C_{19}H_{20}N_6O_5S$ | 444.0 | 445 | 8 | Int. 18 | 3-nitrobenzyl amine |
| 342 | 3-ethyl-N-((2-(3-(3-fluorobenzyl)ureido)thiazol-4-yl)methyl)-N-methyloxetane-3-carboxamide | $C_{19}H_{23}FN_4O_3S$ | 406.0 | 407 | 2 | Int. 5 | 3-Ethyloxetane-3-carboxylic acid (Int. 55) |
| 343 | 2-(2,2-difluoroethoxy)-N-((2-(3-(3-fluorobenzyl)ureido)thiazol-4-yl)methyl)-N-methylpropanamide | $C_{18}H_{21}F_3N_4O_3S$ | 430.0 | 431 | 2 | Int. 5 | 2-(2,2-difluoroethoxy)propanoic acid |
| 344 | N-((2-(3-(3-fluorobenzyl)ureido)thiazol-4-yl)methyl)-2-(4-fluorobenzyloxy)propanamide | $C_{23}H_{24}F_2N_4O_3S$ | 474.0 | 475 | 2 | Int. 5 | 2-(4-fluorobenzyloxy)propanoic acid |
| 345 | 2-(2,2,2-trifluoroethoxy)-N-((2-(3-(3-fluorobenzyl)ureido)thiazol-4-yl)methyl)-N-methylpropanamide | $C_{18}H_{20}F_4N_4O_3S$ | 448.0 | 449 | 2 | Int. 5 | 2-(2,2,2-trifluoroethoxy)propanoic acid |
| 346 | N-((2-(3-(3-fluorobenzyl)ureido)thiazol-4-yl)methyl)-2-(prop-2-ynyloxy)propanamide | $C_{19}H_{21}FN_4O_3S$ | 404.0 | 405 | 2 | Int. 5 | 2-(prop-2-ynyloxy)propanoic acid |
| 347 | N-((2-(3-(3-fluorobenzyl)ureido)thiazol-4-yl)methyl)-2-(5-methylisoxazol-3-yl)methoxy)propanamide | $C_{21}H_{24}FN_5O_4S$ | 462.0 | 462 | 2 | Int. 5 | 2-((5-methylisoxazol-3-yl)methoxy)propanamide |
| 348 | N-((2-(3-(3-fluorobenzyl)ureido)thiazol-4-yl)methyl)-2-(1-methylpyrrolidin-3-yloxy)propanamide | $C_{21}H_{28}FN_5O_3S$ | 450.0 | 450 | 2 | Int. 5 | 2-(1-methylpyrrolidin-3-yloxy)propanoic acid |
| 349 | N-((2-(3-(3-fluorobenzyl)ureido)thiazol-4-yl)methyl)-2-(2-hydroxyethoxy)propanamide | $C_{18}H_{23}FN_4O_4S$ | 410.0 | 411 | 2 | Int. 5 | 2-(2-hydroxyethoxy)propanamide |
| 350 | N-(2-(3-(5-chlorothiophen-2-yl)methyl)ureido)thiazol-4-yl)methyl)-N-methylcyclopentane carboxamide | $C_{17}H_{21}ClN_4O_2S_2$ | 413.0 | 413 | 2 | Int. 29 | Cyclopentane carboxylic acid |
| 351 | N-(2-(3-((5-chlorothiophen-2-yl)methyl)ureido)thiazol-4-yl)methyl)-1-hydroxy-N-methylcyclopropane carboxamide | $C_{15}H_{17}ClN_4O_3S_2$ | 401.0 | 401 | 2 | Int. 29 | 1-hydroxycyclopropane carboxylic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 352 | N-((2-(3-((5-chlorothiophen-2-yl)methyl)ureido)thiazol-4-yl)methyl)-N-methylcyclohexane carboxamide | $C_{18}H_{23}ClN_4O_2S_2$ | 427.0 | 427 | 2 | Int. 29 | Cyclohexane carboxylic acid |
| 353 | 1-cyano-N-((5-fluoro-2-(3-(3-fluorobenzyl)ureido)thiazol-4-yl)methyl)-N-methylcyclopropane carboxamide | $C_{18}H_{17}F_2N_5O_2S$ | 405.0 | 406 | 2 | Int. 5 | 1-cyanocyclopropane carboxylic acid |
| 354 | N-((2-(3-(3-fluorobenzyl)ureido)thiazol-4-yl)methyl)-N-methylcyclopentane carboxamide | $C_{19}H_{23}FN_4O_2S$ | 390.0 | 391 | 2 | Int. 5 | Cyclopentane carboxylic acid |
| 355 | N-((2-(3-(3-fluorobenzyl)ureido)thiazol-4-yl)methyl)-N,2-dimethylcyclohexane carboxamide | $C_{21}H_{27}FN_4O_2S$ | 418.0 | 419 | 2 | Int. 5 | 2-methylcyclohexane carboxylic acid |
| 356 | N-((2-(3-(3-fluorobenzyl)ureido)thiazol-4-yl)methyl)-N-methylcyclohexane carboxamide | $C_{20}H_{25}FN_4O_2S$ | 404.0 | 405 | 2 | Int. 5 | Cyclohexane carboxylic acid |
| 357 | N-((2-(3-(3-fluorobenzyl)ureido)thiazol-4-yl)methyl)-N-methyl-2-oxo-2,3-dihydrobenzoxazole-6-carboxamide | $C_{21}H_{18}FN_5O_4S$ | 455.0 | 456 | 2 | Int. 5 | 2-oxo-2,3-dihydrobenzoxazole-6-carboxamide |
| 358 | 3,3,3-trifluoro-N-(2-(3-(3-fluorobenzyl)ureido)thiazol-4-yl)methyl)-N-methylpropanamide | $C_{16}H_{16}F_4N_4O_2S$ | 404.0 | 405 | 2 | Int. 5 | 3,3,3-trifluoropropanoic acid |
| 359 | N-((2-(3-(3-fluorobenzyl)ureido)thiazol-4-yl)methyl)-2-hydroxy-N,2-dimethylpropanamide | $C_{17}H_{21}FN_4O_3S$ | 380.0 | 381 | 2 | Int. 5 | 2-hydroxy-2-methylpropanoic acid |
| 360 | 2,3-cis-N-(2-(3-(3-fluorobenzyl)ureido)thiazol-4-yl)methyl)-N,3-dimethyltetrahydrofuran-2-carboxamide | $C_{19}H_{23}FN_4O_3S$ | 406.0 | 407 | 2 | Int. 5 | cis-3-methyl-tetrahydrofuran-2-carboxylic acid (Int. 54) |
| 361 | (5R)-N-(2-(3-(3-fluorobenzyl)ureido)thiazol-4-yl)methyl)-5-(hydroxymethyl)-N-methyltetrahydrofuran-2-carboxamide | $C_{19}H_{23}FN_4O_4S$ | 422.0 | 423 | 2; 11 | Int. 5 | (R)-5-(tert-Butyl-diphenyl-silanyloxymethyl)-tetrahydro-furan-2-carboxylic acid (Int. 53) |
| 362 | N-((2-(3-((5-chlorothiophen-2-yl)methyl)ureido)thiazol-4-yl)methyl)-2-hydroxy-N,2-dimethylpropanamide | $C_{15}H_{19}ClN_4O_3S_2$ | 403.0 | 403 | 2 | Int. 5 | 2-hydroxy-2-methylpropanoic acid |

TABLE 1-continued

Preparation of Thiazolyl Amides

| EX # | NAME | MOL FORMULA | MOL WEIGHT | MASS | METHOD | Starting Material 1 (SM1) | Starting Material 2 (SM2) |
|---|---|---|---|---|---|---|---|
| 363 | N-((2-(3-(5-chlorothiophen-2-yl)methyl)ureido)thiazol-4-yl)methyl)-N-methyl-2-oxo-2,3-dihydrobenzoxazole-6-carboxamide | $C_{19}H_{16}ClN_5O_4S_2$ | 478.0 | 478 | 2 | Int. 5 | 2-oxo-2,3-dihydrobenzoxazole-6-carboxamide |
| 364 | (S)-N-((2-(3-((5-chlorothiophen-2-yl)methyl)ureido)thiazol-4-yl)methyl)-2-(4-hydroxy-2-oxopyrrolidin-1-yl)-N-methylacetamide | $C_{17}H_{20}ClN_5O_4S_2$ | 458.0 | 458 | 2 | Int. 5 | (S)-2-(4-hydroxy-2-oxopyrrolidin-1-yl)acetic acid |
| 365 | (R)-N-((2-(3-(benzo[1,2,5]oxadiazol-5-ylmethyl)ureido)thiazol-4-yl)methyl)-N-methyltetrahydrofuran-2-carboxamide | $C_{18}H_{20}N_6O_4S$ | 416.0 | 417 | 7 | Int. 52 | 2,1,3-Benzoxadiazole-5-methanamine hydrochloride [RN 321330-19-2] |
| 366 | (R)-N-((2-(3-(7-chlorobenzo[1,3]dioxol-5-yl)methyl)ureido)thiazol-4-yl)methyl)-N-methyltetrahydrofuran-2-carboxamide | $C_{19}H_{21}ClN_4O_5S$ | 453.0 | 453 | 7 | Int. 52 | 5-Chloropiperonylamine (Int. 66) |
| 367 | 2,3,3,3-tetrafluoro-N-((2-(3-(3-fluorobenzyl)ureido)thiazol-4-yl)methyl)-N-methylpropanamide | $C_{16}H_{15}F_5N_4O_2S$ | 422.0 | 423 | 2 | Int. 5 | 2,3,3,3-tetrafluoropropanoic acid |
| 368 | N-((2-(3-(3-fluorobenzyl)ureido)thiazol-4-yl)methyl)-N-methylcyclopropane carboxamide | $C_{17}H_{19}FN_4O_2S$ | 362.0 | 363 | 2 | Int. 5 | Cyclopropane carboxylic acid |
| 369 | N-((2-(3-(3-fluorobenzyl)ureido)thiazol-4-yl)methyl)-N-methylcyclopropane-1,1-dicarboxamide | $C_{18}H_{20}FN_5O_3S$ | 405.0 | 406 | 2 | Int. 5 | 1-carbamoylcyclopropane carboxylic acid |
| 370 | N-((2-(3-(3-fluorobenzyl)ureido)thiazol-4-yl)methyl)-N,2-dimethylcyclopropane carboxamide | $C_{18}H_{21}FN_4O_2S$ | 376.0 | 377 | 2 | Int. 5 | 2-methylcyclopropane carboxylic acid |
| 371 | (S)-N-((2-(3-(3-fluorobenzyl)ureido)thiazol-4-yl)methyl)-2-(4-hydroxy-2-oxopyrrolidin-1-yl)-N-methylacetamide | $C_{19}H_{22}FN_5O_4S$ | 435.0 | 436 | 2 | Int. 5 | (S)-2-(4-hydroxy-2-oxopyrrolidin-1-yl)acetic acid |

TABLE 2

| | | | | | | Starting | |
|---|---|---|---|---|---|---|---|
| EX# | NAME | MOL FORMULA | MOL WEIGHT | MASS | METHOD | Material 1 (SM1) | Starting Material 2 (SM2) |
| 372 | N-((5-(3-(3-fluorobenzyl) ureido)-1,2,4-thiadiazol-3-yl)methyl)-N,3,5-trimethylisoxazole-4-carboxamide | C18H19FN6O3S | 418.5 | 419 | 2 | Int. 68 | 3,5-Dimethylisoxazole-4-carboxylic acid |
| 373 | N-((5-(3-(3-fluorobenzyl) ureido)-1,2,4-thiadiazol-3-yl)methyl)-N,2,6-trimethylbenzamide | C21H22FN5O2S | 427.5 | 428 | 2 | Int. 68 | 2,6-Dimethylbenzoic acid |
| 374 | N-((5-(3-(3-fluorobenzyl) ureido)-1,2,4-thiadiazol-3-yl)methyl)-N,3-dimethylisonicotinamide | C19H19FN6O2S | 414.5 | 415 | 2 | Int. 68 | 3-Methyl-nicotinic acid |
| 375 | N-((5-(3-(3-fluorobenzyl) ureido)-1,2,4-thiadiazol-3-yl)methyl)-N,3-dimethylpyrazine-2-carboxamide | C18H18FN7O2S | 415.5 | 416 | 2 | Int. 68 | 3-Methylpyrazine-2-carboxylic acid |
| 376 | 1,3,5-Trimethyl-1H-pyrazole-4-carboxylic acid {5-[3-(3-fluoro-benzyl)-ureido]-[1,2,4]thiadiazol-3-ylmethyl}-methyl-amide | $C_{19}H_{22}FN_7O_2S$ | 431.5 | 432 | 2 | Int. 68 | 1,3,5-Trimethyl-1H-pyrazole-4-carboxylic acid |
| 377 | 5-Chloro-1,3-dimethyl-1H-pyrazole-4-carboxylic acid {5-[3-(3-fluoro-benzyl)-ureido]-[1,2,4]thiadiazol-3-ylmethyl}-methyl-amide | $C_{18}H_{19}ClFN_7O_2S$ | 451.9 | 452 | 2 | Int. 68 | 5-Chloro-1,3-dimethyl-1H-pyrazole-4-carboxylic acid |
| 378 | 5-Isopropyl-3-methyl-isoxazole-4-carboxylic acid {5-[3-(3-fluoro-benzyl)-ureido]-[1,2,4]thiadiazol-3-ylmethyl}-methyl-amide | $C_{20}H_{23}FN_6O_3S$ | 446.5 | 447 | 2 | Int. 68 | 5-Isopropyl-3-methyl-isoxazole-4-carboxylic acid |
| 379 | 1,3,5-Trimethyl-1H-pyrazolo[4,3-b]pyridine-7-carboxylic acid {5-[3-(5-chloro-thiophen-2-ylmethyl)-ureido]-[1,2,4]thiadiazol-3-ylmethyl}-methyl-amide | $C_{20}H_{21}ClN_8O_2S_2$ | 505.0 | 505 | 2 | Int. 69 | 1,3,5-Trimethyl-1H-pyrazolo[4,3-b]pyridine-7-carboxylic acid |
| 380 | 1-Methyl-5-pyrrol-1-yl-1H-pyrazole-4-carboxylic acid {5-[3-(3-fluoro-benzyl)-ureido]-[1,2,4]thiadiazol-3-ylmethyl}-methyl-amide | $C_{21}H_{21}FN_8O_2S$ | 468.5 | 469 | 2 | Int. 68 | 1-Methyl-5-pyrrol-1-yl-1H-pyrazole-4-carboxylic acid |
| 381 | 3-Methyl-4-oxo-3,4-dihydro-phthalazine-1-carboxylic acid {5-[3-(3-fluoro-benzyl)-ureido]-[1,2,4]thiadiazol-3-ylmethyl}-methyl-amide | $C_{22}H_{20}FN_7O_3S$ | 481.5 | 482 | 2 | Int. 68 | 3-Methyl-4-oxo-3,4-dihydro-phthalazine-1-carboxylic acid |
| 382 | 2,4-Dimethyl-6-oxo-6H-pyran-3-carboxylic acid {5-[3-(3-fluoro-benzyl)-ureido]-[1,2,4]thiadiazol-3-ylmethyl}-methyl-amide | $C_{20}H_{20}FN_5O_4S$ | 445.5 | 446 | 2 | Int. 68 | 2,4-Dimethyl-6-oxo-6H-pyran-3-carboxylic acid |
| 383 | 3,6-Dimethyl-isoxazolo[5,4-b]pyridine-4-carboxylic acid {5-[3-(3-fluoro-benzyl)-ureido]-[1,2,4]thiadiazol-3-ylmethyl}-methyl-amide | $C_{21}H_{20}FN_7O_3S$ | 469.5 | 470 | 2 | Int. 68 | 3,6-Dimethyl-isoxazolo[5,4-b]pyridine-4-carboxylic acid |
| 384 | 2-(5,7-Dimethyl-[1,2,4]triazolo[1,5-a]pyrimidin-6-yl)-N-{5-[3-(3-fluoro-benzyl)-ureido]-[1,2,4]thiadiazol-3-ylmethyl}-N-methyl-acetamide | $C_{21}H_{22}FN_9O_2S$ | 483.5 | 484 | 2 | Int. 68 | 2-(5,7-Dimethyl-[1,2,4]triazolo[1,5-a]pyrimidin-6-yl)-acetic acid |
| 385 | 3,6-Dimethyl-4-oxo-3,4-dihydro-furo[2,3-d]pyrimidine-5-carboxylic acid {5-[3-(3-fluoro-benzyl)-ureido]-[1,2,4]thiadiazol-3-ylmethyl}-methyl-amide | $C_{21}H_{20}FN_7O_4S$ | 485.5 | 486 | 2 | Int. 68 | 3,6-Dimethyl-4-oxo-3,4-dihydro-furo[2,3-d]pyrimidine-5-carboxylic acid |

TABLE 2-continued

Preparation of Thiadiazolyl Amides

| EX# | NAME | MOL FORMULA | MOL WEIGHT | MASS | METHOD | Starting Material 1 (SM1) | Starting Material 2 (SM2) |
|---|---|---|---|---|---|---|---|
| 386 | N-{5-[3-(3-Fluoro-benzyl)-ureido]-[1,2,4]thiadiazol-3-ylmethyl}-N-methyl-6-[1,2,4]triazol-1-yl-nicotinamide | $C_{20}H_{18}FN_9O_2S$ | 467.5 | 468 | 2 | Int. 68 | [1,2,4]triazol-1-yl-nicotinic acid |
| 387 | 1-(2-Methoxy-ethyl)-6-oxo-1,6-dihydro-pyridazine-3-carboxylic acid {5-[3-(3-fluoro-benzyl)-ureido]-[1,2,4]thiadiazol-3-ylmethyl}-methyl-amide | $C_{20}H_{22}FN_7O_4S$ | 475.5 | 476 | 2 | Int. 68 | 1-(2-Methoxy-ethyl)-6-oxo-1,6-dihydro-pyridazine-3-carboxylic acid |
| 388 | 1-Methyl-4-sulfamoyl-1H-pyrrole-2-carboxylic acid {5-[3-(5-chloro-thiophen-2-ylmethyl)-ureido]-[1,2,4]thiadiazol-3-ylmethyl}-methyl-amide | $C_{16}H_{18}ClN_7O_4S_3$ | 504.0 | 504 | 2 | Int. 69 | 1-Methyl-4-sulfamoyl-1H-pyrrole-2-carboxylic acid |
| 389 | N-{5-[3-(5-Chloro-thiophen-2-ylmethyl)-ureido]-[1,2,4]thiadiazol-3-ylmethyl}-2-(5,7-dimethyl-[1,2,4]triazolo[1,5-a]pyrimidin-6-yl)-N-methyl-acetamide | $C_{19}H_{20}ClN_9O_2S_2$ | 506.0 | 506 | 2 | Int. 69 | (5,7-Dimethyl-[1,2,4]triazolo[1,5-a]pyrimidin-6-yl)-acetic acid |
| 390 | 3,6-Dimethyl-4-oxo-3,4-dihydro-furo[2,3-d]pyrimidine-5-carboxylic acid{5-[3-(5-chloro-thiophen-2-ylmethyl)-ureido]-[1,2,4]thiadiazol-3-ylmethyl}-methyl-amide | $C_{19}H_{18}ClN_7O_4S_2$ | 508.0 | 508 | 2 | Int. 69 | 3,6-Dimethyl-4-oxo-3,4-dihydro-furo[2,3-d]pyrimidine-5-carboxylic acid |
| 391 | (R)-Tetrahydro-furan-2-carboxylic acid {5-[3-(3-fluoro-benzyl)-ureido]-[1,2,4]thiadiazol-3-ylmethyl}-methyl-amide | $C_{17}H_{20}FN_5O_3S$ | 393.4 | 394 | 2; 10 | Int. 70 | (R)-Tetrahydro-furan-2-carboxylic acid |
| 392 | 1,3,5-Trimethyl-1H-pyrazolo[4,3-b]pyridine-7-carboxylic acid {5-[3-(3-fluoro-benzyl)-ureido]-[1,2,4]thiadiazol-3-ylmethyl}-methyl-amide | $C_{22}H_{23}FN_8O_2S$ | 482.5 | 483 | 2 | Int. 68 | 1,3,5-Trimethyl-1H-pyrazolo[4,3-b]pyridine-7-carboxylic acid |
| 393 | 1-Methyl-3-trifluoromethyl-1H-pyrazole-4-carboxylic acid {5-[3-(5-chloro-thiophen-2-ylmethyl)-ureido]-[1,2,4]thiadiazol-3-ylmethyl}-methyl-amide | $C_{16}H_{15}ClF_3N_7O_2S_2$ | 493.9 | 494 | 2 | Int. 69 | 1-Methyl-3-trifluoromethyl-1H-pyrazole-4-carboxylic acid |
| 394 | N-{5-[3-(5-Chloro-thiophen-2-ylmethyl)-ureido]-[1,2,4]thiadiazol-3-ylmethyl}-3-cyano-2-hydroxy-6,N-dimethyl-isonicotinamide | $C_{18}H_{16}ClN_7O_3S_2$ | 478.0 | 478 | 2 | Int. 69 | 3-cyano-2-hydroxy-6,N-dimethyl-isonicotinic acid |
| 395 | 6-Chloro-3-oxo-2,3-dihydro-pyridazine-4-carboxylic acid {5-[3-(3-fluoro-benzyl)-ureido]-[1,2,4]thiadiazol-3-ylmethyl}-methyl-amide | $C_{17}H_{15}ClFN_7O_3S$ | 451.9 | 452 | 2 | Int. 68 | 6-Chloro-3-oxo-2,3-dihydro-pyridazine-4-carboxylic acid |
| 396 | 1-Methyl-6-oxo-1,4,5,6-tetrahydro-pyridazine-3-carboxylic acid {5-[3-(3-fluoro-benzyl)-ureido]-[1,2,4]thiadiazol-3-ylmethyl}-methyl-amide | $C_{18}H_{20}FN_7O_3S$ | 433.5 | 434 | 2 | Int. 68 | 1-Methyl-6-oxo-1,4,5,6-tetrahydro-pyridazine-3-carboxylic acid |
| 397 | 7-Chloro-benzo[1,3]dioxole-5-carboxylic acid {5-[3-(3-fluoro-benzyl)-ureido]-[1,2,4]thiadiazol-3-ylmethyl}-methyl-amide | $C_{20}H_{17}ClFN_5O_4S$ | 477.9 | 478 | 2 | Int. 68 | 7-Chloro-benzo[1,3]dioxole-5-carboxylic acid |
| 398 | 5-Methyl-4-oxo-3,4-dihydro-thieno[2,3-d]pyrimidine-6-carboxylic acid {5-[3-(3-fluoro-benzyl)-ureido]-[1,2,4]thiadiazol-3-ylmethyl}-methyl-amide | $C_{20}H_{18}FN_7O_3S_2$ | 487.5 | 488 | 2 | Int. 68 | 5-Methyl-4-oxo-3,4-dihydro-thieno[2,3-d]pyrimidine-6-carboxylic acid |

TABLE 2-continued

Preparation of Thiadiazolyl Amides

| EX# | NAME | MOL FORMULA | MOL WEIGHT | MASS | METHOD | Starting Material 1 (SM1) | Starting Material 2 (SM2) |
|---|---|---|---|---|---|---|---|
| 399 | 1-Methyl-5-pyrrol-1-yl-1H-pyrazole-4-carboxylic acid {5-[3-(5-chloro-thiophen-2-ylmethyl)-ureido]-[1,2,4]thiadiazol-3-ylmethyl}-methyl-amide | $C_{19}H_{19}ClN_8O_2S_2$ | 491.0 | 491 | 2 | Int. 69 | 1-Methyl-5-pyrrol-1-yl-1H-pyrazole-4-carboxylic acid |
| 400 | 1-Methyl-6-oxo-1,4,5,6-tetrahydro-pyridazine-3-carboxylic acid {5-[3-(5-chloro-thiophen-2-ylmethyl)-ureido]-[1,2,4]thiadiazol-3-ylmethyl}-methyl-amide | $C_{16}H_{18}ClN_7O_3S_2$ | 455.9 | 456 | 2 | Int. 69 | 1-Methyl-6-oxo-1,4,5,6-tetrahydro-pyridazine-3-carboxylic acid |
| 401 | 3-Methyl-4-oxo-3,4-dihydro-phthalazine-1-carboxylic acid {5-[3-(5-chloro-thiophen-2-ylmethyl)-ureido]-[1,2,4]thiadiazol-3-ylmethyl}-methyl-amide | $C_{20}H_{18}ClN_7O_3S_2$ | 504.0 | 504 | 2 | Int. 69 | 3-Methyl-4-oxo-3,4-dihydro-phthalazine-1-carboxylic acid |
| 402 | 2,4-Dimethyl-6-oxo-6H-pyran-3-carboxylic acid {5-[3-(5-chloro-thiophen-2-ylmethyl)-ureido]-[1,2,4]thiadiazol-3-ylmethyl}-methyl-amide | $C_{18}H_{18}ClN_5O_4S_2$ | 468.0 | 468 | 2 | Int. 69 | 2,4-Dimethyl-6-oxo-6H-pyran-3-carboxylic acid |
| 403 | 5-Methyl-4-oxo-3,4-dihydro-thieno[2,3-d]pyrimidine-6-carboxylic acid {5-[3-(5-chloro-thiophen-2-ylmethyl)-ureido]-[1,2,4]thiadiazol-3-ylmethyl}-methyl-amide | $C_{18}H_{16}ClN_7O_3S_3$ | 510.0 | 510 | 2 | Int. 69 | 5-Methyl-4-oxo-3,4-dihydro-thieno[2,3-d]pyrimidine-6-carboxylic acid |
| 404 | N-{5-[3-(5-Chloro-thiophen-2-ylmethyl)-ureido]-[1,2,4]thiadiazol-3-ylmethyl}-N-methyl-6-[1,2,4]triazol-1-yl-nicotinamide | $C_{18}H_{16}ClN_9O_2S_2$ | 490.0 | 490 | 2 | Int. 69 | 6-[1,2,4]triazol-1-yl-nicotinic acid |
| 405 | 1-(2-Methoxy-ethyl)-6-oxo-1,6-dihydro-pyridazine-3-carboxylic acid {5-[3-(5-chloro-thiophen-2-ylmethyl)-ureido]-[1,2,4]thiadiazol-3-ylmethyl}-methyl-amide | $C_{18}H_{20}ClN_7O_4S_2$ | 498.0 | 498 | 2 | Int. 69 | 1-(2-Methoxy-ethyl)-6-oxo-1,6-dihydro-pyridazine-3-carboxylic acid |
| 406 | N-{5-[3-(5-Chloro-thiophen-2-ylmethyl)-ureido]-[1,2,4]thiadiazol-3-ylmethyl}-2,2-difluoro-N-methyl-2-phenyl-acetamide | $C_{18}H_{16}ClF_2N_5O_2S_2$ | 471.9 | 472 | 2 | Int. 69 | Difluoro-phenyl-acetic acid |
| 407 | (R)-Tetrahydro-furan-2-carboxylic acid [5-(3-benzo[1,2,5]oxadiazol-5-ylmethyl-ureido)-[1,2,4]thiadiazol-3-ylmethyl]-methyl-amide | $C_{17}H_{19}N_7O_4S$ | 417.5 | 418 | 2 | Int. 3 | 2,1,3-Benzoxadiazole-5-methanamine hydrochloride [RN 321330-19-2] |
| 408 | 3,5-Dimethyl-1H-pyrazole-4-carboxylic acid {5-[3-(3-fluoro-benzyl)-ureido]-[1,2,4]thiadiazol-3-ylmethyl}-methyl-amide | $C_{18}H_{20}FN_7O_2S$ | 417.5 | 418 | 2; 10 | Int. 70 | 3,5-Dimethyl-1H-pyrazole-4-carboxylic acid |
| 409 | 3,5-Dimethyl-pyridazine-4-carboxylic acid {5-[3-(3-fluoro-benzyl)-ureido]-[1,2,4]thiadiazol-3-ylmethyl}-methyl-amide | $C_{19}H_{20}FN_7O_2S$ | 429.5 | 430 | 2; 10 | Int. 70 | 3,5-Dimethyl-pyridazine-4-carboxylic acid |
| 410 | 5-Isopropyl-3-methyl-isoxazole-4-carboxylic acid {5-[3-(5-chloro-thiophen-2-ylmethyl)-ureido]-[1,2,4]thiadiazol-3-ylmethyl}-methyl-amide | $C_{18}H_{21}ClN_6O_3S_2$ | 469.0 | 469 | 2 | Int. 69 | 5-Isopropyl-3-methyl-isoxazole-4-carboxylic acid |
| 411 | N-{5-[3-(3-Fluoro-benzyl)-ureido]-[1,2,4]thiadiazol-3-ylmethyl}-2,N-dimethyl-5-sulfamoyl-benzamide | $C_{20}H_{21}FN_6O_4S_2$ | 492.6 | 493 | 2 | Int. 68 | 2-Methyl-5-sulfamoyl-benzoic acid |

TABLE 2-continued

Preparation of Thiadiazolyl Amides

| EX# | NAME | MOL FORMULA | MOL WEIGHT | MASS | METHOD | Starting Material 1 (SM1) | Starting Material 2 (SM2) |
|---|---|---|---|---|---|---|---|
| 412 | 1,1-Dioxo-tetrahydrothiophene-3-carboxylic acid {5-[3-(3-fluoro-benzyl)-ureido]-[1,2,4]thiadiazol-3-ylmethyl}-methyl-amide | $C_{17}H_{20}FN_5O_4S_2$ | 441.5 | 442 | 2 | Int. 68 | 1,1-Dioxo-tetrahydrothiophene-3-carboxylic acid |
| 413 | N-{5-[3-(5-Chloro-thiophen-2-ylmethyl)-ureido]-[1,2,4]thiadiazol-3-ylmethyl}-N-methyl-2-morpholin-4-yl-nicotinamide | $C_{20}H_{22}ClN_7O_3S_2$ | 508.0 | 508 | 2 | Int. 69 | 2-Morpholin-4-yl-nicotinic acid |
| 414 | 1-Phenyl-cyclobutane carboxylic acid {5-[3-(5-chloro-thiophen-2-ylmethyl)-ureido]-[1,2,4]thiadiazol-3-ylmethyl}-methyl-amide | $C_{21}H_{22}ClN_5O_2S_2$ | 476.0 | 476 | 2 | Int. 69 | 1-Phenyl-cyclobutane carboxylic acid |
| 415 | 4-Oxo-3,4-dihydro-phthalazine-1-carboxylic acid {5-[3-(5-chloro-thiophen-2-ylmethyl)-ureido]-[1,2,4]thiadiazol-3-ylmethyl}-methyl-amide | $C_{19}H_{16}ClN_7O_3S_2$ | 490.0 | 490 | 2 | Int. 69 | 4-Oxo-3,4-dihydro-phthalazine-1-carboxylic acid |
| 416 | 7-Chloro-benzo[1,3]dioxole-5-carboxylic acid {5-[3-(5-chloro-thiophen-2-ylmethyl)-ureido]-[1,2,4]thiadiazol-3-ylmethyl}-methyl-amide | $C_{18}H_{15}Cl_2N_5O_4S_2$ | 500.4 | 500 | 2 | Int. 69 | 7-Chloro-benzo[1,3]dioxole-5-carboxylic acid |
| 417 | 1-(4-Fluoro-phenyl)-cyclobutane carboxylic acid {5-[3-(5-chloro-thiophen-2-ylmethyl)-ureido]-[1,2,4]thiadiazol-3-ylmethyl}-methyl-amide | $C_{21}H_{21}ClFN_5O_2S_2$ | 494.0 | 494 | 2 | Int. 69 | 1-(4-Fluoro-phenyl)-cyclobutanecarboxylic acid |
| 418 | 1-Methyl-3-trifluoromethyl-1H-pyrazole-4-carboxylic acid {5-[3-(3-fluoro-benzyl)-ureido]-[1,2,4]thiadiazol-3-ylmethyl}-methyl-amide | $C_{18}H_{17}F_4N_7O_2S$ | 471.4 | 472 | 2 | Int. 68 | 1-Methyl-3-trifluoromethyl-1H-pyrazole-4-carboxylic acid |
| 419 | 5-Chloro-1,3-dimethyl-1H-pyrazole-4-carboxylic acid {5-[3-(5-chloro-thiophen-2-ylmethyl)-ureido]-[1,2,4]thiadiazol-3-ylmethyl}-methyl-amide | $C_{16}H_{17}Cl_2N_7O_2S_2$ | 474.4 | 474 | 2 | Int. 69 | 5-Chloro-1,3-dimethyl-1H-pyrazole-4-carboxylic acid |
| 420 | 1-Phenyl-cyclobutane carboxylic acid {5-[3-(3-fluoro-benzyl)-ureido]-[1,2,4]thiadiazol-3-ylmethyl}-methyl-amide | $C_{23}H_{24}FN_5O_2S$ | 453.5 | 454 | 2 | Int. 68 | 1-Phenyl-cyclobutane carboxylic acid |
| 421 | 4-Oxo-3,4-dihydro-phthalazine-1-carboxylic acid {5-[3-(3-fluoro-benzyl)-ureido]-[1,2,4]thiadiazol-3-ylmethyl}-methyl-amide | $C_{21}H_{18}FN_7O_3S$ | 467.5 | 468 | 2 | Int. 68 | 4-Oxo-3,4-dihydro-phthalazine-1-carboxylic acid |
| 422 | 1-(4-Fluoro-phenyl)-cyclobutane carboxylic acid {5-[3-(3-fluoro-benzyl)-ureido]-[1,2,4]thiadiazol-3-ylmethyl}-methyl-amide | $C_{23}H_{23}F_2N_5O_2S$ | 471.5 | 472 | 2 | Int. 68 | 1-(4-Fluoro-phenyl)-cyclobutanecarboxylic acid |
| 423 | 2,2-Difluoro-N-{5-[3-(3-fluoro-benzyl)-ureido]-[1,2,4]thiadiazol-3-ylmethyl}-N-methyl-2-phenyl-acetamide | $C_{20}H_{18}F_3N_5O_2S$ | 449.5 | 450 | 2 | Int. 68 | Difluoro-phenyl-acetic acid |
| 424 | 1,1-Dioxo-tetrahydro-thiophene-3-carboxylic acid {5-[3-(5-chloro-thiophen-2-ylmethyl)-ureido]-[1,2,4]thiadiazol-3-ylmethyl}-methyl-amide | $C_{15}H_{18}ClN_5O_4S_3$ | 464.0 | 464 | 2 | Int. 69 | 1,1-Dioxo-tetrahydro-thiophene-3-carboxylic acid |

TABLE 2-continued

Preparation of Thiadiazolyl Amides

| EX# | NAME | MOL FORMULA | MOL WEIGHT | MASS | METHOD | Starting Material 1 (SM1) | Starting Material 2 (SM2) |
|---|---|---|---|---|---|---|---|
| 425 | 2,2-Dimethyl-tetrahydro-pyran-4-carboxylic acid {5-[3-(5-chloro-thiophen-2-ylmethyl)-ureido]-[1,2,4]thiadiazol-3-ylmethyl}-methyl-amide | $C_{18}H_{24}ClN_5O_3S_2$ | 458.0 | 458 | 2 | Int. 69 | 2,2-Dimethyl-tetrahydro-pyran-4-carboxylic acid |
| 426 | 2,3-Dihydro-benzofuran-2-carboxylic acid {5-[3-(3-fluoro-benzyl)-ureido]-[1,2,4]thiadiazol-3-ylmethyl}-methyl-amide | $C_{21}H_{20}FN_5O_3S$ | 441.5 | 442 | 2 | Int. 68 | 2,3-Dihydro-benzofuran-2-carboxylic acid |
| 427 | (R)-Tetrahydro-furan-2-carboxylic acid {5-[3-(5-chloro-thiophen-2-ylmethyl)-ureido]-[1,2,4]thiadiazol-3-ylmethyl}-methyl-amide | $C_{15}H_{18}ClN_5O_3S_2$ | 415.9 | 416 | 2 | Int. 69 | (R)-Tetrahydro-furan-2-carboxylic acid |
| 428 | 2,2-Dimethyl-tetrahydro-pyran-4-carboxylic acid {5-[3-(3-fluoro-benzyl)-ureido]-[1,2,4]thiadiazol-3-ylmethyl}-methyl-amide | $C_{20}H_{26}FN_5O_3S$ | 435.5 | 436 | 2 | Int. 68 | 2,2-Dimethyl-tetrahydro-pyran-4-carboxylic acid |
| 429 | 1-Methyl-5-nitro-1H-pyrazole-4-carboxylic acid {5-[3-(3-fluoro-benzyl)-ureido]-[1,2,4]thiadiazol-3-ylmethyl}-methyl-amide | $C_{17}H_{17}FN_8O_4S$ | 448.4 | 449 | 2 | Int. 68 | 1-Methyl-5-nitro-1H-pyrazole-4-carboxylic acid |
| 430 | 1-Methyl-5-nitro-1H-pyrazole-4-carboxylic acid {5-[3-(5-chloro-thiophen-2-ylmethyl)-ureido]-[1,2,4]thiadiazol-3-ylmethyl}-methyl-amide | $C_{15}H_{15}ClN_8O_4S_2$ | 470.9 | 471 | 2 | Int. 69 | 1-Methyl-5-nitro-1H-pyrazole-4-carboxylic acid |
| 431 | 2,3-Dihydro-benzofuran-2-carboxylic acid {5-[3-(5-chloro-thiophen-2-ylmethyl)-ureido]-[1,2,4]thiadiazol-3-ylmethyl}-methyl-amide | $C_{19}H_{18}ClN_5O_3S_2$ | 464.0 | 464 | 2 | Int. 69 | 2,3-Dihydro-benzofuran-2-carboxylic acid |
| 432 | (R)—N-{5-[3-(3-Fluoro-benzyl)-ureido]-[1,2,4]thiadiazol-3-ylmethyl}-2-methoxy-N-methyl-propionamide | $C_{16}H_{20}FN_5O_3S$ | 381.4 | 382 | 2; 10 | Int. 70 | (R)-2-Methoxy-propionic acid |
| 433 | (R)—N-{5-[3-(5-chloro-thiophen-2-ylmethyl)-ureido]-[1,2,4]thiadiazol-3-ylmethyl}-2-methoxy-N-methyl-propionamide | $C_{14}H_{18}ClN_5O_3S_2$ | 403.9 | 404 | 2 | Int. 69 | (R)-2-Methoxy-propionic acid |
| 434 | N-{5-[3-(3-Fluoro-benzyl)-ureido]-[1,2,4]thiadiazol-3-ylmethyl}-N-methyl-2-morpholin-4-yl-nicotinamide | $C_{22}H_{24}FN_7O_3S$ | 485.5 | 486 | 2 | Int. 68 | 2-Morpholin-4-yl-nicotinic acid |
| 435 | N-{5-[3-(3-Fluoro-benzyl)-ureido]-[1,2,4]thiadiazol-3-ylmethyl}-N-methyl-2-pyrrolidin-1-yl-nicotinamide | $C_{22}H_{24}FN_7O_2S$ | 469.5 | 470 | 2 | Int. 68 | 2-pyrrolidin-1-yl-nicotinic acid |
| 436 | N-{5-[3-(5-Chloro-thiophen-2-ylmethyl)-ureido]-[1,2,4]thiadiazol-3-ylmethyl}-2,N-dimethyl-5-sulfamoyl-benzamide | $C_{18}H_{19}ClN_6O_4S_3$ | 515.0 | 515 | 2 | Int. 69 | 2-Methyl-5-sulfamoyl-benzoic acid |
| 437 | N-{5-[3-(5-chloro-thiophen-2-ylmethyl)-ureido]-[1,2,4]thiadiazol-3-ylmethyl}-N-methyl-2-pyrrolidin-1-yl-nicotinamide | $C_{20}H_{22}ClN_7O_2S_2$ | 492.0 | 492 | 2 | Int. 69 | 2-pyrrolidin-1-yl-nicotinic acid |
| 438 | 2,2-Difluoro-N-{5-[3-(3-fluoro-benzyl)-ureido]-[1,2,4]thiadiazol-3-ylmethyl}-N-methyl-2-pyridin-2-yl-acetamide | $C_{19}H_{17}F_3N_6O_2S$ | 450.4 | 451 | 2; 10 | Int. 70 | Difluoro-pyridin-2-yl-acetic acid |
| 439 | 1-Methyl-4-sulfamoyl-1H-pyrrole-2-carboxylic acid {5-[3-(3-fluoro-benzyl)-ureido]-[1,2,4]thiadiazol-3-ylmethyl}-methyl-amide | $C_{18}H_{20}FN_7O_4S_2$ | 481.5 | 482 | 2 | Int. 68 | 1-Methyl-4-sulfamoyl-1H-pyrrole-2-carboxylic acid |

TABLE 2-continued

Preparation of Thiadiazolyl Amides

| EX# | NAME | MOL FORMULA | MOL WEIGHT | MASS | METHOD | Starting Material 1 (SM1) | Starting Material 2 (SM2) |
|---|---|---|---|---|---|---|---|
| 440 | 4-Hydroxy-pyrrolidine-1,2-dicarboxylic acid 1-amide 2-({5-[3-(3-fluoro-benzyl)-ureido]-[1,2,4]thiadiazol-3-ylmethyl}-methyl-amide) | $C_{18}H_{22}FN_7O_4S$ | 451.5 | 452 | 2 | Int. 68 | 4-Hydroxy-pyrrolidine-1-carboxamide-2-carboxylic acid |
| 441 | Cyclopentanecarboxylic acid {5-[3-(3-fluoro-benzyl)-ureido]-[1,2,4]thiadiazol-3-ylmethyl}-methyl-amide | $C_{18}H_{22}FN_5O_2S$ | 391.5 | 392 | 2 | Int. 68 | Cyclopentane carboxylic acid |
| 442 | 2-Methyl-cyclohexanecarboxylic acid {5-[3-(3-fluoro-benzyl)-ureido]-[1,2,4]thiadiazol-3-ylmethyl}-methyl-amide | $C_{20}H_{26}FN_5O_2S$ | 419.5 | 420 | 2 | Int. 68 | 2-Methyl-cyclohexanecarboxylic acid |
| 443 | Cyclohexanecarboxylic acid {5-[3-(3-fluoro-benzyl)-ureido]-[1,2,4]thiadiazol-3-ylmethyl}-methyl-amide | $C_{19}H_{24}FN_5O_2S$ | 405.5 | 406 | 2 | Int. 68 | Cyclohexanecarboxylic acid |
| 444 | 2,6-Dioxo-hexahydro-pyrimidine-4-carboxylic acid {5-[3-(3-fluoro-benzyl)-ureido]-[1,2,4]thiadiazol-3-ylmethyl}-methyl-amide | $C_{17}H_{18}FN_7O_4S$ | 435.4 | 436 | 2 | Int. 68 | 2,6-Dioxo-hexahydro-pyrimidine-4-carboxylic acid |
| 445 | 1-Cyano-cyclopropane carboxylic acid {5-[3-(5-chloro-thiophen-2-ylmethyl)-ureido]-[1,2,4]thiadiazol-3-ylmethyl}-methyl-amide | $C_{15}H_{15}ClN_6O_2S_2$ | 410.9 | 411 | 2 | Int. 69 | 1-Cyano-cyclopropane carboxylic acid |
| 446 | 1-Hydroxy-cyclopropane carboxylic acid {5-[3-(3-fluoro-benzyl)-ureido]-[1,2,4]thiadiazol-3-ylmethyl}-methyl-amide | $C_{16}H_{18}FN_5O_3S$ | 379.4 | 380 | 2 | Int. 68 | 1-Hydroxy-cyclopropane carboxylic acid |
| 447 | 2-Oxo-2,3-dihydro-benzooxazole-6-carboxylic acid {5-[3-(3-fluoro-benzyl)-ureido]-[1,2,4]thiadiazol-3-ylmethyl}-methyl-amide | $C_{20}H_{17}FN_6O_4S$ | 456.5 | 457 | 2 | Int. 68 | 2-Oxo-2,3-dihydro-benzooxazole-6-carboxylic acid |
| 448 | N-{5-[3-(3-Fluoro-benzyl)-ureido]-[1,2,4]thiadiazol-3-ylmethyl}-2-hydroxy-2,N-dimethyl-propionamide | $C_{16}H_{20}FN_5O_3S$ | 381.4 | 382 | 2 | Int. 68 | 2-Hydroxy-2-methyl-propionic acid |
| 449 | 1-Cyano-cyclopropane carboxylic acid {5-[3-(3-fluoro-benzyl)-ureido]-[1,2,4]thiadiazol-3-ylmethyl}-methyl-amide | $C_{17}H_{17}FN_6O_2S$ | 388.4 | 389 | 2; 10 | Int. 70 | 1-Cyano-cyclopropane carboxylic acid |
| 450 | N-{5-[3-(3-Fluoro-benzyl)-ureido]-[1,2,4]thiadiazol-3-ylmethyl}-2-((S)-4-hydroxy-2-oxo-pyrrolidin-1-yl)-N-methyl-acetamide | $C_{18}H_{21}FN_6O_4S$ | 436.5 | 437 | 2 | Int. 68 | ((S)-4-Hydroxy-2-oxo-pyrrolidin-1-yl)-acetic acid |

TABLE 3

Preparation of Thiazolyl Sulfonamides

| EX# | NAME | MOL FORMULA | MOL WEIGHT | MASS | METHOD | Starting Material 1 (SM1) | Starting Material 2 (SM2) |
|---|---|---|---|---|---|---|---|
| 451 | 1,1-Dioxo-tetrahydro-1l6-thiophene-3-sulfonic acid {2-[3-(3,4-dichloro-benzyl)-ureido]-thiazol-4-ylmethyl}-methyl-amide | $C_{17}H_{20}Cl_2N_4O_5S_3$ | 527.5 | 527, 529 | 5 | Int. 3 | 1,1-Dioxo-tetrahydrothiophene-3-sulfonyl chloride |
| 452 | N-((2-(3-(3,4-dichlorobenzyl)ureido)thiazol-4-yl)methyl)-N,4-dimethyl benzene sulfonamide | $C_{20}H_{20}Cl_2N_4O_3S_2$ | 499.4 | 499, 501 | 5 | Int. 3 | 4-Toluenesulfonyl chloride |

TABLE 3-continued

Preparation of Thiazolyl Sulfonamides

| EX# | NAME | MOL FORMULA | MOL WEIGHT | MASS | METHOD | Starting Material 1 (SM1) | Starting Material 2 (SM2) |
|---|---|---|---|---|---|---|---|
| 453 | N-((2-(3-(3,4-dichlorobenzyl)ureido)thiazol-4-yl)methyl)-N,3,5-trimethylisoxazole-4-sulfonamide | $C_{18}H_{19}C_{12}N_5O_4S_2$ | 504.4 | 504, 506 | 5 | Int. 3 | 3,5-Dimethylisoxazole-4-sulfonyl chloride |
| 454 | N-((2-(3-(3,4-dichlorobenzyl)ureido)thiazol-4-yl)methyl)-N-methyl methane sulfonamide | $C_{14}H_{16}C_{12}N_4O_3S_2$ | 423.3 | 423 | 5 | Int. 3 | Methanesulfonyl chloride |
| 455 | N-((2-(3-(3-fluorobenzyl)ureido)thiazol-4-yl)methyl)-N-methylmethane sulfonamide | $C_{14}H_{17}FN_4O_3S_2$ | 372.4 | 373 | 5 | Int. 5 | Methanesulfonyl chloride |
| 456 | N-((2-(3-(3-fluorobenzyl)ureido)thiazol-4-yl)methyl)-N-methylpropane-1-sulfonamide | $C_{16}H_{21}FN_4O_3S_2$ | 400.5 | 401 | 5 | Int. 5 | 1-Propanesulfonyl chloride |
| 457 | 5-(2-(3-(3,4-dichlorobenzyl)ureido) thiazol-4-yl)-1-(methylsulfonyl)pyrrolidin-3-yl acetate | $C_{18}H_{20}C_{12}N_4O_5S_2$ | 507.4 | 507, 509 | 5 | Int. 58 | Methanesulfonyl chloride |
| 458 | 1-(3,4-dichlorobenzyl)-3-(4-(4-hydroxy-1-(methylsulfonyl)pyrrolidin-2-yl)thiazol-2-yl)urea | $C_{16}H_{18}C_{12}N_4O_4S_2$ | 465.4 | 465, 467 | 20 | 5-(2-(3-(3,4-dichlorobenzyl)ureido)thiazol-4-yl)-1-(methylsulfonyl)-pyrrolidin-3-yl acetate (EX# 457) | none |
| 459 | N-((2-(3-(3-fluorobenzyl)ureido)thiazol-4-yl)methyl)-N-methylbutane-1-sulfonamide | $C_{17}H_{23}FN_4O_3S_2$ | 414.5 | 415 | 5 | Int. 5 | 1-Butanesulfonyl chloride |
| 460 | N-((2-(3-(3-fluorobenzyl)ureido)thiazol-4-yl)methyl)-N-methylethane sulfonamide | $C_{15}H_{19}FN_4O_3S_2$ | 386.5 | 387 | 5 | Int. 5 | Ethanesulfonyl chloride |
| 461 | N-((2-(3-(3-fluorobenzyl)ureido)thiazol-4-yl)methyl)-N,3,5-trimethylisoxazole-4-sulfonamide | $C_{18}H_{20}FN_5O_4S_2$ | 453.5 | 454 | 5 | Int. 5 | 3,5-Dimethylisoxazole-4-sulfonyl chloride |
| 462 | N-((2-(3-(3-fluorobenzyl)ureido)thiazol-4-yl)methyl)-N-methylcyclopropane sulfonamide | $C_{16}H_{19}FN4O_3S_2$ | 398.5 | 399 | 5 | Int. 5 | Cyclopropanesulfonyl chloride |
| 463 | N-((2-(3-(3-fluorobenzyl)ureido)thiazol-4-yl)methyl)-N-(2-(methylsulfonamido)ethyl)methane sulfonamide | $C_{16}H_{22}FN_5O_5S_3$ | 479.6 | 481 | 5 | Int. 59 | Methanesulfonyl chloride |
| 464 | 1-[4-(1,1-Dioxo-1l6-isothiazolidin-2-ylmethyl)-thiazol-2-yl]-3-(3-fluoro-benzyl)-urea | $C_{15}H_{17}FN_4O_3S_2$ | 384.5 | 385 | 16 | Int. 21 | Isothiazolidine 1,1-dioxide |
| 465 | 1-(3-Fluoro-benzyl)-3-{4-[1-(propane-1-sulfonyl)-pyrrolidin-2-yl]-thiazol-2-yl}-urea | $C_{18}H_{23}FN_4O_3S_2$ | 426.5 | 427 | 5 | Int. 60 | Propanesulfonyl chloride |
| 466 | Ethanesulfonic acid {5-bromo-2-[3-(3-fluoro-benzyl)-ureido]-thiazol-4-ylmethyl}-methyl-amide | $C_{15}H_{18}BrFN_4O_3S_2$ | 465.4 | 465 | 17 | N-((2-(3-(3-fluorobenzyl)ureido)thiazol-4-yl)methyl)-N-methylethane-sulfonamide (EX# 460) | Bromine |
| 467 | N-{2-[3-(3-Fluoro-benzyl)-ureido]-thiazol-4-ylmethyl}-N-methyl-4-morpholin-4-yl-benzenesulfonamide | $C_{23}H_{26}FN_5O_4S_2$ | 519.6 | 521 | 5 | Int. 5 | 4-Morpholin-4-yl-benzenesulfonyl chloride |
| 468 | Furan-2-sulfonic acid {2-[3-(3-fluoro-benzyl)-ureido]-thiazol-4-ylmethyl}-methyl-amide | $C_{17}H_{17}FN_4O_4S_2$ | 424.5 | 425 | 5 | Int. 5 | Furan-2-sulfonyl chloride |

TABLE 3-continued

Preparation of Thiazolyl Sulfonamides

| EX# | NAME | MOL FORMULA | MOL WEIGHT | MASS | METHOD | Starting Material 1 (SM1) | Starting Material 2 (SM2) |
|---|---|---|---|---|---|---|---|
| 469 | Thiophene-2-sulfonic acid {2-[3-(3-fluoro-benzyl)-ureido]-thiazol-4-ylmethyl}-methyl-amide | $C_{17}H_{17}FN_4O_3S_3$ | 440.5 | 441 | 5 | Int. 5 | Thiophene-2-sulfonyl chloride |
| 470 | Pyridine-3-sulfonic acid {2-[3-(3-fluoro-benzyl)-ureido]-thiazol-4-ylmethyl}-methyl-amide | $C_{18}H_{18}FN_5O_3S_2$ | 435.5 | 436 | 5 | Int. 5 | Pyridine-3-sulfonyl chloride |
| 471 | Pyridine-2-sulfonic acid {2-[3-(3-fluoro-benzyl)-ureido]-thiazol-4-ylmethyl}-methyl-amide | $C_{18}H_{18}FN_5O_3S_2$ | 435.5 | 436 | 5 | Int. 5 | Pyridine-2-sulfonyl chloride |
| 472 | 1-Methyl-1H-imidazole-4-sulfonic acid {2-[3-(3-fluoro-benzyl)-ureido]-thiazol-4-ylmethyl}-methyl-amide | $C_{17}H_{19}FN_6O_3S_2$ | 438.5 | 439 | 5 | Int. 5 | 1-Methyl-1H-imidazole-4-sulfonyl chloride |
| 473 | 1,2-Dimethyl-1H-imidazole-4-sulfonic acid {2-[3-(3-fluoro-benzyl)-ureido]-thiazol-4-ylmethyl}-methyl-amide | $C_{18}H_{21}FN_6O_3S_2$ | 452.5 | 453 | 5 | Int. 5 | 1,2-Dimethyl-1H-imidazole-4-sulfonyl chloride |
| 474 | N-{2-[3-(3-Fluoro-benzyl)-ureido]-thiazol-4-ylmethyl}-N-methyl-C-pyridin-3-yl-methanesulfonamide | $C_{19}H_{20}FN_5O_3S_2$ | 449.5 | 450 | 5 | Int. 5 | Pyridin-3-yl-methanesulfonyl chloride |
| 475 | N-(3,5-Dimethyl-isoxazol-4-ylmethyl)-N-{2-[3-(3-fluoro-benzyl)-ureido]-thiazol-4-ylmethyl}-methane sulfonamide | $C_{19}H_{22}FN_5O_4S_2$ | 467.5 | 468 | 5 | Int. 61 | Methanesulfonyl chloride |

Example 476

Intermediates

Intermediate 1: 4-(Chloromethyl)thiazol-2-amine hydrochloride

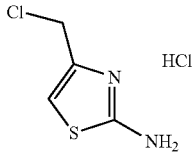

To a solution of 1,3-dichloroacetone (150 g, 1.18 mol) in acetone (600 mL) was added a solution of thiourea (91.7 g, 1.23 mol) in acetone (3000 mL). The mixture was stirred overnight at room temperature. The resulting suspension was concentrated to dryness in vacuo. Ethanol (1.2 L) was added and the mixture was stirred for 3 h. The insolubles were removed by filtration and the filtrate was concentrated to 500 mL. Heptanes (1.5 L) were slowly added resulting in the formation of a white precipitate. This was isolated by filtration, washed with heptane and dried in vacuo to afford 4-(chloromethyl)thiazol-2-amine hydrochloride as a white solid (141.3 g, 0.76 mol, 64%). $^1$H NMR (DMSO-$d_6$): δ 9.50 (bs, 2H); 7.00 (s, 1H); 4.68 (s, 2H).

Alternative Process for Intermediate 1: A mixture of 1,3-dichloroacetone (380.9 g, 3 mol), thiourea (228.3 g, 3 mol), and isopropanol (3.6 L) was stirred at 40° C. under an inert atmosphere, affording a clear solution. The product crystallized after stirring overnight at room temperature. After cooling to −20° C., the product was isolated by filtration, washed with cold isopropanol (0.4 L), and dried in vacuo to afford the title compound as white crystals (408 g, 73.5% yield).

Intermediate 2: 1-(3,4-Dichlorobenzyl)-3-(4-(chloromethyl)thiazol-2-yl) urea

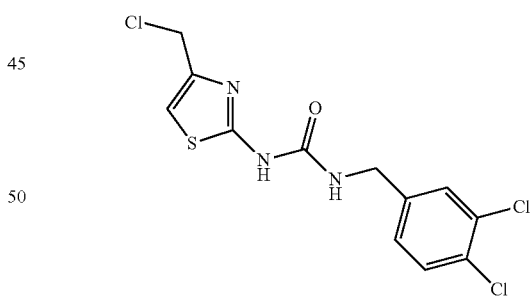

To a suspension of 4-(chloromethyl)thiazol-2-amine hydrochloride (7.55 g, 41 mmol) in DCM (150 mL) at 0° C. was added 3,4-dichlorobenzyl isocyanate (8.27 g, 41 mmol). A solution of DIPEA in DCM (30 mL) was added over a period of 30 minutes and the mixture was stirred overnight at room temperature. Evaporation of the volatiles followed by purification by column chromatography (EtOAc/heptanes 1/1) afforded 1-(3,4-dichlorobenzyl)-3-(4-(chloromethyl) thiazol-2-yl)urea as an off-white solid (10.5 g, 30 mmol) in 73% yield. $^1$H NMR (DMSO-$d_6$): δ 10.80 (bs, 1H); 7.60 (d, 1H); 7.55 (s, 1H); 7.11 (t, 1H); 7.05 (s, 1H); 4.63 (s, 2H); 4.30 (d, 2H).

Intermediate 3: 1-(3,4-Dichlorobenzyl)-3-(4-((methylamino)methyl)thiazol-2-yl)urea

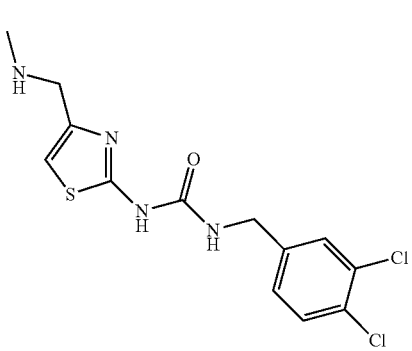

A solution of 1-(3,4-dichlorobenzyl)-3-(4-(chloromethyl) thiazol-2-yl)urea and excess methylamine (2.0 M solution in tetrahydrofuran) was heated for 15 minutes at 60° C. under microwave irradiation. The volatiles were removed in vacuo and the product was purified by column chromatography (DCM/0-15% NH$_3$ saturated MeOH) to afford the title compound.

Intermediate 4: 1-(4-(Chloromethyl)thiazol-2-yl)-3-(3-fluorobenzyl)urea

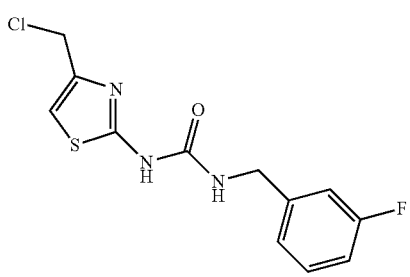

Prepared by same procedure described for Intermediate 2 with 4-(chloromethyl)thiazol-2-amine hydrochloride and 3-fluorobenzyl isocyanate. $^1$H-NMR (ppm, DMSO-d$_6$): 10.70 (bs, 1H), 7.36 (dd, 1H), 7.07 (m, 4H), 4.63 (s, 2H), 4.34 (d, 2H).

Alternative process for Intermediate 4 Using Carbonyl Diimidazole:

A stirred mixture of Intermediate 1: 2-amino-4-chloromethyl-thiazole hydrochloride (27.8 g, 0.15 mol), carbonyl diimidazole (25.5 g, 0.157 mol), and anhydrous THF (0.2 L) was treated dropwise with a solution of DIPEA (26.2 mL, 0.15 mol) in THF (20 mL) at 20-30 C. After 2-3 hours stirring, a solution of 3-fluorobenzylamine (18.5 mL, 0.164 mol) in THF (40 mL) was added. The reaction was diluted with water (200 mL) and THF was evaporated under reduced pressure. The residue was extracted with DCM (2×200 mL). The combined extracts were dried over sodium sulfate and concentrated to leave an orange resin that was purified by silica gel chromatography (acetone/hexane) to afford Intermediate 4 as a pale yellow solid (26 g, 58% yield).

Intermediate 5: 1-(3-Fluorobenzyl)-3-(4-((methylamino)methyl)thiazol-2-yl) urea

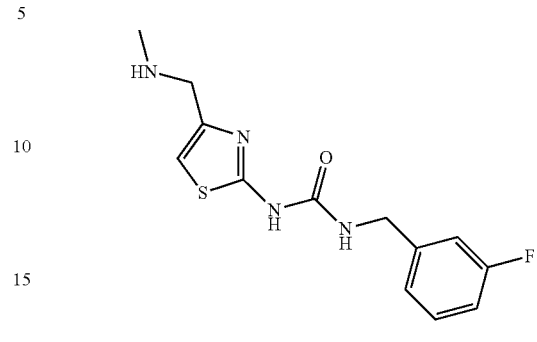

Prepared by reaction of Intermediate 4 with methylamine, following the procedure described for Intermediate 3.

Alternative Process for Intermediate 5 Using N,O-Dimethylhydroxylamine:

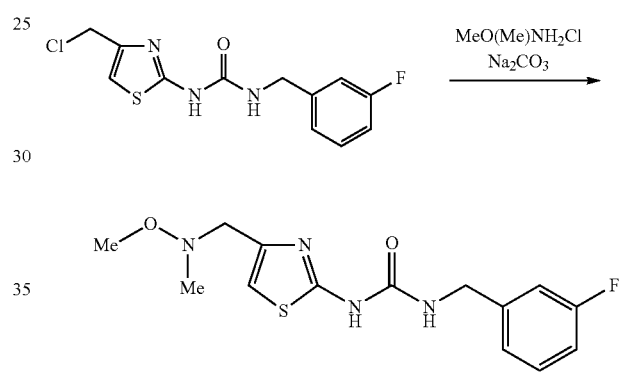

Step 1: 2-(3-(3-Fluorobenzyl)ureido)-4-(N-methoxy-N-methyl-aminomethyl)-thiazole. A mixture of Intermediate 4: 2-(3-(3-fluorobenzyl)ureido)-4-chloromethyl-thiazole (40 g, 0.133 mol), N,O-dimethylhydroxylamine (80 g, 0.820 mol), sodium carbonate (40 g, 0.754 mol), and abs. EtOH (0.2 L) was stirred and heated at 60-70 C for 8-12 hours. The mixture was diluted with water (0.8 L) and cooled to 20 C with continued stirring. The solids were collected by filtration, washed with water, and dried in vacuo to afford the title compound (37 g, 86% yield).

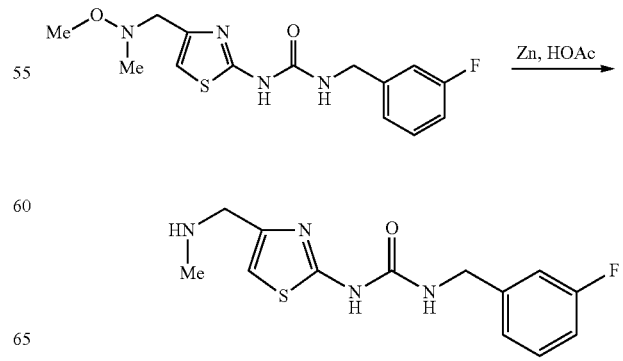

Step 2: Zinc Reduction of methoxyamine to amine (*J. Natural Products* 53(4), 995-999 (1990)). A solution of 2-(3-(3-fluorobenzyl)ureido)-4-(N-methoxy-N-methyl-aminomethyl)-thiazole (10.1 g, 31.1 mmol) in glacial HOAc (140 mL) was treated with micronized zinc dust (50 g) and the mixture was heated to 60-65 C with vigorous agitation. The reduction was complete in 2-16 hours and water (140 mL) was added. The mixture was filtered on Celite, the filter cake was reslurried in 1:1 HOAC:water (150 mL) and refiltered. The combine filtrate was made alkaline to pH 10 with NH$_4$OH and cooled in ice. The solids were collected by filtration, washed with water, and dried in vacuo to afford Intermediate 5 as an off-white solid (8.2 g, 89% yield). This product could be used directly or further purified by crystallization as the hydrochloride salt (1:1 MeOH:EtOH).

Intermediate 6: 1-(3,4-Dichlorobenzyl)-3-(4-(iodomethyl)thiazol-2-yl)urea

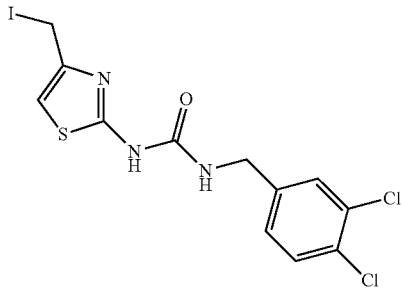

To a solution of 1-(3,4-dichlorobenzyl)-3-(4-(chloromethyl)thiazol-2-yl)urea (Intermediate 2, 1 eq) in acetone was added sodium iodide (10 eq) at once. The mixture was stirred at room temperature for 2 h. The volatiles were removed in vacuo and the mixture was taken up in water and EtOAc. The layers were separated and the organic phase was washed with water and brine, dried over Na$_2$SO$_4$, and concentrated in vacuo to afford 1-(3,4-dichlorobenzyl)-3-(4-(iodomethyl)thiazol-2-yl)urea as a tan-colored solid.

Intermediate 7: 1-(3-Fluorobenzyl)-3-(4-(iodomethyl)thiazol-2-yl) urea

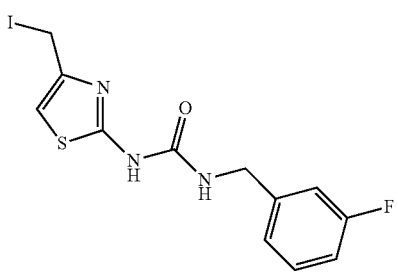

Prepared in a similar manner as 1-(3,4-dichlorobenzyl)-3-(4-(iodomethyl)thiazol-2-yl)urea. $^1$H-NMR (ppm, CDCl$_3$): 7.27 (m, 1H), 7.10 (m, 2H), 6.95 (t, 1H), 6.75 (s, 1H), 4.50 (d, 2H), 4.35 (s, 2H).

Intermediate 8: 1-(3,4-Dichlorobenzyl)-3-(4-((ethylamino)methyl)thiazol-2-yl)urea

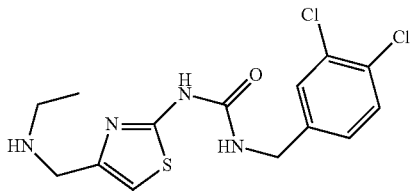

The 1-(3,4-dichloro-benzyl)-3-(4-iodomethyl-thiazol-2-yl)-urea (Intermediate 6, 0.3 mmol) was taken up in a 2.0 M solution of ethylamine in tetrahydrofuran (5 ml). Reaction was stirred at room temperature for 1 hour. The volatiles were removed in vacuo and the crude title compound was taken on as is, ~75% pure.

Intermediate 9: 1-(3,4-Dichlorobenzyl)-3-(4-((isopropylamino)methyl)thiazol-2-yl)urea

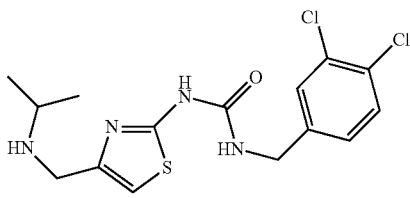

The 1-(3,4-Dichloro-benzyl)-3-(4-iodomethyl-thiazol-2-yl)-urea intermediate (0.3 mmol) was taken up in tetrahydrofuran (5 ml) and isopropyl amine (20 eq.) was added. The reaction was stirred overnight at room temperature. Added a saturated solution of NaSO$_3$ (40 ml). Extracted this with EtOAc twice. The combined organic extracts were dried over Na$_2$SO$_4$, filtered and solvent removed in vacuo. The crude 1-(3,4-dichlorobenzyl)-3-(4-((isopropylamino)methyl)thiazol-2-yl)urea was used as is.

Intermediate 10a: 1-(3,4-Dichlorobenzyl)-3-(4-(1-(methylamino)ethyl)thiazol-2-yl)urea

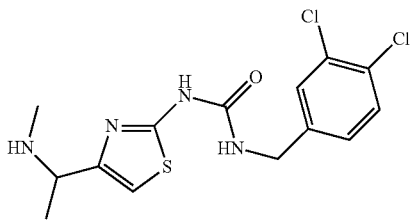

Step 1: The commercial starting material ethyl 2-aminothiazole-4-carboxylate (2 mmol) was dissolved in NMP and DIEA (1 equivalent) was added followed by addition of the 3,4-dichloro-benzyl isocyanate (1 equivalent). Add 5% DMAP. Heat at 160° C. under microwave irradiation for 30 min Added additional isocyanate reagent (1.0 eq) and microwave for another 30 minutes at 160° C. to obtain ethyl 2-(3-(3,4-dichlorobenzyl)ureido)thiazole-4-carboxylate in >90% conversion.

Step 2: Hydrolysis with NaOH to give 2-(3-(3,4-dichlorobenzyl)ureido)thiazole-4-carboxylic acid.

Step 3: Method 2 is followed to couple the above acid with N,O-dimethylhydroxylamine HCl salt to give 2-(3-(3,4-dichlorobenzyl)ureido)-N-methoxy-N-methylthiazole-4-carboxamide.

Step 4: 1 mmol of 2-(3-(3,4-dichlorobenzyl)ureido)-N-methoxy-N-methylthiazole-4-carboxamide was suspended in 10 ml dry tetrahydrofuran and cooled to 0 C. 1.5 ml of 3 M methylmagnesium chloride in tetrahydrofuran was added and stirred for 2 hours. The solution was poured in to 20 ml of 5% concentrate HCl in ethanol. The solution was diluted with brine and the precipitate was filtered, washed with water and dried.

Step 5: 156 mg of 1-(4-acetylthiazol-2-yl)-3-(3,4-dichlorobenzyl)urea was dissolved in 5 ml of 2 M methylamine solution in tetrahydrofuran. To the solution, 2.0 eq. of sodium triacetoxyborohydride was added and stirred overnight at room temp. The volatile was removed by evaporation and the residue was purified by column chromatography using 0-10% gradient of 7 N ammonia/MeOH and DCM to give the title compound.

Intermediate 10b: 1-(3-Fluorobenzyl)-3-(4-(1-(methylamino)ethyl)thiazol-2-yl)urea

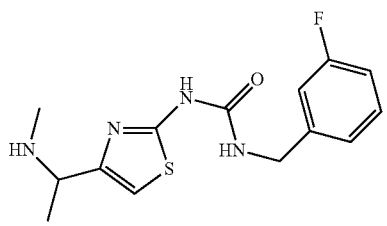

The 1-(3-fluorobenzyl)-3-(4-(1-(methylamino)ethyl)thiazol-2-yl)urea was prepared following the same procedure described for Intermediate 10a using 3-fluoro-benzyl isocyanate in step one.

Intermediate 11: 1-(3,4-Dichlorobenzyl)-3-(4-((2,4-dimethoxybenzylamino) methyl)thiazol-2-yl) urea

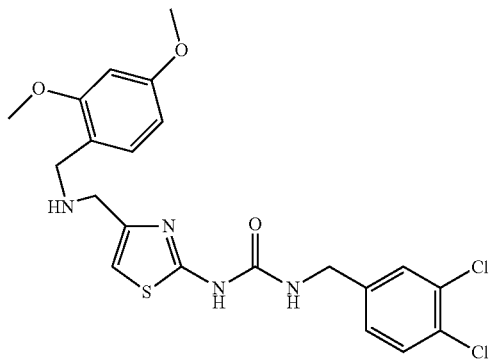

1-(3,4-dichlorobenzyl)-3-(4-(iodomethyl)thiazol-2-yl) urea (Intermediate 6) was taken up in tetrahydrofuran and an excess of the 2,4-dimethoxy-benzylamine (20 eq.) was added. The reaction was allowed to stir overnight at room temperature. The volatiles were removed in vacuo. Resulting oil triturated with water to give a gooey solid. Water was decanted off and resulting residue was purified by column chromatography using 0-8% gradient of 7 N ammonia/MeOH and DCM to give 1-(3,4-Dichloro-benzyl)-3-{4-[(2,4-dimethoxy-benzylamino)-methyl]-thiazol-2-yl}-urea.

Intermediate 12: 1-(3,4-Dichlorobenzyl)-3-(4-((2-methoxyethylamino)methyl)thiazol-2-yl)urea

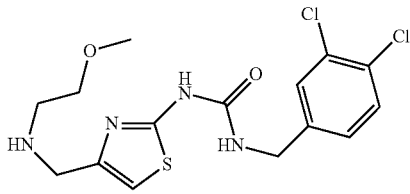

1-(4-Chloromethyl-thiazol-2-yl)-3-(3,4-dichloro-benzyl)-urea (Intermediate 2, 1 eq.) was taken up in NMP (0.3 M) and methoxyethylamine (2.2 eq.) was added. The reaction was heated overnight at 80° C. An aqueous workup was performed. The crude title compound was purified by column chromatography using 0-8% gradient of 7 N ammonia/MeOH and DCM.

Intermediate 13: 2-(2-(3-(3,4-Dichlorobenzyl)ureido)thiazol-4-yl)-N-methyl-2-(methylamino)acetamide

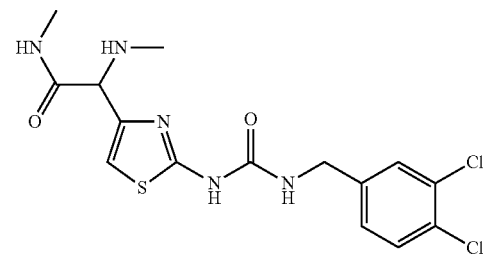

Step 1: Ethyl 2-(2-aminothiazol-4-yl)-2-oxoacetate (2.0 mmol) was dissolved in NMP (5 ml) and 3,4-dichlorobenzyl-isocyanate (2.0 eq.) was added and heated at 130 C under microwave irradiation for 30 minutes. The reaction solution was poured into water. The Ethyl 2-(2-(3-(3,4-dichlorobenzyl)ureido)thiazol-4-yl)-2-oxoacetate precipitate was filtered, washed with water and tetrahydrofuran and dried.

Step 2: Ethyl 2-(2-(3-(3,4-dichlorobenzyl)ureido)thiazol-4-yl)-2-oxoacetate (800 mg) was dissolved in 2 M methylamine in tetrahydrofuran (20 ml) and NaCNBH₃ (2.2 eq.) was added and stirred at room temperature overnight. The title compound was purified by column using 0-10% gradient of 7 N ammonia/MeOH and DCM.

Intermediate 14: 1-(3,4-dichlorobenzyl)-3-(4-((2-hydroxyethylamino)methyl)thiazol-2-yl)urea

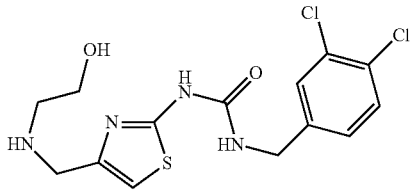

1-(3,4-Dichloro-benzyl)-3-(4-iodomethyl-thiazol-2-yl)-urea (Intermediate 6, 0.3 mmol) was taken up in tetrahydrofuran (5 ml) and 2-Amino-ethanol (20 eq.) was added. The reaction was stirred overnight at room temperature. Added a saturated solution of NaSO₃ (40 ml). Extracted this with EtOAc twice. The combined organic extracts were dried over Na₂SO₄, filtered and solvent removed in vacuo to give the title compound a solid.

Intermediate 15: tert-Butyl 2-(2-(3-(3-fluorobenzyl)ureido)thiazol-4-yl)methylamino)ethylcarbamate

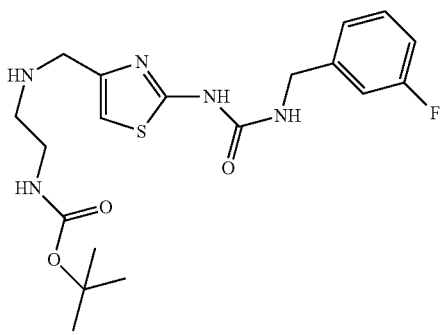

Step 1: Preparation of 2-(3-(3-fluorobenzyl)ureido)thiazole-4-carboxylate according to the procedure described for Intermediate 10b, step 1 and step 2.

Step 2: 2-(3-(3-fluorobenzyl)ureido)thiazole-4-carboxylate (4.08 mmol) is taken up in THF and solution is cooled to −78° C. Added LiAlH₄ (2.6 equivalents, 1M solution in THF). Stir at ambient temperature for 3 hours. Add slowly Na₂SO₄.10H₂O (6.4 g), then NaHSO₄ (1.8 g). Stir for 30 hours. Aqueous workup with EtOAc. Crystallized from DCM/hexanes to give 1-(3-fluorobenzyl)-3-(4-(hydroxymethyl)thiazol-2-yl)urea in 79% yield.

Step 3: The 1-(3-fluorobenzyl)-3-(4-(hydroxymethyl)thiazol-2-yl) urea is taken up in DCM and cooled to 0° C. and Dess-Martin oxidant (1.1 equiv) was added. Stirred at ambient temperature for 1 hour. Washed with dilute Na₂SO₃. Removed solvent in vacuo to give 1-(3-fluorobenzyl)-3-(4-formylthiazol-2-yl)urea (used directly in next step).

Step 4: Reductive amination with tert-butyl 2-aminoethylcarbamate (1.5 equiv) and the aldehyde (1.0 equiv) described in the previous step. The two are combined in DCM and cooled to 0° C., and NaBH(OAc)₃ (2.0 equiv) is added. Stirred at 0° C. for 1 hour. Quenched with dilute NaHCO₃. Purified by column chromatography with a gradient of 2-5% MeOH in DCM to give the title compound.

Intermediate 16: tert-Butyl 4-(chloromethyl)thiazol-2-ylcarbamate

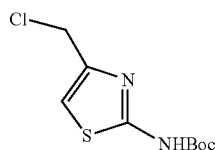

To a solution of N-Boc-thiourea (3.0 g, 17 mmol) in acetone (75 mL) was added 1,3-dichloroacetone (2.4 g, 18.7 mmol) at once. The mixture was stirred at room temperature for 72 h. The reaction mixture was treated with 3 g of NaHCO₃ and stirred for 15 min. The solids were removed by filtration and the filtrate was concentrated in vacuo. Column chromatography (EtOAc/Heptanes 4/1) afforded N-Boc-4-(chloromethyl)thiazol-2-amine (2.9 g, 11.6 mmol, 68%) as a white solid.

Intermediate 17: tert-Butyl 4-((methylamino)methyl)thiazol-2-ylcarbamate

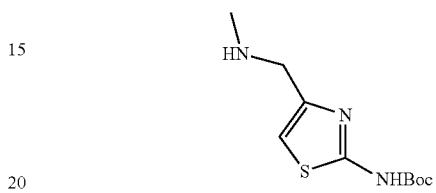

tert-Butyl 4-(chloromethyl)thiazol-2-ylcarbamate (8.0 g, 24.16 mmol) was dissolved in 2.0 M methylamine in tetrahydrofuran (640 mL, ~40 eq.) and heated in the microwave for 60 minutes at 60° C. The precipitate (impurity) was filtered off and the filtrate was concentrated under reduced pressure to furnish 1.97 g product as orange foam. ¹H NMR (DMSO-d₆): δ 11.79 (s, br, 1H), 7.50 (s, 1H), 7.36 (d, 1H), 7.10 (m, 2H), 5.14 (s, br, 1H), 4.63 (s, 2H), 4.36 (s, 2H), 3.83 (t, 2H), 3.43 (t, 2H).

Intermediate 18: (4-{[Methyl(3,5-dimethylisoxazole-4-carbonyl)-amino]-methyl}-thiazol-2-yl) carbamic acid phenyl ester

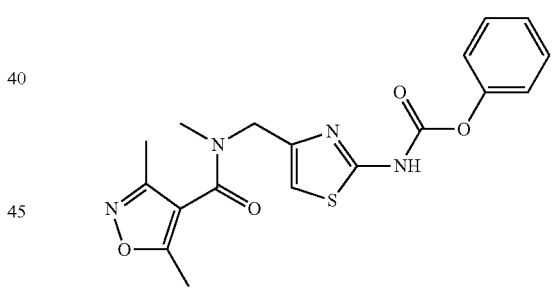

Step 1: The crude tert-butyl 4-((methylamino)methyl)thiazol-2-ylcarbamate (Intermediate 17, 7.78 g, 32 mmol) was dissolved in DCM (100 mL) and DIPEA (6.34 mL, 38 mmol, 1.2 eq.) was added. This mixture was stirred for 5 minutes and 3,5-dimethylisoxazole-4-carbonylchloride (5.45 mL, 0.035 mmol, 1.1 eq.) was added and the reaction mixture was stirred at ambient temperature overnight. After work-up and purification by column chromatography (silica gel, 3% MeOH/DCM) the tert-butyl 4-((N,3,5-trimethylisoxazole-4-carboxamido)methyl) thiazol-2-ylcarbamate was furnished (6.7 g, ca. 80% purity). ¹H NMR (DMSO-d₆): 11.79 (s, br, 1H), 7.50 (s, 1H), 7.36 (d, 1H), 7.10 (m, 2H), 5.14 (s, br, 1H), 4.63 (s, 2H), 4.36 (s, 2H), 3.83 (t, 2H), 3.43 (t, 2H).

Step 2: The crude tert-butyl 4-((N,3,5-trimethylisoxazole-4-carboxamido)methyl) thiazol-2-ylcarbamate (6.7 g) was dissolved in an excess of 4M HCl in dioxane (300 mL). The reaction was stirred at 40 C for 2 hours. Volatiles were removed under reduced pressure and 6.16 g of N-((2-aminothiazol-4-yl)methyl)-N,3,5-trimethylisoxazole-4-carboxamide hydrochloride was obtained. $^1$H-NMR (DMSO-$d_6$): δ 11.79 (s, br, 1H), 7.50 (s, 1H), 7.36 (d, 1H), 7.10 (m, 2H), 5.14 (s, br, 1H), 4.63 (s, 2H), 4.36 (s, 2H), 3.83 (t, 2H), 3.43 (t, 2H).

Step 3: N-((2-aminothiazol-4-yl)methyl)-N,3,5-trimethylisoxazole-4-carboxamide hydrochloride (6.16 g, 20.34 mmol) was dissolved in pyridine (35 mL) and DMAP (150 mg, 5 mol %) was added. The solution was cooled to 0° C. and a solution of phenylchloroformate (2.55 mL, 3.18 g, 20.34 mmol) in tetrahydrofuran (35 mL) was added dropwise. The mixture was stirred overnight at room temperature and the volatiles were evaporated in vacuo. The residue was taken up in water/EtOAc. The organic phase was dried over MgSO$_4$ and the volatiles were evaporated under reduced pressure. The material was crystallized from EtOAc/i-Pr$_2$O to afford (4-{[methyl(3,5-dimethylisoxazole-4-carbonyl)-amino]-methyl}-thiazol-2-yl) carbamic acid phenyl ester (1.80 g) as a tan-colored solid (purity ~85%). $^1$H NMR (CDCl$_3$): δ 9.85 (bs, 1H), 7.45 (m, 2H), 7.25 (m, 2H), 7.20 (m, 2H), 6.80 (b, 1H), 4.75 (bs, 1H), 4.45 (bs, 1H), 3.00 (bs, 3H), 2.36 (s, 3H), 2.24 (s, 3H).

Intermediate 19: 1-(3-Fluorobenzyl)-3-(4-((2-hydroxyethylamino)methyl)thiazol-2-yl)urea

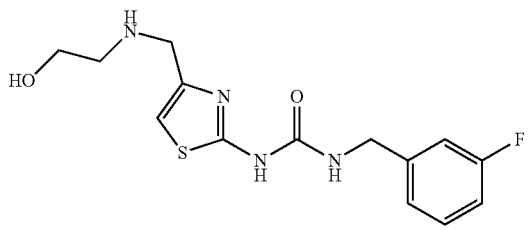

1-(3-Fluorobenzyl)-3-(4-(iodomethyl)thiazol-2-yl)urea (Intermediate 7) was taken up in tetrahydrofuran and an excess of the 2-amino-ethanol (20 equiv.) was added. The reaction was allowed to stir overnight at room temperature. The reaction was poured into water and extracted with EtOAc, partitioned with brine, dried over Na$_2$SO$_4$, filtered, and volatiles were removed in vacuo. The resulting solid was triturated with EtOAc, followed by diethyl ether to give the title compound.

Intermediate 20: 1-(3,5-Difluorobenzyl)-3-(4-((methylamino)methyl)thiazol-2-yl)urea

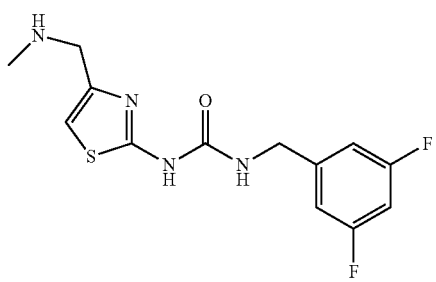

Step 1: A 3-neck 500 ml round bottle flask was charged with 4-Chloromethyl-thiazol-2-ylamine hydrochloride (Intermediate 1, 1 eq.) and CDI (1.05 eq.) and purged with nitrogen. Anhydrous THF was added via cannula. To the resulting stirring granular suspension was added DIPEA (1.05 eq.) dropwise via an addition funnel. After the addition of DIPEA was complete, the 3,5-difluoro-benzyl amine (1.0 eq.) was added dropwise in the same manner. The reaction was quenched with DI water and the THF was removed in vacuo. The resulting orange residue was partitioned with water and DCM. The organic layer was dried with Na$_2$SO$_4$, filtered and solvent was removed in vacuo. The crude was purified by column chromatography (acetone/hexanes) followed by recrystallization from iPrOAc and hexanes. The solid was isolated via filtration and dried under vacuum to give 1-(4-Chloromethyl-thiazol-2-yl)-3-(3,5-difluoro-benzyl)-urea.

Step 2: The title compound was prepared from the above 1-(4-Chloromethyl-thiazol-2-yl)-3-(3,5-difluoro-benzyl)-urea following the procedure described for Intermediate 3.

Intermediate 21: 1-(4-(Chloromethyl)thiazol-2-yl)-1-(2,4-dimethoxybenzyl)-3-(3-fluorobenzyl)urea

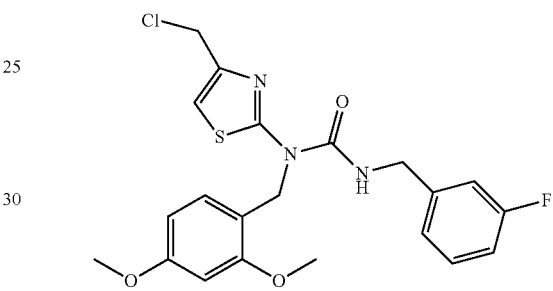

Step 1: The HCl salt of 4-(chloromethyl)thiazol-2-amine (10 mmol) was suspended in DCM (50 ml), and 2,4-dimethoxybenzaldehyde (1.0 eq. of) and DIEA (1.0 eq.) were added. To the mixture, acetic acid (1 ml) was added followed by addition of sodium triacetoxyborohydride (2.5 eq.) and the reaction was stirred at room temperature overnight. The reaction mixture was filtered through Celite and washed with DCM. The filtrate was concentrated and purified by column chromatography using 0-10% gradient of 7 N ammonia/MeOH and DCM to give 4-(chloromethyl)-N-(2,4-dimethoxybenzyl)thiazol-2-amine.

Step 2: The 4-(chloromethyl)-N-(2,4-dimethoxybenzyl) thiazol-2-amine was dissolved in DCM (50 ml) and 3-fluorobenzylisocyanate (1.2 eq.) was added and stirred overnight. The mixture was concentrated and the residue was purified on a column using 0-100% gradient of EtOAc and hexanes to give the title compound.

Intermediate 22: (4-{[Methyl-(3-methyl-pyrazine-2-carbonyl)-amino]-methyl}-thiazol-2-yl)-carbamic acid phenyl ester

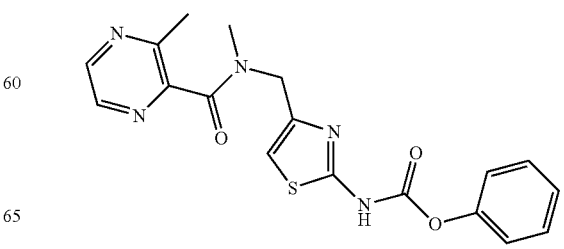

Step 1: To a solution of tert-butyl 4-((methylamino)methyl)thiazol-2-ylcarbamate (Intermediate 17, 1.30 g, 5.3 mmol) and 3-methylpyrazine-2-carboxylic acid (1.1 g, 8 mmol) in CH2Cl2 (25 mL) was added DCC (1.64 g, 8 mmol). The mixture was stirred for 2 hours and the solids were removed by filtration. The filtrate was concentrated in vacuo and purified by column chromatography (2% MeOH in CH2Cl2, Rf=0.15) to afford tert-butyl 4-((N,2-dimethylpyrazine-3-carboxamido)methyl)thiazol-2-ylcarbamate (1.30 g, 3.6 mmol) as an off-white solid in 68% yield.

Step 2: A solution of tert-butyl 4-((N,2-dimethylpyrazine-3-carboxamido)methyl)thiazol-2-ylcarbamate (1.30 g, 3.6 mmol) in dioxane (10 mL) was treated with 4N HCl in dioxane (10 mL) for 2 hours. The resulting suspension was concentrated in vacuo to afford N-((2-aminothiazol-4-yl)methyl)-N,3-dimethylpyrazine-2-carboxamide (1.10 g).

Step 3: A mixture of N-((2-aminothiazol-4-yl)methyl)-N,3-dimethylpyrazine-2-carboxamide (555 mg, 1.84 mmol) and DMAP (20 mg) in pyridine (10 mL) was cooled to 0° C. and a solution of phenyl chloroformate (433 mg, 2.8 mmol) in THF was added drop wise. The mixture was stirred overnight and all volatiles were removed in vacuo at 30° C. The residue was triturated with TBME to afford (4-{[Methyl-(3-methyl-pyrazine-2-carbonyl)-amino]-methyl}-thiazol-2-yl)-carbamic acid phenyl ester (125 mg) as a tan colored solid (purity 96%).

Intermediate 23: 3-((2-(3-(3,4-Dichlorobenzyl)ureido)thiazol-4-yl)methylamino) propylphosphonic acid

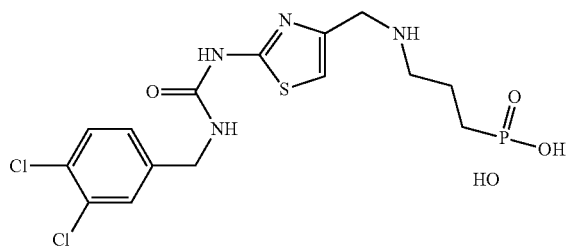

Step 1: 0.58 g of 2-(3-(3,4-dichlorobenzyl)ureido)thiazole-4-carboxylic acid was dissolved in 15 ml of DMF and 3.0 eq. of DIEA and 1.05 eq. of TBTU was added. To the mixture, 1.2 eq. of N,O-dimethylhydroxylamine HCl salt was added and the reaction was stirred at room temp. overnight. The product was precipitated from water, filtered, washed with water and dried to give 2-(3-(3,4-dichlorobenzyl)ureido)-N-methoxy-N-methylthiazole-4-carboxamide.

Step 2: 1.0 g of 2-(3-(3,4-dichlorobenzyl)ureido)-N-methoxy-N-methylthiazole-4-carboxamide was dissolved in 20 ml dry tetrahydrofuran and cooled to −78 C. 1.10 eq. of 1 N lithium aluminum hydride in tetrahydrofuran was added slowly. The reaction was stirred at 0 C for 2 hours. The reaction was cooled to −78 C again and quenched with 1 N HCl and extracted with EtOAc three times. The organic was combined, dried over sodium sulfate and concentrated. The residue was purified by column chromatography using 0-100% gradient of EtOAc and hexanes to give 1-(3,4-dichlorobenzyl)-3-(4-formylthiazol-2-yl)urea.

Step 3: 300 mg of 1-(3,4-dichlorobenzyl)-3-(4-formylthiazol-2-yl) urea was dissolved in 5 ml MeOH. 1.0 eq. of tetrabutylammonium bromide and 1.0 eq. of sodium hydroxide were added followed by addition of 1.0 eq. of 3-aminopropylphosphonic acid. To the mixture, 3.0 eq. of sodium cyanoborohydride was added and the reaction was stirred at room temp. overnight. The reaction mixture was loaded to reverse phase column and purified by HPLC to give 3-((2-(3-(3,4-dichlorobenzyl)ureido)thiazol-4-yl)methylamino)propylphosphonic acid.

Intermediate 24: 1-(4-(1-Amino-2-hydroxyethyl)thiazol-2-yl)-3-(3-fluorobenzyl)urea

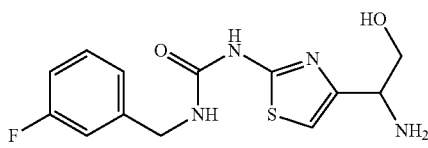

Step 1: An N-methylpyrrolidinone (5 mL) solution of ethyl 2-(2-aminothiazol-4-yl)-2-oxoacetate (commercial, 1.00 g, 5.0 mmol) and 1-fluoro-3-(isocyanatomethyl)benzene (831 mg, 5.5 mmol) was heated in a microwave reactor at 120 C for 30 minutes. Upon cooling, water (50 mL) was added with vigorous stiffing. Filtration of the precipitate afforded ethyl 2-(2-(3-(3-fluorobenzyl)ureido)thiazol-4-yl)-2-oxoacetate. M/Z 352 (M+H)+. The filtrate was dissolved in EtOH (100 mL) then hydroxylamine hydrochloride (700 mg, 10 mmol) and sodium acetate (1.07 g, 13 mmol) were added to the mix. The solution was stirred at 75 C for 4 hours and filtered while hot. Evaporation of the mixture and Flash chromatography afforded ethyl 2-(2-(3-(3-fluorobenzyl)ureido)thiazol-4-yl)-2-(hydroxyimino)acetate as a mixture of isomers. M/Z 367 (M+H)+.

Step 2: LiAlH$_4$ (10 mL, 10 mmol, 1 M in THF) was added to a THF (20 mL) solution of ethyl 2-(2-(3-(3-fluorobenzyl)ureido)thiazol-4-yl)-2-(hydroxyimino)acetate (1.05 g, 2.86 mmol). The mixture was stirred for a day at 50 C. Upon cooling the mixture to 0 C, Na$_2$SO$_4$x10H$_2$O (9.2 g, 28.6 mmol) was added carefully. The suspension was stirred for two days at ambient temperature which was followed by the addition of NaHSO$_4$ (1.2 g, 28.6 mmol) and MeOH (20 mL). The mixture is further stirred for an hour then HCl (5 mL, 2 M in ether) was added. Stirring was continued for another hour. Filtration, evaporation of the filtrate and Flash chromatography afforded 1-(4-(1-amino-2-hydroxyethyl)thiazol-2-yl)-3-(3-fluorobenzyl)urea. $^1$H NMR (400 MHz, MeOH): δ 7.28 (m, 1H), 7.09 (d, 1H), 7.01 (d, 1H), 6.92 (td, 1H), 6.81 (s, 1H), 4.42 (s, 2H), 4.10 (m, 1H), 3.84 (dd, 1H), 3.72 (dd, 1H). MS (ES+): M/Z 311 (M+H)+.

Intermediate 25: 1-(3-Fluorobenzyl)-3-(5-isopropyl-4-((methylamino)methyl)thiazol-2-yl)urea

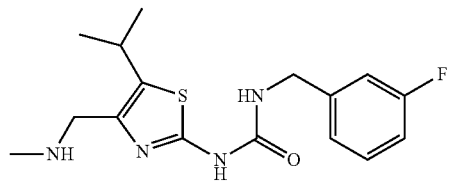

Step 1: A THF (5 mL) solution of methy; 2-amino-5-isopropylthiazole-4-carboxylate (commercially available, 200 mg, 1 mmol) and 1-fluoro-3-(isocyanatomethyl)benzene (140 μL, 1.1 mmol) was microwave irradiated at 160 C for 35 minutes. Usual work-up concluded with recrystallization from MeOH afforded methyl 2-(3-(3-fluorobenzyl)ureido)-5-isopropylthiazole-4-carboxylate. $^1$H NMR (400 MHz, DMSO-d6): δ7.35 (m, 1H), 7.08 (m, 3H), 4.34 (d, 2H), 3.94 (m, 1H), 3.76 (s, 3H), 1.24 (d, 6H). MS (ES+): M/Z 452 (M+H)+.

Step 2: LiAlH$_4$ (5.5 mL, 5.5 mmol, 1 M in THF) was added to a THF (30 mL) solution of methyl 2-(3-(3-fluorobenzyl) ureido)-5-isopropylthiazole-4-carboxylate (780 mg, 2.22 mmol) at 0 C. Upon completion of the reaction Na$_2$SO$_4$x10H$_2$O (1.5 g, 4.5 mmol) was added carefully. The suspension was stirred for a day at ambient temperature which was followed by the addition of NaHSO$_4$ (0.5 g, 4.5 mmol) and MeOH (5 mL). The mixture extracted with CH$_2$Cl$_2$, washed with dilute HCl, dried and evaporated to afford 1-(3-fluorobenzyl)-3-(4-(hydroxymethyl)-5-isopropylthiazol-2-yl)urea. $^1$H NMR (400 MHz, CDCl$_3$): δ 7.70 (s, 1H, br), 7.24 (m, 1H), 7.05 (d, 1H), 6.99 (d, 1H), 6.92 (td, 1H), 4.55 (s, 2H), 4.41 (d, 2H), 3.20 (m, 1H), 1.27 (d, 6H). MS (ES+): M/Z 324 (M+H)+.

Step 3: 1-(3-Fluorobenzyl)-3-(4-(hydroxymethyl)-5-isopropylthiazol-2-yl)urea (32 mg, 0.1 mmol) was oxidized with MnO$_2$ (87 mg, 1.0 mmol) in CH$_2$Cl$_2$ (5 mL). Filtration and evaporation afforded 1-(3-fluorobenzyl)-3-(4-formyl-5-isopropylthiazol-2-yl)urea. $^1$H NMR (400 MHz, CDCl$_3$): δ 9.83 (s, 1H), 7.60 (s, 1H, br), 7.27 (m, 1H), 7.12 (d, 1H), 7.06 (d, 1H), 6.93 (td, 1H), 4.48 (d, 2H), 3.80 (m, 1H), 1.42 (d, 6H). MS (ES+): M/Z 322 (M+H)+.

Step 4: NaBH$_4$ (100 mg, 3 mmol) was added in portions to a mixture of MeNH$_2$ (5 mL, 30% in EtOH) and 1-(3-fluorobenzyl)-3-(4-formyl-5-isopropylthiazol-2-yl)urea (322 mg, 1 mmol) at 0 C. The mixture was stirred for 6 hours then quenched with dilute HCl solution. Basic aqueous work-up with CH$_2$Cl$_2$ followed by flash chromatography afforded 1-(3-fluorobenzyl)-3-(5-isopropyl-4-((methylamino)methyl)thiazol-2-yl)urea. MS (ES+): M/Z 337 (M+H)+.

Intermediate 26: 1-(4-((2,2-Difluoroethylamino) methyl)thiazol-2-yl)-3-(3-fluorobenzyl)urea

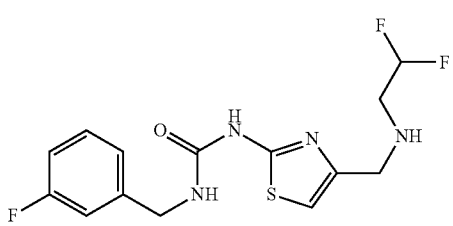

1-(4-Iodomethyl-thiazol-2-yl)-3-(3-fluorobenzyl)-urea (Intermediate 7, 1 eq.) was taken up in THF (0.3 M) and 2,2-difluoroethanamine (20 eq.) was added. The reaction was stirred overnight at ambient temperature. Some of the starting material, Intermediate 7 remained. Added additional 2,2-difluoroethanamine (10 equivalents). The reaction was complete after 2-4 hours. Removed solvent; coevaporated twice with MeOH. Crude is a 1:1 mixture of title compound and bis addition impurity. (used as is in subsequent step).

Intermediate 27: Not used

Intermediate 28: N-(4-((methoxy(methyl)amino) methyl)thiazol-2-yl)-1H-imidazole-1-carboxamide

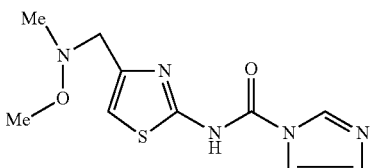

Step 1: 2-Amino-4-(N-methoxy-N-methyl-aminomethyl) thiazole. A mixture of 2-amino-4-chloromethyl-thiazole hydrochloride (27.8 g, 0.15 mol), N,O-dimethylhydroxylamine hydrochloride (87.8 g, 0.90 mol), and anhydrous THF (300 mL) was rapidly stirred and DIPEA (157 mL, 0.90 mol) was added. The resulting mixture was heated at 60 C for 10-15 hours. The mixture was cooled in an ice/salt bath and the solid byproduct (DIPEA hydrochloride) was removed by filtration and washed with cold THF (300 mL). The combined filtrate was concentrated to afford the title compound as a dark oil (31 g, >100% theory), which partially crystallized on standing. This product was used in the next step without further purification.

Step 2: 2-(N-Imidazocarbonylamino)-4-(N-methoxy-N-methyl-aminomethyl)thiazole. A flask was purged with dry nitrogen and charged with carbonyl diimidazole (37.2 g, 0.222 mol) and anhydrous THF (0.4 L). The mixture was stirred and heated to 27-32 C, affording a clear solution. A solution of crude 2-amino-4-(N-methoxy-N-methyl-aminomethyl)thiazole (31 g (as is), ~0.15 mol) in anhydrous THF (0.1 L) was added dropwise. The resulting cloudy reaction mixture was cooled to room temperature and stirred overnight affording a thick slurry. The solids were isolated by filtration, washed with diethyl ether (80 mL), and dried in vacuo (no heat) to afford the title compound as an off-white solid (20.0 g, 0.075 mol, 50% yield for 2-steps).

Intermediate 29: 1-[(5-Chlorothiophen-2-yl)methyl)- 3-(4-((methylamino)methyl) thiazol-2-yl]urea

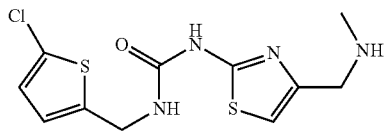

Step 1: Intermediate 28 (imidazolide) was reacted with C-(5-chlorothiophen-2-yl)methylamine using Method 7.
Step 2: The methoxyamine-urea product obtained in Step 1 was reduced with micronized zinc dust in acetic acid, following the procedure for Intermediate 5/Alternative Process/Step 2, to afford Intermediate 29.

Intermediate 30: 1-((5-Chlorothiophen-3-yl)methyl)- 3-(4-((methylamino)methyl) thiazol-2-yl) urea

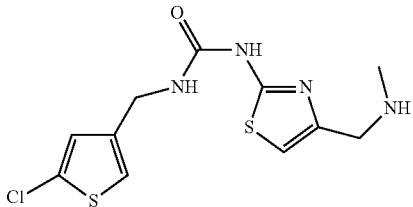

Step 1: Intermediate 28 (imidazolide) was reacted with Intermediate 37 (amine) using Method 7.
Step 2: The methoxyamine-urea product obtained in Step 1 was reduced with micronized zinc dust in acetic acid, following the procedure for Intermediate 5/Alternative Process/Step 2, to afford intermediate 30.

Intermediate 31: 5-(Methoxymethyl)-3-methylisoxazole-4-carboxylic acid

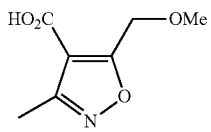

Step 1: A mixture of methyl 4-methoxyacetoacetate (34.2 mmol, 5 g) and pyrrolidine (1.1 eq, 37.6 mmol, 2.6 g) in toluene (50 ml) was refluxed under Dean-Stark-conditions for 14 h. The solvent was then removed under reduced pressure. The remaining oil was dissolved in chloroform (50 ml) and nitroethane (3 eq, 102.6 mmol, 7.69 g) and triethylamine (1.1 eq, 37.6 mmol, 3.79 g) were added. The mixture was cooled to 0° C. before dropwise addition of a solution of phosphorus oxychloride (1.1 eq, 37.6 mmol, 5.75 g) in chloroform (20 ml). The mixture was stirred over night at room temperature and then poured into water (20 ml). The organic layer was washed successively with hydrochloric acid (20 ml), aqueous sodium hydroxide (5% w/v, 50 mL) and brine (50 mL), dried ($Na_2SO_4$) and concentrated. After column chromatography, 1.47 g of methyl 5-(methoxymethyl)-3-methylisoxazole-4-carboxylyate was isolated. $^1$H NMR (300 MHz, $CDCl_3$), δ 4.80 (s, 2H), 3.87 (s, 3H), 3.45 (s, 3H), 2.45 (s, 3H).

Step 2: The methyl ester obtained in Step 1 (7.8 mmol, 1.4 g) was dissolved in tetrahydrofuran/water (20 ml, 10:1). Lithium hydroxide (1.1 eq, 8.68 mmol, 0.21 g) was added and the mixture was stirred at room temperature over night. The solvent was removed under reduced pressure to give the title compound as a white solid (0.85 g, 60% yield). $^1$H NMR (300 MHz, $CD_3OD$): δ 4.83 (s, 2H), 3.41 (s, 3H), 2.42 (s, 3H).

Intermediate 32: 5-Methylpyridazine-4-carboxylic acid

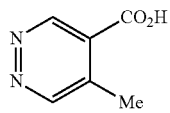

Intermediate 33: 4-Methylpyridazine-3-carboxylic acid

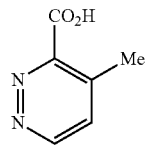

Step: 1: Ethyl pyruvate (4.5 eq, 66.9 g) was cooled to −10° C. and $H_2O_2$ (3.0 eq, 37.3 g) was added drop wise keeping the temperature below 0° C. Subsequently, the mixture was stirred for 15 minutes. A solution of 4-methylpyridazine (12.05 g, 128 mmol), $FeSO_4 7H_2O$ (3.0 eq, 106.8 g), $H_2SO_4$ (36 g) in $H_2O$ (35 mL)/$CH_2Cl_2$ (270 mL) was cooled to −5° C. The mixture of $H_2O_2$ and ethyl pyruvate was added drop wise keeping the temperature below 0° C. and stirred for 15 minutes. The reaction mixture was poured into $H_2O$/EtOAc mixture and stirred for 3 hours. The $H_2O$-layer was removed and the organic layer was stirred overnight with aq. $Na_2SO_3$. Subsequently, the layers were separated and the organic layer was washed twice with $H_2O$ and dried over $MgSO_4$. Removal of the volatiles afforded a mixture of ethyl 5-methylpyridazine-4-carboxylate and ethyl 4-methylpyridazine-3-carboxylate and 3 other compounds (29.0 g) as a yellow/orange oil.

The crude material was purified by silica chromatography, affording a mixture of ethyl 5-methylpyridazine-4-carboxylate and ethyl 4-methylpyridazine-3-carboxylate and another compound (3.7 g) as a yellow oil. The mixture was again purified by column chromatography ($SiO_2$; $CH_2Cl_2$/EtOAc 9:1-8:2) affording Ethyl 5-methylpyridazine-4-carboxylate (614 mg, 29% yield) as a yellow oil and Ethyl 4-methylpyridazine-3-carboxylate (447 mg, 23% yield) as a yellow oil/solid.

Intermediate 32: To a solution of ethyl 5-methylpyridazine-4-carboxylate (240 mg, 1.4 mmol) in $H_2O$/THF was added 7.5 N aq. NaOH (1.25 eq, 0.25 mL) and the mixture was stirred for 1 hour at 60° C. Concentrated HCl was added to pH 2 and subsequently the volatiles were removed in vacuo. The residue was first stirred with EtOAc and the solids were collected by filtration. Then stirred with THF and the solids were again collected by filtration. The solids were extracted with MeOH and removal of the volatiles afforded 5-methylpyridazine-4-carboxylic acid (358 mg) as a brown solid.

Intermediate 33: To a solution of ethyl 4-methylpyridazine-3-carboxylate (240 mg, 1.4 mmol) in $H_2O$/THF was added 7.5 N aq. NaOH (1.25 eq, 0.25 mL) and the mixture was stirred for 1 hour at 60° C. Concentrated HCl was added to pH 2 and subsequently the volatiles were removed in vacuo. The residue was first stirred with EtOAc and the solids were collected by filtration then stirred with THF and the solids were again collected by filtration. The solids were extracted with MeOH and removal of the volatiles afforded 4-methylpyridazine-3-carboxylic acid (328 mg) as a brown solid.

Intermediate 34: 3-Methyl-pyrazine-2-carboxylic acid

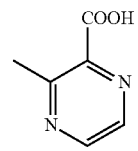

A solution of dimethylpyrazine (25 g, 231 mmol) in water (250 mL) was heated at 70° C. and a solution of $KMnO_4$ (82.2 g, 520 mmol) in water was added at such a rate to maintain the temperature between 70 and 75° C. The mixture was stirred until the purple color vanished and was filtered over Celite. The aqueous solution was extracted with EtOAc (6×800 mL), dried over $Na_2SO_4$ and concentrated in vacuo. The residue

Intermediate 35: 3-(Ethoxycarbonyl)-5-methylisoxazole-4-carboxylic acid

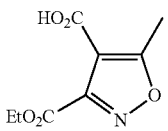

Step 1: To a solution of tert-butyl acetoacetate (42.1 mmol, 6.6 g) and ethyl cyanoformate (1.2 eq, 50.5 mmol, 5.0 g) in dry DCM (20 ml) [Zn(acac)$_2$] (2.1 mmol, 0.55 g) was added. After stirring at room temperature for 2 hours, TLC indicated complete conversion. The solvent was evaporated under reduced pressure, the residue was dissolved in ethyl ether and the suspension was filtered through Celite. After concentration, 2-acetyl-3-oxo-succinic acid 1-tert-butyl ester 4-ethyl ester (8.93 g, 82% yield) was obtained as a yellow oil.

Step 2: The 1,3-diketone obtained in Step 1 (34.7 mmol, 8.9 g) was dissolved in chloroform (50 ml). 4.91 g of triethylamine (1.4 eq, 48.6 mmol) and hydroxylamine-HCl salt (1.3 eq, 45.1 mmol, 3.13 g) were added and the mixture was refluxed for 3 h. The reaction was cooled to room temperature and 1N aq. HCl (100 ml) was added followed by extraction with DCM (3×100 mL). The combined organic layers were dried over sodium sulfate, filtered and concentrated. Column purification by silica gel yielded (6.89 g, 77% yield) of tert-butyl 3-(ethoxycarbonyl)-5-methylisoxazole-4-carboxylate. $^1$H NMR (300 MHz, CDCl$_3$), δ 4.42 (q, 2H), 2.66 (s, 3H), 1.53 (s, 15H), 1.39 (t, 3H).

Step 3: The tert-butyl ester obtained in Step 2 (0.8 g, 3.13 mmol) was dissolved in formic acid (20 mL) and stirred at room temperature overnight. 6N aq. HCl (50 ml) was added. The mixture was extracted with DCM (3×50 mL). The combined organic layers were dried over sodium sulfate and concentrated to give the title compound, Intermediate 35: 3-(ethoxycarbonyl)-5-methylisoxazole-4-carboxylic acid, as a brownish oil (0.4 g, 64%). $^1$H NMR (300 MHz, MeOH-d$_4$): δ 4.40 (q, 2H), 2.68 (s, 3H), 1.35 (t, 3H).

Intermediate 36: C-(5-Fluoro-thiophen-2-yl)-methylamine

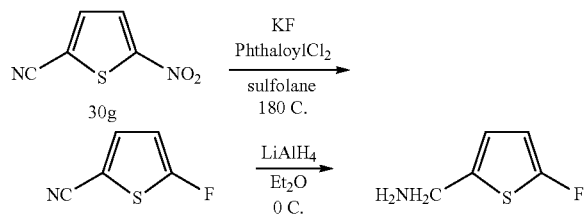

Step 1: Synthesis of 5-fluoro-thiophene-2-carbonitrile starting from 5-nitro-thiophene-2-carbonitrile following a literature procedure: Syn Comm 30 (19) 3629-3632 (2000).

Step 2: A 500 ml 3 neck flask was fitted with septum, N$_2$ inlet, and an addition funnel. Under N$_2$, the flask was charged with LAH (130 ml of a 1M solution of LAH in diethyl ether), and cooled in an ice bath with stirring. Added the 5-Fluorothiophene-2-carbonitrile (9.43 g) as a solution in dry diethyl ether (15 mL) over 30 minutes via addition funnel. After addition, the reaction was allowed to warm to room temperature over an hour. The resulting thin mixture was diluted with diethyl ether (200 ml) and then slowly, 2N NaOH (25 ml) was added dropwise. Stirred overnight; a tan mass was present. Filtered the diethyl ether layer. The tan mass was broken up and titrated with diethyl ether (50 ml) and then filtered. The diethyl ether portions were combined and the solvent removed in vacuo. Dried overnight under reduced pressure to give a clear orange oil. Distilled at 68-70° C. (10 mm) to give C-(5-fluoro-thiophen-2-yl)-methylamine as a clear colorless liquid.

Intermediate 37: (5-Chlorothiophen-3-yl)methanamine hydrochloride

Step 1: To a solution of N-chlorosuccinimide (1.0 eq, 12.2 g) in hexane (100 mL) were added thiophene-3-carbonitrile (10 g, 91.6 mmol) and 70% HClO$_4$ (1 mol %, 0.1 mL). The reaction mixture was stirred overnight at room temperature and subsequently K$_2$CO$_3$ was added. Removal of the solids and the volatiles afforded the crude product as a yellow oil. (This was a mixture of starting material: desired product: wrong isomer: dichlorinated 48%:26%:19%:6%.) Purification twice by column chromatography afforded 5-chlorothiophene-3-carbonitrile (1.71 g, 13%) as a yellow oil.

Step 2: To a pre-cooled (ice-water bath) solution of BH$_3$.THF (3.4 eq, 11.8 mL) was added a solution of 5-chlorothiophene-3-carbonitrile (0.5 g, 3.48 mmol) in THF (11.5 ml). The reaction mixture was stirred for 4 hours at room temperature and subsequently 6 N HCl (17 ml) was added slowly followed by H$_2$O/MeOH (17/114 mL). The reaction mixture was stirred overnight. Removal of the volatiles afforded the title product (1.0 g) as an off-white solid.

Intermediate 38: 3-Chloromethyl-[1,2,4]thiadiazol-5-ylamine

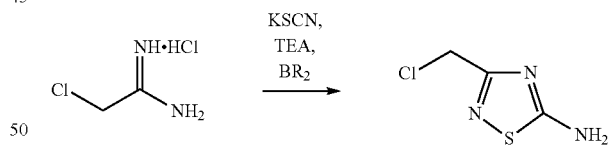

2-Chloroacetamidine hydrochloride (10.3 g, 80 mmol) was dissolved in anhydrous MeOH (300 mL) and then cooled to 0 C. TEA (20.2 g, 200 mol) was added followed by bromine (11.5 g, 72 mmol, dropwise over 5 minutes at 0 C). Potassium thiocyanate (8.15 g, 84 mmol) in MeOH (100 mL) was added dropwise over 1 hour and the resultant mixture was stirred at 0 C for 2 hours. Reaction was maintained at ambient temperature for 1 h. Solid was removed by filtration and filtrate concentrated in vacuo. This syrupy residue was treated with EtOAc (300 mL) followed by filtration and purification by silica gel chromatography (PE:EA=4:1 to 3:1) to afford Intermediate 67: 3-chloromethyl-[1,2,4]thiadiazol-5-ylamine as white solid (5 g, 42%). $^1$H-NMR (400 MHz, DMSO-d$_6$) δ: 8.03 (s, 2H, —NH$_2$), 4.51 (s, 2H, —CH$_2$Cl); LC-MS (m/z): 150.1 μM+Hr.

Intermediate 39: (3-{[Methyl-((R)-tetrahydro-furan-2-carbonyl)-amino]-methyl}-[1,2,4]thiadiazol-5-yl)-carbamic acid phenyl ester

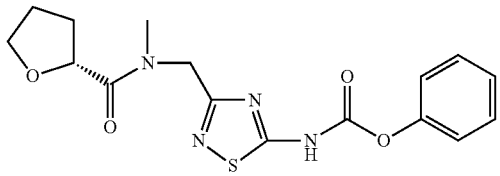

Step 1: 3-Chloromethyl-[1,2,4]thiadiazol-5-ylamine (Intermediate 38) (1.5 g, 10 mmol) was dissolved in 27% methylamine alcohol solution (20 mL, 174 mmol) to give a yellowish solution. The solution was heated in microwave reactor at 60 C for 15 min After cooling to room temperature, the reaction mixtures were combined and concentrated at room temperature (20-25 C; attention: the product is sensitive to heat). A solution of potassium carbonate (9.7 g, 70 mmol) in water (15 mL) was added into the residue and the resultant mixture was concentrated to dryness. The crude product was purified by silica gel column chromatography (DCM:MeOH=5:1) to afford 3-(N-methylaminomethyl)[1,2,4]thiadiazol-5-ylamine (14.0 g, yield: 69%) as a yellow solid. LC-MS (m/z): 145.1 [M+H]$^+$.

Step 2: To a solution of (R)-tetrahydrofuran-2-carboxylic acid (5.0 g, 43 mmol) in DMF (100 mL) was added carbonyl diimidazole (7.68 g, 47 mmol) at 0 C under $N_2$. After 2 hours agitation at 0 C, the product obtained from Step 1 (7.0 g, 49 mmol) in DMF (20 mL) was added and the mixture was stirred at room temperature overnight. The reaction mixture was then diluted with water (800 mL), extracted with EA (10×200 mL). The combined organic layers were washed twice with brine (100 mL) and concentrated. The residue was purified by silica gel column chromatography (PE:EA=1:3) to afford (R)-tetrahydro-furan-2-carboxylic acid (5-amino-[1,2,4]thiadiazol-3-ylmethyl)-methyl-amide (5.9 g, yield: 59%) as a red syrup. LC-MS (m/z): 243.1 [M+H]$^+$.

Step 3: To a solution of the product from Step 2, (R)-tetrahydro-furan-2-carboxylic acid (5-amino-[1,2,4]thiadiazol-3-ylmethyl)-methyl-amide (3.0 g, 12.4 mmol), and pyridine (1.08 g, 13.6 mmol) in DCM (120 mL) was added phenyl chloroformate (1.95 g, 12.4 mmol) by syringe at 0 C under $N_2$. The reaction mixture was stirred at room temperature overnight, concentrated and purified by silica gel column chromatography (PE:EA=1:1) to afford Intermediate 39: (3-{[methyl-((R)-tetrahydro-furan-2-carbonyl)-amino]-methyl}-[1,2,4]thiadiazol-5-yl)-carbamic acid phenyl ester (3.0 g, yield: 67%) as a pale solid. LC-MS (m/z): 363.1 [M+H]$^+$.

Intermediate 40: 2-(3-(3-Fluorobenzyl)ureido)-4-(N-methyl-aminomethyl)-5-fluorothiazole

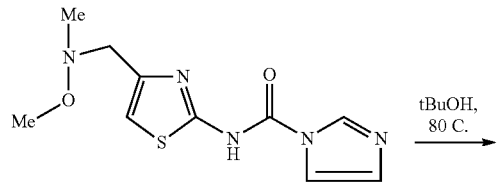

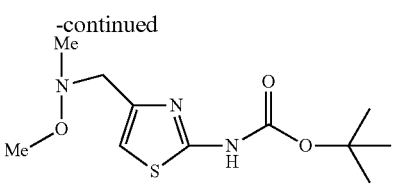

Step 1: 2-(tert-Butoxycarbonylamino)-4-(N-methoxy-N-methyl-aminomethyl)thiazole. A mixture of Intermediate 28: 2-(N-imidazocarbonylamino)-4-(N-methoxy-N-methyl-aminomethyl)thiazole (23.3 g, 87.2 mmol) and anhydrous tert-butanol (140 mL) was stirred under an inert atmosphere and heated to 80 C. After 20 minutes, a clear solution was obtained. tert-Butanol was evaporated at reduced pressure and the oily residue was dissolved in hexane (200 mL) and washed with water (2×100 mL). The organic layer was dried over sodium sulfate, filtered and evaporated to afford the title compound as a colorless oil which crystallized on standing (21.4 g, 90% yield).

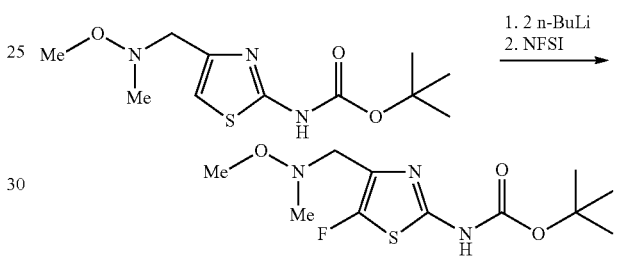

Step 2: Fluorination of Thiazole 5-Position (*Organic Process R & D* (10), 346-348 (2006)). 2-(tert-Butoxycarbonylamino)-4-(N-methoxy-N-methyl-aminomethyl)-5-fluorothiazole. A solution of 2-(tert-butoxycarbonylamino)-4-(N-methoxy-N-methyl-aminomethyl)thiazole (34.4 g, 0.126 mol) and anhydrous THF (0.71 L) was cooled to −78 C under an inert atmosphere. A solution of 1.6 M n-BuLi in hexane (165 mL, 0.264 mol) was added dropwise over 45 minutes. The resulting mixture was stirred at −78 C for 2-3 hours, then treated dropwise with a solution of N-fluorobenzenesulfonimide (51.6 g, 0.164 mol) in THF (0.3 L). The reaction was warmed to −10 C and quenched with 1 N HCl (0.28 L). The mixture was made alkaline with saturated sodium bicarbonate solution (~200 mL) and extracted with diethyl ether (0.5 L). The organic layer was dried with magnesium sulfate and concentrated to leave a red oil (51 g) which was purified by silica gel chromatography (40% EtOAc/hexane) to afford the title compound as a yellow resin (15.1 g, 41% yield).

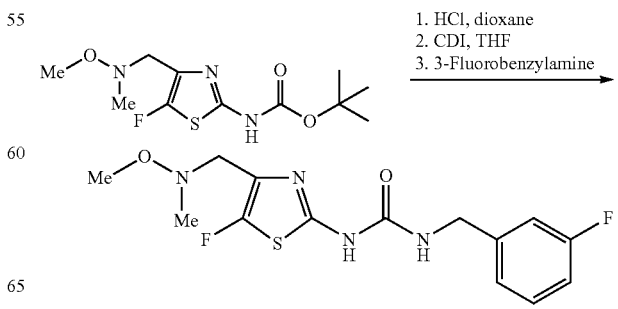

Step 3: 2-(3-(3-fluorobenzyl)ureido)-4-(N-methoxy-N-methyl-aminomethyl)-5-fluorothiazole. A solution of 2-(tert-butoxycarbonylamino)-4-(N-methoxy-N-methyl-aminomethyl)-5-fluorothiazole (3.6 g, 12.4 mmol) in 1,4-dioxane (60 mL) was saturated with dry HCl gas and held overnight. The mixture was evaporated to dryness to leave the 2-amino-5-fluorothiazole dihydrochloride salt (3.3 g, 100% yield).

Step 4: The salt was suspended in anhydrous THF (50 mL) and DIPEA (4.3 mL, 25 mmol) was added. The resulting mixture was added to a solution of carbonyl diimidazole (2.07 g, 12.8 mmol) in THF (30 mL) at 30-35 C. After stirring overnight at room temperature, the solids were collected and washed with diethyl ether (5 mL) to give a 2-(N-imidazocarbonylamino)-5-fluorothiazole intermediate (2.1 g, 55% yield).

Step 5: The imidazolide intermediate (2.0 g, 6 mmol) was suspended in THF (40 mL) and 3-fluorobenzylamine (0.71 mL, 6 mmol) was added slowly. After 1 hour, water (40 mL) was added and THF was evaporated at reduced pressure. Extraction with DCM (60 mL), drying over sodium sulfate, and concentration afforded the title compound as a pale yellow foam (2.05 g, 100% yield).

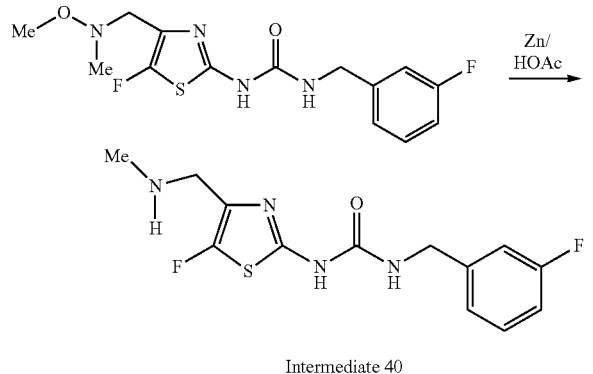

Intermediate 40

Step 6: 2-(3-(3-Fluorobenzyl)ureido)-4-(N-methyl-aminomethyl)-5-fluorothiazole (Intermediate 40). A solution of 2-(3-(3-fluorobenzyl)ureido)-4-(N-methoxy-N-methyl-aminomethyl)-5-fluorothiazole (2.05 g, 6 mmol) in glacial acetic acid (30 mL) was treated with micronized zinc dust (12 g) and stirred at 60 C for 1-2 hours. The mixture was diluted with water (30 mL) and filtered on Celite. The filter cake was washed with 1:1 HOAc:water (3×20 mL) and the combined filtrate were brought to pH 10 with ammonium hydroxide (~82 mL). The resulting mixture was stirred in ice and the crude product was collected by filtration and washed with water (4 mL). The crude product was further purified by silica gel chromatography (5:94:1 MeOH:DCM:NH$_4$OH) to afford Intermediate 40 as a white solid (1.25 g, 67% yield).

Intermediate 41: 1-[4-(Cyano-methylamino-methyl)-thiazol-2-yl]-3-(3-fluoro-benzyl)-urea

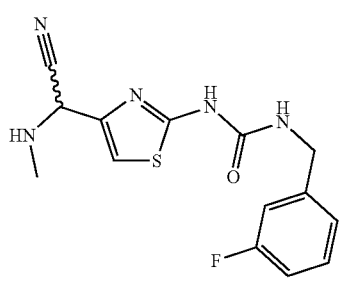

Step 1: Preparation of acetic acid 2-amino-thiazol-4-ylm-ethyl ester. 1-Chloro-3-hydroxy-propan-2-one (15.06 g) and thiourea (8.36 g) were dissolved in EtOH (55 mL) and heated at reflux over 30 min. The reaction mixture was concentrated under reduced pressure to afford the desired product.

Step 2: Preparation of -(3-fluoro-benzyl)-3-(4-hydroxymethyl-thiazol-2-yl)-urea. To a solution of acetic acid 2-amino-thiazol-4-ylmethyl ester (6.89 g) in THF (50 mL) were 3-fluorobenzylisocyanate (5.50 g) and TEA (5.03 mL) added. The resultant solution was heated at 70° C. over 2 h. Then, MeOH (30 mL) and NaOH (6N, 15 mL) were added to the above solution. The reaction mixture was heated at 60° C. for 30 min After cooling down, the reaction mixture was diluted with EtOAc (150 mL) and was washed with water. The organic solvents were concentrated and the residue was purified by silica-gel column chromatography to afford 8.29 g of the desired product-1-(3-fluoro-benzyl)-3-(4-hydroxymethyl-thiazol-2-yl)-urea.

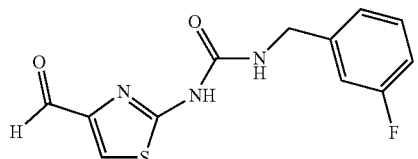

Step 3: Preparation of 1-(3-fluoro-benzyl)-3-(4-formyl-thiazol-2-yl)-urea. (3-Fluoro-benzyl)-3-(4-hydroxymethyl-thiazol-2-yl)-urea (909.52 mg) was added in a solution of Dess-Martin periodinane (0.3 M, 10.8 mL) in DCM (100 mL) at 0° C. The reaction mixture was stirred at room temperature over a couple of hours until all starting materials were consumed. After concentration, the residue was recrystallized from DCM/Hexane to afford the desired product (580 mg).

Step 4: Preparation of 1-[4-(cyano-methylamino-methyl)-thiazol-2-yl]-3-(3-fluoro-benzyl)-urea. Trimethylsilyl cyanide (161 µL) was added to a solution of 1-(3-fluoro-benzyl)-3-(4-formyl-thiazol-2-yl)-urea (409 mg) and MeNH$_2$ (8 M, 0.4 mL) in (EtOH 10 mL) at 0° C. The reaction mixture was stirred at room temperature for 2 hours. The additional of 170 µL of trimethylsilyl cyanide was added to convert all starting material into the product. The product was purified by aqueous work-up and chromatography.

Intermediate 42: 1-(2-Methoxyethyl)-3,5-dimethyl-1H-pyrazole-4-carboxylic acid

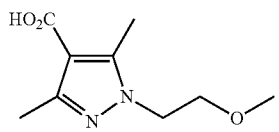

Sodium hydride (60%, 120 mg, 3.0 mmol) was suspended in THF (2 ml) at 0 C. Ethyl 3,5-dimethyl-1H-pyrazole-4-carboxylate (168 mg, 1.0 mmol) dissolved in THF (2 mL) was added drop-wise. Stirring was maintained until the evolution of hydrogen stopped. 1-Bromo-2-methoxyethane (208 mg, 1.5 mmol) was added and the reaction was heated at reflux at 70 C for 48 hours. Reaction was quenched with water at 0 C, acidified to pH=1-2 with HCl (2M) and was extracted with EtOAc. The organic layer was washed with water, NH$_4$Cl aq., and brine, and dried with Na$_2$SO$_4$, and concentrated. The residue was subjected to HPLC purification. White solid (67 mg, 0.34 mmol, 34%) was obtained after stripping of solvents and drying. ESI-MS m/z 199.4 (M+H).

Intermediate 43: Tetrahydro-2H-pyran-2-carboxylic acid

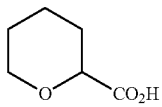

(Tetrahydro-2H-pyran-2-yl)methanol (0.51 g, 4.30 mmol) was dissolved in 10 mL of 1:1 ACN/water mixture, and bis-acetoxyiodobenzene [BAIB] (3.04 g, 9.46 mmol) was added to the mixture. It was then cooled to 0 C in an ice bath, and TEMPO (0.134 g, 0.86 mmol) was added under argon flow. The mixture was stirred at room temperature for 3 hours, and the reaction was quenched by addition of 2×20 mL of 1 M NaOH. Basic solution was washed 3×30 mL of EtOAc, and re-acidified with 1 M HCl to ca. pH 2. Aqueous layer was then extracted 6×30 mL of EtOAc, organic layers were combined, dried over sodium sulfate and evaporated. The title compound was isolated as an oil (0.34 g, 61%) was used in the next step without further purification. $^1$H NMR (300 MHz, CDCl$_3$) δ4.11 (d, 1H, J=10.5 Hz), 3.98 (d, 1H, J=9.9 Hz), 3.53 (m, 1H), 2.10-1.92 (m, 3H), 1.60-1.54 (m, 3H).

Intermediate 44: (R)-5-Methoxytetrahydrofuran-2-carboxylic acid

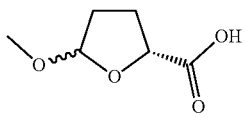

Step 1: ((R)-5-methoxy-tetrahydro-furan-2-yl)-methanol. ((R)-5-Methoxy-tetrahydro-furan-2-ylmethoxy)-methyl-diphenylsilane (Pilli, R. A.; Riatto, V. B. *Tet. Asymm.* (2000)), 11, 3675) (0.80 g, 2.25 mmol) was dissolved in 35 mL of anhydrous MeOH and 5 mL of formic acid was added to the mixture. The mixture was stirred at room temperature for 30 minutes at which point TLC (9:1 hexanes:EtOAc) indicated complete conversion to the product. Volatiles were removed in vacuo and 0.83 g, 100% of the title compound was obtained as clear oil.

Step 2: (R)-5-methoxytetrahydrofuran-2-carboxylic acid. Material from Step 1 was oxidized via the same method in Step 2 of the synthesis of Intermediate 47, it was prepared as oil. $^1$H NMR (300 MHz, CDCl$_3$) δ 5.19 (d, 0.6H, J=4.2 Hz), 5.10 (d, 0.4H, J=4.5 Hz), 4.63-4.58 (m, 1H), 3.42 (s, 1.2H), 3.34 (s, 1.8H), 2.28-1.88 (m, 4H).

Intermediate 45: 1-(4-methoxybutanyl)-3,5-dimethyl-1H-pyrazole-4-carboxylic acid

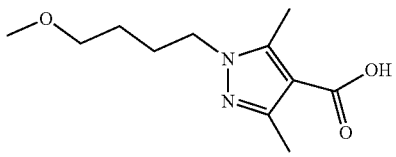

Prepared by following the same method as the preparation of Intermediate 42, ethyl 3,5-dimethyl-1H-pyrazole-4-carboxylate (280 mg) was reacted with 1-bromo-2-methoxybutane (367 mg) to afford white solid (185 mg, 41%). ESI-MS m/z 227.4 (M+H).

Intermediate 46: 1-(3-methoxypropyl)-3,5-dimethyl-1H-pyrazole-4-carboxylic acid

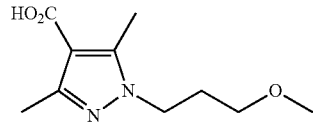

Prepared by following the same method as the preparation of intermediate 42: ethyl 3,5-dimethyl-1H-pyrazole-4-carboxylate (280 mg) was reacted with 1-bromo-2-methoxybutane (337 mg) to afford white solid (42 mg, 0.20 mmol, 10%). ESI-MS m/z 213.2 (M+H).

Intermediate 47: (R)-5-methyltetrahydrofuran-2-carboxylic acid

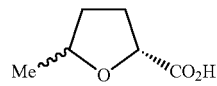

Step 1: (R)-tert-butyl((5-methyltetrahydrofuran-2-yl)methoxy)diphenylsilane (*Tet. Asym.* (2000), 11, 3675) (0.523 g, 1.48 mmol) was dissolved in 5 mL of anhydrous THF, TBAF (1 M solution in THF, 1.48 mL) was added to the solution and it was stirred at room temperature under argon flow overnight. Volatiles were then removed in vacuo and resulting oil was used in the next step with no purification Step 2: Crude (R)-(5-methyltetrahydrofuran-2-yl)methanol was dissolved in 6 mL of 1:1 ACN/water mixture, and bis-acetoxyiodobenzene [BAIB] (0.71 g, 2.20 mmol) was added to the mixture. It was then cooled to 0 C in an ice bath, and TEMPO (0.031 g, 0.2 mmol) was added under argon flow. The mixture was stirred at room temperature for 3 h, and the reaction was quenched by addition of 20 mL of 1 M NaOH. Basic solution was washed 3×15 mL of EtOAc, and re-acidified with 1 M HCl to ca. pH 2. Aqueous layer was then extracted 6×15 mL of EtOAc, organic layers combined, dried over sodium sulfate and evaporated. Resulting oil (0.05 g, 26%) was used in the next step with no purification. $^1$H NMR (300 MHz, CDCl$_3$) δ 4.48-4.43 (m, 1H), 4.20-4.17 (m, 1H), 2.33-2.21 (m, 3H), 2.08-2.02 (m, 1H), 1.35 (dd, 3H, J1=6.3 Hz, J2=1.8 Hz).

Intermediate 48: 3-Methyloxetane-3-carboxylic acid

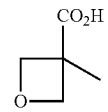

The title compound was prepared following the same method described in step 2 of the preparation of intermediate 47 from (3-methyloxetan-3-yl)methanol (0.51 g, 5 mmol). ¹H NMR (300 MHz, CDCl₃) δ 4.98 (d, 2H, J=6.0 Hz), 4.44 (d, 2H, J=6.0 Hz), 1.65 (s, 3H).

Intermediate 49: 3,6-Dichloropyridazine-4-carbonyl chloride

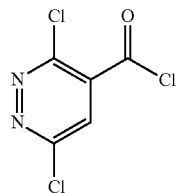

To a suspension of 3,6-dichloropyridazine-4-carboxylic acid (1.16 g, 6 mmol) in toluene (20 mL) were added DMF (2 drops) and SOCl₂ (4 mL) and the mixture was heated at reflux temperature for 3 h. The volatiles were removed and the residue was stripped with toluene. The resulting brown oil (3,6-dichloropyridazine-4-carbonyl chloride) was used without purification.

Intermediate 50: 3,5-Dimethylpyridazine-4-carboxylic acid

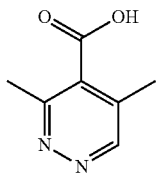

Step 1: Ethyl 2,3-dimethylcycloprop-2-enecarboxylate. Under a nitrogen atmosphere 2-butyn (9.50 g, 176 mmol) was cooled to 0° C. and Rh₂(OAc)₄ (195 mg) was added. To the resulting suspension was added slowly over a period of 4.5 hours ethyl diazoacetate (8.02 g, 70 mmol). The mixture was stirred for 30 minutes and pentane (30 mL) was added. The solids were removed by filtration over Celite and the filtrate was concentrated in vacuo to afford ethyl 2,3-dimethylcycloprop-2-enecarboxylate (below) as a mixture with ethyl diazoacetate.

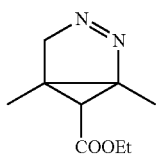

Step 2: Ethyl 1,5-dimethyl-2,3-diaza-bicyclo[3.1.0]hex-2-ene-6-carboxylate. Diazomethane was prepared from Diazald (21.5 g), KOH (6.6 g) in 2-(2-ethoxyethoxy)ethanol (35 mL). To the diazomethane solution in Et₂O was added ethyl 2,3-dimethylcycloprop-2-enecarboxylate as obtained above. The mixture was stirred at 0° C. for 14 days in the dark. A solution of acetic acid in Et₂O was added to quench off remaining diazomethane and the volatiles were removed in vacuo. Remaining starting material was removed by Kugelrohr distillation to afford ethyl 1,5-dimethyl-2,3-diaza-bicyclo[3.1.0]hex-2-ene-6-carboxylate (1.25 g, 6.9 mmol) as a yellowish oil in 10% yield over 2 steps.

Step 3: Ethyl 3,5-dimethyl-1,4-dihydropyridazine-4-carboxylate. To a solution of ethyl 1,5-dimethyl-2,3-diaza-bicyclo[3.1.0]hex-2-ene-6-carboxylate (1.25 g, 6.9 mmol) in ethanol (20 mL) was added a solution of NaOEt in ethanol (7 mL 0.2N) and the mixture was stirred for 10 min The resulting solution was partitioned between diethyl ether and water. The organic phase was isolated and the aqueous phase was extracted with diethyl ether. The combined organic phases were dried over MgSO₄ and the volatiles were removed in vacuo to afford ethyl 3,5-dimethyl-1,4-dihydropyridazine-4-carboxylate (1.0 g, 5.5 mmol, 80%) which was partially (circa 50%) oxidized to the pyridazine analog.

Step 4: Ethyl 3,5-dimethylpyridazine-4-carboxylate. To a solution of ethyl 3,5-dimethyl-1,4-dihydropyridazine-4-carboxylate (1.0 g, 5.5 mmol) as obtained above in acetone (30 mL) was added a solution of KMnO₄ (0.48 g, 3.0 mmol) in water (6 mL). The mixture was stirred for 30 minutes at room temperature and the solids were removed by filtration. The filtrate was concentrated and purified by column chromatography (SiO₂, EtOAc/Heptane 1/1) to afford ethyl 3,5-dimethylpyridazine-4-carboxylate (600 mg, 3.3 mmol) as a colorless oil in 60% yield.

Step 5: 3,5-Dimethylpyridazine-4-carboxylic acid (Intermediate 50). To a solution of ethyl 3,5-dimethylpyridazine-4-carboxylate (600 mg, 3.3 mmol) in ethanol (1 mL) was added a solution of NaOH (166 mg, 4.16 mmol) in water (5 mL). The mixture was heated at 50° C. for 1 hour and a clear solution was obtained. The solution was acidified by addition of aq. HCl until pH 5 and all volatiles were removed in vacuo. The residue was extracted with DCM/MeOH 4/1. The extract was concentrated to dryness to afford Intermediate 50: 3,5-dimethylpyridazine-4-carboxylic acid (550 mg) as an off-white solid.

Intermediate 51: 1-(5-Fluoro-thiophen-2-ylmethyl)-3-(4-methylaminomethyl-thiazol-2-yl)-urea

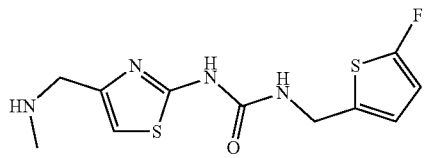

It was prepared following the same method of the preparation of Intermediate 29, starting from (5-fluoro-thiophen-2-yl)-methylamine.

Intermediate 52: Imidazole-1-carboxylic acid (4-{[methyl-((R)-tetrahydro-furan-2-carbonyl)-amino]-methyl}-thiazol-2-yl)-amide

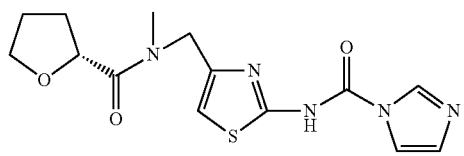

Step 1: tert-Butyl 4-((methylamino)methyl)thiazol-2-yl-carbamate (Intermediate 17) was coupled with (R)-2-tetrahydrofuroic acid using TBTU (Method 2) to afford (4-{[methyl- ((R)-tetrahydro-furan-2-carbonyl)-amino]-methyl}-thiazol-2-yl)-carbamic acid tert-butyl ester.

Step 2: The product from Step 1 was treated with TFA to cleave the BOC group (Method 1) to afford (R)-tetrahydro-furan-2-carboxylic acid (2-amino-thiazol-4-ylmethyl)-methyl-amide.

Step 3: (R)-Tetrahydro-furan-2-carboxylic acid (2-amino-thiazol-4-ylmethyl)-methyl-amide (1.65 g, 6.5 mmol) was dissolved in THF (5 mL) and added dropwise to a solution of carbonyl diimidazole (1.1. eq) in THF (10 mL) at 35° C. After stirring overnight at 20° C., the mixture was cooled in ice. The solids were collected by filtration and washed with Et$_2$O to afford Intermediate 52: Imidazole-1-carboxylic acid (4-{[methyl-((R)-tetrahydro-furan-2-carbonyl)-amino]-methyl}-thiazol-2-yl)-amide (1.2 g, 55% yield) as felty white crystals.

Intermediate 53: (R)-5-(tert-Butyl-diphenyl-silanyloxymethyl)-tetrahydro-furan-2-carboxylic acid

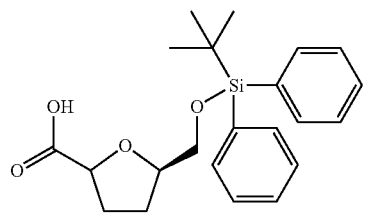

Prepared from the corresponding 2-nitrile via a 3 step procedure:

Step 1: (R)-5-(tert-Butyl-diphenyl-silanyloxymethyl)-tetrahydro-furan-2-carbonitrile was treated with sodium methoxide in MeOH to afford (R)-5-(tert-Butyl-diphenyl-silanyloxymethyl)-tetrahydro-furan-2-carboxylic acid methyl ester.

Step 2: The methyl ester obtained in Step 1 was reduced with LAH in THF to afford the alcohol: (R)-5-(tert-Butyl-diphenyl-silanyloxymethyl)-tetrahydro-furan-2-methanol.

Step 3: The alcohol obtained in Step 2 was oxidized with BAIB/TEMPO (using the procedure for Intermediate 55) to afford Intermediate 53: (R)-5-(tert-Butyl-diphenyl-silanyloxymethyl)-tetrahydro-furan-2-carboxylic acid.

Intermediate 54:
cis-3-Methyl-tetrahydrofuran-2-carboxylic acid

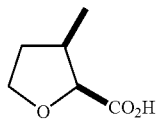

Prepared by catalytic hydrogenation (Rh/C, 50 psi, MeOH) of 3-methyl-2-furoic acid.

Intermediate 55: 3-Ethyloxetane-3-carboxylic acid

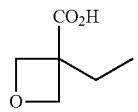

(3-Ethyloxetan-3-yl)methanol (0.58 g, 5.00 mmol) was dissolved in 10 mL of a 1:1 ACN-water mixture, and bis-acetoxyiodobenzene (BAIB, 3.54 g, 11.0 mmol) was added. The mixture was cooled in an ice bath, and TEMPO (0.156 g, 1.00 mmol) was added under argon flow. The mixture was stirred at room temperature for 1 hr, and then treated with 1 M aqueous sodium hydroxide (20 mL). The solution was washed twice with EtOAc and then acidified to pH 2. The aqueous solution was extract six times with EtOAc and these combined extracts were dried over sodium sulfate and concentrated to afford 0.37 g (57%) of Intermediate 55 as oil, which was used without further purification.

Intermediate 56:
cis-3-methoxy-tetrahydrofuran-2-carboxylic acid

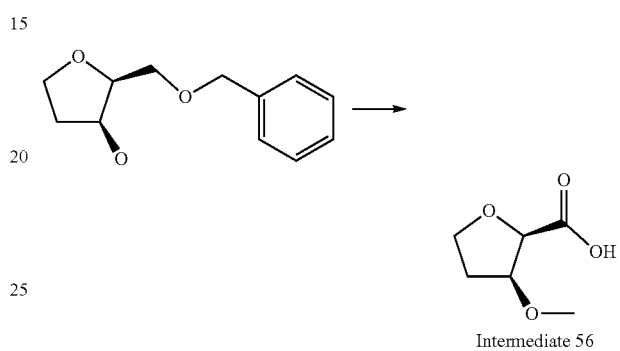

Intermediate 56

Step 1: cis-2-Benzyloxymethyl-tetrahydro-furan-3-ol was O-methylated using methyliodide and sodium hydride in DMF.

Step 2: The 3-methoxy-compound obtained in Step 1 was hydrogenated over palladium on carbon in acetic acid to cleave the O-benzyl protecting group.

Step 3: The 2-hydroxymethyl group in the product form Step 2 was oxidized to the carboxylic acid using BAIB/TEMPO to afford Intermediate 56, which was purified by chromatography.

Intermediate 57: Benzooxazol-6-yl-methylamine
[RN 872047-63-7]

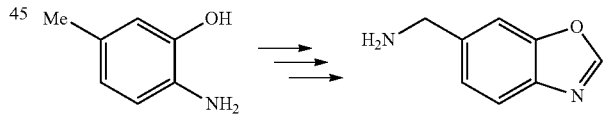

Step 1: 6-Methyl-benzooxazole. A 50 ml flask was charged with 6-amino-m-cresol (2 g, 16.24 mmole), 20 ml toluene and 5.4 ml triethyl orthoformate. The reaction mixture was refluxed for 2 hours. The mixture was concentrated down to about 2.3 g crude. Purification by silicagel column chromatography using 20% EtOAc/hexane provided 1.45 g brown oil (69% yield) that solidified in the freezer.

Step 2: 6-Bromo-methyl-benzooxazole. To a 100 ml flask equipped with magnetic stirre and condenser were added: 6-methyl-benzooxazole (1.4 g, 10.52 mmole), 50 ml carbon tertrachloride, NBS (1.7 g, 9.5 mmole) and AIBN (200 mg, 1.21 mmole). The reaction mixture was refluxed for 4 hours. The mixture was cooled down, concentrated and purified by silicagel column chromatography using 10 to 15% EtOAc/hexane. 1.81 g (75% yield) yellow solid was obtained.

Step 3: 6-Azidomethyl-benzooxazole. A 100 ml flask was loaded with 6-bromo-methyl-benzooxazole (1.8 g, 8.5 mmole), 40 ml DMF and sodium azide (1.1 g, 16.98 mmole). The reaction mixture was stirred at room temperature, overnight. The reaction mixture was diluted with 40 ml water and extracted 2×50 ml EtOAc. Combined organic layers were washed with water, brine, dried over sodium sulfate, filtered and concentrated to afford 2 g oily crude. HNMR shows 90% pure product. This was used for next step.

Step 4: Benzooxazol-6-yl-methylamine (Int. 57). To a solution of 6-azidomethyl-benzooxazole (500 mg, 2.87 mmole) in 25 ml MeOH, 10% Pd/C (300 mg, 10% eq.) was added. The reaction mixture was stirred at ambient temperature under hydrogen atmosphere for 24 hours. The reaction mixture was filtered trough a pad of celite and washed with MeOH. The filtrate was concentrated to give Intermediate 57 as a brown oil (400 mg).

Intermediate 58: Acetic acid (R)-5-{2-[3-(3,4-dichloro-benzyl)-ureido]-thiazol-4-yl}-pyrrolidin-3-yl ester Hydrochloride

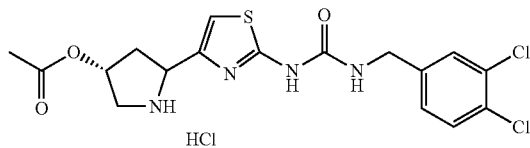

Step 1: (R)-4-Acetoxy-pyrrolidin-2-yl chloromethyl ketone was condensed with thiourea in ethanol in the manner described for Intermediate 1, to afford (R)-4-Acetoxy-2-(2-amino-thiazol-4-yl)-pyrrolidine-1-carboxylic acid tert-butyl ester.

Step 2: (R)-4-Acetoxy-2-(2-amino-thiazol-4-yl)-pyrrolidine-1-carboxylic acid tert-butyl ester (327 mg, 1 mmol) was combined with 3,4-dichlorobenzyl isocyanate (303 mg, 1.5 mmol) in DCM (10 mL) and stirred overnight. The reaction mixture was concentrated and purified by chromatography (silica gel, DCM/MeOH/NH$_4$OH) to afford (R)-4-acetoxy-2-{2-[3-(3,4-dichloro-benzyl)-ureido]-thiazol-4-yl}-pyrrolidine-1-carboxylic acid tert-butyl ester.

Step 3: The product obtained in Step 2 was dissolved in 4M HCl in 1,4-dioxane (7 mL). After stirring overnight the reaction mixture was concentrated and the residue was crystalized from THF/Et$_2$O to afford Intermediate 58: acetic acid (R)-5-{2-[3-(3,4-dichloro-benzyl)-ureido]-thiazol-4-yl}-pyrrolidin-3-yl ester hydrochloride, as a white solid (224 mg, 52% yield).

Intermediate 59: 1-{4-[(2-Amino-ethylamino)-methyl]-thiazol-2-yl}-3-(3-fluoro-benzyl)-urea bis-Trifluoroacetate

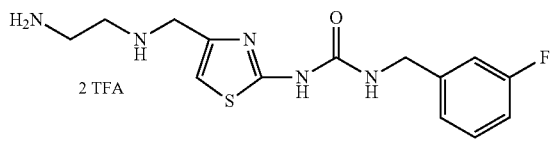

Step 1: Sodium triacetoxyborohydride (937 mg, 4.42 mmol) was added to a CH$_2$Cl$_2$ (50 mL) solution of 1-(3-fluorobenzyl)-3-(4-formylthiazol-2-yl)urea (620 mg, 2.21 mmol) and tert-butyl 2-aminoethylcarbamate (532 mg, 3.32 mmol) at 0 C. Upon completion of the reaction, it was quenched with dilute NaHCO$_3$. The organics were dried and evaporated. Flash chromatography afforded tert-butyl 2-((2-(3-(3-fluorobenzyl)ureido)thiazol-4-yl)methylamino)ethylcarbamate. $^1$H NMR (400 MHz, CDCl$_3$): δ 8.05 (1H, br), 7.28 (m, 1H), 7.00 (m, 3H), 6.61 (s, 1H), 4.80 (s, 1H), 4.49 (d, 2H), 3.73 (s, 2H), 3.17 (m, 2H), 2.63 (t, 2H), 1.41 (s, 9H). MS (ES+): M/Z 424 (M+H)$^+$.

Step 2: [Method 1]: Trifluoroacetic acid (1 mL) was added to a CH$_2$Cl$_2$ (5 mL) solution of tert-butyl 2-((2-(3-(3-fluorobenzyl)ureido)thiazol-4-yl)methylamino)ethylcarbamate (70 mg, 0.16 mmol). Upon completion of the reaction, the mixture was evaporated to dryness to afford Intermediate 59: 1-{4-[(2-amino-ethylamino)-methyl]-thiazol-2-yl}-3-(3-fluoro-benzyl)-urea bis-trifluoroacetate as a white solid.

Intermediate 60: 1-(3-Fluorobenzyl)-3-(4-(pyrrolidin-2-yl)thiazol-2-yl)urea Hydrochloride

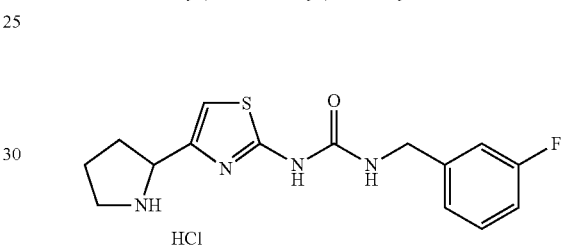

Step 1: An ethanol (20 mL) solution of tert-butyl 2-(2-chloroacetyl)pyrrolidine-1-carboxylate (1.08 g, 4.4 mol) and thiourea (334 mg, 4.4 mmol) was stirred at 55 C for 70 hours. Upon completion of the condensation, the solution was evaporated. The solid was dissolved in CH$_2$Cl$_2$ (100 mL). It was washed with dilute NaHCO$_3$ solution, dried and evaporated. Recrystallization from CH$_2$Cl$_2$/hexane afforded tert-butyl 2-(2-aminothiazol-4-yl)pyrrolidine-1-carboxylate. $^1$H NMR (400 MHz, CDCl$_3$): mixture of rotamers: δ 8.81 (s, 2H, br), 6.22 and 6.15 (2s, 1H), 4.84 and 4.78 (2s, 1H), 3.62 and 3.44 (2m, 2H), 2.4-1.8 (m, 4H), 1.46 and 1.36 (2s, 9H). MS (ES+): M/Z 270 (M+H)$^+$, 170 (M–C$_5$H$_8$O$_2$)$^+$.

Step 2: A THF (5 mL) solution of tert-butyl 2-(2-aminothiazol-4-yl)pyrrolidine-1-carboxylate (270 mg, 1 mmol) and 3-fluororbenzyl isocyanate (140 μL, 1.1 mmol) was microwave irradiated at 120 C for 60 minutes. Aqueous work-up, followed by flash chromatography afforded tert-butyl 2-(2-(3-(3-fluorobenzyl)ureido)thiazol-4-yl)pyrrolidine-1-carboxylate. MS (ES+): M/Z 421 (M+H)$^+$, 321 (M–C$_5$H$_8$O$_2$)$^+$.

Step 3: tert-Butyl 2-(2-aminothiazol-4-yl)pyrrolidine-1-carboxylate (870 mg, 2.1 mmol) was deprotected with trifluoroacetic acid (5 mL) in CH$_2$Cl$_2$ (20 mL). Evaporation of the reaction mixture and treatment with HCl (5 mL, 10 mmol, 2M in ether) afforded Intermediate 60: 1-(3-fluorobenzyl)-3-(4-(pyrrolidin-2-yl)thiazol-2-yl)urea hydrochloride as a white solid. $^1$H NMR (400 MHz, DMSO): δ 11.93 (s, 1H, 9.96 (s, 1H), 8.85 (s, 1H), 7.76 (t, 1H), 7.38 (m, 1H), 7.1 (m, 4H), 4.56 (t, 1H), 4.37 (d, 2H), 2.30 (m, 1H), 2.08 (m, 3H). MS (ES+): M/Z 321 (M+H)$^+$.

Intermediate 61: 1-(4-(((3,5-Dimethylisoxazol-4-yl)methylamino)methyl)thiazol-2-yl)-3-(3-fluorobenzyl)urea

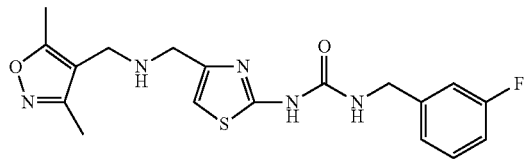

Step 1: Sodium azide (390 mg, 6.0 mmol) was added to a DMSO (5 mL) solution of Intermediate 4: 1-(4-(chloro-methyl)thiazol-2-yl)-3-(3-fluorobenzyl)urea (600 mg, 2 mmol). The mixture was stirred for 4 hours at 40 C. Upon completion of the reaction, water was added at 10 C and the mixture was extracted with EtOAc. Organics were washed with brine, dried and evaporated. Recrystallization from CH$_2$Cl$_2$/hexane afforded 1-(4-(azidomethyl)thiazol-2-yl)-3-(3-fluorobenzyl)urea. $^1$H NMR (400 MHz, CDCl$_3$): δ 10.3 (1H, br), 7.27 (m, 1H), 7.1-6.9 (m, 3H), 6.74 (s, 1H), 4.50 (d, 2H), 4.27 (s, 2H). MS (ES+): M/Z 307 (M+H)$^+$.

Step 2: Trimethylphosphine (107 μL, 1.2 mmol) was added dropwise to a THF (5 mL) solution of 1-(4-(azidomethyl)thiazol-2-yl)-3-(3-fluorobenzyl)urea (307 mg, 1.0 mmol) at 0 C under a nitrogen atmosphere. The mixture was stirred for 22 hours then HCl (0.5 mL, 4M in water) was added and the stirring was continued for 22 hours. Upon evaporation of the mixture, the product was recrystallized from acetonitrile to afford 1-(4-(aminomethyl) thiazol-2-yl)-3-(3-fluorobenzyl)urea hydrochloride. $^1$H NMR (400 MHz, CD$_3$OD): δ 10.3 (1H, br), 7.34 (m, 1H), 7.17-6.95 (m, 4H), 4.45 (s, 2H), 4.08 (s, 2H). MS (ES+): M/Z 281 (M+H)$^+$.

Step 3: NaBH$_4$ (35 mg, 1 mmol) was added in portions to a MeOH (5 mL) solution of 3,5-dimethylisoxazole-4-carbaldehyde (65 mg, 0.5 mmol) and 1-(4-(aminomethyl) thiazol-2-yl)-3-(3-fluorobenzyl)urea hydrochloride (157 mg, 0.5 mmol) at 0 C. The mixture was stirred for 6 hours then quenched with dilute HCl solution. Basic aqueous work-up with CH$_2$Cl$_2$ followed by flash chromatography afforded Intermediate 61: 1-(4-(((3,5-dimethylisoxazol-4-yl)methylamino)methyl)thiazol-2-yl)-3-(3-fluorobenzyl)urea. $^1$H NMR (400 MHz, CDCl$_3$): δ 8.2 (1H, br), 7.27 (m, 1H), 6.92 (m, 3H), 6.60 (s, 1H), 4.37 (d, 2H), 3.66 (s, 2H), 3.33 (s, 2H), 2.22 (s, 3H), 2.11 (s, 3H). MS (ES+): M/Z 390 (M+H)$^+$.

Intermediates 62-65: Not used

Intermediate 66: Chlorobenzo[1,3]dioxol-5-ylmethylamine (alt. name: 5-Chloro-piperonyl amine)

Step 1: 5-Chloropiperonal was prepared by the literature method (*Berichte der Deutschen Chemischen Gesellschaft*, 43, 2605-2606 (1911)).

Step 2: Reductive amination of 5-chloropiperonal was performed by borane reduction of the O-methyloxime derivative by literature method (*J. Org. Chem.* 34(6), 1817-1821, (1969)).

Intermediate 67: Not used

Intermediate 68: 1-(3-Fluorobenzyl)-3-(3-methylaminomethyl-[1,2,4]thiadiazol-5-yl)-urea

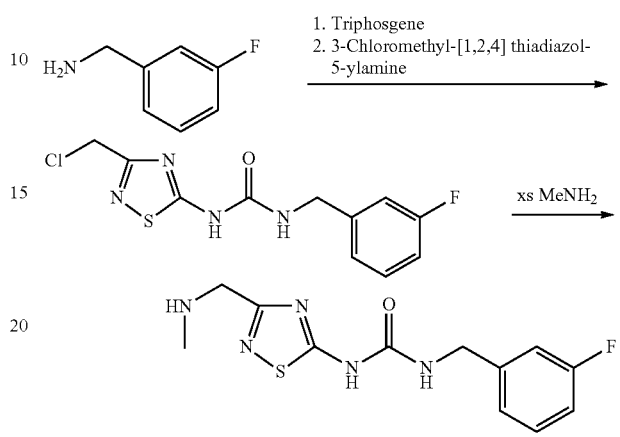

Step 1: To a solution of triphosgene (2.37 g, 8 mmol) in CH$_2$Cl$_2$ (48 mL) was added dropwise a mixture of 3-fluorobenzylamine (2.0 g, 16 mmol) and DIPEA (4.14 g, 32 mmol) in CH$_2$Cl$_2$ (32 mL) over 2 hours at 0 C under N$_2$ atmosphere. After addition was complete, the mixture was refluxed for 1 hour and then cooled to ambient temperature. The mixture was washed with aq. KHSO$_4$, brine, dried over Na$_2$SO$_4$, and concentrated to give 3-fluorobenzyl isocyanate as a yellow liquid (1.34 g, yield 100%), which was used in the next step without further purification.

Step 2: 3-Fluorobenzyl isocyanate (1.3 g, 8 mmol) was added into a mixture of Intermediate 38: 3-chloromethyl-[1,2,4]thiadiazol-5-ylamine (0.83 g, 5.5 mmol), and DMAP (22 mg, 0.14 mmol) in NMP (11 mL). The reaction mixture was heated in a microwave reactor for 1 hour at 100 C and then cooled to ambient temperature. The reaction mixture was diluted with EtOAc (75 mL) and washed with water (30 mL×2). The aqueous phase was extracted with EtOAc (40 mL×2). The combined organic layers were washed with brine, dried over Na$_2$SO$_4$, filtered and evaporated to give the crude product, which was purified by silica gel column chromatography to afford 1-(3-chloromethyl-[1,2,4]thiadiazol-5-yl)-3-(3-fluoro-benzyl)-urea as an off-white solid (1.2 g, 72%). LC-MS (m/z): 303.0 (M+H)

Step 3: A solution of the urea obtained above (8.5 g, 28.3 mmol) and excess methylamine (27% alcohol solution, 54 mL) was heated in a microwave reactor for 15 minutes at 60 C. After cooling to room temperature, a solution of K$_2$CO$_3$ (1.8 g) in water (5 mL) was added, and the volatiles were removed in vacuo. The crude product was purified by column chromatography DCM:MeOH:Et$_3$N=20:1:0.151 to give Intermediate 68: 1-(3-fluorobenzyl)-3-(3-methyl aminomethyl-[1,2,4]thiadiazol-5-yl)-urea as a yellowish solid (4.4 g, yield: 52.7%, purity detected by LC-MS: >97%). $^1$H NMR (400 MHz, DMSO-d$_6$) δ: 7.95 (s, 1H), 7.90 (s, 1H), 7.37 (m, 1H), 7.10 (m, 3H), 4.37 (d, J=5.6 Hz, 2H), 3.71 (s, 2H), 2.31 (s, 3H).

Intermediate 69: 1-(5-Chloro-thiophen-2-ylmethyl)-3-(3-methylaminomethyl-[1,2,4]thiadiazol-5-yl)-urea

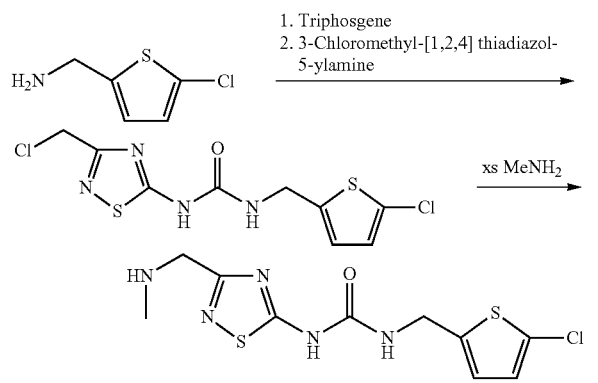

Step 1: To a solution of triphosgene (1.15 g, 3.9 mmol) in CH₂Cl₂ (30 mL) was added dropwise a mixture of (5-chlorothiophen-2-yl)methanamine (1.14 g, 7.8 mmol) and DIPEA (2.0 g, 15.6 mmol) in CH₂Cl₂ (32 mL) over 2 hours at 0 C under N₂ atmosphere. After addition was complete, the mixture was refluxed for 1 hour and then cooled to ambient temperature. The mixture was washed with aq. KHSO₄, brine, dried over Na₂SO₄, and concentrated to give 5-chlorothiophen-2-yl-methyl isocynate a yellow liquid (1.34 g, yield 100%), which was used in the next step without further purification.

Step 2: The isocyanate obtained above was added into a mixture of Intermediate 38: 3-chloromethyl-[1,2,4]thiadiazol-5-ylamine (0.96 g, 6.4 mmol), and DMAP (26 mg, 0.17 mmol) in NMP (7 mL). The reaction mixture was heated in a microwave reactor for 1 hour at 100 C and then cooled to ambient temperature. The reaction mixture was diluted with EtOAc (50 mL) and washed with water (20 mL×2). The aqueous phase was extracted with EtOAc (25 mL×2). The combined organic layers were washed with brine, dried over Na₂SO₄, filtered and evaporated to give the crude product, which was purified by silica gel column chromatography [petroleum ether:EtOAc (PE:EA)=3:1] to give 1-(3-chloromethyl-[1,2,4]thiadiazol-5-yl)-3-(5-chloro-thiophen-2-ylmethyl)-urea as a brown oil (1.74 g, 70%).

Step 3: A solution of the urea obtained above (7.33 g, 22.7 mmol) and excess methylamine (27% alcohol solution, 36 mL) was heated in a microwave oven for 15 minutes at 60 C. After having been cooled to room temperature, a solution of K₂CO₃ (1.7 g) in water (3 mL) was added and the volatiles were removed in vacuo. The crude product was purified by column chromatography [EtOAc, then DCM:MeOH: Et₃N=20:1:0.15] to give Intermediate 69: 1-(5-chlorothiophen-2-ylmethyl)-3-(3-methylaminomethyl-[1,2,4]thiadiazol-5-yl)-urea as a yellowish solid (2.22 g, yield: 31%). ¹H NMR (400 MHz, DMSO-d₆) δ: 7.74 (s, 1H), 6.94 (d, J=4.0 Hz, 1H), 6.85 (d, J=3.2 Hz, 1H), 4.42 (d, J=6.0 Hz, 2H), 3.70 (s, 2H), 2.31 (s, 3H).

Intermediate 70: 1-(2,4-Dimethoxy-benzyl)-3-(3-fluoro-benzyl)-1-(3-methylamino-methyl-[1,2,4]thiadiazol-5-yl)-urea

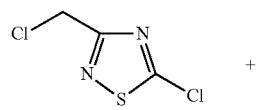 +

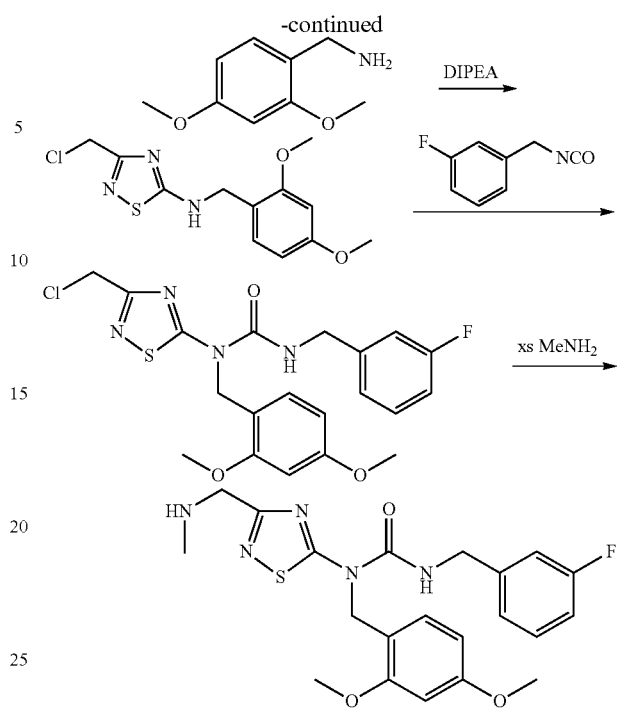

Step 1: A solution of 5-chloro-3-chloromethyl-[1,2,4]thiadiazole (3 g, 18 mmol, [74461-64-6]) in DCM (20 mL) was treated with DIPEA (1 eq), followed by 2,4-dimethoxybenzylamine (1 eq). After stirring overnight, the mixture was concentrated and purified by silica gel chromatography (10% MeOH/EtOAc) to afford (3-chloromethyl-[1,2,4]thiadiazol-5-yl)-(2,4-dimethoxy-benzyl)-amine, which was used directly in the next step.

Step 2: The amine obtained above was dissolved in THF (45 mL) and treated with 3-fluorobenzylisocyanate (1 eq). The resulting solution was heated at 140 C for 20 minutes in a sealed tube. The reaction mixture was concentrated and purified by silica gel chromatography (50% EtOAc/hexanes to afford 1-(3-chloromethyl-[1,2,4]thiadiazol-5-yl)-1-(2,4-dimethoxy-benzyl)-3-(3-fluoro-benzyl)-urea (3.8 g, 47% yield for two steps).

Step 3: The urea product obtained above (1.0 g, 2.2 mmol) was dissolved in a solution of 33% methylamine in ethanol. The solution was heated in a sealed tube at 60 C for 15 minutes, then concentrated and purified by silica gel chromatography (4% 7N ammonia/MeOH: 96% DCM) to afford Intermediate 70: 1-(2,4-dimethoxy-benzyl)-3-(3-fluoro-benzyl)-1-(3-methylamino-methyl-[1,2,4]thiadiazol-5-yl)-urea, as a white solid (825 mg, 83% yield).

End of Intermediates.

Example 477

Synthesis Methods For Compounds of Tables 1-3

Method 1: BOC Deprotection Method using TFA

The BOC-protected thiazole urea analog (0.2-0.5 mmol) was dissolved in trifluoroacetic acid (2 ml) and the solution is stirred overnight. The volatiles were removed by evaporation and the residue was triturated with ether to afford the TFA salt of the final product; or purified by column chromatography using 0-10% gradient of 7 N ammonia/MeOH and DCM. In cases where the HCl salt was desired, this was treated with HCl (4.0M in dioxane) to give the HCl salt.

Method 2: Amide Formation by TBTU Coupling of Carboxylic Acid and Amine

Carboxylic acid (0.25 mmol) was dissolved in 3 ml DMF, and TBTU (1.1 eq) and base ($K_2CO_3$ or DIEA, 1.1 eq.) were added. To the stirred mixture, N-alkylaminomethyl thia(dia)zolylurea was added and stirred overnight. 10 ml of water was added. If the product precipitated from the solution, it was filtered and washed with water and dried. The crude was purified by column chromatography using 0-100% gradient of 10% MeOH/EtOAc and hexanes. If the product remained in the solution, the product was extracted three times with EtOAc and back washed with brine twice. The organic was dried, concentrated and purified by column chromatography using 0-10% gradient of 7 N ammonia/MeOH and DCM.

Method 3: Amide Formation by Condensation of an Acid Chloride and Amine

Carboxylic chloride (0.25 mmol) was added to a mixture of 1.0 eq. of N-alkylaminomethylthi(dia)azolylurea and base ($K_2CO_3$ or DIEA, 1 eq.) in 3 ml DMF. The reaction was stirred overnight. 10 ml of water was added. If the product precipitated from the solution, it was filtered and washed with water and dried. The crude was purified by column chromatography using 0-100% gradient of 10% MeOH/EtOAc and hexanes. If the product remained in the solution, the product was extracted three times with EtOAc and back washed with brine twice. The organic was dried, concentrated and purified by column chromatography using 0-10% 7 N ammonia/MeOH and DCM.

Method 4: TBTU Coupling Followed by Deprotection with HCl

Step 1: Thiazole urea intermediate (SM1) and acid (SM2) are coupled following Method 2.
Step 2: The protected thiazole urea analog was dissolved in 4.0M HCl in dioxane and the solution is stirred 2-24 hours. Diethyl ether is added. In most cases, product precipitates and is isolated as a solid. If necessary, the product is purified by column chromatography using 0-10% gradient of 7 N ammonia/MeOH and DCM.

Method 5: Sulfonamide Formation by Condensation of a Sulfonyl Chloride and Amine Sulfonyl chloride (SM2, 0.25 mmol) was added to a mixture of an advanced intermediate, N-alkylaminomethylthiazolylurea (SM1, 1.0 eq.) and base ($K_2CO_3$ or DIEA, 1.0 eq.) in 3 mL inert solvent such as DCM or THF or DMF. The reaction was stirred overnight. 10 mL of water was added. If the product precipitated from the solution, filtered and washed with water and dried. The crude was purified by column chromatography using 0-100% gradient of 10% MeOH/EtOAc and hexanes. If the product remained in the solution, the product was extracted three times with EtOAc and back washed with brine twice. The organic was dried, concentrated and purified by column chromatography using 0-10% gradient of 7 N ammonia/MeOH and DCM.

Method 6: General Method For Removing N-Fmoc Protecting Group

The advanced thia(dia)zole intermediate (0.2 mmol) bearing an N-Fmoc (N-9-Fluorenylmethyl Carbamate) protecting group was dissolved in DMF (2 mL) treated with excess morpholine (1 mL). When the reaction was complete the solution was concentrated in vacuo and purified by chromatography to afford the N-deprotected product.

Method 7: Urea Formation by Reaction of an N-Acyl-imidazolide with Amine

An N-acyl-imidazolide (SM 1, 1 mmol), typically formed by condensing a 2-aminothiazole derivative with carbonyl diimidazole, is suspended in THF (10 mL) and the amine component (SM2, 1 eq) is added. If the amine (SM2) is used in the form of a salt (ex. hydrochloride), then a base (1 eq) such as DIPEA is also added. The reaction is stirred at 20-50° C. until complete, then concentrated, and purified by chromatography (silica gel, MeOH/EtOAc) to afford the desired thiazole urea product.

Method 8: Urea Formation by Reaction of a Phenyl Carbamate with Amine

A phenylcarbamate (SM1, 1 eq.) was taken up in dioxane and the amine (SM2, 1.1 eq.) was added. The reaction was heated in the microwave at 100-140° C. until complete. The solvent was removed and the crude material was purified by column chromatography using 10% saturated ammonia/MeOH in DCM or 10% MeOH/EtOAc in hexanes to give product. In some cases, the HCl salt of the product was prepared by adding HCl in dioxane, followed by the addition of diethyl ether to give a white solid.

Method 9: Carboxylic Acid Formation by Hydrolysis of Corresponding Ester

The carboxylic acid ester is saponified with aqueous sodium hydroxide in an alcoholic cosolvent. The carboxylic acid product is isolated by acidification and aqueous work-up.
Example: Ethyl 4-(((2-(3-(3-fluorobenzyl)ureido)thiazol-4-yl)methyl)(methyl)-carbamoyl)-5-methylisoxazole-3-carboxylate (105 mg) was dissolved in ethanol (5 ml) and 1 N sodium hydroxide (5.0 eq) was added and stirred for 2 hours. The reaction was acidified to pH=2 and concentrated. The precipitate was filtered, washed with water and dried to give 4-(((2-(3-(3-fluorobenzyl)ureido)thiazol-4-yl)methyl)(methyl)carbamoyl)-5-methylisoxazole-3-carboxylic acid.

Method 10: General DMB Deprotection Method Using TFA

The advanced thia(dia)zole intermediate (0.25-0.5 mmol) with a 2,4-dimethoxybenzyl-protecting group (DMB) was dissolved in trifluoroacetic acid (4 ml) with anisole (5 drop) and the reaction was stirred at room temperature overnight. The volatiles were evaporated and the residue was purified by column chromatography using 0-10% gradient of 7 N ammonia/MeOH and DCM to afford the deprotected product.

Method 11: General Deprotection Method For O—Silyl Protecting Groups

The advanced thia(dia)zole intermediate (0.25-0.5 mmol) bearing an O-silyl protecting group (such as tert-butyldiphenylsilyl or tert-butyldimethylsilyl) is cleaved by treatment with tetra-n-butylammonium fluoride (TBAF) in THF or ACN solvent (*Can. J. Chem.* 55, 562 (1977)). The deprotected product is purified by chromatography, if necessary.

Method 12: Reduction of Ester to Alcohol

A carboxylic ester is reduced with lithium borohydride in an inert solvent such as THF to afford the corresponding alcohol, after aqueous work-up and chromatography.

Example: Ethyl 4-(((2-(3-(3-fluorobenzyl)ureido)thiazol-4-yl)methyl)(methyl)carbamoyl)-5-methylisoxazole-3-carboxylate (60 mg) was suspended in tetrahydrofuran (6 ml) and LiBH$_4$ (3.0 mg) was added and stirred at room temperature overnight. Additional LiBH$_4$ (6.0 mg) was added and stirred overnight. The reaction was concentrated and the residue was purified by column chromatography using 0-100% gradient of 9:1 EtOAc/MeOH and hexanes.

Method 13: Preparation of 2,4-Dimethoxybenzyl-protected Amines

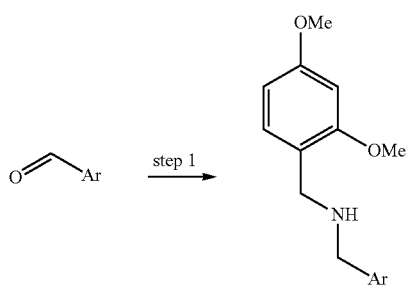

Step 1: Aryl aldehyde (10 mmol) was mixed with 2,4-dimethoxybenzylamine (1.0 eq.) in DCM (50 ml) and acetic acid (1.0 ml) was added. To the mixture, sodium triacetoxyborohydride (2.5 eq.) was added the mixture was stirred at room temperature overnight. The mixture was filtered through Celite and washed with DCM. The filtrate was concentrated and purified by column chromatography using 0-10% gradient of 7 N ammonia/MeOH and DCM to afford the 2,4-DMB-protected amine product.

Method 14: Alkylation of Thiazolidine-2,4-Dione

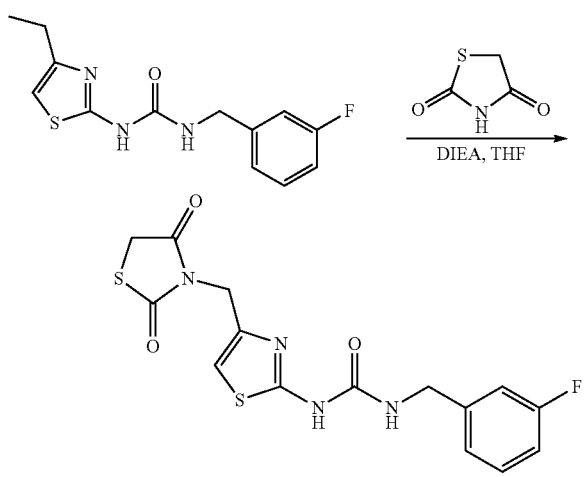

1-(3-Fluoro-benzyl)-3-(4-iodomethyl-thiazol-2-yl)-urea (Intermediate 7, 0.3 mmol) was taken up in THF (3 ml) and DIPEA (1 eq.) and potassium carbonate (1 eq.) was added, followed by thiazolidine-2,4-dione (1 eq.). The reaction was stirred at room temperature overnight. Solvent is removed in vacuo and the crude material was purified by column chromatography with a gradient of 0-60% of (9:1 EtOAc/MeOH) and hexanes to afford 1-(4-((2,4-dioxothiazolidin-3-yl)methyl)thiazol-2-yl)-3-(3-fluorobenzyl)urea (EX #109) as a white solid.

Method 15: Alkylation of Oxazolidin-2-one

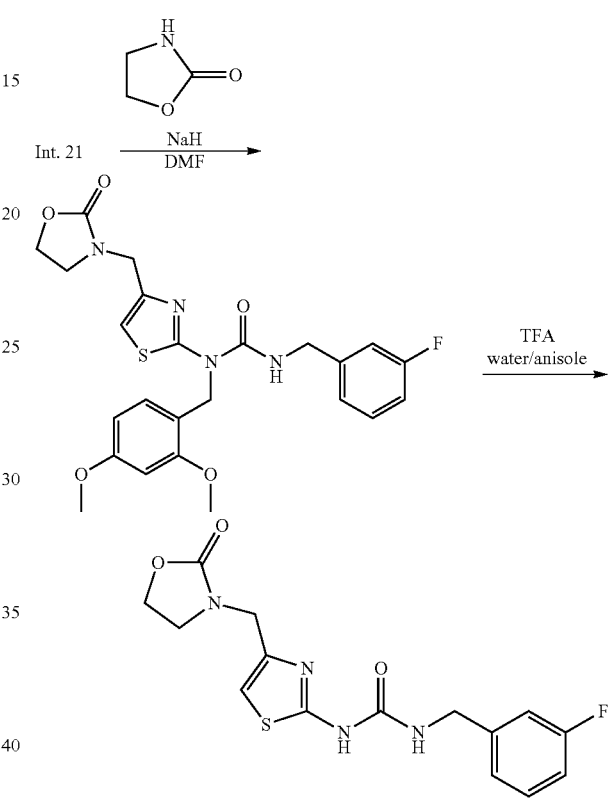

Step 1: 1-(4-Chloromethyl-thiazol-2-yl)-1-(2,4-dimethoxy-benzyl)-3-(3-fluoro-benzyl)-urea (Intermediate 21, 0.3 mmol) was taken up in DMF (2 ml). A solution of the oxazolidin-2-one (or sultam) (1 eq.) with NaH (1 eq.) in DMF (2 ml) was added. The reaction was allowed to stir at room temperature for 2 hours. An aqueous workup with EtOAc was performed. Purified by column chromatography using a gradient of 0-100% EtOAc/hexanes to give 1-(2,4-dimethoxybenzyl)-3-(3-fluorobenzyl)-1-(4-((2-oxooxazolidin-3-yl)methyl)thiazol-2-yl)urea.

Step 2: The 1-(2,4-dimethoxybenzyl)-3-(3-fluorobenzyl)-1-(4-((2-oxooxazolidin-3-yl)methyl)thiazol-2-yl)urea was treated with TFA. Anisole (1 drop) was added. The reaction was stirred for 1 hour. Solvent was removed in vacuo. Purified by column chromatography with a gradient of 0-100% of 9:1 EtOAc/MeOH and hexanes. Resulting solid was triturated with diethyl ether to give the pure urea product.

Method 16: Alkylation of Isothiazolidinine 1,1-Dioxide

Intermediate 21 and isothiazolidine 1,1-dioxide were reacted and deprotected following the procedure in Method 15.

Method 17: Bromination of Thiazole 5-Position

Bromine (120 µL, 0.12 mmol, 1M in $CH_2Cl_2$) was added dropwise to a $CH_2Cl_2$ (5 mL) solution of the thiazole urea compound (0.1 mmol). The bromination was instantaneous. The mixture was washed with dilute $Na_2SO_3$ solution, dried and evaporated to afford the 5-bromo-compound.

Method 18: Chlorination of Thiazole 5-Position

The thiazole urea compound was taken up in DCM and treated with N-chlror-succinimide (1.2 equiv). The mixture was stirred overnight at ambient temperature. An aqueous work-up was performed with dilute sodium sulfite solution. The organic layer was filtered through a silica plug and eluted with 3% MeOH in DCM to give the 5-chloro-compound.

Method 19: Cyanation of Thiazole 5-Position

Example: A mixture of 3,5-dimethyl-isoxazole-4-carboxylic acid {5-bromo-2-[3-(3-fluoro-benzyl)-ureido]-thiazol-4-ylmethyl}-methyl-amide (Ex. 151) (100 mg, 0.2 mmol), CuCN (180 mg, 2.0 mmol) and KCN (13 mg, 0.2 mmol) in DMF (1 mL) was heated to 120 C for 5 hours. Upon cooling the mix was diluted with EtOAc (50 mL), filtered, washed with brine, dried and evaporated. Flash chromatography afforded 3,5-dimethyl-isoxazole-4-carboxylic acid {5-cyano-2-[3-(3-fluoro-benzyl)-ureido]-thiazol-4-ylmethyl}-methyl-amide.

Method 20: Hydrolysis of Acetate Protecting Group to Afford Alcohol

The acetate thiazole urea (0.5 mmol) was dissolved in ethanol (2 ml) and 1 N sodium hydroxide (2.5 ml) was added and stirred overnight. The ethanol was removed by evaporation. If precipitation occurred, the product was isolated by filtration and washing with water. The product can be isolated by extraction of the mixture three times with EtOAc. The organic was combined and dried over sodium sulfate. The organic was filtered and washed with EtOAc and the filtrate was concentrated to dryness. The residue was purified by column chromatography using gradient of 0-10% gradient of 7 N ammonia/MeOH and DCM.

Method 21-43: Not used

Method 44: Synthesis of 3-chloro-6-methoxypyridazine-4-carboxylic acid {2-[3-(3-fluoro-benzyl)-ureido]-thiazol-4-ylmethyl}-methyl-amide 3,6-Dichloro-pyridazine-4-carboxylic acid {2-[3-(3-fluoro-benzyl)-ureido]-thiazol-4-ylmethyl}-methyl-amide (47 mg) was treated with potassium hydroxide (56 mg) in MeOH (5 mL) over night. The resultant mixture was diluted with water (10 mL) and the pH was adjusted to 9-10 by sodium bicarbonate. After evaporation of MeOH, the resultant precipitate-3-chloro-6-methoxypyridazine-4-carboxylic acid {2-[3-(3-fluoro-benzyl)-ureido]-thiazol-4-ylmethyl}-methyl-amide was collected, briefly rinsed with water and dried. The desired product was confirmed by 1HNMR and LC-MS.

Method 45: Synthesis of 3-chloro-6-hydroxypyridazine-4-carboxylic acid {2-[3-(3-fluoro-benzyl)-ureido]-thiazol-4-ylmethyl}-methyl-amide 3,6-Dichloro-pyridazine-4-carboxylic acid {2-[3-(3-fluoro-benzyl)-ureido]-thiazol-4-ylmethyl}-methyl-amide (150 mg) in acetic acid (10 mL) was heated at reflux for 2 h. The resultant mixture was concentrated and purified by a preparative C-18 reverse phase HPLC. About 15 mg of the desired product-3-chloro-6-hydroxypyridazine-4-carboxylic acid {2-[3-(3-fluoro-benzyl)-ureido]-thiazol-4-ylmethyl}-methyl-amide was obtained. The desired product was confirmed by 1HNMR and LC-MS.

Method 46: Synthesis of tetrahydro-furan-2-carboxylic acid (2-amino-1-{2-[3-(3-fluoro-benzyl)-ureido]-thiazol-4-yl}-ethyl)-methyl-amide Tetrahydro-furan-2-carboxylic acid (cyano-{2-[3-(3-fluoro-benzyl)-ureido]-thiazol-4-yl}-methyl)-methyl-amide (420 mg) was dissolved in MeOH (10 mL) and treated with Raney®-Nickel under a pressurized hydrogen (45 psi) over a couple of hours until all starting materials were consumed. The final product was purified by column chromatography. The product was confirmed by $^1H$ NMR and LC-MS.

Method 47: Synthesis of 6-methoxy-3-methyl-pyridazine-4-carboxylic acid {2-[3-(3-fluoro-benzyl)-ureido]-thiazol-4-ylmethyl}-methyl-amide $N_2$ was bubbled for 15 minutes through a solution of 1-(3-fluorobenzyl)-3-(4-((3-chloro-6-methoxy-N-methylpyridazine-4-carboxamido)methyl)-thiazol-2-yl)urea (118 mg, 0.25 mmol) in 1,4-dioxane. $Pd(PPh_3)_4$ (15 mg, 13 µmol) was added followed by $AlMe_3$ (250 µl, 2 M in toluene, 0.51 mmol). The mixture was refluxed for 4 hours and MeOH was added. Silica (300 mg) was added and the volatiles were removed in vacuo. The residue was brought on a column and purified by chromatography ($CH_2Cl_2$+5% 7N $NH_3$ in MeOH) to afford the title product (60 mg, 0.13 mmol) as an off-white solid in 52% yield.

Method 48: Synthesis of 6-hydroxy-3-methyl-pyridazine-4-carboxylic acid {2-[3-(3-fluoro-benzyl)-ureido]-thiazol-4-ylmethyl}-methyl-amide 6-Methoxy-3-methyl-pyridazine-4-carboxylic acid {2-[3-(3-fluoro-benzyl)-ureido]-thiazol-4-ylmethyl}-methyl-amide was dissolved in DCM and treated with an excess of BBr3 at room temperature for a couple of hours. Column chromatography afforded the title product.

Method 49: Synthesis of 3-(dimethylamino)-N-((2-(3-(3-fluorobenzyl)ureido)thiazol-4-yl)methyl)-6-methoxy-N-methylpyridazine-4-carboxamide 3-Chloro-6-methoxypyridazine-4-carboxylic acid {2-[3-(3-fluoro-benzyl)-ureido]-thiazol-4-ylmethyl}-methyl-amide was treated with dimethylamine in 1,4-dioxane to afford the desired product.

Method 50: Synthesis of N-((2-(3-(3-fluorobenzyl)ureido)thiazol-4-yl)methyl)-6-hydroxy-N-methyl-3-(methylamino)pyridazine-4-carboxamide 3-(Dimethylamino)-N-((2-(3-(3-fluorobenzyBureido)thiazol-4-yl)methyl)-6-methoxy-N-methylpyridazine-4-carboxamide was treated with BBr3 (12 equivalent) in DCM to afford the title product.

Method 51: Synthesis of 6-chloro-N-((2-(3-(3-fluorobenzyl)ureido)thiazol-4-yl)methyl)-3-hydroxy-N-methylpyridazine-4-carboxamide Step 1: Synthesis of 6-chloro-N-((2-(3-(3-fluorobenzyl)ureido)thiazol-4-yl)methyl)-3-methoxy-N-methylpyridazine-4-carboxamide. A solution of 3,6-dichloro-pyridazine-4-carboxylic acid {2-[3-(3-fluoro-benzyl)-ureido]-thiazol-4-ylmethyl}-methyl-amide (235 mg, 0.5 mmol) and MeOH (160 mg, 5 mmol) in 1,4-dioxane (10 mL) was added NaOH (20 mg, 0.5 mmol). The mixture was stirred overnight at room temperature and concentrated in vacuo. The residue was dissolved in $CH_2Cl_2$+5% MeOH and filtered over a small plug of silica. The volatiles were evaporated and the desired product (230 mg) was obtained as a 5:1 mixture with starting material-3,6-dichloro-pyridazine-4-carboxylic acid {2-[3-(3-fluoro-benzyl)-ureido]-thiazol-4-ylmethyl}-methyl-amide. This mixture was used as such in the subsequent steps.

Step 2: Synthesis of 6-chloro-N-((2-(3-(3-fluorobenzyl) ureido)thiazol-4-yl)methyl)-3-hydroxy-N-methylpyridazine-4-carboxamide. A solution of 6-chloro-N-((2-(3-(3-fluorobenzyBureido)thiazol-4-yl)methyl)-3-methoxy-N-methylpyridazine-4-carboxamide (113 mg, 0.24 mmol) and NaOAc (100 mg, 1.21 mmol) in AcOH (7 mL) was heated at 100° C. overnight. The volatiles were removed in vacuo and the residue was purified by column chromatography ($SiO_2$, $CH_2Cl_2$/5% 7N $NH_3$ in MeOH). The title product was confirmed by $^1$H-NMR and LC-MS.

End of Methods Section.

Example 478

Demonstration of Antibacterial Effect and Mechanism of Action

The polC gene from Streptococcus pyogenes was overexpressed and PolC was purified as described in PCT/US05/15548. Primer extension activity of PolC was measured using 1 μM oligonucleotide primer-template (primer strand 5'-ACCAGTGAGACGGGCAACA, template strand 5'-TGAAT-TATAGGCCCTGTTGCCCGTCTCACTGGT). Reactions contained 10 mM magnesium acetate, 50 mM Tricine/Tris pH 7.8, 2.4% (w/v) polyethylene glycol (8000 MW), 0.024% pluronic F68, 1 mM dithiothreitol, 20 μM dATP, 20 μM dCTP, 0.5 μM dGTP, 0.72 μM dTTP, 0.28 μM 3H-dTTP (0.005 μCi/μL), 8% DMSO and 15 nM PolC. Reactions (25 μL) were incubated for 10 minutes at room temperature and stopped by addition of an equal volume of 100 mM EDTA. Incorporation of radiolabelled dTTP was measured by scintillation proximity assay by addition of 100 μL of 1 mg/mL PEI-PVT beads in 300 mM citrate pH 3.0.

Compounds of Formula (I) were tested for inhibition of S. pyogenes PolC activity. Serial 2-fold dilutions of compounds were tested for inhibition of PolC activity and $IC_{50}$'s were determined (XLfit). Compounds described in Examples 1, 3-6, 8, 10-17, 19-21, 24-31, 33, 36, 38, 40, 54, 56-57, 59-71, 74-105, 107-108, 110-112, 114, 117-120, 122-142, 144-159, 162-179, 181-182, 184-225, 227-242, 244-319, 321-355, and 357-475 had $IC_{50}$'s of 0.01-25 μM. These compounds were specific for prokaryotic DNA polymerase, showing little or no inhibition of eukaryotic S. cerevisiae polymerase delta at concentrations up to 160 μM.

A subset of these analogs were tested for inhibition of macromolecular biosynthesis in whole cell S. aureus assays as described by Ochsner, et al. (Antimicrob Agents Chemo. 49:4253-62 (2005)). All tested analogs were potent inhibitors of DNA synthesis, with $IC_{50}$'s of <0.06-4.5 μg/mL; the compounds showed little or no inhibition of other macromolecular synthesis pathways (RNA, protein or cell wall biosynthesis) at concentrations as high as 64 μg/mL.

Compounds of the present invention were tested for antibacterial activity against a variety of pathogenic organisms including S. aureus, S. pneumoniae, S. pyogenes, E. faecalis, H. influenza and M. catarrhalis using a standard broth microdilution method to determine their minimum inhibitory concentrations (MICs). All compounds were tested using standard methods in accordance with CLSI guidelines (Clinical and Laboratory Standards Institute). Compounds described in Examples 1, 3-6, 8, 10-17, 19-21, 24-31, 33, 36, 38, 40, 54, 56-57, 59-71, 74-105, 107-108, 110-112, 114, 117-120, 122-142, 144-159, 162-179, 181-182, 184-225, 227-242, 244-319, 321-355, and 357-475 had MIC's of <0.12-4.0 μg/mL against some strains of the major Gram-positive organisms S. aureus, S. pneumoniae, S. pyogenes, and E. faecalis. The compounds showed weak Gram-negative activity with MICs of 1->128 μg/mL against some strains of the major Gram-negative organisms E. coli tolC, P. aeruginosa, H. influenze and M. catarrhalis. Compounds described in Examples 11, 54, 60, and 208 shown to be bactericidal in S. aureus, E. faecalis, E. faecium, S. pyogenes, S. epidermidis and S. pneumoniae.

Compounds of the present invention were not compromised by existing resistance to all drug classes tested, including β-lactams, glycopeptides, oxazolidinones, macrolides, and fluoroquinolones. In particular, compounds described in Examples 11, 54, 60, and 208 were active against methicillin-(oxacillin-) resistant S. aureus (MRSA), vancomycin-intermediate S. aureus (VISA), linezolid-resistant S. aureus, methicillin-(oxacillin-) resistant and mupirocin resistant S. epidermidis, macrolide-resistant S. pyogenes, macrolide-, penicillin-, and levofloxacin-resistant S. pneumoniae, vancomycin-, macrolide-, and ciprofloxacin-resistant E. faecalis (VRE) and vancomycin-, macrolide-, and ciprofloxacin-resistant E. faecium. MICs were comparable in sensitive versus drug resistant strains, and ranged from 0.25-4 μg/mL in clinically relevant resistant strains.

Compounds of the present invention showed broad spectrum antibacterial activity against Gram-positive bacteria. Compounds described in Examples 54, 60, 96, 107, 208, and 214 exhibited $MIC_{90}$'s ranging from 1-4 μg/mL for methicillin-(oxacillin-) resistant S. aureus (MRSA), vancomycin-resistant E. faecalis (VRE), vancomycin-resistant E. faecium, penicillin-intermediate S. pneumoniae and macrolide-resistant S. pyogenes.

It will be clear that the invention is well adapted to attain the ends and advantages mentioned as well as those inherent therein. While several presently preferred embodiments have been described for purposes of this disclosure, various changes and modifications may be made which are well within the scope of the invention. Numerous other changes may be made which will readily suggest themselves to those skilled in the art and which are encompassed in the spirit of the invention disclosed herein and as defined in the appended claims.

The entire disclosure and all publications cited herein are hereby incorporated by reference.

What is claimed is:

1. A compound of Formula (I):

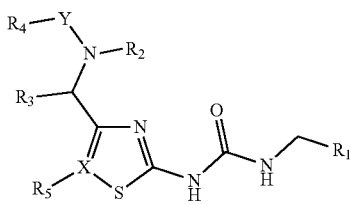

(I)

in which:
- $R_1$ is selected from the group consisting of a substituted or unsubstituted aryl, substituted or unsubstituted arylalkyl and substituted or unsubstituted heteroaryl;
- X is selected from the group consisting of a C and N atom;
- Y is selected from the group consisting of CO and $SO_2$;
- $R_2$, $R_3$ and $R_4$ are independently selected from the group consisting of H, OH, substituted or unsubstituted aryl, substituted or unsubstituted arylalkyl, substituted or unsubstituted linear, cyclic or branched alkyl, cyano, and perfluoroalkyl; and
- $R_5$ is selected from the group consisting of H, halogen, alkyl, cyano and null, wherein $R_5$ is null when X is N;
- wherein $R_2$, $R_4$, Y and N or $R_2$, $R_3$, CH and N do not form a substituted or unsubstituted 4-7 member saturated ring.

2. A compound of Formula (I):

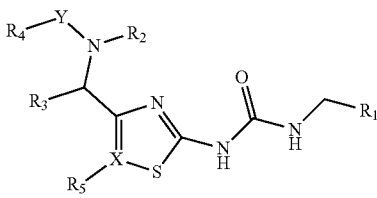

(I)

in which:
- $R_1$ is selected from the group consisting of a substituted or unsubstituted aryl, substituted or unsubstituted arylalkyl and substituted or unsubstituted heteroaryl;
- X is selected from the group consisting of a C and N atom;
- Y is selected from the group consisting of CO and $SO_2$;
- $R_3$ is selected from the group consisting of H, OH, substituted or unsubstituted aryl, substituted or unsubstituted arylalkyl, substituted or unsubstituted linear, cyclic or branched alkyl, cyano, and perfluoroalkyl; and
- $R_5$ is selected from the group consisting of H, halogen, alkyl, cyano and null, wherein $R_5$ is null when X is N,
- wherein $R_2$, $R_4$, Y and N form a substituted or unsubstituted 4-7 member saturated ring.

3. A compound of Formula (I):

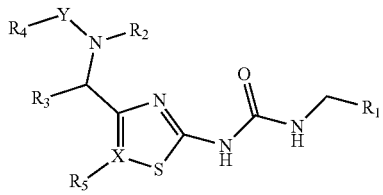

(I)

in which:
- $R_1$ is selected from the group consisting of a substituted or unsubstituted aryl, substituted or unsubstituted arylalkyl and substituted or unsubstituted heteroaryl;
- X is selected from the group consisting of a C and N atom;
- Y is selected from the group consisting of CO and $SO_2$;
- $R_4$ is selected from the group consisting of H, OH, substituted or unsubstituted aryl, substituted or unsubstituted arylalkyl, substituted or unsubstituted linear, cyclic or branched alkyl, cyano, and perfluoroalkyl; and
- $R_5$ is selected from the group consisting of H, halogen, alkyl, cyano and null, wherein $R_5$ is null when X is N,
- wherein $R_2$, $R_3$, CH and N form a substituted or unsubstituted 4-7 member saturated ring.

4. The compound of claim 1, wherein $R_1$ is a substituted or unsubstituted phenyl or thiophene group.

5. The compound of claim 4, wherein $R_1$ is a phenyl group having one or more substituents selected from the group consisting of halogen, cyano, $(C_{1-6})$alkyl, mono to perfluoro $(C_{1-3})$alkyl, $(C_{3-7})$cycloalkyl, $(C_{2-6})$alkenyl, $(C_{1-6})$alkoxy, $(C_{2-6})$alkenoxy, hydroxy, amino, mono- or di-$(C_{1-6})$alkylamino, acylamino, nitro, carboxy, $(C_{1-6})$alkoxycarbonyl, $(C_{1-6})$alkenyloxycarbonyl, $(C_{1-6})$alkoxycarbonyl$(C_{1-6})$alkyl, carboxy$(C_{1-6})$alkyl, $(C_{1-6})$alkylcarbonyloxy, carboxy$(C_{1-6})$alkyloxy, $(C_{1-6})$alkoxycarbonyl$(C_{1-6})$alkoxy, $(C_{1-6})$alkylthio, $(C_{1-6})$alkylsulphinyl, $(C_{1-6})$alkylsulphonyl, sulphamoyl, mono- and di-$(C_{1-6})$-alkylsulphamoyl, and carbamoyl.

6. The compound of claim 1, wherein $R_1$ is selected from the group consisting of 3-fluorophenyl, 4-fluorophenyl, 3-chlorophenyl, 4-chlorophenyl, 3-bromophenyl, 4-bromophenyl, 3-iodophenyl, 4-iodophenyl, 3-methoxyphenyl, 4-methoxyphenyl, 3-methylphenyl, 4-methylphenyl, 3-trifluoromethylphenyl, 4-trifluoromethylphenyl, 3-4-methylendioxyphenyl, 3-4-difluorophenyl, 3-4-dichlorophenyl, 3-4-dibromophenyl, 3-4-dimethylphenyl, 3-4-(—CH$_2$CH$_2$CH$_2$—)phenyl, 3-4-(—OCH$_2$CH$_2$O—)phenyl, 3-chloro-4-fluorophenyl, benzo[1,3]dioxyl-5-yl, and 3-3-cyanophenyl, 3,5-difluorophenyl, thiophen-2-yl, thiophen-3-yl, 4,5-di-bromo-thiophen-2yl, 5-chloro-thiophen-2yl, and 5-bromo-thiophen-2yl, 5-fluoro-thiophen-2-yl, 5-chloro-thiophen-3-yl, 1,1,-difluoro-benzo[1,3]dioxyl-5-yl, 7-chlorobenzo[1,3]dioxol-5-yl, 3-nitrophenyl, 2,1,3-benzoxadiazol-5-yl, and 4-nitrophenyl.

7. The compound of claim 1, wherein Y is a CO group.

8. The compound of claim 7, wherein X is C atom.

9. The compound of claim 7, wherein X is N atom.

10. The compound of claim 1, wherein Y is a SO$_2$ group.

11. The compound of claim 10, wherein X is a C atom.

12. The compound of claim 10, wherein X is an N atom.

13. The compound of claim 1, wherein $R_2$ is selected from the group consisting of H, methyl, ethyl, 2-hydroxyethyl, 2-methoxyethyl, 2-aminoethyl, propyl, cyclopropyl, isopropyl, 2,4-dimethoxybenzyl, 2-methanesulfonylaminoethyl, 2,2-Difluoro-ethyl, and 3,5-dimethylisoxazole-4-yl-methyl.

14. The compound of claim 1, wherein $R_3$ is selected from the group consisting of H, methyl, ethyl, 2-hydroxyethyl, 2-hydroxymethyl, 2-methoxyethyl, 2-aminoethyl, propyl, cyclopropyl, isopropyl, 2,4-dimethoxybenzyl, and 2-methanesulfonylaminoethyl.

15. The compound of claim 1, wherein $R_4$ is selected from the group consisting of methyl, 2-(2-methoxyethoxy)-methyl, 2-methoxymethyl, 4-methylisoxazole-5-yl, isoxazole-5-yl, 3-phenylpropanyl, furan-2-yl, 4-phenoxybutanyl, 1,1-dioxo-tetrahydro-1-lamda6-thiophen-3-ylmethylaminoyl, 3,5-dimethylisoxazole-4-yl, 1-methyl-1H-imidazole-5-yl, furan-3-yl, 3-methylfuran-2-yl, 5-methyl-3-phenylisoxazole-4-yl, 5-methyl-2-phenyl-2H-1,2,3-triazole-4-yl, 5-methylisoxazole-3-yl, 3-methyl-5-phenylisoxazole-4-yl, 3-methyl-5-(4-methyl-1,2,3-thiadiazol-5-yl)isoxazole-4-yl, 2-(2H-tetrazol-5-yl)methyl, benzofuran-2-yl, 1,2,5-oxadiazole-3-yl, (3,5-dimethylisoxazol-4-yl)-methyl, 3-methylisoxazole-4-yl, 5-methylisoxazole-4-yl, 5-cyclopropyl-isoxazole-4-yl, 2,6-dimethylphenyl, 5-(furan-2-yl)-isoxazole-3-yl, 2,5-dimethyloxazole-4-yl, 2-phenylthiazole-4-yl, 2-(thiophen-2-yl)thiazole-4-yl, 3-hydroxy-isoxazole-5-yl, 5-phenyl-1,3,4-oxadiazole-2-yl, 5-methylfuran-2-yl, 4-methyl-1,2,5-oxadiazole-3-yl, 4-methyl-2-(pyrazin-2-yl)thiazole-5-yl, 2,4-dimethoxy-phenyl, 4-methoxy-phenyl, 3,4-dimethoxy-phenyl, benzo[1,3]dioxole-5-yl, 3,4,5-trimethoxy-phenyl, 5-methyl-3-(trifluoromethyl)isoxazole-4-yl, pyridin-3-ylmethyl, 2,4-dimethylpyridine-3-yl, 2,4,6-trimethylphenyl, 5-(methoxymethyl)-3-methylisoxazole-4-yl, 2-methoxy-methyl, 2-methoxyformyl, 3-ethyl-5-methylisoxazole-4-yl, pyrimidine-5-yl, pyrazine-2-yl, 5-methylpyrazine-2-yl, furan-3-yl, 4-methyloxazole-5-yl, 2-tosylmethyl, 3-ethylcarboxy-5-methylisoxazole-4-yl, 3-carboxy-5-methylisoxazole-4-yl, 2-methylpyridine-3-yl, 4-methylpyridine-3-yl, 3-chloro-4-(methylsulfonyl)thiophene-2-yl, 4-methylthiazole-5-yl, 5-oxo-3,5-dihydro-2H-thiazolo[3,2-a]pyrimidine-6-yl, 4-methyl-2-(methylthio)pyrimidine-5-yl, 2-methylprop-1-enyl, 2-methylphenyl, quinoxaline-2,3-methylpyridine-4-yl, 3-methylisoxazole-4-yl, 4-amino-pyrimidine-5-yl, 2-amino-4-methylpyrimidine-5-yl, 4,6-dimethyl-2-oxo-1,2-dihydropyridine-3-yl, 2,4,6-trimethylpyrimidine-5-yl, 3-methylpyrazine-2-yl, 4-Boc-amino-1-methyl-1H-imidazole-2-yl, 4-amino-1-methyl-1H-imidazole-2-yl, 4-acetamido-1-methyl-1H-imidazole-2-yl, 4,6-dimethylpyrimidine-5-yl, 3-(hydroxymethyl)-5-methyl-isoxazole-4-yl, 3-methylpyridine-2-yl, 2-amino-4,6-dimethylpyrimidine-5-yl, 2-methylimidazo[1,2-a]pyridine-3-yl, tetrahydrofuran-2-yl, 2-methoxypyridine-3-yl, tetrahydrofuran-3-yl, methoxyformyl, 2-chloropyridine-3-yl, 1,3,5-tetramethyl-1H-pyrazole-4-yl, (S)-tetrahydrofuran-2-yl, (R)-tetrahydrofuran-2-yl, 3-propoxypyridine-4-yl, N-Boc-morpholine-2-yl, morpholine-2-yl, pyridazine-4-yl, 3,5-dimethyl-1H-pyrazole-4-yl, pyridazine-3-yl, tetrahydro-2H-pyran-4-yl, 1,5-dimethyl-1H-pyrazole-4-yl, morpholine-3-yl, 4-methylpyrrolidine-3-yl, (S)-pyrrolidine-2-yl, 1,1-Dioxo-tetrahydro-1-lamda6-thiophene-3-yl, 4-methylphenyl, methyl, ethyl, propyl, butyl, cyclopropyl, and 1,1-Dioxo-1-isothiazolidin-2-yl, 2-methyl-5,6-dihydro-4H-pyran-3-yl, 2-methyl-5-morpholin-4-ylmethyl-furan-3-yl, 2-methyl-but-2-enyl, [1,2,3]thiadiazole-4-yl, 2-pyridin-3-yl-thiazole-4-yl, 2,5-dimethyl-2H-pyrazole-3-yl, 4-methylfurazan-3-yl, 2-morpholin-4-ylmethyl-furan-3-yl, 1-methylpyrrolidine-2-yl, 1-methyl-1H-pyrrole-2-yl, 1,5-dimethyl-1H-[1,2,3]triazole-4-yl, 5-fluoro-thiophene-2-yl, 4-methylpyrimidine-5-yl, 4-methyl-2-phenyl-pyrimidine-5-yl, 2-methylsulfanyl-nicotinyl, acetonitrile, 6-morpholin-4-yl-nicotinyl, 4-methyl-thiazole-5-yl, 3-methyl-1H-pyrazole-4-yl, 2,4-dimethyl-pyrimidine-5-yl, 2-methyl-[1,6]naphthyridine-3-yl, 6-(4-methoxy-phenyl)-pyridazine-3-yl, 2,6-bis-dimethylamino-pyrimidine-4-yl, 2,6-di-morpholin-4-yl-pyrimidine-4-yl, 3-pyridin-3-yl-acrylonitrile-2-yl, 2-methyl-[1,8]naphthyridine-3-yl, 2-dimethylamino-6-methyl-pyrimidine-4-yl, acetic acid 1-yl-ethyl ester, 1-ethyl-3-methyl-1H-pyrazole-4-yl, 2-methyl-pyrazolo[1,5-a]pyrimidine-3-yl, 1-hydroxy-ethyl, 1-ethyl-5-methyl-1H-pyrazole-4-yl, 5,7-dimethyl-pyrazolo[1,5-a]pyrimidine-3-yl, 1-methyl-1H-indole-3-yl, 1-methyl-1H-indazole-3-yl, pyrazolo[1,5-a]pyridine-3-yl, 2-furan-2-yl-oxo, 5-oxo-pyrrolidine-2-yl, 4-methyl-pyridazine-3-yl, 5-methyl-pyridazine-4-yl, 3-amino-1H-pyrazole-4-yl, 3,6-dimethoxy-pyridazine-4-yl, 3,6-dichloro-pyridazine-4-yl, pyridine-3-yl, pyridine-2-yl, 1-methyl-1H-imidazole-4-yl, 1,2-dimethyl-1H-imidazole-4-yl, pyridin-3-yl-methyl, 3-chloro-6-methoxy-pyridazin-4-yl, 3,5-dimethyl-pyridazin-4-yl, 1-methyl-3-trifluoromethyl-1H-pyrazol-4-yl, 3-chloro-6-hydroxy-pyridazin-4-yl, 2-methyl-tetrahydrofuran-2-yl, 4-chloro-1-methyl-1H-pyrazol-3-yl, 5-chloro-1-methyl-1H-pyrazol-4-yl, 4-chloro-2-methyl-2H-pyrazol-3-yl, 4-chloro-1H-pyrazol-3-yl, 1,3,6-trimethyl-1H-pyrazolo[3,4-b]pyridin-3-yl, 2-methyl-5-sulfamoyl-phenyl, 1-methyl-6-oxo-1,4,5,6-tetrahydropyridazin-3-yl, 1-phenyl-cyclobutyl, 3-methyl-4-oxo-3,4-dihydrophthalazin-1-yl, 7-chloro-benzo[1,3]dioxol-5-yl, 6-[1,2,4]triazol-1-yl-pyridin-3-yl, 1-(2-methoxyethyl)-6-oxo-1,6-dihydropyridazin-3-yl, 2-(2,4-dioxo-3,4-dihydropyrimidin-1-(2H)-yl)methyl, 6-chloro-3-hydroxy-pyridazin-4-yl, 3-cyano-2-hydroxy-6-methyl-pyridin-4-yl, 1-methyl-5-(1H-pyrrol-1-yl)-1H-pyrazol-4-yl, 4-oxo-3,4-dihydrophthalazin-1-yl, 4,6-dimethyl-2-oxo-2H-pyran-5-yl, 1-methyl-4-sulfamoyl-1H-pyrrol-2-yl, (5,7-dimethyl-[1,2,4]triazolo[1,5-a]pyrimidin-6-yl)methyl, 3,6-dimethyl-4-oxo-3,4-dihydrofuro[2,3-d]pyrimidin-5-yl, 5-methyl-4-oxo-3,4-dihydrothieno[2,3-b]pyrimidin-6-yl, phenyl-difluoromethyl, 4-hydroxyl-1-carbamoyl-pyrrolidin-2-yl, 2-(1-morpholino)-pyridin-3-yl, 1-(3-fluorophenyl)-cyclobutyl, 1-methyl-5-trifluoromethyl-1H-pyrazol-4-yl, (S)-1-methoxyethyl, 3-methyl-5,6-dihydro-1,4-dioxin-2-yl, (R)-5-oxo-tetrahydrofuran-2-yl, 5-chloro-1,3-dimethyl-1H-pyraozol-4-yl, 2-methoxy-ethyl, 1-(2-hydroxyethyl)-3,5-dimethyl-1H- pyrazol-4-yl, (R)-1-methoxy-ethyl, 1-(2-methoxyethyl)-3,5-dimethyl-1H-pyrazol-4-yl, tetrahydro-2H-pyran-2-yl, 3,6-dimethylisoxazolo[5,4-b]pyridine-4-yl, 5-methoxy-tetrahydrofuran-2-yl, 1-(4-methoxybutyl)-3,5-dimethyl-1H-pyrazol-4-yl, 1-(3-methoxypropyl)-3,5-dimethyl-1H-pyrazol-4-yl, 1-(4-fluorophenyl)-cyclobutyl, 5-methyl-tetrahydrofuran-2-yl, 3-methyl-oxetan-3-yl, 5-chloro-1H-pyrazol-4-yl, (R)-2,2-dimethyl-1,3-dioxolan-4-yl, (S)-2,2-dimethyl-1,3-dioxolan-4-yl, 3,6-dichloro-5-methyl-pyridazin-4-yl, 6-methoxyl-3-methyl-pyridazin-4-yl, 1-methyl-5-nitro-1H pyrazol-4-yl, 2,3-dihydrobenzofuran-2-yl, 6-hydroxy-3-methyl-pyridazin-4-yl, 2-(1-pyrrolidinyl)-pyridin-3-yl, 3-oxo-3-(2-thiophenyl)-propyl, 3-oxo-3-phenyl-propyl, 3-fluoro-4-methoxy-benzyl, 3,4-dimethoxy-benzyl, 4-(hydroxymethyl)-phenoxy-methyl, 3-methylsulfonyl-benzyl, 2-mercapto-4-methyl-thiazol-5-yl, 5-trifluoromethyl-furan-2-yl, 6-hydroxy-3-methylamino-pyridazin-4-yl, 3-(dimethylamino)-6-methoxy-pyridazin-4-yl, 2,2-dimethyl-tetrahydro-2H-pyran-4-yl, 4-(dimethylamino)-benzyl, 7-hydroxy-1,2,3,4-tetrahydroisoquinolin-3-yl, 1H-benzoimidazol-2-yl, naphthalene-2-yl-methyl, 4-methoxy-3-methyl-benzyl, 1-amino-2-benzyloxy-ethyl, 1,4-dioxo-1,2,3,4-tetrahydrophthalazin-6-yl, 2,4-dioxo-3,4-dihydropyrimidin-1(2H)-yl)-methyl, 5-nitro-1H-pyrazol-4-yl, (S)-3,3-difluoro-tetrahydrofuran-2-yl, chroman-2-yl, 3,5-dimethyl-1H-pyrazol-4-yl, 4-butynyl, 2-methyl-1,2,34-tetrahydroisoquinolin-3-yl, (S)-2-(4-pyridinyl), 1-amino-ethyl, cis-3-methoxy-tetrahydrofuran-2-yl, 1-cyano-cyclopropyl, ethynyl, 1-ethoxy-ethyl, 1-(4-methoxy-phenoxy)ethyl, 1-(cyclopropylmethoxy)ethyl, 1,4-diamino-butyl, 1-(2-phenoxyethoxy)ethyl, cyclopropylmethyl, 3-ethyl-3-oxetan-3-yl, 1-(2,2-difluoroethoxy)ethyl, 1-(4-fluoro-benzyloxy)ethyl, 1-(2,2,2-trifluoroethoxy)ethyl, 1-(prop-2-ynyloxy)ethyl, 5-methyl-isoxazol-3-yl, 1-((1-methyl-pyrrolidin-3-yl)oxy)ethyl, 1-(2-hydroxyethoxy)ethyl, cyclopentyl, 1-hydroxy-cyclopropyl, cyclohexyl, 2-methyl cyclohexyl, 2-oxo-2,3-dihydrobenzoxazol-6-yl, 2,2,2-trifluoroethyl, 1-hydroxy-1-methyl-ethyl, (R)-5-(hydroxymethyl)tetrahydrofuran-2-yl, (4-hydroxy-2-oxo-pyrrolidin-1-yl)methyl, 1,2,2,2-tetrafluoroethyl, 1-carbamoyl-cyclopropyl, 2-methyl-cyclopropyl, 5-chloro-1,3-dimethyl-1H-pyrazol-4-yl, 5-isopropyl-3-methyl-isoxazol-4-yl, and 1,3,5-trimethyl-1H-pyrazolo[4,3-b]pyridin-7-yl.

16. The compound of claim 2, wherein $R_2$, $R_4$, Y and N together form 2,4-dioxothiazolidin-3-yl.

17. The compound of claim 2, wherein $R_2$, $R_4$, Y and N together form 2-oxooxazolidin-3-yl.

18. The compound of claim 3, wherein $R_2$, $R_3$, CH and N together form 4-aceoxy-1-(methylsulfonyl)pyrrolidin-2-yl.

19. The compound of claim 3, wherein $R_2$, $R_3$, CH and N together form 4-hydroxy-1-(methylsulfonyl)pyrrolidin-2-yl.

20. A compound selected from the group consisting of:
N-((2-(3-(3,4-dichlorobenzyl)ureido)thiazol-4-yl)methyl)-N-(2-methoxyethyl)acetamide;
3-(N-((2-(3-(3,4-dichlorobenzyl)ureido)thiazol-4-yl)methyl)acetamido)propylphosphonic acid;
N-((2-(3-(3,4-dichlorobenzyl)ureido)thiazol-4-yl)methyl)-2-(2-methoxyethoxy)-N-methylacetamide;
N-((2-(3-(3,4-dichlorobenzyl)ureido)thiazol-4-yl)methyl)-2-methoxy-N-methylacetamide;
N-((2-(3-(3,4-dichlorobenzyl)ureido)thiazol-4-yl)methyl)-N,4-dimethylisoxazole-5-carboxamide;
N-((2-(3-(3,4-dichlorobenzyl)ureido)thiazol-4-yl)methyl)-N-methylisoxazole-5-carboxamide;
N-((2-(3-(3,4-dichlorobenzyl)ureido)thiazol-4-yl)methyl)-N-methyl-3-phenylpropanamide;
N-((2-(3-(3,4-dichlorobenzyl)ureido)thiazol-4-yl)methyl)-N-methylfuran-2-carboxamide;
N-((2-(3-(3,4-dichlorobenzyl)ureido)thiazol-4-yl)methyl)-N-methyl-4-phenoxybutanamide;
1-(3,4-Dichloro-benzyl)-3-{4-[3-(1,1-dioxo-tetrahydro-1,6-thiophen-3-ylmethyl)-1-methyl-ureidomethyl]-thiazol-2-yl}-urea;
N-((2-(3-(3,4-dichlorobenzyl)ureido)thiazol-4-yl)methyl)-N,3,5-trimethylisoxazole-4-carboxamide;
N-((2-(3-(3,4-dichlorobenzyl)ureido)thiazol-4-yl)methyl)-N,1-dimethyl-1H-imidazole-5-carboxamide;
N-((2-(3-(3,4-dichlorobenzyl)ureido)thiazol-4-yl)methyl)-N-methylfuran-3-carboxamide;
N-((2-(3-(3,4-dichlorobenzyl)ureido)thiazol-4-yl)methyl)-N,3-dimethylfuran-2-carboxamide;
N-((2-(3-(3,4-dichlorobenzyl)ureido)thiazol-4-yl)methyl)-N,5-dimethyl-3-phenylisoxazole-4-carboxamide;
N-((2-(3-(3,4-dichlorobenzyl)ureido)thiazol-4-yl)methyl)-N-ethyl-3,5-dimethylisoxazole-4-carboxamide;
N-((2-(3-(3,4-dichlorobenzyl)ureido)thiazol-4-yl)methyl)-N-isopropyl-3,5-dimethylisoxazole-4-carboxamide;
N-((2-(3-(3,4-dichlorobenzyl)ureido)thiazol-4-yl)methyl)-N,5-dimethyl-2-phenyl-2H-1,2,3-triazole-4-carboxamide;
N-((2-(3-(3,4-dichlorobenzyl)ureido)thiazol-4-yl)methyl)-N,5-dimethylisoxazole-3-carboxamide;
N-((2-(3-(3,4-dichlorobenzyl)ureido)thiazol-4-yl)methyl)-N,3-dimethyl-5-phenylisoxazole-4-carboxamide;
N-((2-(3-(3,4-dichlorobenzyl)ureido)thiazol-4-yl)methyl)-N,3-dimethyl-5-(4-methyl-1,2,3-thiadiazol-5-yl)isoxazole-4-carboxamide;
N-((2-(3-(3,4-dichlorobenzyl)ureido)thiazol-4-yl)methyl)-N-methyl-2-(2H-tetrazol-5-yl)acetamide;
N-((2-(3-(3,4-dichlorobenzyl)ureido)thiazol-4-yl)methyl)-N-methylbenzofuran-2-carboxamide;
N-(1-(2-(3-(3,4-dichlorobenzyl)ureido)thiazol-4-yl)ethyl)-N,3,5-trimethylisoxazole-4-carboxamide;
N-((2-(3-(3,4-dichlorobenzyl)ureido)thiazol-4-yl)methyl)-N-methyl-1,2,5-oxadiazole-3-carboxamide;
N-((2-(3-(3,4-dichlorobenzyl)ureido)thiazol-4-yl)methyl)-2-(3,5-dimethylisoxazol-4-yl)-N-methylacetamide;
N-((2-(3-(3,4-dichlorobenzyl)ureido)thiazol-4-yl)methyl)-3-ethyl-N,5-dimethylisoxazole-4-carboxamide;
N-((2-(3-(3,4-dichlorobenzyl)ureido)thiazol-4-yl)methyl)-N,3-dimethylisoxazole-4-carboxamide;
N-((2-(3-(3,4-dichlorobenzyl)ureido)thiazol-4-yl)methyl)-N,5-dimethylisoxazole-4-carboxamide;
5-cyclopropyl-N-((2-(3-(3,4-dichlorobenzyl)ureido)thiazol-4-yl)methyl)-N-methylisoxazole-4-carboxamide;
N-((2-(3-(3,4-dichlorobenzyl)ureido)thiazol-4-yl)methyl)-N,2,6-trimethylbenzamide;
N-((2-(3-(3,4-dichlorobenzyl)ureido)thiazol-4-yl)methyl)-5-(furan-2-yl)-N-methylisoxazole-3-carboxamide;
N-((2-(3-(3,4-dichlorobenzyl)ureido)thiazol-4-yl)methyl)-N,2,5-trimethyloxazole-4-carboxamide;
N-((2-(3-(3,4-dichlorobenzyl)ureido)thiazol-4-yl)methyl)-N-methyl-2-phenylthiazole-4-carboxamide;
N-((2-(3-(3,4-dichlorobenzyl)ureido)thiazol-4-yl)methyl)-N-(2,4-dimethoxybenzyl)-3,5-dimethylisoxazole-4-carboxamide;
N-((2-(3-(3,4-dichlorobenzyl)ureido)thiazol-4-yl)methyl)-N-(2-methoxyethyl)-3,5-dimethylisoxazole-4-carboxamide;

N-((2-(3-(3,4-dichlorobenzyl)ureido)thiazol-4-yl)methyl)-N-methyl-2-(thiophen-2-yl)thiazole-4-carboxamide;
N-((2-(3-(3,4-dichlorobenzyl)ureido)thiazol-4-yl)methyl)-3-hydroxy-N-methylisoxazole-5-carboxamide;
N-((2-(3-(3,4-dichlorobenzyl)ureido)thiazol-4-yl)methyl)-N-methyl-5-phenyl-1,3,4-oxadiazole-2-carboxamide;
N-((2-(3-(3,4-dichlorobenzyl)ureido)thiazol-4-yl)methyl)-N,5-dimethylfuran-2-carboxamide;
N-((2-(3-(3,4-dichlorobenzyl)ureido)thiazol-4-yl)methyl)-N,4-dimethyl-1,2,5-oxadiazole-3-carboxamide;
4-Methyl-2-pyrazin-2-yl-thiazole-5-carboxylic acid {2-[3-(3,4-dichlorobenzyl)ureido]-thiazol-4-ylmethyl}-methyl-amide;
N-((2-(3-(3,4-dichlorobenzyl)ureido)thiazol-4-yl)methyl)-2,4-dimethoxy-N-methylbenzamide;
N-((2-(3-(3,4-dichlorobenzyl)ureido)thiazol-4-yl)methyl)-4-methoxy-N-methylbenzamide;
N-((2-(3-(3,4-dichlorobenzyl)ureido)thiazol-4-yl)methyl)-3,4-dimethoxy-N-methylbenzamide;
N-((2-(3-(3,4-dichlorobenzyl)ureido)thiazol-4-yl)methyl)-N-methylbenzo[1,3]dioxole-5-carboxamide;
N-((2-(3-(3,4-dichlorobenzyl)ureido)thiazol-4-yl)methyl)-3,4,5-trimethoxy-N-methylbenzamide;
N-((2-(3-(3,4-dichlorobenzyl)ureido)thiazol-4-yl)methyl)-N,5-dimethyl-3-(trifluoromethyl)isoxazole-4-carboxamide;
N-((2-(3-(3,4-dichlorobenzyl)ureido)thiazol-4-yl)methyl)-N-methyl-2-(pyridin-3-yl)acetamide;
N-(1-(2-(3-(3,4-dichlorobenzyl)ureido)thiazol-4-yl)-2-(methylamino)-2-oxoethyl)-N,3,5-trimethylisoxazole-4-carboxamide;
N-((2-(3-(3,4-dichlorobenzyl)ureido)thiazol-4-yl)methyl)-N,2,4-trimethylnicotinamide;
N-((2-(3-(3,4-dichlorobenzyl)ureido)thiazol-4-yl)methyl)-N,2,4,6-tetramethylbenzamide;
N-((2-(3-(3,4-dichlorobenzyl)ureido)thiazol-4-yl)methyl)-N-(2-hydroxyethyl)-3,5-dimethylisoxazole-4-carboxamide;
N-((2-(3-(3-fluorobenzyl)ureido)thiazol-4-yl)methyl)-N,3,5-trimethylisoxazole-4-carboxamide;
N-((2-(3-(3-fluorobenzyl)ureido)thiazol-4-yl)methyl)-5-(methoxymethyl)-N,3-dimethylisoxazole-4-carboxamide;
N-((2-(3-(3,4-dichlorobenzyl)ureido)thiazol-4-yl)methyl)-5-(methoxymethyl)-N,3-dimethylisoxazole-4-carboxamide;
N-((2-(3-(3-fluorobenzyl)ureido)thiazol-4-yl)methyl)-2-methoxy-N-methylacetamide;
methyl 2-(((2-(3-(3-fluorobenzyl)ureido)thiazol-4-yl)methyl)(methyl)amino)-2-oxoacetate;
N-((2-(3-(3-fluorobenzyl)ureido)thiazol-4-yl)methyl)-N,3-dimethylisoxazole-4-carboxamide;
3-ethyl-N-((2-(3-(3-fluorobenzyl)ureido)thiazol-4-yl)methyl)-N,5-dimethylisoxazole-4-carboxamide;
N-((2-(3-(3-fluorobenzyl)ureido)thiazol-4-yl)methyl)-N,2,4-trimethylnicotinamide;
N-((2-(3-(3-fluorobenzyl)ureido)thiazol-4-yl)methyl)-N-methylpyrazine-2-carboxamide;
N-((2-(3-(3,4-dichlorobenzyl)ureido)thiazol-4-yl)methyl)-N-methylpyrimidine-5-carboxamide;
N-((2-(3-(3-fluorobenzyl)ureido)thiazol-4-yl)methyl)-N-methylpyrimidine-5-carboxamide;
N-((2-(3-(3,4-dichlorobenzyl)ureido)thiazol-4-yl)methyl)-N-methylpyrazine-2-carboxamide;
N-((2-(3-(3-fluorobenzyl)ureido)thiazol-4-yl)methyl)-N-methylacetamide;
N-((2-(3-(3-fluorobenzyl)ureido)thiazol-4-yl)methyl)-N,5-dimethylpyrazine-2-carboxamide;
N-((2-(3-(3-fluorobenzyl)ureido)thiazol-4-yl)methyl)-N-methylfuran-3-carboxamide;
N-((2-(3-(3-fluorobenzyl)ureido)thiazol-4-yl)methyl)-N,4-dimethyloxazole-5-carboxamide;
N-((2-(3-(3-fluorobenzyl)ureido)thiazol-4-yl)methyl)-N,5-dimethylisoxazole-3-carboxamide;
N-((2-(3-(3-fluorobenzyl)ureido)thiazol-4-yl)methyl)-N-methyl-2-tosylacetamide;
Ethyl 4-(((2-(3-(3-fluorobenzyl)ureido)thiazol-4-yl)methyl)(methyl)carbamoyl)-5-methylisoxazole-3-carboxylate;
4-(((2-(3-(3-fluorobenzyl)ureido)thiazol-4-yl)methyl)(methyl)carbamoyl)-5-methylisoxazole-3-carboxylic acid;
N-((2-(3-(3-fluorobenzyl)ureido)thiazol-4-yl)methyl)-N,2-dimethylnicotinamide;
N-((2-(3-(3-fluorobenzyl)ureido)thiazol-4-yl)methyl)-N,5-dimethylisoxazole-4-carboxamide;
N-((2-(3-(3-fluorobenzyl)ureido)thiazol-4-yl)methyl)-N,4-dimethylnicotinamide;
3-chloro-N-((2-(3-(3-fluorobenzyl)ureido)thiazol-4-yl)methyl)-N-methyl-4-(methylsulfonyl)thiophene-2-carboxamide;
N-((2-(3-(3-fluorobenzyl)ureido)thiazol-4-yl)methyl)-N,4-dimethylthiazole-5-carboxamide;
N-((2-(3-(3-fluorobenzyl)ureido)thiazol-4-yl)methyl)-N-methyl-5-oxo-3,5-dihydro-2H-thiazolo[3,2-a]pyrimidine-6-carboxamide;
N-((2-(3-(3-fluorobenzyl)ureido)thiazol-4-yl)methyl)-N,4-dimethyl-2-(methylthio)pyrimidine-5-carboxamide;
N-((2-(3-(3-fluorobenzyl)ureido)thiazol-4-yl)methyl)-N,3-dimethylbut-2-enamide;
N-((2-(3-(3-fluorobenzyl)ureido)thiazol-4-yl)methyl)-N,2-dimethylbenzamide;
N-((2-(3-(3-fluorobenzyl)ureido)thiazol-4-yl)methyl)-N-methylquinoxaline-2-carboxamide;
N-((2-(3-(3-fluorobenzyl)ureido)thiazol-4-yl)methyl)-N,3-dimethylpicolinamide;
N-((2-(3-(3-fluorobenzyl)ureido)thiazol-4-yl)methyl)-5-((4-methoxybenzyloxy)methyl)-N,3-dimethylisoxazole-4-carboxamide;
N-(2-Aminoethyl)-N-((2-(3-(3-fluorobenzyl)ureido)thiazol-4-yl)methyl)-3,5-dimethylisoxazole-4-carboxamide;
4-amino-N-((2-(3-(3-fluorobenzyl)ureido)thiazol-4-yl)methyl)-N-methylpyrimidine-5-carboxamide;
2-amino-N-((2-(3-(3-fluorobenzyl)ureido)thiazol-4-yl)methyl)-N,4-dimethylpyrimidine-5-carboxamide;
N-((2-(3-(3-fluorobenzyl)ureido)thiazol-4-yl)methyl)-3,5-dimethyl-N-(2-(methylsulfonamido)ethyl)isoxazole-4-carboxamide;
N-((2-(3-(3-fluorobenzyl)ureido)thiazol-4-yl)methyl)-N,4,6-trimethyl-2-oxo-1,2-dihydropyridine-3-carboxamide;
N-((2-(3-(3-fluorobenzyl)ureido)thiazol-4-yl)methyl)-N,2,4,6-tetramethylpyrimidine-5-carboxamide;
N-((2-(3-(3-fluorobenzyl)ureido)thiazol-4-yl)methyl)-N,3-dimethylpyrazine-2-carboxamide;
tert-butyl 2-(((2-(3-(3-fluorobenzyl)ureido)thiazol-4-yl)methyl)(methyl)carbamoyl)-1-methyl-1H-imidazol-4-ylcarbamate;
4-amino-N-((2-(3-(3-fluorobenzyl)ureido)thiazol-4-yl)methyl)-N,1-dimethyl-1H-imidazole-2-carboxamide;

4-acetamido-N-((2-(3-(3-fluorobenzyl)ureido)thiazol-4-yl)methyl)-N,1-dimethyl-1H-imidazole-2-carboxamide;
N-((2-(3-(3-fluorobenzyl)ureido)thiazol-4-yl)methyl)-N,4,6-trimethylpyrimidine-5-carboxamide;
N-((2-(3-(3-fluorobenzyl)ureido)thiazol-4-yl)methyl)-3-(hydroxymethyl)-N,5-dimethylisoxazole-4-carboxamide;
N-((2-(3-(4-fluorobenzyl)ureido)thiazol-4-yl)methyl)-N,3,5-trimethylisoxazole-4-carboxamide;
N-((2-(3-(3,5-difluorobenzyl)ureido)thiazol-4-yl)methyl)-N,3,5-trimethylisoxazole-4-carboxamide;
N-((2-(3-(3-fluorobenzyl)ureido)thiazol-4-yl)methyl)-N,3-dimethylisonicotinamide;
N-((2-(3-(3-chlorobenzyl)ureido)thiazol-4-yl)methyl)-N,3,5-trimethylisoxazole-4-carboxamide;
N-((2-(3-(benzo[1,3]dioxol-5-ylmethyl)ureido)thiazol-4-yl)methyl)-N,3,5-trimethylisoxazole-4-carboxamide;
2-amino-N-((2-(3-(3-fluorobenzyl)ureido)thiazol-4-yl)methyl)-N,4,6-trimethylpyrimidine-5-carboxamide;
N-((2-(3-((2,2-difluorobenzo[1,3]dioxol-5-yl)methyl)ureido)thiazol-4-yl)methyl)-N,3,5-trimethylisoxazole-4-carboxamide;
N-((2-(3-(3-fluorobenzyl)ureido)thiazol-4-yl)methyl)-N,2-dimethylimidazo[1,2-a]pyridine-3-carboxamide;
N,3,5-trimethyl-N-((2-(3-(3-(N-methylacetamido)benzyl)ureido)thiazol-4-yl)methyl)isoxazole-4-carboxamide;
N-((2-(3-((5-chlorothiophen-2-yl)methyl)ureido)thiazol-4-yl)methyl)-N,3,5-trimethylisoxazole-4-carboxamide;
N-((2-(3-(3-fluorobenzyl)ureido)thiazol-4-yl)methyl)-N-methyltetrahydrofuran-2-carboxamide;
1-(4-((2,4-dioxothiazolidin-3-yl)methyl)thiazol-2-yl)-3-(3-fluorobenzyl)urea;
N-((2-(3-(3-fluorobenzyl)ureido)thiazol-4-yl)methyl)-2-methoxy-N-methylnicotinamide;
N-((2-(3-(3-fluorobenzyl)ureido)thiazol-4-yl)methyl)-N-methyltetrahydrofuran-3-carboxamide;
N,3,5-trimethyl-N-((2-(3-(thiophen-3-ylmethyl)ureido)thiazol-4-yl)methyl)isoxazole-4-carboxamide;
methyl (2-(3-(3-fluorobenzyl)ureido)thiazol-4-yl)methyl (2-hydroxyethyl)carbamate;
N-((2-(3-(3-fluorobenzyl)ureido)thiazol-4-yl)methyl)-N-(2-hydroxyethyl)-3-methylisonicotinamide;
1-(3-fluorobenzyl)-3-(4-((2-oxooxazolidin-3-yl)methyl)thiazol-2-yl)urea;
2-chloro-N-((2-(3-(3-fluorobenzyl)ureido)thiazol-4-yl)methyl)-N-methylnicotinamide;
N-((2-(3-(3-fluorobenzyl)ureido)thiazol-4-yl)methyl)-N,1,3,5-tetramethyl-1H-pyrazole-4-carboxamide;
(S)—N-((2-(3-(3-fluorobenzyl)ureido)thiazol-4-yl)methyl)-N-methyltetrahydrofuran-2-carboxamide;
(R)—N-((2-(3-(3-fluorobenzyl)ureido)thiazol-4-yl)methyl)-N-methyltetrahydrofuran-2-carboxamide;
N-((2-(3-(3-fluorobenzyl)ureido)thiazol-4-yl)methyl)-N-methyl-3-propoxypicolinamide;
tert-butyl 2-(((2-(3-(3-fluorobenzyl)ureido)thiazol-4-yl)methyl)(methyl)carbamoyl)morpholine-4-carboxylate;
N-((2-(3-(3-fluorobenzyl)ureido)thiazol-4-yl)methyl)-N-methylmorpholine-2-carboxamide;
N-((2-(3-(3,5-difluorobenzyl)ureido)thiazol-4-yl)methyl)-N,3-dimethylpyrazine-2-carboxamide;
N-((2-(3-(3,5-difluorobenzyl)ureido)thiazol-4-yl)methyl)-N,3-dimethylisonicotinamide;
N-((2-(3-(3-fluorobenzyl)ureido)thiazol-4-yl)methyl)-N-methylpyridazine-4-carboxamide;
N-((2-(3-(3-fluorobenzyl)ureido)thiazol-4-yl)methyl)-N,3,5-trimethyl-1H-pyrazole-4-carboxamide;
N-((2-(3-(3-fluorobenzyl)ureido)thiazol-4-yl)methyl)-N-methylpyridazine-3-carboxamide;
N-((2-(3-(3-fluorobenzyl)ureido)thiazol-4-yl)methyl)-N-methyltetrahydro-2H-pyran-4-carboxamide;
N-((2-(3-(3-fluorobenzyl)ureido)thiazol-4-yl)methyl)-N,1,5-trimethyl-1H-pyrazole-4-carboxamide;
N-((2-(3-((5-chlorofuran-2-yl)methyl)ureido)thiazol-4-yl)methyl)-N,3,5-trimethylisoxazole-4-carboxamide;
N-((2-(3-(3-fluorobenzyl)ureido)thiazol-4-yl)methyl)-N-methylmorpholine-3-carboxamide;
N-((2-(3-(3-fluorobenzyl)ureido)thiazol-4-yl)methyl)-N,4-dimethylpyrrolidine-3-carboxamide;
(S)—N-((2-(3-(3-fluorobenzyl)ureido)thiazol-4-yl)methyl)-N-methylpyrrolidine-2-carboxamide;
2-Methyl-5,6-dihydro-4H-pyran-3-carboxylic acid {2-[3-(3-fluoro-benzyl)-ureido]-thiazol-4-ylmethyl}-methyl-amide;
2-Methyl-5-morpholin-4-ylmethyl-furan-3-carboxylic acid {2-[3-(3-fluoro-benzyl)-ureido]-thiazol-4-ylmethyl}-methyl-amide;
2-Methyl-but-2-enoic acid {2-[3-(3-fluoro-benzyl)-ureido]-thiazol-4-ylmethyl}-methyl-amide;
1,2,3-Thiadiazole-4-carboxylic acid {2-[3-(3-fluoro-benzyl)-ureido]-thiazol-4-ylmethyl}-methyl-amide;
3,5-Dimethyl-isoxazole-4-carboxylic acid {2-[3-(5-fluoro-thiophen-2-ylmethyl)-ureido]-thiazol-4-ylmethyl}-methyl-amide;
2-Pyridin-3-yl-thiazole-4-carboxylic acid {2-[3-(3-fluoro-benzyl)-ureido]-thiazol-4-ylmethyl}-methyl-amide;
2,5-Dimethyl-2H-pyrazole-3-carboxylic acid {2-[3-(3-fluoro-benzyl)-ureido]-thiazol-4-ylmethyl}-methyl-amide;
4-Methyl-furazan-3-carboxylic acid {2-[3-(3-fluoro-benzyl)-ureido]-thiazol-4-ylmethyl}-methyl-amide;
2-Morpholin-4-ylmethyl-furan-3-carboxylic acid {2-[3-(3-fluoro-benzyl)-ureido]-thiazol-4-ylmethyl}-methyl-amide;
1-Methyl-pyrrolidine-2-carboxylic acid {2-[3-(3-fluoro-benzyl)-ureido]-thiazol-4-ylmethyl}-methyl-amide;
1-Methyl-1H-pyrrole-2-carboxylic acid {2-[3-(3-fluoro-benzyl)-ureido]-thiazol-4-ylmethyl}-methyl-amide;
1,5-Dimethyl-1H-[1,2,3]triazole-4-carboxylic acid {2-[3-(3-fluoro-benzyl)-ureido]-thiazol-4-ylmethyl}-methyl-amide;
5-Fluoro-thiophene-2-carboxylic acid {2-[3-(3-fluoro-benzyl)-ureido]-thiazol-4-ylmethyl}-methyl-amide;
4-Methyl-pyrimidine-5-carboxylic acid {2-[3-(3-fluoro-benzyl)-ureido]-thiazol-4-ylmethyl}-methyl-amide;
4-Methyl-2-phenyl-pyrimidine-5-carboxylic acid {2-[3-(3-fluoro-benzyl)-ureido]-thiazol-4-ylmethyl}-methyl-amide;
N-{2-[3-(3-Fluoro-benzyl)-ureido]-thiazol-4-ylmethyl}-N-methyl-2-methylsulfanyl-nicotinamide;
2-Cyano-N-{2-[3-(3-fluoro-benzyl)-ureido]-thiazol-4-ylmethyl}-N-methyl-acetamide;
3,5-Dimethyl-isoxazole-4-carboxylic acid {5-bromo-2-[3-(3-fluoro-benzyl)-ureido]-thiazol-4-ylmethyl}-methyl-amide;
N-{2-[3-(3-Fluoro-benzyl)-ureido]-thiazol-4-ylmethyl}-N-methyl-6-morpholin-4-yl-nicotinamide;
4-Methyl-thiazole-5-carboxylic acid {2-[3-(3-fluoro-benzyl)-ureido]-thiazol-4-ylmethyl}-methyl-amide;
3-Methyl-1H-pyrazole-4-carboxylic acid {2-[3-(3-fluoro-benzyl)-ureido]-thiazol-4-ylmethyl}-methyl-amide;

2,4-Dimethyl-pyrimidine-5-carboxylic acid {2-[3-(3-fluoro-benzyl)-ureido]-thiazol-4-ylmethyl}-methyl-amide;

2-Methyl-[1,6]naphthyridine-3-carboxylic acid {2-[3-(3-fluoro-benzyl)-ureido]-thiazol-4-ylmethyl}-methyl-amide;

6-(4-Methoxy-phenyl)-pyridazine-3-carboxylic acid {2-[3-(3-fluoro-benzyl)-ureido]-thiazol-4-ylmethyl}-methyl-amide;

3-Methyl-pyrazine-2-carboxylic acid {5-bromo-2-[3-(3-fluoro-benzyl)-ureido]-thiazol-4-ylmethyl}-methyl-amide;

3-Methyl-pyrazine-2-carboxylic acid {5-chloro-2-[3-(3-fluoro-benzyl)-ureido]-thiazol-4-ylmethyl}-methyl-amide;

2,6-Bis-dimethylamino-pyrimidine-4-carboxylic acid {2-[3-(3-fluoro-benzyl)-ureido]-thiazol-4-ylmethyl}-methyl-amide;

2,6-Di-morpholin-4-yl-pyrimidine-4-carboxylic acid {2-[3-(3-fluoro-benzyl)-ureido]-thiazol-4-ylmethyl}-methyl-amide;

2-Cyano-N-{2-[3-(3-fluoro-benzyl)-ureido]-thiazol-4-ylmethyl}-N-methyl-3-pyridin-3-yl-acrylamide;

2-Methyl-[1,8]naphthyridine-3-carboxylic acid {2-[3-(3-fluoro-benzyl)-ureido]-thiazol-4-ylmethyl}-methyl-amide;

2-Dimethylamino-6-methyl-pyrimidine-4-carboxylic acid {2-[3-(3-fluoro-benzyl)-ureido]-thiazol-4-ylmethyl}-methyl-amide;

N-{2-[3-(3-Fluoro-benzyl)-ureido]-thiazol-4-ylmethyl}-2-methoxy-N-methyl-2-phenyl-acetamide;

3-Methyl-pyrazine-2-carboxylic acid {2-[3-(5-fluoro-thiophen-2-ylmethyl)-ureido]-thiazol-4-ylmethyl}-methyl-amide;

3-Methyl-pyrazine-2-carboxylic acid methyl-[2-(3-thiophen-3-ylmethyl-ureido)-thiazol-4-ylmethyl]-amide;

3,5-Dimethyl-isoxazole-4-carboxylic acid {5-cyano-2-[3-(3-fluoro-benzyl)-ureido]-thiazol-4-ylmethyl}-methyl-amide;

Acetic acid 1-({2-[3-(3-fluoro-benzyl)-ureido]-thiazol-4-ylmethyl}-methyl-carbamoyl)-ethyl ester;

1-Ethyl-3-methyl-1H-pyrazole-4-carboxylic acid {2-[3-(3-fluoro-benzyl)-ureido]-thiazol-4-ylmethyl}-methyl-amide;

2-Methyl-pyrazolo[1,5-a]pyrimidine-3-carboxylic acid {2-[3-(3-fluoro-benzyl)-ureido]-thiazol-4-ylmethyl}-methyl-amide;

N-{2-[3-(3-Fluoro-benzyl)-ureido]-thiazol-4-ylmethyl}-2-hydroxy-N-methyl-propionamide;

3,5-Dimethyl-isoxazole-4-carboxylic acid (1-{2-[3-(3-fluoro-benzyl)-ureido]-thiazol-4-yl}-ethyl)-amide;

1-Ethyl-5-methyl-1H-pyrazole-4-carboxylic acid {2-[3-(3-fluoro-benzyl)-ureido]-thiazol-4-ylmethyl}-methyl-amide;

5,7-Dimethyl-pyrazolo[1,5-a]pyrimidine-3-carboxylic acid {2-[3-(3-fluoro-benzyl)-ureido]-thiazol-4-ylmethyl}-methyl-amide;

3,5-Dimethyl-isoxazole-4-carboxylic acid (1-{2-[3-(3-fluoro-benzyl)-ureido]-thiazol-4-yl}-2-hydroxy-ethyl)-amide;

1-Methyl-1H-indole-3-carboxylic acid {2-[3-(3-fluoro-benzyl)-ureido]-thiazol-4-ylmethyl}-methyl-amide;

1-Methyl-1H-indazole-3-carboxylic acid {2-[3-(3-fluoro-benzyl)-ureido]-thiazol-4-ylmethyl}-methyl-amide;

Pyrazolo[1,5-a]pyridine-3-carboxylic acid {2-[3-(3-fluoro-benzyl)-ureido]-thiazol-4-ylmethyl}-methyl-amide;

N-{2-[3-(3-Fluoro-benzyl)-ureido]-thiazol-4-ylmethyl}-2-furan-2-yl-N-methyl-2-oxo-acetamide;

3,5-Dimethyl-isoxazole-4-carboxylic acid [2-(3-benzyl-ureido)-thiazol-4-ylmethyl]-methyl-amide;

3-Methyl-pyrazine-2-carboxylic acid {2-[3-(5-chloro-thiophen-2-ylmethyl)-ureido]-thiazol-4-ylmethyl}-methyl-amide;

3,5-Dimethyl-isoxazole-4-carboxylic acid {2-[3-(3-fluoro-benzyl)-ureido]-5-isopropyl-thiazol-4-ylmethyl}-methyl-amide;

5-Oxo-pyrrolidine-2-carboxylic acid {2-[3-(3-fluoro-benzyl)-ureido]-thiazol-4-ylmethyl}-methyl-amide;

3-Methyl-pyrazine-2-carboxylic acid {2-[3-(5-chloro-thiophen-3-ylmethyl)-ureido]-thiazol-4-ylmethyl}-methyl-amide;

3,5-Dimethyl-isoxazole-4-carboxylic acid (2,2-difluoro-ethyl)-{2-[3-(3-fluoro-benzyl)-ureido]-thiazol-4-ylmethyl}-amide;

4-Methyl-pyridazine-3-carboxylic acid {2-[3-(3-fluoro-benzyl)-ureido]-thiazol-4-ylmethyl}-methyl-amide;

5-Methyl-pyridazine-4-carboxylic acid {2-[3-(3-fluoro-benzyl)-ureido]-thiazol-4-ylmethyl}-methyl-amide;

3-Amino-1H-pyrazole-4-carboxylic acid {2-[3-(3-fluoro-benzyl)-ureido]-thiazol-4-ylmethyl}-methyl-amide;

3,6-Dimethoxy-pyridazine-4-carboxylic acid {2-[3-(3-fluoro-benzyl)-ureido]-thiazol-4-ylmethyl}-methyl-amide;

(3,5-Dimethyl-isoxazol-4-ylmethyl)-{2-[3-(3-fluoro-benzyl)-ureido]-thiazol-4-ylmethyl}-carbamic acid methyl ester;

(R)-Tetrahydro-furan-2-carboxylic acid {2-[3-(5-chloro-thiophen-2-ylmethyl)-ureido]-thiazol-4-ylmethyl}-methyl-amide;

5-Methyl-pyridazine-4-carboxylic acid {2-[3-(5-chloro-thiophen-2-ylmethyl)-ureido]-thiazol-4-ylmethyl}-methyl-amide;

3,5-Dimethyl-1H-pyrazole-4-carboxylic acid {2-[3-(5-chloro-thiophen-2-ylmethyl)-ureido]-thiazol-4-ylmethyl}-methyl-amide;

5-Methyl-pyridazine-4-carboxylic acid {2-[3-(5-chloro-thiophen-3-ylmethyl)-ureido]-thiazol-4-ylmethyl}-methyl-amide;

Tetrahydro-furan-2-carboxylic acid {2-[3-(5-chloro-thiophen-3-ylmethyl)-ureido]-thiazol-4-ylmethyl}-methyl-amide;

3,5-Dimethyl-1H-pyrazole-4-carboxylic acid {2-[3-(5-chloro-thiophen-3-ylmethyl)-ureido]-thiazol-4-ylmethyl}-methyl-amide;

1,3,5-Trimethyl-1H-pyrazole-4-carboxylic acid {2-[3-(5-chloro-thiophen-3-ylmethyl)-ureido]-thiazol-4-ylmethyl}-methyl-amide;

3,6-Dichloro-pyridazine-4-carboxylic acid {2-[3-(3-fluoro-benzyl)-ureido]-thiazol-4-ylmethyl}-methyl-amide;

3-Chloro-6-methoxy-pyridazine-4-carboxylic acid {2-[3-(3-fluoro-benzyl)-ureido]-thiazol-4-ylmethyl}-methyl-amide;

3,5-Dimethyl-isoxazole-4-carboxylic acid {5-fluoro-2-[3-(3-fluoro-benzyl)-ureido]-thiazol-4-ylmethyl}-methyl-amide;

(R)-Tetrahydro-furan-2-carboxylic acid {5-fluoro-2-[3-(3-fluoro-benzyl)-ureido]-thiazol-4-ylmethyl}-methyl-amide;

3,5-Dimethyl-pyridazine-4-carboxylic acid {2-[3-(3-fluoro-benzyl)-ureido]-thiazol-4-ylmethyl}-methyl-amide;
N-{5-Fluoro-2-[3-(3-fluoro-benzyl)-ureido]-thiazol-4-ylmethyl}-N-methyl-acetamide;
1-Methyl-3-trifluoromethyl-1H-pyrazole-4-carboxylic acid {2-[3-(3-fluoro-benzyl)-ureido]-thiazol-4-ylmethyl}-methyl-amide;
1,3,5-Trimethyl-1H-pyrazole-4-carboxylic acid {5-fluoro-2-[3-(3-fluoro-benzyl)-ureido]-thiazol-4-ylmethyl}-methyl-amide;
1,3,5-Trimethyl-1H-pyrazole-4-carboxylic acid {2-[3-(5-chloro-thiophen-2-ylmethyl)-ureido]-thiazol-4-ylmethyl}-methyl-amide;
3-Chloro-6-hydroxy-pyridazine-4-carboxylic acid {2-[3-(3-fluoro-benzyl)-ureido]-thiazol-4-ylmethyl}-methyl-amide;
2-Methyl-tetrahydro-furan-2-carboxylic acid {2-[3-(3-fluoro-benzyl)-ureido]-thiazol-4-ylmethyl}-methyl-amide;
4-Chloro-1-methyl-1H-pyrazole-3-carboxylic acid {2-[3-(3-fluoro-benzyl)-ureido]-thiazol-4-ylmethyl}-methyl-amide;
5-Chloro-1-methyl-1H-pyrazole-4-carboxylic acid {2-[3-(3-fluoro-benzyl)-ureido]-thiazol-4-ylmethyl}-methyl-amide;
4-Chloro-2-methyl-2H-pyrazole-3-carboxylic acid {2-[3-(3-fluoro-benzyl)-ureido]-thiazol-4-ylmethyl}-methyl-amide;
4-Chloro-1H-pyrazole-3-carboxylic acid {2-[3-(3-fluoro-benzyl)-ureido]-thiazol-4-ylmethyl}-methyl-amide;
3,5-Dimethyl-isoxazole-4-carboxylic acid (cyano-{2-[3-(3-fluoro-benzyl)-ureido]-thiazol-4-yl}-methyl)-methyl-amide;
1-Methyl-3-trifluoromethyl-1H-pyrazole-4-carboxylic acid {2-[3-(5-chloro-thiophen-2-ylmethyl)-ureido]-thiazol-4-ylmethyl}-methyl-amide;
1-Methyl-3-trifluoromethyl-1H-pyrazole-4-carboxylic acid {2-[3-(5-chloro-thiophen-2-ylmethyl)-ureido]-thiazol-4-ylmethyl}-methyl-amide;
1,3,6-Trimethyl-1H-pyrazolo[3,4-b]pyridine-4-carboxylic acid {2-[3-(5-chloro-thiophen-2-ylmethyl)-ureido]-thiazol-4-ylmethyl}-methyl-amide;
N-{2-[3-(5-Chloro-thiophen-2-ylmethyl)-ureido]-thiazol-4-ylmethyl}-2,N-dimethyl-5-sulfamoyl-benzamide;
1-Methyl-6-oxo-1,4,5,6-tetrahydro-pyridazine-3-carboxylic acid {2-[3-(5-chloro-thiophen-2-ylmethyl)-ureido]-thiazol-4-ylmethyl}-methyl-amide;
1-Phenyl-cyclobutanecarboxylic acid {2-[3-(5-chloro-thiophen-2-ylmethyl)-ureido]-thiazol-4-ylmethyl}-methyl-amide;
3-Methyl-4-oxo-3,4-dihydro-phthalazine-1-carboxylic acid {2-[3-(5-chloro-thiophen-2-ylmethyl)-ureido]-thiazol-4-ylmethyl}-methyl-amide;
7-Chloro-benzo[1,3]dioxole-5-carboxylic acid {2-[3-(5-chloro-thiophen-2-ylmethyl)-ureido]-thiazol-4-ylmethyl}-methyl-amide;
N-{2-[3-(5-Chloro-thiophen-2-ylmethyl)-ureido]-thiazol-4-ylmethyl}-N-methyl-6-[1,2,4]triazol-1-yl-nicotinamide;
1-(2-Methoxy-ethyl)-6-oxo-1,6-dihydro-pyridazine-3-carboxylic acid {2-[3-(5-chloro-thiophen-2-ylmethyl)-ureido]-thiazol-4-ylmethyl}-methyl-amide;
N-((2-(3-((5-chlorothiophen-2-yl)methyl)ureido)thiazol-4-yl)methyl)-2-(2,4-dioxo-3,4-dihydropyrimidin-1(2H)-yl)-N-methylacetamide;
1,1-Dioxo-tetrahydrothiophene-3-carboxylic acid {2-[3-(5-chlorothiophen-2-yl)methyl)-ureido]-thiazol-4-ylmethyl}-methyl-amide;
6-chloro-N-((2-(3-(3-fluorobenzyl)ureido)thiazol-4-yl)methyl)-3-hydroxy-N-methylpyridazine-4-carboxamide;
5-chloro-N-((2-(3-(3-fluorobenzyl)ureido)thiazol-4-yl)methyl)-N,1,3-trimethyl-1H-pyrazole-4-carboxamide;
N-((2-(3-(3-fluorobenzyl)ureido)thiazol-4-yl)methyl)-5-isopropyl-N,3-dimethylisoxazole-4-carboxamide;
3-cyano-N-((2-(3-(3-fluorobenzyl)ureido)thiazol-4-yl)methyl)-2-hydroxy-N,6-dimethylisonicotinamide;
6-chloro-N-((2-(3-(3-fluorobenzyl)ureido)thiazol-4-yl)methyl)-N-methyl-3-oxo-2,3-dihydropyridazine-4-carboxamide;
N-((2-(3-(3-fluorobenzyl)ureido)thiazol-4-yl)methyl)-N,1-dimethyl-5-(1H-pyrrol-1-yl)-1H-pyrazole-4-carboxamide;
N-((2-(3-(3-fluorobenzyl)ureido)thiazol-4-yl)methyl)-N,2-dimethyl-5-sulfamoylbenzamide;
N-((2-(3-(3-fluorobenzyl)ureido)thiazol-4-yl)methyl)-N-methyl-1-phenylcyclobutanecarboxamide;
N-((2-(3-(3-fluorobenzyl)ureido)thiazol-4-yl)methyl)-N-methyl-4-oxo-3,4-dihydrophthalazine-1-carboxamide;
N-((2-(3-(3-fluorobenzyl)ureido)thiazol-4-yl)methyl)-N,4,6-trimethyl-2-oxo-2H-pyran-5-carboxamide;
7-chloro-N-((2-(3-(3-fluorobenzyl)ureido)thiazol-4-yl)methyl)-N-methylbenzo[1,3]dioxole-5-carboxamide;
N-((2-(3-(3-fluorobenzyl)ureido)thiazol-4-yl)methyl)-N,1-dimethyl-4-sulfamoyl-1H-pyrrole-2-carboxamide;
2-(5,7-dimethyl-[1,2,4]triazolo[1,5-a]pyrimidin-6-yl)-N-((2-(3-(3-fluorobenzyl)ureido)thiazol-4-yl)methyl)-N-methylacetamide;
N-((2-(3-(3-fluorobenzyl)ureido)thiazol-4-yl)methyl)-N,3,6-trimethyl-4-oxo-3,4-dihydrofuro[2,3-d]pyrimidine-5-carboxamide;
N-((2-(3-(3-fluorobenzyl)ureido)thiazol-4-yl)methyl)-N,5-dimethyl-4-oxo-3,4-dihydrothieno[2,3-d]pyrimidine-6-carboxamide;
2,2-difluoro-N-((2-(3-(3-fluorobenzyl)ureido)thiazol-4-yl)methyl)-N-methyl-2-phenylacetamide;
N2-((2-(3-(3-fluorobenzyl)ureido)thiazol-4-yl)methyl)-4-hydroxy-N2-methylpyrrolidine-1,2-dicarboxamide;
N-((2-(3-((5-chlorothiophen-2-yl)methyl)ureido)thiazol-4-yl)methyl)-N-methyl-2-morpholinonicotinamide;
N-((2-(3-((5-chlorothiophen-2-yl)methyl)ureido)thiazol-4-yl)methyl)-N-methyl-4-oxo-3,4-dihydrophthalazine-1-carboxamide;
N-((2-(3-((5-chlorothiophen-2-yl)methyl)ureido)thiazol-4-yl)methyl)-N,4,6-trimethyl-2-oxo-2H-pyran-5-carboxamide;
N-((2-(3-((5-chlorothiophen-2-yl)methyl)ureido)thiazol-4-yl)methyl)-N,1-dimethyl-4-sulfamoyl-1H-pyrrole-2-carboxamide;
N-((2-(3-((5-chlorothiophen-2-yl)methyl)ureido)thiazol-4-yl)methyl)-2-(5,7-dimethyl-[1,2,4]triazolo[1,5-a]pyrimidin-6-yl)-N-methylacetamide;
N-((2-(3-((5-chlorothiophen-2-yl)methyl)ureido)thiazol-4-yl)methyl)-N,5-dimethyl-4-oxo-3,4-dihydrothieno[2,3-d]pyrimidine-6-carboxamide;
N-((2-(3-((5-chlorothiophen-2-yl)methyl)ureido)thiazol-4-yl)methyl)-1-(3-fluorophenyl)-N-methylcyclobutanecarboxamide;
N-((2-(3-((5-chlorothiophen-2-yl)methyl)ureido)thiazol-4-yl)methyl)-2,2-difluoro-N-methyl-2-phenylacetamide;

N-((2-(3-(3-fluorobenzyl)ureido)thiazol-4-yl)methyl)-N-methyl-5-(trifluoromethyl)-1H-pyrazole-4-carboxamide;

N-((2-(3-(3-fluorobenzyl)ureido)thiazol-4-yl)methyl)-N,1-dimethyl-5-(trifluoromethyl)-1H-pyrazole-4-carboxamide;

(S)—N-((2-(3-(3-fluorobenzyl)ureido)thiazol-4-yl)methyl)-2-methoxy-N-methylpropanamide;

N-((2-(3-(3-fluorobenzyl)ureido)thiazol-4-yl)methyl)-N,3-dimethyl-5,6-dihydro-1,4-dioxine-2-carboxamide;

(R)—N-((2-(3-(3-fluorobenzyl)ureido)thiazol-4-yl)methyl)-N-methyl-5-oxotetrahydrofuran-2-carboxamide;

5-chloro-N-((2-(3-((5-chlorothiophen-2-yl)methyl)ureido)thiazol-4-yl)methyl)-N,1,3-trimethyl-1H-pyrazole-4-carboxamide;

N-((2-(3-(3-fluorobenzyl)ureido)thiazol-4-yl)methyl)-N,1-dimethyl-6-oxo-1,4,5,6-tetrahydropyridazine-3-carboxamide;

N-((2-(3-(3-fluorobenzyl)ureido)thiazol-4-yl)methyl)-N,3-dimethyl-4-oxo-3,4-dihydrophthalazine-1-carboxamide;

N-((2-(3-((5-chlorothiophen-2-yl)methyl)ureido)thiazol-4-yl)methyl)-N,1-dimethyl-5-(1H-pyrrol-1-yl)-1H-pyrazole-4-carboxamide;

N-((2-(3-((5-chlorothiophen-2-yl)methyl)ureido)thiazol-4-yl)methyl)-N,3,6-trimethyl-4-oxo-3,4-dihydrofuro[2,3-d]pyrimidine-5-carboxamide;

N-((2-(3-(3-fluorobenzyl)ureido)thiazol-4-yl)methyl)-3-methoxy-N-methylpropanamide;

N-((2-(3-(3-fluorobenzyl)ureido)thiazol-4-yl)methyl)-1-(2-hydroxyethyl)-N,3,5-trimethyl-1H-pyrazole-4-carboxamide;

(R)—N-((2-(3-(3-fluorobenzyl)ureido)thiazol-4-yl)methyl)-2-methoxy-N-methylpropanamide;

N-((2-(3-(3-fluorobenzyl)ureido)thiazol-4-yl)methyl)-1-(2-methoxyethyl)-N,3,5-trimethyl-1H-pyrazole-4-carboxamide;

N-((2-(3-(3-fluorobenzyl)ureido)thiazol-4-yl)methyl)-N-methyltetrahydro-2H-pyran-2-carboxamide;

N-(cyano(2-(3-(3-fluorobenzyl)ureido)thiazol-4-yl)methyl)-N,3-dimethylpyrazine-2-carboxamide;

N-(cyano(2-(3-(3-fluorobenzyl)ureido)thiazol-4-yl)methyl)-N-methyltetrahydrofuran-2-carboxamide;

N-((2-(3-((5-chlorothiophen-2-yl)methyl)ureido)thiazol-4-yl)methyl)-N,3,6-trimethylisoxazolo[5,4-b]pyridine-4-carboxamide;

N-((2-(3-(3-fluorobenzyl)ureido)thiazol-4-yl)methyl)-5-methoxy-N-methyltetrahydrofuran-2-carboxamide;

N-((2-(3-(3-fluorobenzyl)ureido)thiazol-4-yl)methyl)-1-(4-methoxybutyl)-N,3,5-trimethyl-1H-pyrazole-4-carboxamide;

N-((2-(3-(3-fluorobenzyl)ureido)thiazol-4-yl)methyl)-1-(3-methoxypropyl)-N,3,5-trimethyl-1H-pyrazole-4-carboxamide;

N-((5-fluoro-2-(3-(3-fluorobenzyl)ureido)thiazol-4-yl)methyl)-N,3,5-trimethylpyridazine-4-carboxamide;

N-((2-(3-(3-fluorobenzyl)ureido)thiazol-4-yl)methyl)-N-methyl-2-morpholinonicotinamide;

N-((2-(3-(3-fluorobenzyl)ureido)thiazol-4-yl)methyl)-N,3,6-trimethylisoxazolo[5,4-b]pyridine-4-carboxamide;

N-((2-(3-(3-fluorobenzyl)ureido)thiazol-4-yl)methyl)-1-(4-fluorophenyl)-N-methylcyclobutanecarboxamide;

1,1-Dioxo-tetrahydrothiophene-3-carboxylic acid {2-[3-(3-fluoro-benzyl)-ureido]-thiazol-4-ylmethyl}-methylamide;

N-((2-(3-(3-fluorobenzyl)ureido)thiazol-4-yl)methyl)-N,5-dimethyltetrahydrofuran-2-carboxamide;

N-((2-(3-(3-fluorobenzyl)ureido)thiazol-4-yl)methyl)-N,3-dimethyloxetane-3-carboxamide;

5-chloro-N-((2-(3-(3-fluorobenzyl)ureido)thiazol-4-yl)methyl)-N-methyl-1H-pyrazole-4-carboxamide;

(R)—N-((2-(3-(3-fluorobenzyl)ureido)thiazol-4-yl)methyl)-N,2,2-trimethyl-1,3-dioxolane-4-carboxamide;

(S)—N-((2-(3-(3-fluorobenzyl)ureido)thiazol-4-yl)methyl)-N,2,2-trimethyl-1,3-dioxolane-4-carboxamide;

N-(2-amino-1-(2-(3-(3-fluorobenzyl)ureido)thiazol-4-yl)ethyl)-N-methyltetrahydrofuran-2-carboxamide;

(R)—N-((2-(3-((5-fluorothiophen-2-yl)methyl)ureido)thiazol-4-yl)methyl)-N-methyltetrahydrofuran-2-carboxamide;

3,6-dichloro-N-((2-(3-(3-fluorobenzyl)ureido)thiazol-4-yl)methyl)-N,5-dimethylpyridazine-4-carboxamide;

N-((2-(3-(3-fluorobenzyl)ureido)thiazol-4-yl)methyl)-6-methoxy-N,3-dimethylpyridazine-4-carboxamide;

N-((2-(3-(3-fluorobenzyl)ureido)thiazol-4-yl)methyl)-N,1,3,6-tetramethyl-1H-pyrazolo[3,4-b]pyridine-4-carboxamide;

N-((2-(3-(3-fluorobenzyl)ureido)thiazol-4-yl)methyl)-N,1-dimethyl-5-nitro-1H-pyrazole-4-carboxamide;

N-((2-(3-(3-fluorobenzyl)ureido)thiazol-4-yl)methyl)-N-methyl-2,3-dihydrobenzofuran-2-carboxamide;

N-((2-(3-((5-chlorothiophen-2-yl)methyl)ureido)thiazol-4-yl)methyl)-N-methyl-2,3-dihydrobenzofuran-2-carboxamide;

N-((2-(3-(3-fluorobenzyl)ureido)thiazol-4-yl)methyl)-6-hydroxy-N,3-dimethylpyridazine-4-carboxamide;

N-((2-(3-(3-fluorobenzyl)ureido)thiazol-4-yl)methyl)-N-methyl-2-(pyrrolidin-1-yl)nicotinamide;

N-((2-(3-(3-fluorobenzyl)ureido)thiazol-4-yl)methyl)-N-methyl-4-oxo-4-(thiophen-2-yl)butanamide;

N-((2-(3-(3-fluorobenzyl)ureido)thiazol-4-yl)methyl)-N-methyl-4-oxo-4-phenylbutanamide;

2-(3-fluoro-4-methoxyphenyl)-N-((2-(3-(3-fluorobenzyl)ureido)thiazol-4-yl)methyl)-N-methylacetamide;

2-(3,4-dimethoxyphenyl)-N-((2-(3-(3-fluorobenzyl)ureido)thiazol-4-yl)methyl)-N-methylacetamide;

N-((2-(3-(3-fluorobenzyl)ureido)thiazol-4-yl)methyl)-2-(4-(hydroxymethyl)phenoxy)-N-methylacetamide;

N-((2-(3-(3-fluorobenzyl)ureido)thiazol-4-yl)methyl)-N-methyl-2-(3-(methylsulfonyl)phenyl)acetamide;

N-((2-(3-(3-fluorobenzyl)ureido)thiazol-4-yl)methyl)-2-(2-mercapto-4-methylthiazol-5-yl)-N-methylacetamide;

N-((2-(3-(3-fluorobenzyl)ureido)thiazol-4-yl)methyl)-N-methyl-5-(trifluoromethyl)furan-2-carboxamide;

(R)—N-((5-fluoro-2-(3-(3-fluorobenzyl)ureido)thiazol-4-yl)methyl)-2-methoxy-N-methylpropanamide;

N-((2-(3-(3-fluorobenzyl)ureido)thiazol-4-yl)methyl)-6-hydroxy-N-methyl-3-(methylamino)pyridazine-4-carboxamide;

3-(dimethylamino)-N-((2-(3-(3-fluorobenzyl)ureido)thiazol-4-yl)methyl)-6-methoxy-N-methylpyridazine-4-carboxamide;

N-((2-(3-(3-fluorobenzyl)ureido)thiazol-4-yl)methyl)-1-(2-methoxyethyl)-N-methyl-6-oxo-1,6-dihydropyridazine-3-carboxamide;

N-((2-(3-((5-chlorothiophen-2-yl)methyl)ureido)thiazol-4-yl)methyl)-N-methyl-2-(pyrrolidin-1-yl)nicotinamide;

N-((2-(3-(3-fluorobenzyl)ureido)thiazol-4-yl)methyl)-N,2,2-trimethyltetrahydro-2H-pyran-4-carboxamide;

N-((2-(3-((5-chlorothiophen-2-yl)methyl)ureido)thiazol-4-yl)methyl)-N,2,2-trimethyltetrahydro-2H-pyran-4-carboxamide;

N-((2-(3-((1H-indol-5-yl)methyl)ureido)thiazol-4-yl)methyl)-N,3,5-trimethylisoxazole-4-carboxamide;
N-((2-(3-(benzo[1,2,5]oxadiazol-5-ylmethyl)ureido)thiazol-4-yl)methyl)-N,3,5-trimethylisoxazole-4-carboxamide;
N-((2-(3-(benzo[1,2,5]thiadiazol-5-ylmethyl)ureido)thiazol-4-yl)methyl)-N,3,5-trimethylisoxazole-4-carboxamide;
2-(4-(dimethylamino)phenyl)-N-((2-(3-(3-fluorobenzyl)ureido)thiazol-4-yl)methyl)-N-methylacetamide;
N-((2-(3-(3-fluorobenzyl)ureido)thiazol-4-yl)methyl)-7-hydroxy-N-methyl-1,2,3,4-tetrahydroisoquinoline-3-carboxamide;
3-(1H-benzoimidazol-2-yl)-N-((2-(3-(3-fluorobenzyl)ureido)thiazol-4-yl)methyl)-N-methylpropanamide;
N-((2-(3-(3-fluorobenzyl)ureido)thiazol-4-yl)methyl)-N-methyl-2-(naphthalen-2-yl)acetamide;
N-((2-(3-(3-fluorobenzyl)ureido)thiazol-4-yl)methyl)-2-(4-methoxy-3-methylphenyl)-N-methylacetamide;
2-amino-3-(benzyloxy)-N-((2-(3-(3-fluorobenzyl)ureido)thiazol-4-yl)methyl)-N-methylpropanamide;
N-((2-(3-(3-fluorobenzyl)ureido)thiazol-4-yl)methyl)-N-methyl-1,4-dioxo-1,2,3,4-tetrahydrophthalazine-6-carboxamide;
N-((2-(3-(3-fluorobenzyl)ureido)thiazol-4-yl)methyl)-N-methyl-6-(1H-1,2,4-triazol-1-yl)nicotinamide;
2-(2,4-dioxo-3,4-dihydropyrimidin-1(2H)-yl)-N-((2-(3-(3-fluorobenzyl)ureido)thiazol-4-yl)methyl)-N-methylacetamide;
N-((2-(3-((5-chlorothiophen-2-yl)methyl)ureido)thiazol-4-yl)methyl)-N-methyl-1,4-dioxo-1,2,3,4-tetrahydrophthalazine-6-carboxamide;
N2-((2-(3-((5-chlorothiophen-2-yl)methyl)ureido)thiazol-4-yl)methyl)-4-hydroxy-N2-methylpyrrolidine-1,2-dicarboxamide;
N-((2-(3-((5-chlorothiophen-2-yl)methyl)ureido)thiazol-4-yl)methyl)-N,1-dimethyl-5-nitro-1H-pyrazole-4-carboxamide;
(S)-3,3-difluoro-N-((2-(3-(3-fluorobenzyl)ureido)thiazol-4-yl)methyl)-N-methyltetrahydrofuran-2-carboxamide;
N-((2-(3-(3-fluorobenzyl)ureido)thiazol-4-yl)methyl)-N-methylchroman-2-carboxamide;
4-(3,5-dimethyl-1H-pyrazol-4-yl)-N-((2-(3-(3-fluorobenzyl)ureido)thiazol-4-yl)methyl)-N-methylbenzamide;
N-((2-(3-(3-fluorobenzyl)ureido)thiazol-4-yl)methyl)-N-methylpent-4-ynamide;
N-((2-(3-(3-fluorobenzyl)ureido)thiazol-4-yl)methyl)-N,2-dimethyl-1,2,3,4-tetrahydroisoquinoline-3-carboxamide;
(S)-2-amino-N-((2-(3-(3-fluorobenzyl)ureido)thiazol-4-yl)methyl)-N-methyl-3-(pyridin-4-yl)propanamide;
cis-N-((2-(3-(3-fluorobenzyl)ureido)thiazol-4-yl)methyl)-3-methoxy-N-methyltetrahydrofuran-2-carboxamide;
1-cyano-N-((2-(3-(3-fluorobenzyl)ureido)thiazol-4-yl)methyl)-N-methylcyclopropanecarboxamide;
N-((2-(3-(3-fluorobenzyl)ureido)thiazol-4-yl)methyl)-N-methylpropiolamide;
N-((2-(3-((1H-indol-2-yl)methyl)ureido)thiazol-4-yl)methyl)-N,3,5-trimethylisoxazole-4-carboxamide;
N-((2-(3-(benzoxazol-6-ylmethyl)ureido)thiazol-4-yl)methyl)-N,3,5-trimethylisoxazole-4-carboxamide;
2-ethoxy-N-((2-(3-(3-fluorobenzyl)ureido)thiazol-4-yl)methyl)-N-methylpropanamide;
N-((2-(3-(3-fluorobenzyl)ureido)thiazol-4-yl)methyl)-2-(4-methoxyphenoxy)-N-methylpropanamide;
2-(cyclopropylmethoxy)-N-((2-(3-(3-fluorobenzyl)ureido)thiazol-4-yl)methyl)-N-methylpropanamide;
2,5-diamino-N-((2-(3-(3-fluorobenzyl)ureido)thiazol-4-yl)methyl)-N-methylpentanamide;
N-((2-(3-(3-fluorobenzyl)ureido)thiazol-4-yl)methyl)-N-methyl-2-(2-phenoxyethoxy)propanamide;
2-cyclopropyl-N-((2-(3-(3-fluorobenzyl)ureido)thiazol-4-yl)methyl)-N-methylacetamide;
N,3,5-trimethyl-N-((2-(3-(4-nitrobenzyl)ureido)thiazol-4-yl)methyl)isoxazole-4-carboxamide;
N,3,5-trimethyl-N-((2-(3-(3-nitrobenzyl)ureido)thiazol-4-yl)methyl)isoxazole-4-carboxamide;
3-ethyl-N-((2-(3-(3-fluorobenzyl)ureido)thiazol-4-yl)methyl)-N-methyloxetane-3-carboxamide;
2-(2,2-difluoroethoxy)-N-((2-(3-(3-fluorobenzyl)ureido)thiazol-4-yl)methyl)-N-methylpropanamide;
N-((2-(3-(3-fluorobenzyl)ureido)thiazol-4-yl)methyl)-2-(4-fluorobenzyloxy)propanamide;
2-(2,2,2-trifluoroethoxy)-N-((2-(3-(3-fluorobenzyl)ureido)thiazol-4-yl)methyl)-N-methylpropanamide;
N-((2-(3-(3-fluorobenzyl)ureido)thiazol-4-yl)methyl)-2-(prop-2-ynyloxy)propanamide;
N-((2-(3-(3-fluorobenzyl)ureido)thiazol-4-yl)methyl)-N-methyl-2-((5-methylisoxazol-3-yl)methoxy)propanamide;
N-((2-(3-(3-fluorobenzyl)ureido)thiazol-4-yl)methyl)-N-methyl-2-(1-methylpyrrolidin-3-yloxy)propanamide;
N-((2-(3-(3-fluorobenzyl)ureido)thiazol-4-yl)methyl)-2-(2-hydroxyethoxy)propanamide;
N-((2-(3-((5-chlorothiophen-2-yl)methyl)ureido)thiazol-4-yl)methyl)-N-methylcyclopentanecarboxamide;
N-((2-(3-((5-chlorothiophen-2-yl)methyl)ureido)thiazol-4-yl)methyl)-1-hydroxy-N-methylcyclopropanecarboxamide;
N-((2-(3-((5-chlorothiophen-2-yl)methyl)ureido)thiazol-4-yl)methyl)-N-methylcyclohexanecarboxamide;
1-cyano-N-((5-fluoro-2-(3-(3-fluorobenzyl)ureido)thiazol-4-yl)methyl)-N-methylcyclopropanecarboxamide;
N-((2-(3-(3-fluorobenzyl)ureido)thiazol-4-yl)methyl)-N-methylcyclopentanecarboxamide;
N-((2-(3-(3-fluorobenzyl)ureido)thiazol-4-yl)methyl)-N,2-dimethylcyclohexanecarboxamide;
N-((2-(3-(3-fluorobenzyl)ureido)thiazol-4-yl)methyl)-N-methylcyclohexanecarboxamide;
N-((2-(3-(3-fluorobenzyl)ureido)thiazol-4-yl)methyl)-N-methyl-2-oxo-2,3-dihydrobenzoxazole-6-carboxamide;
3,3,3-trifluoro-N-((2-(3-(3-fluorobenzyl)ureido)thiazol-4-yl)methyl)-N-methylpropanamide;
N-((2-(3-(3-fluorobenzyl)ureido)thiazol-4-yl)methyl)-2-hydroxy-N,2-dimethylpropanamide;
2,3-cis-N-((2-(3-(3-fluorobenzyl)ureido)thiazol-4-yl)methyl)-N,3-dimethyltetrahydrofuran-2-carboxamide;
(5R)—N-((2-(3-(3-fluorobenzyl)ureido)thiazol-4-yl)methyl)-5-(hydroxymethyl)-N-methyltetrahydrofuran-2-carboxamide;
N-((2-(3-((5-chlorothiophen-2-yl)methyl)ureido)thiazol-4-yl)methyl)-2-hydroxy-N,2-dimethylpropanamide;
N-((2-(3-(5-chlorothiophen-2-yl)methyl)ureido)thiazol-4-yl)methyl)-N-methyl-2-oxo-2,3-dihydrobenzoxazole-6-carboxamide;
(S)—N-((2-(3-((5-chlorothiophen-2-yl)methyl)ureido)thiazol-4-yl)methyl)-2-(4-hydroxy-2-oxopyrrolidin-1-yl)-N-methylacetamide;
(R)—N-((2-(3-(benzo[1,2,5]oxadiazol-5-ylmethyl)ureido)thiazol-4-yl)methyl)-N-methyltetrahydrofuran-2-carboxamide;

(R)—N-((2-(3-((7-chlorobenzo[1,3]dioxol-5-yl)methyl) ureido)thiazol-4-yl)methyl)-N-methyltetrahydrofuran-2-carboxamide;
2,3,3,3-tetrafluoro-N-((2-(3-(3-fluorobenzyl)ureido)thiazol-4-yl)methyl)-N-methylpropanamide;
N-((2-(3-(3-fluorobenzyl)ureido)thiazol-4-yl)methyl)-N-methylcyclopropanecarboxamide;
N-((2-(3-(3-fluorobenzyl)ureido)thiazol-4-yl)methyl)-N-methylcyclopropane-1,1-dicarboxamide;
N-((2-(3-(3-fluorobenzyl)ureido)thiazol-4-yl)methyl)-N,2-dimethylcyclopropanecarboxamide;
(S)—N-((2-(3-(3-fluorobenzyl)ureido)thiazol-4-yl)methyl)-2-(4-hydroxy-2-oxopyrrolidin-1-yl)-N-methylacetamide;
N-((5-(3-(3-fluorobenzyl)ureido)-1,2,4-thiadiazol-3-yl)methyl)-N,3,5-trimethylisoxazole-4-carboxamide;
N-((5-(3-(3-fluorobenzyl)ureido)-1,2,4-thiadiazol-3-yl)methyl)-N,2,6-trimethylbenzamide;
N-((5-(3-(3-fluorobenzyl)ureido)-1,2,4-thiadiazol-3-yl)methyl)-N,3-dimethylisonicotinamide;
N-((5-(3-(3-fluorobenzyl)ureido)-1,2,4-thiadiazol-3-yl)methyl)-N,3-dimethylpyrazine-2-carboxamide;
1,3,5-Trimethyl-1H-pyrazole-4-carboxylic acid {5-[3-(3-fluoro-benzyl)-ureido]-[1,2,4]thiadiazol-3-ylmethyl}-methyl-amide;
5-Chloro-1,3-dimethyl-1H-pyrazole-4-carboxylic acid {5-[3-(3-fluoro-benzyl)-ureido]-[1,2,4]thiadiazol-3-ylmethyl}-methyl-amide;
5-Isopropyl-3-methyl-isoxazole-4-carboxylic acid {5-[3-(3-fluoro-benzyl)-ureido]-[1,2,4]thiadiazol-3-ylmethyl}-methyl-amide;
1,3,5-Trimethyl-1H-pyrazolo[4,3-b]pyridine-7-carboxylic acid {5-[3-(5-chloro-thiophen-2-ylmethyl)-ureido]-[1,2,4]thiadiazol-3-ylmethyl}-methyl-amide;
1-Methyl-5-pyrrol-1-yl-1H-pyrazole-4-carboxylic acid {5-[3-(3-fluoro-benzyl)-ureido]-[1,2,4]thiadiazol-3-ylmethyl}-methyl-amide;
3-Methyl-4-oxo-3,4-dihydro-phthalazine-1-carboxylic acid {5-[3-(3-fluoro-benzyl)-ureido]-[1,2,4]thiadiazol-3-ylmethyl}-methyl-amide;
2,4-Dimethyl-6-oxo-6H-pyran-3-carboxylic acid {5-[3-(3-fluoro-benzyl)-ureido]-[1,2,4]thiadiazol-3-ylmethyl}-methyl-amide;
3,6-Dimethyl-isoxazolo[5,4-b]pyridine-4-carboxylic acid {5-[3-(3-fluoro-benzyl)-ureido]-[1,2,4]thiadiazol-3-ylmethyl}-methyl-amide;
2-(5,7-Dimethyl-[1,2,4]triazolo[1,5-a]pyrimidin-6-yl)-N-{5-[3-(3-fluoro-benzyl)-ureido]-[1,2,4]thiadiazol-3-ylmethyl}-N-methyl-acetamide;
3,6-Dimethyl-4-oxo-3,4-dihydro-furo[2,3-d]pyrimidine-5-carboxylic acid {5-[3-(3-fluoro-benzyl)-ureido]-[1,2,4]thiadiazol-3-ylmethyl}-methyl-amide;
N-{5-[3-(3-Fluoro-benzyl)-ureido]-[1,2,4]thiadiazol-3-ylmethyl}-N-methyl-6-[1,2,4]triazol-1-yl-nicotinamide;
1-(2-Methoxy-ethyl)-6-oxo-1,6-dihydro-pyridazine-3-carboxylic acid {5-[3-(3-fluoro-benzyl)-ureido]-[1,2,4]thiadiazol-3-ylmethyl}-methyl-amide;
1-Methyl-4-sulfamoyl-1H-pyrrole-2-carboxylic acid {5-[3-(5-chloro-thiophen-2-ylmethyl)-ureido]-[1,2,4]thiadiazol-3-ylmethyl}-methyl-amide;
N-{5-[3-(5-Chloro-thiophen-2-ylmethyl)-ureido]-[1,2,4]thiadiazol-3-ylmethyl}-2-(5,7-dimethyl-[1,2,4]triazolo[1,5-a]pyrimidin-6-yl)-N-methyl-acetamide;
3,6-Dimethyl-4-oxo-3,4-dihydro-furo[2,3-d]pyrimidine-5-carboxylic acid{5-[3-(5-chloro-thiophen-2-ylmethyl)-ureido]-[1,2,4]thiadiazol-3-ylmethyl}-methyl-amide;
(R)-Tetrahydro-furan-2-carboxylic acid {5-[3-(3-fluoro-benzyl)-ureido]-[1,2,4]thiadiazol-3-ylmethyl}-methyl-amide;
1,3,5-Trimethyl-1H-pyrazolo[4,3-b]pyridine-7-carboxylic acid {5-[3-(3-fluoro-benzyl)-ureido]-[1,2,4]thiadiazol-3-ylmethyl}-methyl-amide;
1-Methyl-3-trifluoromethyl-1H-pyrazole-4-carboxylic acid {5-[3-(5-chloro-thiophen-2-ylmethyl)-ureido]-[1,2,4]thiadiazol-3-ylmethyl}-methyl-amide;
N-{5-[3-(5-Chloro-thiophen-2-ylmethyl)-ureido]-[1,2,4]thiadiazol-3-ylmethyl}-3-cyano-2-hydroxy-6,N-dimethyl-isonicotinamide;
6-Chloro-3-oxo-2,3-dihydro-pyridazine-4-carboxylic acid {5-[3-(3-fluoro-benzyl)-ureido]-[1,2,4]thiadiazol-3-ylmethyl}-methyl-amide;
1-Methyl-6-oxo-1,4,5,6-tetrahydro-pyridazine-3-carboxylic acid {5-[3-(3-fluoro-benzyl)-ureido]-[1,2,4]thiadiazol-3-ylmethyl}-methyl-amide;
7-Chloro-benzo[1,3]dioxole-5-carboxylic acid {5-[3-(3-fluoro-benzyl)-ureido]-[1,2,4]thiadiazol-3-ylmethyl}-methyl-amide;
5-Methyl-4-oxo-3,4-dihydro-thieno[2,3-d]pyrimidine-6-carboxylic acid {5-[3-(3-fluoro-benzyl)-ureido]-[1,2,4]thiadiazol-3-ylmethyl}-methyl-amide;
1-Methyl-5-pyrrol-1-yl-1H-pyrazole-4-carboxylic acid {5-[3-(5-chloro-thiophen-2-ylmethyl)-ureido]-[1,2,4]thiadiazol-3-ylmethyl}-methyl-amide;
1-Methyl-6-oxo-1,4,5,6-tetrahydro-pyridazine-3-carboxylic acid {5-[3-(5-chloro-thiophen-2-ylmethyl)-ureido]-[1,2,4]thiadiazol-3-ylmethyl}-methyl-amide;
3-Methyl-4-oxo-3,4-dihydro-phthalazine-1-carboxylic acid {5-[3-(5-chloro-thiophen-2-ylmethyl)-ureido]-[1,2,4]thiadiazol-3-ylmethyl}-methyl-amide;
2,4-Dimethyl-6-oxo-6H-pyran-3-carboxylic acid {5-[3-(5-chloro-thiophen-2-ylmethyl)-ureido]-[1,2,4]thiadiazol-3-ylmethyl}-methyl-amide;
5-Methyl-4-oxo-3,4-dihydro-thieno[2,3-d]pyrimidine-6-carboxylic acid {5-[3-(5-chloro-thiophen-2-ylmethyl)-ureido]-[1,2,4]thiadiazol-3-ylmethyl}-methyl-amide;
N-{5-[3-(5-Chloro-thiophen-2-ylmethyl)-ureido]-[1,2,4]thiadiazol-3-ylmethyl}-N-methyl-6-[1,2,4]triazol-1-yl-nicotinamide;
1-(2-Methoxy-ethyl)-6-oxo-1,6-dihydro-pyridazine-3-carboxylic acid {5-[3-(5-chloro-thiophen-2-ylmethyl)-ureido]-[1,2,4]thiadiazol-3-ylmethyl}-methyl-amide;
N-{5-[3-(5-Chloro-thiophen-2-ylmethyl)-ureido]-[1,2,4]thiadiazol-3-ylmethyl}-2,2-difluoro-N-methyl-2-phenyl-acetamide;
(R)-Tetrahydro-furan-2-carboxylic acid [5-(3-benzo[1,2,5]oxadiazol-5-ylmethyl-ureido)-[1,2,4]thiadiazol-3-ylmethyl]-methyl-amide;
3,5-Dimethyl-1H-pyrazole-4-carboxylic acid {5-[3-(3-fluoro-benzyl)-ureido]-[1,2,4]thiadiazol-3-ylmethyl}-methyl-amide;
3,5-Dimethyl-pyridazine-4-carboxylic acid {5-[3-(3-fluoro-benzyl)-ureido]-[1,2,4]thiadiazol-3-ylmethyl}-methyl-amide;
5-Isopropyl-3-methyl-isoxazole-4-carboxylic acid {5-[3-(5-chloro-thiophen-2-ylmethyl)-ureido]-[1,2,4]thiadiazol-3-ylmethyl}-methyl-amide;
N-{5-[3-(3-Fluoro-benzyl)-ureido]-[1,2,4]thiadiazol-3-ylmethyl}-2,N-dimethyl-5-sulfamoyl-benzamide;

1,1-Dioxo-tetrahydrothiophene-3-carboxylic acid {5-[3-(3-fluoro-benzyl)-ureido]-[1,2,4]thiadiazol-3-ylmethyl}-methyl-amide;

N-{5-[3-(5-Chloro-thiophen-2-ylmethyl)-ureido]-[1,2,4]thiadiazol-3-ylmethyl}-N-methyl-2-morpholin-4-yl-nicotinamide;

1-Phenyl-cyclobutanecarboxylic acid {5-[3-(5-chloro-thiophen-2-ylmethyl)-ureido]-[1,2,4]thiadiazol-3-ylmethyl}-methyl-amide;

4-Oxo-3,4-dihydro-phthalazine-1-carboxylic acid {5-[3-(5-chloro-thiophen-2-ylmethyl)-ureido]-[1,2,4]thiadiazol-3-ylmethyl}-methyl-amide;

7-Chloro-benzo[1,3]dioxole-5-carboxylic acid {5-[3-(5-chloro-thiophen-2-ylmethyl)-ureido]-[1,2,4]thiadiazol-3-ylmethyl}-methyl-amide;

1-(4-Fluoro-phenyl)-cyclobutanecarboxylic acid {5-[3-(5-chloro-thiophen-2-ylmethyl)-ureido]-[1,2,4]thiadiazol-3-ylmethyl}-methyl-amide;

1-Methyl-3-trifluoromethyl-1H-pyrazole-4-carboxylic acid {5-[3-(3-fluoro-benzyl)-ureido]-[1,2,4]thiadiazol-3-ylmethyl}-methyl-amide;

5-Chloro-1,3-dimethyl-1H-pyrazole-4-carboxylic acid {5-[3-(5-chloro-thiophen-2-ylmethyl)-ureido]-[1,2,4]thiadiazol-3-ylmethyl}-methyl-amide;

1-Phenyl-cyclobutanecarboxylic acid {5-[3-(3-fluoro-benzyl)-ureido]-[1,2,4]thiadiazol-3-ylmethyl}-methyl-amide;

4-Oxo-3,4-dihydro-phthalazine-1-carboxylic acid {5-[3-(3-fluoro-benzyl)-ureido]-[1,2,4]thiadiazol-3-ylmethyl}-methyl-amide;

1-(4-Fluoro-phenyl)-cyclobutanecarboxylic acid {5-[3-(3-fluoro-benzyl)-ureido]-[1,2,4]thiadiazol-3-ylmethyl}-methyl-amide;

2,2-Difluoro-N-{5-[3-(3-fluoro-benzyl)-ureido]-[1,2,4]thiadiazol-3-ylmethyl}-N-methyl-2-phenyl-acetamide;

1,1-Dioxo-tetrahydro-1lambda*6*-thiophene-3-carboxylic acid {5-[3-(5-chloro-thiophen-2-ylmethyl)-ureido]-[1,2,4]thiadiazol-3-ylmethyl}-methyl-amide;

2,2-Dimethyl-tetrahydro-pyran-4-carboxylic acid {5-[3-(5-chloro-thiophen-2-ylmethyl)-ureido]-[1,2,4]thiadiazol-3-ylmethyl}-methyl-amide;

2,3-Dihydro-benzofuran-2-carboxylic acid {5-[3-(3-fluoro-benzyl)-ureido]-[1,2,4]thiadiazol-3-ylmethyl}-methyl-amide;

(R)-Tetrahydro-furan-2-carboxylic acid {5-[3-(5-chloro-thiophen-2-ylmethyl)-ureido]-[1,2,4]thiadiazol-3-ylmethyl}-methyl-amide;

2,2-Dimethyl-tetrahydro-pyran-4-carboxylic acid {5-[3-(3-fluoro-benzyl)-ureido]-[1,2,4]thiadiazol-3-ylmethyl}-methyl-amide;

1-Methyl-5-nitro-1H-pyrazole-4-carboxylic acid {5-[3-(3-fluoro-benzyl)-ureido]-[1,2,4]thiadiazol-3-ylmethyl}-methyl-amide;

1-Methyl-5-nitro-1H-pyrazole-4-carboxylic acid {5-[3-(5-chloro-thiophen-2-ylmethyl)-ureido]-[1,2,4]thiadiazol-3-ylmethyl}-methyl-amide;

2,3-Dihydro-benzofuran-2-carboxylic acid {5-[3-(5-chloro-thiophen-2-ylmethyl)-ureido]-[1,2,4]thiadiazol-3-ylmethyl}-methyl-amide;

(R)—N-{5-[3-(3-Fluoro-benzyl)-ureido]-[1,2,4]thiadiazol-3-ylmethyl}-2-methoxy-N-methyl-propionamide;

(R)—N-{5-[3-(5-chloro-thiophen-2-ylmethyl)-ureido]-[1,2,4]thiadiazol-3-ylmethyl}-2-methoxy-N-methyl-propionamide;

N-{5-[3-(3-Fluoro-benzyl)-ureido]-[1,2,4]thiadiazol-3-ylmethyl}-N-methyl-2-morpholin-4-yl-nicotinamide;

N-{5-[3-(3-Fluoro-benzyl)-ureido]-[1,2,4]thiadiazol-3-ylmethyl}-N-methyl-2-pyrrolidin-1-yl-nicotinamide;

N-{5-[3-(5-Chloro-thiophen-2-ylmethyl)-ureido]-[1,2,4]thiadiazol-3-ylmethyl}-2,N-dimethyl-5-sulfamoyl-benzamide;

N-{5-[3-(5-chloro-thiophen-2-ylmethyl)-ureido]-[1,2,4]thiadiazol-3-ylmethyl}-N-methyl-2-pyrrolidin-1-yl-nicotinamide;

2,2-Difluoro-N-{5-[3-(3-fluoro-benzyl)-ureido]-[1,2,4]thiadiazol-3-ylmethyl}-N-methyl-2-pyridin-2-yl-acetamide;

1-Methyl-4-sulfamoyl-1H-pyrrole-2-carboxylic acid {5-[3-(3-fluoro-benzyl)-ureido]-[1,2,4]thiadiazol-3-ylmethyl}-methyl-amide;

4-Hydroxy-pyrrolidine-1,2-dicarboxylic acid 1-amide 2-({5-[3-(3-fluoro-benzyl)-ureido]-[1,2,4]thiadiazol-3-ylmethyl}-methyl-amide);

Cyclopentanecarboxylic acid {5-[3-(3-fluoro-benzyl)-ureido]-[1,2,4]thiadiazol-3-ylmethyl}-methyl-amide;

2-Methyl-cyclohexanecarboxylic acid {5-[3-(3-fluoro-benzyl)-ureido]-[1,2,4]thiadiazol-3-ylmethyl}-methyl-amide;

Cyclohexanecarboxylic acid {5-[3-(3-fluoro-benzyl)-ureido]-[1,2,4]thiadiazol-3-ylmethyl}-methyl-amide;

2,6-Dioxo-hexahydro-pyrimidine-4-carboxylic acid {5-[3-(3-fluoro-benzyl)-ureido]-[1,2,4]thiadiazol-3-ylmethyl}-methyl-amide;

1-Cyano-cyclopropanecarboxylic acid {5-[3-(5-chloro-thiophen-2-ylmethyl)-ureido]-[1,2,4]thiadiazol-3-ylmethyl}-methyl-amide;

1-Hydroxy-cyclopropanecarboxylic acid {5-[3-(3-fluoro-benzyl)-ureido]-[1,2,4]thiadiazol-3-ylmethyl}-methyl-amide;

2-Oxo-2,3-dihydro-benzooxazole-6-carboxylic acid {5-[3-(3-fluoro-benzyl)-ureido]-[1,2,4]thiadiazol-3-ylmethyl}-methyl-amide;

N-{5-[3-(3-Fluoro-benzyl)-ureido]-[1,2,4]thiadiazol-3-ylmethyl}-2-hydroxy-2,N-dimethyl-propionamide;

1-Cyano-cyclopropanecarboxylic acid {5-[3-(3-fluoro-benzyl)-ureido]-[1,2,4]thiadiazol-3-ylmethyl}-methyl-amide;

N-{5-[3-(3-Fluoro-benzyl)-ureido]-[1,2,4]thiadiazol-3-ylmethyl}-2-((S)-4-hydroxy-2-oxo-pyrrolidin-1-yl)-N-methyl-acetamide;

1,1-Dioxo-tetrahydro-116-thiophene-3-sulfonic acid {2-[3-(3,4-dichloro-benzyl)-ureido]-thiazol-4-ylmethyl}-methyl-amide;

N-((2-(3-(3,4-dichlorobenzyl)ureido)thiazol-4-yl)methyl)-N,4-dimethylbenzenesulfonamide;

N-((2-(3-(3,4-dichlorobenzyl)ureido)thiazol-4-yl)methyl)-N,3,5-trimethylisoxazole-4-sulfonamide;

N-((2-(3-(3,4-dichlorobenzyl)ureido)thiazol-4-yl)methyl)-N-methylmethanesulfonamide;

N-((2-(3-(3-fluorobenzyl)ureido)thiazol-4-yl)methyl)-N-methylmethanesulfonamide;

N-((2-(3-(3-fluorobenzyl)ureido)thiazol-4-yl)methyl)-N-methylpropane-1-sulfonamide;

1-(3,4-dichlorobenzyl)-3-(4-(4-hydroxy-1-(methylsulfonyl)pyrrolidin-2-yl)thiazol-2-yl)urea;

N-((2-(3-(3-fluorobenzyl)ureido)thiazol-4-yl)methyl)-N-methylbutane-1-sulfonamide;

N-((2-(3-(3-fluorobenzyl)ureido)thiazol-4-yl)methyl)-N-methylethanesulfonamide;

N-((2-(3-(3-fluorobenzyl)ureido)thiazol-4-yl)methyl)-N,3,5-trimethylisoxazole-4-sulfonamide;

N-((2-(3-(3-fluorobenzyl)ureido)thiazol-4-yl)methyl)-N-methylcyclopropanesulfonamide;

N-((2-(3-(3-fluorobenzyl)ureido)thiazol-4-yl)methyl)-N-(2-(methylsulfonamido)ethyl)methanesulfonamide;

1-[4-(1,1-Dioxo-1l6-isothiazolidin-2-ylmethyl)-thiazol-2-yl]-3-(3-fluoro-benzyl)-urea;

Ethanesulfonic acid {5-bromo-2-[3-(3-fluoro-benzyl)-ureido]-thiazol-4-ylmethyl}-methyl-amide;

N-{2-[3-(3-Fluoro-benzyl)-ureido]-thiazol-4-ylmethyl}-N-methyl-4-morpholin-4-yl-benzenesulfonamide;

Furan-2-sulfonic acid {2-[3-(3-fluoro-benzyl)-ureido]-thiazol-4-ylmethyl}-methyl-amide;

Thiophene-2-sulfonic acid {2-[3-(3-fluoro-benzyl)-ureido]-thiazol-4-ylmethyl}-methyl-amide;

Pyridine-3-sulfonic acid {2-[3-(3-fluoro-benzyl)-ureido]-thiazol-4-ylmethyl}-methyl-amide;

Pyridine-2-sulfonic acid {2-[3-(3-fluoro-benzyl)-ureido]-thiazol-4-ylmethyl}-methyl-amide;

1-Methyl-1H-imidazole-4-sulfonic acid {2-[3-(3-fluoro-benzyl)-ureido]-thiazol-4-ylmethyl}-methyl-amide;

1,2-Dimethyl-1H-imidazole-4-sulfonic acid {2-[3-(3-fluoro-benzyl)-ureido]-thiazol-4-ylmethyl}-methyl-amide;

N-{2-[3-(3-Fluoro-benzyl)-ureido]-thiazol-4-ylmethyl}-N-methyl-C-pyridin-3-yl-methanesulfonamide;

N-(3,5-Dimethyl-isoxazol-4-ylmethyl)-N-{2-[3-(3-fluoro-benzyl)-ureido]-thiazol-4-ylmethyl}-methanesulfonamide.

21. A pharmaceutical composition comprising a therapeutically effective amount of a compound according to claim 1 or a pharmaceutically acceptable salt of a compound of claim 1.

22. A pharmaceutical composition comprising a therapeutically effective amount of a compound according to claim 20 or a pharmaceutically acceptable salt of a compound of claim 20.

23. The compound of claim 3, selected from the group consisting of 5-(2-(3-(3,4-dichlorobenzyl)ureido)thiazol-4-yl)-1-(methylsulfonyl)pyrrolidin-3-yl acetate and 1-(3-Fluoro-benzyl)-3-{4-[1-(propane-1-sulfonyl)-pyrrolidin-2-yl]-thiazol-2-yl}-urea.

* * * * *